United States Patent
Liu et al.

(10) Patent No.: US 12,428,632 B2
(45) Date of Patent: *Sep. 30, 2025

(54) POLYPEPTIDES HAVING LYZOZYME ACTIVITY, POLUNUCLEOTIDES ENCODING SAME AND USES AND COMPOSITIONS THEREOF

(71) Applicant: Novozymes A/S, Bagsvaerd (DK)

(72) Inventors: Ye Liu, Beijing (CN); Ming Li, Beijing (CN); Kirk Matthew Schnorr, Holte (DK); Peter Bjarke Olsen, Copenhagen (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/506,179

(22) Filed: Nov. 10, 2023

(65) Prior Publication Data

US 2024/0124862 A1    Apr. 18, 2024

Related U.S. Application Data

(62) Division of application No. 16/607,404, filed as application No. PCT/CN2018/086528 on May 11, 2018, now Pat. No. 11,859,170.

(30) Foreign Application Priority Data

May 12, 2017    (WO) ................ PCT/CN2017/084074

(51) Int. Cl.
| | | |
|---|---|---|
| C12N 9/36 | (2006.01) |
| A23K 10/30 | (2016.01) |
| A23K 20/189 | (2016.01) |
| A23K 40/10 | (2016.01) |
| A23K 40/30 | (2016.01) |
| A23K 50/30 | (2016.01) |
| A23K 50/75 | (2016.01) |
| A23K 50/80 | (2016.01) |

(52) U.S. Cl.
CPC ............ *C12N 9/2462* (2013.01); *A23K 10/30* (2016.05); *A23K 20/189* (2016.05); *A23K 40/10* (2016.05); *A23K 40/30* (2016.05); *A23K 50/30* (2016.05); *A23K 50/75* (2016.05); *A23K 50/80* (2016.05); *C12Y 302/01017* (2013.01)

(58) Field of Classification Search
CPC .......... C12N 9/2462; C12Y 302/01017; A23K 20/189
See application file for complete search history.

(56) References Cited

U.S. PATENT DOCUMENTS

| | | | |
|---|---|---|---|
| 4,355,022 A | 10/1982 | Rabussay | |
| 5,041,236 A | 8/1991 | Carpenter et al. | |
| 9,663,775 B2 | 5/2017 | Schnorr | |
| 10,945,449 B2 * | 3/2021 | Liu | ............. A23K 20/147 |
| 11,859,170 B2 * | 1/2024 | Liu | ............. A23K 10/30 |
| 2012/0288490 A1 | 11/2012 | De Maria | |
| 2014/0325711 A1 | 10/2014 | Schnorr et al. | |

FOREIGN PATENT DOCUMENTS

| | | |
|---|---|---|
| CN | 102858968 A | 1/2013 |
| CN | 103957929 A | 7/2014 |
| EP | 0425016 A2 | 10/1990 |
| WO | 2000021381 A1 | 4/2000 |
| WO | 2004017988 A1 | 3/2004 |
| WO | 2004026334 A1 | 4/2004 |
| WO | 2005080559 A1 | 9/2005 |
| WO | 2008124764 A1 | 10/2008 |
| WO | 2013076253 A1 | 5/2013 |
| WO | 2017000922 A1 | 1/2017 |
| WO | 2017001701 A1 | 1/2017 |
| WO | 2017001703 A1 | 1/2017 |
| WO | 2017064092 A1 | 4/2017 |

OTHER PUBLICATIONS

Search results #26, #30 showing SEQ ID No. 3 of U.S. Appl. No. 11/859,170 (Year: 2024).*
Anonymous, 2020, What is the true definition of Plant-based and why does it matter, article on the website of Root the future.
Hughey et al, 1987, Appl Environ Microbiol, vol. 53, pp. 2165-2170.
Masschalck et al., 2002, Journal of Food Protection, vol. 65, No. 12, pp. 1916-1923.
Vries et al., 2017, Uniprot No. A0A1Q5TMG8.
Zhu et al., 2017, Uniprot No. A0A0F7TVL0.

* cited by examiner

*Primary Examiner* — Ruth A Davis
(74) *Attorney, Agent, or Firm* — Adam Rucker

(57) ABSTRACT

Novel polypeptides having lysozyme activity, polynucleotides encoding polypeptides having lysozyme activity, and nucleic acid constructs, vectors, and host cells comprising polynucleotides that encode polypeptides having lysozyme activity, as well as methods of producing and using such polypeptides, polynucleotides, constructs, vectors, and host cells, including, but not limited to, animal feed and animal feed additives comprising polypeptides having lysozyme activity.

26 Claims, 2 Drawing Sheets

Specification includes a Sequence Listing.

SEQUENCE LISTING

```
Sequence total quantity: 329
SEQ ID NO: 1            moltype = DNA  length = 809
FEATURE                 Location/Qualifiers
sig_peptide             1..57
mat_peptide             58..806
source                  1..809
                        mol_type = genomic DNA
                        organism = Penicillium simplicissimum
CDS                     1..429
CDS                     501..806
SEQUENCE: 1
atgcacttct cgctcctcgc catctccgca gccattgcct tgcccctggc cagtgcctat   60
cccgtcaacg cggacgatct ccactgccgc tctggtcctg gcaccaacta tggcatcgtg  120
aagtcctaca agcgcggaac cgacctcagc atcacctgcc aggccaccgg caccgacgtc  180
aacggtgacg agctctggga caagacctcc gacggctgct acgtgagcga ctactatgtc  240
aagaccggct ccagcagcta cgttaccaag cactgcgacg gcagctccgg cggcggcagc  300
agcggtggca acctgcccgg cctgactgct actcagtcca agcacgccaa ggaaatcatc  360
gccgaggcca agcgtgagga tctgggtctg cacggctgct ctgccggtat tgcgactgcc  420
```

```
cttgttgagg tatgaacatt gacattccgc cccttgatag caatctccct cgaaatacga   480
tcgactaaca attcctctag tcgaacatct tgatctatgc caacaaggct gtccctctt    540
ccctcaacta cccccacgac gccgttggct cggaccacga cagtgttggt atcttccagc   600
agcgcgctat gtattacccc aacattgccg ctgatatgga tgccgccaag tctgctgccc   660
agttctttga gaagatgaag aacgttagtg gctggaagtc aatggctgtt ggaagccctt   720
gccagaaggt ccagggctcc gcttatccta ctcgctatgc tgagcgtgtt tctgaggctg   780
agaagatctg caaagctggt ggcatctaa                                     809

SEQ ID NO: 2              moltype = AA  length = 245
FEATURE                   Location/Qualifiers
source                    1..245
                          mol_type = protein
                          organism = Penicillium simplicissimum
SEQUENCE: 2
MHFSLLAISA AIALPLASAY PVNADDLHCR SGPGTNYGIV KSYKRGTDLS ITCQATGTDV   60
NGDELWDKTS DGCYVSDYYV KTGSSSYVTK HCDGSSGGGS SGGNLPGLTA TQSKHAKEII   120
AEAKREDLGL HGCSAGIATA LVESNILIYA NKAVPSSLNY PHDAVGSDHD SVGIFQQRAM   180
YYPNIAADMD AAKSAAQFFE KMKNVSGWKS MAVGSLCQKV QGSAYPTRYA ERVSEAEKIC   240
KAGGI                                                               245

SEQ ID NO: 3              moltype = AA  length = 226
FEATURE                   Location/Qualifiers
source                    1..226
                          mol_type = protein
                          organism = Penicillium simplicissimum
SEQUENCE: 3
YPVNADDLHC RSGPGTNYGI VKSYKRGTDL SITCQATGTD VNGDELWDKT SDGCYVSDYY   60
VKTGSSSYVT KHCDGSSGGG SSGGNLPGLT ATQSKHAKEI IAEAKREDLG LHGCSAGIAT   120
ALVESNILIY ANKAVPSSLN YPHDAVGSDH DSVGIFQQRA MYYPNIAADM DAAKSAAQFF   180
EKMKNVSGWK SMAVGSLCQK VQGSAYPTRY AERVSEAEKI CKAGGI                  226

SEQ ID NO: 4              moltype = DNA  length = 808
FEATURE                   Location/Qualifiers
sig_peptide               1..57
mat_peptide               58..805
source                    1..808
                          mol_type = genomic DNA
                          organism = Penicillium vasconiae
CDS                       1..429
CDS                       500..805
SEQUENCE: 4
atgcacttct cgctcctcgc catctccgca gccattgccc tgcccctggc cagcgcctat   60
cccgtcaacg ctgacgatct ccactgccgc tctggtccgg gcaccagcta cggcattgtc   120
aagtcctaca gcgcggaac tgacctcacc atcacctgcc aggccgccgg cacccgatgtc  180
aacggtgatg agctctggga caagaccccc gacggctgct atgtgagcga ctactacgtc   240
aagaccggcc cagcagcta cgttgccaag cactgtgacg gcggctctag cggtggcagc   300
agcggcggtg acttgcctgg tctgagtgct actcagtcca agcacgccag ggctatcatc   360
gccgaggcga agagtgagga tctgggtctg cacggctgct cggctggtat tgcgactgcc   420
cttgtggagg taagaacact ccttaatcac aattcctcct tataagatca atagtatcat   480
caactaacaa cctctatagt cgagcatcct gatctatgcc aacgggatg tccccacttc    540
cctgaactac ccccatgacg ctattggctc ggacaacgaa agtgtcggca tcttccagca   600
gcgcgccatt tactaccccg acattgcggc tgatatggat gccgccaagt ctgctgccca   660
gttcttcaag aagatgaaga acattagcgg ctggaagtct atggctgttg gaacccttg    720
ccagaaggtc cagggctctg cttatcctac tcgctatgct gagcgtgttg ctgaggcgga   780
gaagatttgc aatgctggtg gtatttaa                                      808

SEQ ID NO: 5              moltype = AA  length = 245
FEATURE                   Location/Qualifiers
source                    1..245
                          mol_type = protein
                          organism = Penicillium vasconiae
SEQUENCE: 5
MHFSLLAISA AIALPLASAY PVNADDLHCR SGPGTSYGIV KSYKRGTDLT ITCQAAGTDV   60
NGDELWDKTS DGCYVSDYYV KTGSSSYVAK HCDGGSSGGS SGGDLPGLSA TQSKHARAII   120
AEAKSEDLGL HGCSAGIATA LVESSILIYA NRDVPTSLNY PHDAIGSDND SVGIFQQRAI   180
YYPDIAADMD AAKSAAQFFK KMKNISGWKS MAVGTLCQKV QGSAYPTRYA ERVAEAEKIC   240
NAGGI                                                               245

SEQ ID NO: 6              moltype = AA  length = 226
FEATURE                   Location/Qualifiers
source                    1..226
                          mol_type = protein
                          organism = Penicillium vasconiae
SEQUENCE: 6
YPVNADDLHC RSGPGTSYGI VKSYKRGTDL TITCQAAGTD VNGDELWDKT SDGCYVSDYY   60
VKTGSSSYVA KHCDGGSSGG SSGGDLPGLS ATQSKHARAI IAEAKSEDLG LHGCSAGIAT   120
ALVESSILIY ANRDVPTSLN YPHDAIGSDN DSVGIFQQRA IYYPDIAADM DAAKSAAQFF   180
KKMKNISGWK SMAVGTLCQK VQGSAYPTRY AERVAEAEKI CNAGGI                  226
```

```
SEQ ID NO: 7                moltype = DNA   length = 802
FEATURE                     Location/Qualifiers
sig_peptide                 1..60
mat_peptide                 61..799
source                      1..802
                            mol_type = genomic DNA
                            organism = Talaromyces proteolyticus
CDS                         1..423
CDS                         494..799
SEQUENCE: 7
atgtttgcta cttcgctcat tgcactgtcc ctcgtgacaa tcctccccat ctccaacgcc   60
tatcccatca aaaccgatgg tcttcactgc cgttccggac cgggaacggg ttattcgatc  120
gtgaagacct acaacaaggg cgaagaggtc tcgatcactc gccaggcccc tggaactgat  180
gttaatgcag actcccttg  ggataagact tctgatggct gctatgtcac tgattactac  240
gttagcacag gcactagtgg ctacgtcact ggtgagtgtg gtagtaccgg tggcagtggt  300
ggaaaacttc cgggtcttga ctctacacaa tcgtcccatg cccgagccat atcgcagag   360
gccaaaaagg agagtctagg tcgtcagggc tgccttgccg gcattgcaac tgctttgact  420
gaggtatggc ttaaccctac tcataaattc cccttacatt gttttttac caatcatgtc   480
taactgagcg cagtcgagca ttctggtcta cgcaaacgag gccgttccag aatcgatgaa  540
atacaagcac gatgccgttg gcagcgacca cgatagcatt ggcatcttcc agcagcgcgc  600
aatgtactat cccaatatcg ccgcagacat ggatccagca aagtcggctg cacagttctt  660
tgctaaaatg aaggaggtta gtggatggcg aagcatgaac gttggtgaac tctgccagaa  720
ggttcaagga tctgcctatc ctactcgata tgaacagcat ctgtctgctg ctgaagcgat  780
ctgctctgct gacagtgatt ga                                           802

SEQ ID NO: 8                moltype = AA    length = 243
FEATURE                     Location/Qualifiers
source                      1..243
                            mol_type = protein
                            organism = Talaromyces proteolyticus
SEQUENCE: 8
MFATSLIALS LVTILPISNA YPIKTDGLHC RSGPGTGYSI VKTYNKGEEV SITCQAPGTD    60
VNGDSLWDKT SDGCYVTDYY VSTGTSGYVT GECGSTGGSG GKLPGLDSTQ SSHARAIIAE   120
AKKESLGRQG CLAGIATALT ESSILVYANE AVPESMKYKH DAVGSDHDSI GIFQQRAMYY   180
PNIAADMDPA KSAAQFFAKM KEVSGWRSMN VGELCQKVQG SAYPTRYEQH LSAAEAICSA   240
DSD                                                                243

SEQ ID NO: 9                moltype = AA    length = 223
FEATURE                     Location/Qualifiers
source                      1..223
                            mol_type = protein
                            organism = Talaromyces proteolyticus
SEQUENCE: 9
YPIKTDGLHC RSGPGTGYSI VKTYNKGEEV SITCQAPGTD VNGDSLWDKT SDGCYVTDYY    60
VSTGTSGYVT GECGSTGGSG GKLPGLDSTQ SSHARAIIAE AKKESLGRQG CLAGIATALT   120
ESSILVYANE AVPESMKYKH DAVGSDHDSI GIFQQRAMYY PNIAADMDPA KSAAQFFAKM   180
KEVSGWRSMN VGELCQKVQG SAYPTRYEQH LSAAEAICSA DSD                     223

SEQ ID NO: 10               moltype = DNA   length = 1043
FEATURE                     Location/Qualifiers
sig_peptide                 1..60
mat_peptide                 61..1040
source                      1..1043
                            mol_type = genomic DNA
                            organism = Aspergillus sp.
CDS                         1..666
CDS                         735..1040
SEQUENCE: 10
atgatgttca ttccactcgt cactctttgc tttgcagctg ctatcccgt tgtccgagca    60
tacccagtca aagctgatgt ccattgccgt tcgggccctg gaaccagcta ttccattgtc   120
aagacataca gcacggggac tcagatctcg gttagctgcc aggctgctgg tacagatgtt   180
gatggtgacc agctgtggga caagacctct gatggctgct atgtctccga ctattatgtg   240
tccacaggca gcagcaacta tgttaccagc cactgcccta ccgagtacgc cattaaaact   300
gatgtcaact gtcgttccgg tcccggaacc aattatgga  ttgtcaagac atacaatcag   360
ggagtgatgg tttctctcaa ctgccaggct tccggcaccg atgtcgatgg cgattctctc   420
tgggacaaga catccgatgg ctgctatgtc tctgactact acgtggccac cggcagcagc   480
agttatgtga caagcgcttg cagcggcagc agcagcagtg gcggtggtgg aagcagcagc   540
agcggcaacc tgcccagtct cgattccacc cagtctgccc acgcccgcgc cattatcgga   600
gaagccaaga gccaaaatgt tggtcgtcaa ggctgccttg ctggcattgc aactgccctg   660
gttgaggtaa gaggttcccc atatctcaag gtaccatttt tactggatga atgattgcta   720
actgtgtaca ccagtcgagc atgcttatgt atgctaacag caatgtcgcc gcatcgctca   780
gctatcctca tgatgctgtc ggctcggact acgatagcgt cggcctcttc agcagcgtg    840
tgtcgattta taccaacctc gctgctgata tggatgctgc acaatctgcc ggccagtttt   900
ttgatgagat gaagaaagtc agtggctggg agactatgaa cgttgtgat ctttgccagg    960
aggtgcagag gtcagcctat ccagaccgat atggggga  agtttcgact gctgagtcaa   1020
tctgctctgc tggtggtttg taa                                          1043

SEQ ID NO: 11               moltype = AA    length = 324
FEATURE                     Location/Qualifiers
```

```
source                    1..324
                          mol_type = protein
                          organism = Aspergillus sp.
SEQUENCE: 11
MMFIPLVTLC FAAAIPVVRA YPVKADVHCR SGPGTSYSIV KTYSTGTQIS VSCQAAGTDV    60
DGDQLWDKTS DGCYVSDYYV STGSSNYVTS HCPTEYAIKT DVNCRSGPGT NYGIVKTYNQ   120
GVMVSLNCQA SGTDVDGDSL WDKTSDGCYV SDYYVATGSS SYVTSACSGS SSSGGGGSSS   180
SGNLPSLDST QSAHARAIIG EAKSQNVGRQ GCLAGIATAL VESSMLMYAN SNVAASLSYP   240
HDAVGSDYDS VGLFQQRVSI YTNLAADMDA AQSAGOFFDE MKKVSGWETM NVGDLCQEVQ   300
RSAYPDRYAG EVSTAESICS AGGL                                         324

SEQ ID NO: 12             moltype = AA  length = 304
FEATURE                   Location/Qualifiers
source                    1..304
                          mol_type = protein
                          organism = Aspergillus sp.
SEQUENCE: 12
YPVKADVHCR SGPGTSYSIV KTYSTGTQIS VSCQAAGTDV DGDQLWDKTS DGCYVSDYYV    60
STGSSNYVTS HCPTEYAIKT DVNCRSGPGT NYGIVKTYNQ GVMVSLNCQA SGTDVDGDSL   120
WDKTSDGCYV SDYYVATGSS SYVTSACSGS SSSGGGGSSS SGNLPSLDST QSAHARAIIG   180
EAKSQNVGRQ GCLAGIATAL VESSMLMYAN SNVAASLSYP HDAVGSDYDS VGLFQQRVSI   240
YTNLAADMDA AQSAGOFFDE MKKVSGWETM NVGDLCQEVQ RSAYPDRYAG EVSTAESICS   300
AGGL                                                               304

SEQ ID NO: 13             moltype = DNA  length = 797
FEATURE                   Location/Qualifiers
sig_peptide               1..57
mat_peptide               58..794
source                    1..797
                          mol_type = genomic DNA
                          organism = Penicillium antarcticum
CDS                       1..435
CDS                       489..794
SEQUENCE: 13
atgcatttcc aactcgtgac tctctccgtt gccttgctct cccgtttat caacgcctac     60
cccatcaccg gtgacaccgt caactgccgc tccggtccag aacatccta ctcagtagtc    120
aagtcctaca aaagggcgc agatgttgca attacctgcc aagcatccgg cacagacatc    180
aaaggcgata gcatctggga caagaccgcc gatggctgct atgtcgcgga cttctacgtg   240
aaaacaggta gctccagcta cgtgacgaag aaatgcaagc tggcagcgg tggtggtggt    300
ggcagcagca gcggaaatct acctggcctt acatccactc agtccaagca tgccaaagct   360
atcatcggag aagcgaagaa ggaggatcta ggtcgccagg gctgtcttgc tggtattgca   420
actgctcttg ttgaggtgag gtctagtcta attctgcagt tccttgaatc attcttaaca   480
cattctagtc aaatattctc atctatgcca acaaaaaagt cccctcttca cttaactacc   540
cccacgatgc cgtgggctcg gactatgata tgtgttggcat cttccagcag cgcgccaagt   600
actatcccag tattgctgcc gatatggatc cggccaaatc ggctgcgcag ttctttaagg   660
gtatgaaggg tgtcagtggg tggaagacta tggaggttgg gaagctttgc cagaaggtgc   720
agggttcggc ttatcccact cgatatgcgg gacgtgtcga tgaggctgag aagatttgtg   780
ctgctggtgg tttgtag                                                  797

SEQ ID NO: 14             moltype = AA  length = 247
FEATURE                   Location/Qualifiers
source                    1..247
                          mol_type = protein
                          organism = Penicillium antarcticum
SEQUENCE: 14
MHFQLVTLSV ALLSPFINAY PITGDTVNCR SGPGTSYSVV KSYKKGADVA ITCQASGTDI    60
KGDSIWDKTA DGCYVADFYV KTGSSSYVTK KCNSGSGGGG GSSSGNLPGL TSTQSKHAKA   120
IIGEAKKEDL GRQGCLAGIA TALVESNILI YANKKVPSSL NYPHDAVGSD YDSVGIFQQR   180
AKYYPSIAAD MDPAKSAAQF FKGMKGVSGW KTMEVGKLCQ KVQGSAYPTR YAGRVDEAEK   240
ICAAGGL                                                            247

SEQ ID NO: 15             moltype = AA  length = 228
FEATURE                   Location/Qualifiers
source                    1..228
                          mol_type = protein
                          organism = Penicillium antarcticum
SEQUENCE: 15
YPITGDTVNC RSGPGTSYSV VKSYKKGADV AITCQASGTD IKGDSIWDKT ADGCYVADFY    60
VKTGSSSYVT KKCNSGSGGG GGSSSGNLPG LTSTQSKHAK AIIGEAKKED LGRQGCLAGI   120
ATALVESNIL IYANKKVPSS LNYPHDAVGS DYDSVGIFQQ RAKYYPSIAA DMDPAKSAAQ   180
FFKGMKGVSG WKTMEVGKLC QKVQGSAYPT RYAGRVDEAE KICAAGGL               228

SEQ ID NO: 16             moltype = DNA  length = 817
FEATURE                   Location/Qualifiers
sig_peptide               1..60
mat_peptide               61..814
source                    1..817
                          mol_type = genomic DNA
                          organism = Ovatospora brasiliensis
```

```
CDS                       1..444
CDS                       509..814
SEQUENCE: 16
atgcaaatct ccctgatcgc cctcaccctc gcggccgccg tcctcccagc ggtcagcgcc    60
tacccgtca aggccgactc gctcaactgc cgcagcggcc cgggcaccag ctacaaggtc    120
gtcaagacct acaagaaggg cgccgacatc aagatctcgt gccagaccga aggccccagc    180
gtcaacggcg acaacctctg gatcaagacc caggacgggt gctacgtcgc cgactactac    240
gtcaagacgg gcaccaacgg ctatgttgcc aagaagtgct cttctggtgg aagcactggt    300
ggcggcagcg gcggcggcaa gggtaacctg cccggtctga tgccaagca gtcgtctcta    360
gctcgggcta tcgtcgccca ggcgaagaag gacggtgtcg gtctccacgg ctgcgaggcc    420
ggtattgcga ccgctcttgt cgaggtaagc ttcttccacg gtataccatc cagattcata    480
ttgaaaccca tgactaaccc tccaccagtc cggcatcaag gtctacgcca acaaaaaggt    540
gcccgcctcg ctcaagtacc cgcacgacgc cgtcggctcc gaccacgaca gcatcggcat    600
cttccagcag cgcgccgtct actacccaa catcgccgct ccgcgcgctc    660
cgcccaccag ttctttgcca agatgaaggg cgtctcgggc tggaagacca tggctgtcgg    720
caagctctgc cagaaggtcc aggtctcggc ttacccggac cgctatgcca agcgggtgtc    780
ggaggccacc aagatttgca aggctgctgg gatctga                             817

SEQ ID NO: 17             moltype = AA  length = 250
FEATURE                   Location/Qualifiers
source                    1..250
                          mol_type = protein
                          organism = Ovatospora brasiliensis
SEQUENCE: 17
MQISLIALTL AAAVLPAVSA YPVKADSLNC RSGPGTSYKV VKTYKKGADI KISCQTEGPS    60
VNGDNLWIKT QDGCYVADYY VKTGTNGYVA KKCSSGGSTG GGSGGGKGNL PGLNAKQSSH    120
ARAIVAQAKK DGVGLHGCEA GIATALVESG IKVYANKKVP ASLKYPHDAV GSDHDSIGIF    180
QQRAVYYPNI AADMDPARSA HQFFAKMKGV SGWKTMAVGK LCQKVQVSAY PDRYAKRVSE    240
ATKICKAAGI                                                           250

SEQ ID NO: 18             moltype = AA  length = 230
FEATURE                   Location/Qualifiers
source                    1..230
                          mol_type = protein
                          organism = Ovatospora brasiliensis
SEQUENCE: 18
YPVKADSLNC RSGPGTSYKV VKTYKKGADI KISCQTEGPS VNGDNLWIKT QDGCYVADYY    60
VKTGTNGYVA KKCSSGGSTG GGSGGGKGNL PGLNAKQSSH ARAIVAQAKK DGVGLHGCEA    120
GIATALVESG IKVYANKKVP ASLKYPHDAV GSDHDSIGIF QQRAVYYPNI AADMDPARSA    180
HQFFAKMKGV SGWKTMAVGK LCQKVQVSAY PDRYAKRVSE ATKICKAAGI               230

SEQ ID NO: 19             moltype = DNA  length = 821
FEATURE                   Location/Qualifiers
sig_peptide               1..63
mat_peptide               64..818
source                    1..821
                          mol_type = genomic DNA
                          organism = Penicillium wellingtonense
CDS                       1..447
CDS                       513..818
SEQUENCE: 19
atgcctttga caaatttct ccccgtcctc gccctctccc tcctaacacc cttcgcaacc    60
gcctacccca taactggcga cgtggtaaac tgccgctccg gccccaggaac acctacgac    120
gtcgtcaaat cctacaaaact aaacgccgat gtctcgatta catgccaagc acccggcacc    180
gatgtcaagg gtgattcggt ctgggacaag accgccgacg gctgctatgt tcggattac    240
tacgtgaaaa ccggtagcag cagctacgtg acaaccgaagt gtggtggtga tgacgacggc    300
ggtgataatg atggtggtag ttccggaaat cttcccggtc tgacatcgac tcagtccaag    360
catgcgaagg atatcattgc cgaggcgaag agtgaggatc ttgggcggca gggatgtctg    420
gctgtattg ctactgctat tgttgaggtg agcagccct tcgcatttc tttcttgtcc    480
ttttaccgga tattcagctc taacgcattc agtcaaatat cctcatatac gctaacagtg    540
gcgtccccga gtctctgaaa tacccgcatg acgcagtcgg ttctgatcac gatagtgtcg    600
ggattttcca gcagcgcgct atgtttata aggatattgc ggctgatatg gatgcgggta    660
aatctgctgg gcaattttt gggaaaatga aggctgttag tgggtggaag agtatggatg    720
tgggcacttt tgtgtcagaag gtgcagggtt ctgcttatcc ttcgaggtat gcggagcagg    780
tgtcgaaggc tgagaagatt tgtaaggcgg tgggctttg a                         821

SEQ ID NO: 20             moltype = AA  length = 251
FEATURE                   Location/Qualifiers
source                    1..251
                          mol_type = protein
                          organism = Penicillium wellingtonense
SEQUENCE: 20
MPLTKFLPVL ALSLLTPFAT AYPITGDVVN CRSGPGTTYD VVKSYKLNAD VSITCQAPGT    60
DVKGDSVWDK TADGCYVADY YVKTGSSSYV TTKCGGDDDG GDNDGGSSGN LPGLTSTQSK    120
HAKDIIAEAK SEDLGRQGCL AGIATAIVES NILIYANSGV PESLKYPHDA VGSDHDSVGI    180
FQQRAMFYKD IAADMDAGKS AGQFFGKMKA VSGWKSMDVG TLCQKVQGSA YPSRYAEQVS    240
KAEKICKAGG L                                                         251

SEQ ID NO: 21             moltype = AA  length = 230
```

```
FEATURE                 Location/Qualifiers
source                  1..230
                        mol_type = protein
                        organism = Penicillium wellingtonense
SEQUENCE: 21
YPITGDVVNC RSGPGTTYDV VKSYKLNADV SITCQAPGTD VKGDSVWDKT ADGCYVADYY    60
VKTGSSSYVT TKCGGDDDGG DNDGGSSGNL PGLTSTQSKH AKDIIAEAKS EDLGRQGCLA   120
GIATAIVESN ILIYANSGVP ESLKYPHDAV GSDHDSVGIF QQRAMFYKDI AADMDAGKSA   180
GQFFGKMKAV SGWKSMDVGT LCQKVQGSAY PSRYAEQVSK AEKICKAGGL             230

SEQ ID NO: 22           moltype = DNA   length = 817
FEATURE                 Location/Qualifiers
sig_peptide             1..66
mat_peptide             67..814
source                  1..817
                        mol_type = genomic DNA
                        organism = Penicillium roseopurpureum
CDS                     1..456
CDS                     509..814
SEQUENCE: 22
atgccttcca ccaagttcct gcccttcgtc gccatcgctc tcatcgctgc gcctctctcc    60
agcgcatacc ccatcaccgg cgatgtcgtg aactgtcgct ccggcccgg taccagctac   120
gatgtagtca agtcctacaa gctggactcc gatgtcacaa tcaagtgcca agcatctgga   180
accgatgtca agggcgacag tatctgggac aagacctccg acggctgcta tgtcgcggac   240
tactacgtga agaccggcag cagcagctac gttacgacca gtgtgatgac aaccggaggc   300
gatgatgatg atgatgaagg tggcagctcg ggtggaaact tgcccggtct aacctccacc   360
cagtcgaagc atgcgaagga aatcattgcc gaagcaaaga gcgagaatct aggacatcga   420
ggatgcaccg ctggtattgc gactgcgatc gttgaggtaa gacactcctc gtgaataata   480
ttaaaaaatc acctctgaca ttttctagtc aaatattcta atctacgcca ataacgccgt   540
tcccgagtct ctgaaatacc cccacgataa ggtgggctct gaccacgaca gcgtcggcat   600
cttccagcag cgcgccatgt tctacaagga tattgcggct gatatggatg ctggcaagtc   660
tgctgctcaa ttctttgaga agatgacggg tatcagcggg tggaagagta tggatgttgg   720
tactttgtgc cagaaggtgc agggctccgc ttatcctact cggtatgctg agcaggtttc   780
aaaggccgag aagatttgct ctgcaggtgg tctttga                           817

SEQ ID NO: 23           moltype = AA   length = 254
FEATURE                 Location/Qualifiers
source                  1..254
                        mol_type = protein
                        organism = Penicillium roseopurpureum
SEQUENCE: 23
MPSTKFLPFV AIALIAAPLS SAYPITGDVV NCRSGPGTSY DVVKSYKLDS DVTIKCQASG    60
TDVKGDSIWD KTSDGCYVAD YYVKTGSSSY VTTKCDDNGG DDDDEGGSS GGNLPGLTST   120
QSKHAKEIIA EAKSENLGHR GCTAGIATAI VESNILIYAN NAVPESLKYP HDKVGSDHDS   180
VGIFQQRAMF YKDIAADMDA GKSAAQFFEK MTAISGWKSM DVGTLCQKVQ GSAYPTRYAE   240
QVSKAEKICS AGGL                                                   254

SEQ ID NO: 24           moltype = AA   length = 232
FEATURE                 Location/Qualifiers
source                  1..232
                        mol_type = protein
                        organism = Penicillium roseopurpureum
SEQUENCE: 24
YPITGDVVNC RSGPGTSYDV VKSYKLDSDV TIKCQASGTD VKGDSIWDKT SDGCYVADYY    60
VKTGSSSYVT TKCDDNGGDD DDEGGSSGG NLPGLTSTQS KHAKEIIAEA KSENLGHRGC   120
TAGIATAIVE SNILIYANNA VPESLKYPHD KVGSDHDSVG IFQQRAMFYK DIAADMDAGK   180
SAAQFFEKMT AISGWKSMDV GTLCQKVQGS AYPTRYAEQV SKAEKICSAG GL          232

SEQ ID NO: 25           moltype = DNA   length = 810
FEATURE                 Location/Qualifiers
sig_peptide             1..60
mat_peptide             61..807
source                  1..810
                        mol_type = genomic DNA
                        organism = Penicillium virgatum
CDS                     1..438
CDS                     502..807
SEQUENCE: 25
atgatgttca ctcctctttt ggctcttact tttgccgcca tcgcgccgat tgtcaatgct    60
tatcctatca ccggcgacgg tgtcaattgc cgctctggtc ctggaacctc ctattctgta   120
gtcaagagct accagaaggg agccgatgtt gcaattacgt gccaagcacc tggcactgat   180
gtcaaaggtg acaacatctg ggacaagact gccgacggct gctatgttgc cgactactat   240
atcaaaactg gaagcagtag ctacgttact gcgaaatgcg atgacagcgg gagcggcagt   300
ggaggcgaca gcagtggaaa cctccctggt ttgacgtcca ctcagtccaa catgcaaaag   360
gccattatcg gtgaagcgaa gaaagaagac ctgggccgcc agggctgtct tgctggtatc   420
gcaactgcac ttgtagaggt aagcttcaac gaagatactt aatccaggta tgtttaatta   480
gatactgact gacgatcaca gtctaatatc tacatctatg ccaacaaaaa ggtgccctcg   540
tcccttaact acccgcacga caaggtcggc tccgattacg acagcgtggg catcttccag   600
cagcgtgccg tttactatcc caacatcgct gccgatatgg atgccgcaaa gtcagctgga   660
```

```
cagttctttg ccaagatgaa gggtatcagt ggttggaagt ccatggaggt tggtaagctt  720
tgccagaagg tgcaaggctc ggcgtaccct acccgatatg cggaacgtct ttctgaggcg  780
aagaagattt gtgctgctgg tggcttgtaa                                   810
```

SEQ ID NO: 26          moltype = AA   length = 248
FEATURE                Location/Qualifiers
source                 1..248
                       mol_type = protein
                       organism = Penicillium virgatum
SEQUENCE: 26
```
MMFTPLLALT FAAIAPIVNA YPITGDGVNC RSGPGTSYSV VKSYQKGADV AITCQAPGTD   60
VKGDNIWDKT ADGCYVADYY IKTGSSSYVT AKCDDSGSGS GGDSSGNLPG LTSTQSKHAK  120
AIIGEAKKED LGRQGCLAGI ATALVESNIY IYANKKVPSS LNYPHDKVGS DYDSVGIFQQ  180
RAVYYPNIAA DMDAAKSAGQ FFAKMKGISG WKSMEVGKLC QKVQGSAYPT RYAERLSEAK  240
KICAAGGL                                                           248
```

SEQ ID NO: 27          moltype = AA   length = 228
FEATURE                Location/Qualifiers
source                 1..228
                       mol_type = protein
                       organism = Penicillium virgatum
SEQUENCE: 27
```
YPITGDGVNC RSGPGTSYSV VKSYQKGADV AITCQAPGTD VKGDNIWDKT ADGCYVADYY   60
IKTGSSSYVT AKCDDSGSGS GGDSSGNLPG LTSTQSKHAK AIIGEAKKED LGRQGCLAGI  120
ATALVESNIY IYANKKVPSS LNYPHDKVGS DYDSVGIFQQ RAVYYPNIAA DMDAAKSAGQ  180
FFAKMKGISG WKSMEVGKLC QKVQGSAYPT RYAERLSEAK KICAAGGL               228
```

SEQ ID NO: 28          moltype = DNA   length = 809
FEATURE                Location/Qualifiers
sig_peptide            1..60
mat_peptide            61..806
source                 1..809
                       mol_type = genomic DNA
                       organism = Aspergillus niveus
CDS                    1..438
CDS                    501..806
SEQUENCE: 28
```
atgctgtatc tttttctcac tgcccttttcg tttgctgcca ctgctcccct ggtaggcgca   60
tatcccatta ctggtgatgg agtcaactgc cgttctggtc ctggtacaag ccatgccgtg  120
gtcaagtcct accccaaggg ccacgagata tccattgtct gccaagctgc cggaaccgac  180
gtcaagggag atgatctctg ggataagacg tctgacggct gctacgtcgc cgattactac  240
gtgaagactg gacgaccgg ctatgtcacc aagcactgcg atggcggcag tgatggtggc  300
agcagtggcg gcagcggcaa tcttcctggc ctcactgcca ctcagtcctc tcacgcccat  360
aagattattg gcgaagcaaa gaaggaaggc ctgggtcgtc aaggttgtct ggctgggatt  420
gcaactgctt tggtcgaggt gagtcgctcc gagcttttct ccttccattt gggtactgta  480
ctgacgctga acgtgtatag tccaacatct tagtttatgc caacagcaag gtcccggcgt  540
ctctcaacta ccctcatgac gccgtcggcc acgactacga cagcgttggc atcttccagc  600
agcgtgctgt ctactatccc gacatcgccg ccgatatgga ccccgcacgt tctgccgctc  660
agttctttgc caagatgaag aatatcagcg gctggaagac gatggatgtt ggcaagcttt  720
gccagaaggt gcaggtctct gcctatcccg atcggtatgc agagcgtgtt cctgctgcca  780
aaaagatctg ctctgctggg ggctatag                                     809
```

SEQ ID NO: 29          moltype = AA   length = 248
FEATURE                Location/Qualifiers
source                 1..248
                       mol_type = protein
                       organism = Aspergillus niveus
SEQUENCE: 29
```
MLYLFLTALS FAATAPLVGA YPITGDGVNC RSGPGTSHAV VKSYPKGHEI SIVCQAAGTD   60
VKGDDLWDKT SDGCYVADYY VKTGTTGYVT KHCDGGSDGG SSGGSGNLPG LTATQSSHAH  120
KIIGEAKKEG LGRQGCLAGI ATALVESNIL VYANSKVPAS LNYPHDAVGH DYDSVGIFQQ  180
RAVYYPDIAA DMDPARSAAQ FFAKMKNISG WKTMDVGKLC QKVQVSAYPD RYAERVPAAE  240
KICSAGGL                                                           248
```

SEQ ID NO: 30          moltype = AA   length = 228
FEATURE                Location/Qualifiers
source                 1..228
                       mol_type = protein
                       organism = Aspergillus niveus
SEQUENCE: 30
```
YPITGDGVNC RSGPGTSHAV VKSYPKGHEI SIVCQAAGTD VKGDDLWDKT SDGCYVADYY   60
VKTGTTGYVT KHCDGGSDGG SSGGSGNLPG LTATQSSHAH KIIGEAKKEG LGRQGCLAGI  120
ATALVESNIL VYANSKVPAS LNYPHDAVGH DYDSVGIFQQ RAVYYPDIAA DMDPARSAAQ  180
FFAKMKNISG WKTMDVGKLC QKVQVSAYPD RYAERVPAAE KICSAGGL               228
```

SEQ ID NO: 31          moltype = DNA   length = 813
FEATURE                Location/Qualifiers
sig_peptide            1..57
mat_peptide            58..810

```
source                  1..813
                        mol_type = genomic DNA
                        organism = Chaetomium sp.
CDS                     1..429
CDS                     505..810
SEQUENCE: 31
atgcaactct cactcacggc tctggccctc gcggccgctc tccccatggt cagcgcctac   60
cccgtcaagg cggacttgct caactgccgc actggccccg gaaccagcta cgaccttgtc  120
acgcaataca agaagggcac cgacgtcaag atcacctgcc agacgacagg cacggtcgtc  180
gagggtcata acctctggga caagacctcg gacgggtgct acgttgccga cttctacatc  240
cagacgggca cttccggcta tgtcgcggac aaatgcggcg agaccggcgg tggcggtgac  300
accggcggca acctccccgg gctcaccgcg gtgcagtcca ggaacgccag ggctatcatc  360
ggcgaggcga agaaggaagg gcttggccgc cagggctgtg aggcgggcat tgcgaccgcc  420
attgtcgagg tgagatccaa tgacccacgg gactatgaag tgcttgtgtc actacaaggt  480
gaacccctta ctaacaccac ccagtccaac atcctaattt acgccaataa gaaggtcaag  540
gagtcgtaca actacccgca cgacgccgtg ggcgaggacc acgacagcgt cggcatcttc  600
cagcagcgcg tgaccttcta ccccgacatc gaggccagca tggacccggc ccggtccgcg  660
gcccagtttt tcaccgagat gaagcggatc agcggctgga agaccatgga cgttgggacg  720
ctgtgccaga aggtgcagcg ctccgcgtac ccagaccgct atggcaagca ggtcgacaag  780
gctgggaaga tttgtgctgc tggcggtatg taa                                813

SEQ ID NO: 32           moltype = AA  length = 245
FEATURE                 Location/Qualifiers
source                  1..245
                        mol_type = protein
                        organism = Chaetomium sp.
SEQUENCE: 32
MQLSLTALAL AAALPMVSAY PVKADLLNCR TGPGTSYDLV TQYKKGTDVK ITCQTTGTVV   60
EGHNLWDKTS DGCYVADFYI QTGTSGYVAD KCGETGGGGD TGGNLPGLTA VQSRNARAII  120
GEAKKEGLGR QGCEAGIATA IVESNILIYA NKKVKESYNY PHDAVGEDHD SVGIFQQRVT  180
FYPDIEASMD PARSAAQFFT EMKRISGWKT MDVGTLCQKV QRSAYPDRYG KQVDKAGKIC  240
AAGGM                                                              245

SEQ ID NO: 33           moltype = AA  length = 226
FEATURE                 Location/Qualifiers
source                  1..226
                        mol_type = protein
                        organism = Chaetomium sp.
SEQUENCE: 33
YPVKADLLNC RTGPGTSYDL VTQYKKGTDV KITCQTTGTV VEGHNLWDKT SDGCYVADFY   60
IQTGTSGYVA DKCGETGGGG DTGGNLPGLT AVQSRNARAI IGEAKKEGLG RQGCEAGIAT  120
AIVESNILIY ANKKVKESYN YPHDAVGEDH DSVGIFQQRV TFYPDIEASM DPARSAAQFF  180
TEMKRISGWK TMDVGTLCQK VQRSAYPDRY GKQVDKAGKI CAAGGM                 226

SEQ ID NO: 34           moltype = DNA  length = 804
FEATURE                 Location/Qualifiers
sig_peptide             1..60
mat_peptide             61..801
source                  1..804
                        mol_type = genomic DNA
                        organism = Talaromyces atricola
CDS                     1..429
CDS                     496..801
SEQUENCE: 34
atgtttgcca cctcgctcat tgcactgtcc ctcgcgacaa ttctccccat ctcgaacgcg   60
tatcccatta agactgatgg acttcactgt cgctcggggc ctggaactgg ttattcagtt  120
gtgaagacct ataataaggg tgaagaggtc tcaatcaaat gccaggctcc tggaaccaac  180
atcaatggag atattctctg ggatctgact gagaatggct gttatgtcgc ggattactac  240
gttagtactg gtactagtgg ctacgtcact gataagtgtg gtagcagtgg tggcggtggc  300
agcgatggaa atcttccggg tctcaactct gtacaatcgt cccacgcccg agccattatc  360
gcggaggcca agcaggagag tcttggtcac cagggctgtc tagctggcat tgcaactgct  420
ctgactgagg taggcttcga tcccactcgt ctctaagtgt ctcattttca gcaaccatta  480
ctaattgagc tgcagtcgag catttttagtt tacgcaaaca aggctgttcc agcttcgatg  540
aactacaaat acgacgcggt tggcagcgat cacgatagca ttggcatctt ccaacaacgc  600
gctatgtact atcccgatat cgctgccgac atggatcctg ctaagtccgc cgcacagttc  660
ttcgccaaga tgaaggggt tagtggatgg caaaccatgg atgttggtga cctatgccag  720
aaggttcaag gatctgctta tccgacccga tatgaacagc atttgtccgc tgctaaatcg  780
atctgctctg ctgatagtga ttaa                                         804

SEQ ID NO: 35           moltype = AA  length = 245
FEATURE                 Location/Qualifiers
source                  1..245
                        mol_type = protein
                        organism = Talaromyces atricola
SEQUENCE: 35
MFATSLIALS LATILPISNA YPIKTDGLHC RSGPGTGYSV VKTYNKGEEV SIKCQAPGTN   60
INGDILWDLT ENGCYVADYY VSTGTSGYVT DKCGSSGGGG SDGDLPGLNS VQSSHARAII  120
AEAKQESLGH QGCLAGIATA LTESSILVYA NKAVPASMNY KYDAVGSDHD SIGIFQQRAM  180
YYPDIAADMD PAKSAAQFFA KMKGVSGWQT MDVGDLCQKV QGSAYPTRYE QHLSAAKSIC  240
```

```
SADSD                                                                 245

SEQ ID NO: 37           moltype = AA   length = 225
FEATURE                 Location/Qualifiers
source                  1..225
                        mol_type = protein
                        organism = Talaromyces atricola
SEQUENCE: 36
YPIKTDGLHC RSGPGTGYSV VKTYNKGEEV SIKCQAPGTN INGDILWDLT ENGCYVADYY    60
VSTGTSGYVT DKCGSSGGGG SDGDLPGLNS VQSSHARAII AEAKQESLGH QGCLAGIATA   120
LTESSILVYA NKAVPASMNY KYDAVGSDHD SIGIFQQRAM YYPDIAADMD PAKSAAQFFA   180
KMKGVSGWQT MDVGDLCQKV QGSAYPTRYE QHLSAAKSIC SADSD                   225

SEQ ID NO: 37           moltype = DNA   length = 794
FEATURE                 Location/Qualifiers
sig_peptide             1..57
mat_peptide             58..791
source                  1..794
                        mol_type = genomic DNA
                        organism = Trichocladium asperum
CDS                     1..426
CDS                     486..791
SEQUENCE: 37
atgcagctct cgctcatcgc gctcacccct gcggccgctg tccccatagt cagcgcgtac    60
cctgtcaagg aaacactcaa ctgccgctct ggtcccggaa ccagctacaa agttgtcaag   120
acatacaagc agggtgcgga tgtcaagatc acctgccaga ccaccggtcc aaccatcaag   180
ggttccaata tctgggacaa gacccaagat gggtgctacg tcgccgacta ttacatcaag   240
acagggtctt cgggctatgt tgccgccaag tgtggtgcca gtggtggtga tggcggcggc   300
agtggcaccc tccctggcct aaacgcggtt cagtccaagc acgccaaagc catcgttggc   360
caagcgaaga aagacggtgt cggccgccac ggctgtgagg ccggtattgc aactgccctt   420
gtcgaggtaa gaccccatcc catgactgtc cgggataaga accgccatct aacgccgcga   480
tttagtcgac catgtatgtc tacgccaaca acaaggttcc caaatcgctc aactacccgc   540
atgaccgggt cggctcggat tacgacacgc tcggcatctt ccagcagcgc gccatctact   600
atcccaacat cgccgccgat atggaccctg ccaggtctgc agggcagttc tttgccaaga   660
tgaagggggt cagcggctgg aagacgatgg ctgttggcaa gttgtgccag aaggtgcagg   720
tctcggccta ccctgaccgc tatgcgcagc aggtctccaa agccaccaag atttgtgctg   780
ctgctggtct ctag                                                    794

SEQ ID NO: 38           moltype = AA   length = 244
FEATURE                 Location/Qualifiers
source                  1..244
                        mol_type = protein
                        organism = Trichocladium asperum
SEQUENCE: 38
MQLSLIALTL AAAVPIVSAY PVKETLNCRS GPGTSYKVVK TYKQGADVKI TCQTTGPTIK    60
GSNIWDKTQD GCYVADYYIK TGSSGYVAAK CGASGGDGGG SGTLPGLNAV QSKHAKAIVG   120
QAKKDGVGRH GCEAGIATAL VESTMYVYAN NKVPKSLNYP HDRVGSDYDS VGIFQQRAIY   180
YPNIAADMDP ARSAGQFFAK MKGVSGWKTM AVGKLCQKVQ VSAYPDRYAQ QVSKATKICA   240
AAGL                                                               244

SEQ ID NO: 39           moltype = AA   length = 225
FEATURE                 Location/Qualifiers
source                  1..225
                        mol_type = protein
                        organism = Trichocladium asperum
SEQUENCE: 39
YPVKETLNCR SGPGTSYKVV KTYKQGADVK ITCQTTGPTI KGSNIWDKTQ DGCYVADYYI    60
KTGSSGYVAA KCGASGGDGG GSGTLPGLNA VQSKHAKAIV GQAKKDGVGR HGCEAGIATA   120
LVESTMYVYA NNKVPKSLNY PHDRVGSDYD SVGIFQQRAI YYPNIAADMD PARSAGQFFA   180
KMKGVSGWKT MAVGKLCQKV QVSAYPDRYA QQVSKATKIC AAAGL                  225

SEQ ID NO: 40           moltype = DNA   length = 1063
FEATURE                 Location/Qualifiers
sig_peptide             1..57
mat_peptide             58..1060
source                  1..1063
                        mol_type = genomic DNA
                        organism = Metarhizium carneum
CDS                     1..663
CDS                     755..1060
SEQUENCE: 40
atgcatctca cttccctctc cgtatacttg gccgtcggcg gctccatggt ggcggcatac    60
cccatcaagg acaacaatgt aaactgccgc tccggcccgg aaccagcttc tccgtcgtc   120
aaacagtaca agctcgacca agagctcaca gtcagctgcc agaaccacgg ggagagcatt   180
tccggcgaca cgctctggga caagacgtcg gacgggtgct acgtggccga ctggtacgtg   240
aggacgggca cgtccaacat ggtcaccgga cagtgcggca cggcatatcc catcaaggag   300
gacaatgtcc actgccgctc aggtcccggg acgacctttg gcgtcgtcaa gacgtacccc   360
aaggggcaaa aggtcgagct gtcctgccag acccagggcg agaccgtatc gggcaacagc   420
ctctgggaca agacgaccga cggctgctac gtgtccgact cgctcgtcca gacgggcaca   480
```

```
tcaaacatgg tcgctggcca gtgtgccggc gcccccagca gtccccctc tggaggatca    540
ggaaatctcc ccggcctgag tgctactcag agccgcacg cccgcgccat catcgcccag    600
gtgaagaagg agggacttgg cagacagggc tgtgaagccg gcctggccac cggactcact    660
gaggtatgtc taccatgaat gagcaccagc gtgattatga ttgtgcagac agacagacga    720
cgagaacagt aaaggctaac atgaaccaaa acagtcgatc ttgcgcatcc tggccaacaa    780
cgctgtgccg gcgtccttga agtacgcgca cgacggcatg ggctctgacc acgcagcgt    840
gggcattttc cagcagcgcg ccatgtatta caccgatatt gcctgcgaca tggacgctgc    900
ctgctccgcg agcagcttct tcaagggcat gacgggcata tccggctggc ggaccatgga    960
tgttgccaag ctctgccagg ccgtgcagcg gtcggcctat cctgatgcct accagaagta   1020
tgttggtgcg gctgctgaga tctgcgctgc tggagggtcg taa                    1063

SEQ ID NO: 41          moltype = AA   length = 323
FEATURE                Location/Qualifiers
source                 1..323
                       mol_type = protein
                       organism = Metarhizium carneum
SEQUENCE: 41
MHLTSLSVYL AVGGSMVAAY PIKDNNVNCR SGPGTSFSVV KQYKLDQDVT VSCQTHGESI    60
SGDTLWDKTS DGCYVADWYV RTGTSNMVTG QCGSGYPIKE DNVHCRSGPG TTFGVVKTYP   120
KGQKVELSCQ TQGETVSGNS LWDKTTDGCY VSDSLVQTGT SNMVAGQCAG APSSPPSGGS   180
GNLPGLSATQ SAHARAIIAQ VKKEGLGRQG CEAGLATGLT ESSLRILANN AVPASLKYAH   240
DGMGSDHDSV GIFQQRAMYY TDIACDMDAA CSASSFFKGM TGISGWRTMD VAKLCQAVQR   300
SAYPDAYQKY VGAAAEICAA GGS                                          323

SEQ ID NO: 42          moltype = AA   length = 304
FEATURE                Location/Qualifiers
source                 1..304
                       mol_type = protein
                       organism = Metarhizium carneum
SEQUENCE: 42
YPIKDNNVNC RSGPGTSFSV VKQYKLDQDV TVSCQTHGES ISGDTLWDKT SDGCYVADWY    60
VRTGTSNMVT GQCGSGYPIK EDNVHCRSGP GTTFGVVKTY PKGQKVELSC QTQGETVSGN   120
SLWDKTTDGC YVSDSLVQTG TSNMVAGQCA GAPSSPPSGG SGNLPGLSAT QSAHARAIIA   180
QVKKEGLGRQ GCEAGLATGL TESSLRILAN NAVPASLKYA HDGMGSDHDS VGIFQQRAMY   240
YTDIACDMDA ACSASSFFKG MTGISGWRTM DVAKLCQAVQ RSAYPDAYQK YVGAAAEICA   300
AGGS                                                               304

SEQ ID NO: 43          moltype = DNA   length = 838
FEATURE                Location/Qualifiers
sig_peptide            1..57
mat_peptide            58..835
source                 1..838
                       mol_type = genomic DNA
                       organism = Thielavia terrestris
CDS                    1..432
CDS                    530..835
SEQUENCE: 43
atgcagctct ccctcctcgt cctctcccte gtggccgctg tgcccatggc cagcgcgtac    60
ccggtcaagg ccgacactct caactgccgc tcccgcccgg gcaccagtta caaggtcatc   120
aagacctaca gaagggcac cgatctcaag atcacctgcc agacgccgg cacctcggtc   180
aacggcgaca acctgtggga caagacctcg gacggctgct acgtggccga ttactacgtc   240
aagaccggca cctccggcta cgtcacggcc cattgcgatg ccggcagcgg cagcggcagc   300
agcggcggcg gcaacctgcc aggactcaac tcggtccagt cctcgcacgc ccgggccatc   360
atcggcgagg cgaagaagga gggcgtcggc cgccacggct gcgaggccgg catcgcgacc   420
gcgcttgtcg aggtacgttg catcctaaca tcaaacttta cttgccttga ccccactgtg   480
accgccagaa aaaaccaaaa ctaacacatc acctcttccc ctcacacagt ccaacatcct   540
gatctacgcc aacaaggcgg tcccggcctc gctcaagtac ccgcacgacg cggtgggctc   600
ggaccacgac agcgtcggca tcttccagca gcgcgccaag tactacccca catcgcggc   660
cgacatggac ccggcgcgct cggccgccca gttcttcgcc aagatgaagg gcatcaaggg   720
ctggcagagc atggccgtcg gcacgctctg ccagaaggtc cagggctccg cgtacccgga   780
ccgctatgcc aagcgggtct cggaggcgac caagatttgc cagggctggtg ggttgtaa    838

SEQ ID NO: 44          moltype = AA   length = 246
FEATURE                Location/Qualifiers
source                 1..246
                       mol_type = protein
                       organism = Thielavia terrestris
SEQUENCE: 44
MQLSLLVLSL VAAVPMASAY PVKADTLNCR SGPGTSYKVI KTYKKGTDLK ITCQTPGTSV    60
NGDNLWDKTS DGCYVADYYV KTGTSGYVTA HCDAGSGSGS SGGNLPGLN SVQSSHARAI   120
IGEAKKEGVG RHGCEAGIAT ALVESNILIY ANKAVPASLK YPHDAVGSDH DSVGIFQQRA   180
KYYPNIAADM DPARSAAQFF AKMKGIKGWQ SMAVGTLCQK VQGSAYPDRY AKRVSEATKI   240
CQAGGL                                                             246

SEQ ID NO: 45          moltype = AA   length = 227
FEATURE                Location/Qualifiers
source                 1..227
                       mol_type = protein
                       organism = Thielavia terrestris
```

```
SEQUENCE: 45
YPVKADTLNC RSGPGTSYKV IKTYKKGTDL KITCQTPGTS VNGDNLWDKT SDGCYVADYY     60
VKTGTSGYVT AHCDAGSGSG SSGGGNLPGL NSVQSSHARA IIGEAKKEGV GRHGCEAGIA    120
TALVESNILI YANKAVPASL KYPHDAVGSD HDSVGIFQQR AKYYPNIAAD MDPARSAAQF    180
FAKMKGIKGW QSMAVGTLCQ KVQGSAYPDR YAKRVSEATK ICQAGGL                  227

SEQ ID NO: 46           moltype = AA   length = 144
FEATURE                 Location/Qualifiers
source                  1..144
                        mol_type = protein
                        organism = Aspergillus clavatus
SEQUENCE: 46
SGNLPGLTAT QSSHARDIIG EAKKENLGRQ GCLAGIATGL VESNLLIYAN SKVPASLKYK     60
HDAVGHDYDS VGIFQQRAIY YPDIAADMDP ARSAAQFFAK MKNISGWKTM NVGKLCQKVQ    120
VSAYPDRYAQ RVSAAEKICA AGGL                                          144

SEQ ID NO: 47           moltype = AA   length = 137
FEATURE                 Location/Qualifiers
source                  1..137
                        mol_type = protein
                        organism = Salinispora tropica
SEQUENCE: 47
GLTQTQMDNA KTIVDVGTDM NIPHRGLVVA IATAMQESTL LNYANAGVPE SQNYPHEAVG     60
WDHDSVGLFQ QRSSTGWGSI AELMTPTYAA EAFYQALLQV PGWQGMSVAW AAQSVQVSAF    120
PDAYAQHETR ATTIVSA                                                  137

SEQ ID NO: 48           moltype = AA   length = 137
FEATURE                 Location/Qualifiers
source                  1..137
                        mol_type = protein
                        organism = Salinispora arenicola
SEQUENCE: 48
GLTQAQMDNA KVIVDVGTRM DIPHRGLIVA IATAMQESTL LNYANGGVPE SRNYPHQAVG     60
WDHDSVGLFQ QRPSSGWGSV AQLMRPTYAA EAFYQALLTI PGWQEMSVAW AAQSVQVSAF    120
PDAYAQHVTR ATTVVTA                                                  137

SEQ ID NO: 49           moltype = AA   length = 135
FEATURE                 Location/Qualifiers
source                  1..135
                        mol_type = protein
                        organism = Rhodococcus erythropolis
SEQUENCE: 49
GLNASQTALA KQAVAIGESM GVPDQGIVVA LATMSQESTY RMLASSNVPE SLQYPHDGVG     60
SDHLSVNQYQ QQVGIWGTAE DLMNPVTANV KFFDALLKVS GWQSMPVTVA AQTVQGSAHP    120
EAYADDETLA RQLAS                                                    135

SEQ ID NO: 50           moltype = AA   length = 135
FEATURE                 Location/Qualifiers
source                  1..135
                        mol_type = protein
                        organism = Mycobacterium phage
SEQUENCE: 50
MTHTNDTYAR EILRAGNDLG ITPRGIVIAF ATVFVESDWY MWANAKVPES LRLPHERVGN     60
DGRSVGLFQQ QVVWGNGAWW WGDAATCMDP YKSARLFFER LKTRDYSTGD PGAHAQAIQR    120
SAYPDRYGQR MSEAQ                                                    135

SEQ ID NO: 51           moltype = AA   length = 144
FEATURE                 Location/Qualifiers
source                  1..144
                        mol_type = protein
                        organism = Penicillium rubens
SEQUENCE: 51
SGNLPGLTST QSKHAKDIIG EAKKEDLGRQ GCLAGIATGL VESNMLMYAN KKVPESLKYP     60
HDAVGSDYDS VGIFQQRAVY YPDIAADMDA AKSAAQFFKG MKAISGWKTM EVGKLCQKVQ    120
RSAYPSRYSE RVAEAKKICA AGGL                                          144

SEQ ID NO: 52           moltype = AA   length = 136
FEATURE                 Location/Qualifiers
source                  1..136
                        mol_type = protein
                        organism = Micromonospora aurantiaca
SEQUENCE: 52
GLDRTQMNNA KKIVQAGKEM GMPRRALVIA VATAMQESTL LNYASGVLPE SQSYPHQAIG     60
WDHDSVGLFQ QRPSSGWGTV EQLMDPEYAT KAFLSALAEI PGWQSLPLSV AAQAVQISAF    120
PDAYAQHEWR AGEVVA                                                   136

SEQ ID NO: 53           moltype = AA   length = 147
FEATURE                 Location/Qualifiers
source                  1..147
```

```
                            mol_type = protein
                            organism = Micromonospora aurantiaca
SEQUENCE: 53
TGDMPRFAEY GERQLRNAAV IIKVGQDMKL PARGWVIALA TAMQESALRN LANSTVPASL    60
ALPHEGVGAD HDSLGLFQQR PGWGSVEQRM TPSYAARKFY QKMEKVPDWQ QRPLTVVAQK   120
VQVSAYPDAY AKHEELAGAI VDALAGG                                       147

SEQ ID NO: 54               moltype = AA  length = 137
FEATURE                     Location/Qualifiers
source                      1..137
                            mol_type = protein
                            organism = Micromonospora aurantiaca
SEQUENCE: 54
GLDQRQMDNA KAIVDVGREM KMPRRALVVA VATAMQESNL YNLASDVLPQ SFDHPHQGSG    60
SDHDSVGLFQ QRPSSGWGTV AQLMRPAYAA RAFYAALREV PGWEDMSVTA AAQAVQVSAY   120
PDAYARHEKR ATTVVSA                                                  137

SEQ ID NO: 55               moltype = AA  length = 143
FEATURE                     Location/Qualifiers
source                      1..143
                            mol_type = protein
                            organism = Tuber melanosporum
SEQUENCE: 55
GNLPGLDATQ SRHARTIIAV AREYGVGNRG CQVSIVTAMQ ESRIRVLANP SVPDSNKYPH    60
DGTGSDHDSV GIFQQRPQFW GTVKDCMDPK TSAGKFFTAL KKVNGWERME IGRAAQSVQR   120
SAFPDAYTKH TPLAKGVCEA GGI                                           143

SEQ ID NO: 56               moltype = AA  length = 142
FEATURE                     Location/Qualifiers
source                      1..142
                            mol_type = protein
                            organism = Hypocrea atroviridis
SEQUENCE: 56
NLPGLNAVQT KYANAIIAKA KADDVGSHGC QAAIATAMVE SSIIMYANKA VPGSLKYPHD    60
RIGSDHDRVG LFQQRASIYK NVKCDMDAAC SAGQFFAEMK KVSGWQTMAV GTLCQKIQRS   120
AYPDRYAKQV GLATNVCKAG GL                                            142

SEQ ID NO: 57               moltype = AA  length = 137
FEATURE                     Location/Qualifiers
source                      1..137
                            mol_type = protein
                            organism = Metarhizium acridum
SEQUENCE: 57
LTELQAKYAR GIIAQAKKER LGAQGCRAGI ATALVESTLI MHANYAVPDS LVYDYDRLGY    60
DRDSVGLFQQ RASIYTDIKC SMNAACSAHQ FFTEMKGVPE WRYMDVGTLC QEVQRSENPE   120
QYHEFIDQAV DICKEGG                                                  137

SEQ ID NO: 58               moltype = AA  length = 142
FEATURE                     Location/Qualifiers
source                      1..142
                            mol_type = protein
                            organism = Metarhizium robertsii
SEQUENCE: 58
NLPSLNAAQS GYAKSIIAKA KAAGVQRHGC QAAIATGLVE SKLLMYANNA VPASLTYRHG    60
GISSDNDSIG IFQQRASVYK NIACSMDAGC SAGQFFSQMK RIGGWQTLSV GALCQKIQQS   120
SFPDRYEKQV AAAASICAAG GL                                            142

SEQ ID NO: 59               moltype = AA  length = 137
FEATURE                     Location/Qualifiers
source                      1..137
                            mol_type = protein
                            organism = Verrucosispora maris
SEQUENCE: 59
GLTQAQMDNA KVIVDVGVDM KIPRKGLVVA VATAMQESTL LNYASGVLPE SQNYPHQAIG    60
WDHDSVGLFQ QRPSSGWGTV RDLMRPAYSA RAFYEALLEV PGWEQMSLTL AAQAVQISAF   120
PYAYAQHEER ANTIVAA                                                  137

SEQ ID NO: 60               moltype = AA  length = 133
FEATURE                     Location/Qualifiers
source                      1..133
                            mol_type = protein
                            organism = Verrucosispora maris
SEQUENCE: 60
SGAQVANAVV IVTAGRQRQV PARGYVIALA TAMQESTLRN LANANVPESL ALPHEGVGRD    60
HDSVGLFQQR PGWGTVRERM TPSYAADRFY EALARVDGWE RMRLTDAAQA VQRSAYPEEY   120
QKWEDDAELL AAA                                                      133

SEQ ID NO: 61               moltype = AA  length = 142
FEATURE                     Location/Qualifiers
```

```
source                  1..142
                        mol_type = protein
                        organism = Beauveria bassiana
SEQUENCE: 61
NLPGLNALQT KYANAIIAQA KKDGVGAHGC QAGIATAMVE STLVMYANKA VPASLKYPHD    60
RVGSDHDSVG LFQQRASIYK NVKCDMDAAC SAGQFFAEMK RINGWQKIAV GTLCQKVQRS    120
AYPDRYAKQV GLATNVCKAG GL                                            142

SEQ ID NO: 62           moltype = AA   length = 143
FEATURE                 Location/Qualifiers
source                  1..143
                        mol_type = protein
                        organism = Thielavia terrestris
SEQUENCE: 62
GNLPGLNSVQ SSHARAIIGE AKKEGVGRHG CEAGIATALV ESNILIYANK AVPASLKYPH    60
DAVGSDHDSV GIFQQRAKYY PNIAADMDPA RSAAQFFAKM KGIKGWQSMA VGTLCQKVQG    120
SAYPDRYAKR VSEATKICQA GGL                                            143

SEQ ID NO: 63           moltype = AA   length = 137
FEATURE                 Location/Qualifiers
source                  1..137
                        mol_type = protein
                        organism = Micromonospora peucetia
SEQUENCE: 63
GLTQAQMDNA KVIVDVGVEL KMPRRALVVA VATSMQESRL YNLASDVLPE STRYPHQGSG    60
SDHDSVGLFQ QRPSSGWGTV RELMRPSYAA RAFYEALRDV PGWQQMSVAG AAQAVQVSAF    120
PDAYAQHEGL ATTVVAA                                                   137

SEQ ID NO: 64           moltype = AA   length = 153
FEATURE                 Location/Qualifiers
source                  1..153
                        mol_type = protein
                        organism = Microbacterium laevaniformans
SEQUENCE: 64
GSTRTLGATE LGHAATILSV ARSLGVSARG QQIAIMTALQ ESGLKMYANS SVPESLDYPH    60
DAVGSDHDSV NYFQQRVSGW GTVEELMDPL YAAKAFFGGE EGPNGGSPRG LLDIPGWEDM    120
GLGEAAQTVQ VSAYPTAYDK WEPAAQQIIT AVG                                153

SEQ ID NO: 65           moltype = AA   length = 134
FEATURE                 Location/Qualifiers
source                  1..134
                        mol_type = protein
                        organism = Mycobacterium abscessus
SEQUENCE: 65
ASRDDYARAI IAEGKRRGIT ARGIQIGLAT AIVESALKMW ANEKVPESFN YPHDAVGDDG    60
YSVGLFQQQI VKGPNGWWWA DCATCMNPAR SAGLFFDRLA KLPYNDALRL PGSFAQQVQQ    120
SDFPERYDQR FAEA                                                     134

SEQ ID NO: 66           moltype = AA   length = 137
FEATURE                 Location/Qualifiers
source                  1..137
                        mol_type = protein
                        organism = Micromonospora lupini
SEQUENCE: 66
GLDDDQMENA EAIVRAGRKM GVPRRGLVIA VATAMQESNL YNVASGVLPE SQDYPHQGVG    60
WDHDSVGLFQ QRSSSGWGPV GRLMDPEFAT RQFLTALEQV PGWQQMRLTD AAQAVQVSAY    120
PEHYQQHEWR ATRVVDA                                                   137

SEQ ID NO: 67           moltype = AA   length = 137
FEATURE                 Location/Qualifiers
source                  1..137
                        mol_type = protein
                        organism = Micromonospora lupini
SEQUENCE: 67
GLDQVQMDNA KIIVDVGREL KMPRRALVVA LATAMQESNL YNLASDVLPE STQYPHQGSG    60
ADHDSVGLFQ QRPSSGWGTV AELMRPSYAA RAFYTALAEI PGWEDMSVTA AAQAVQISAF    120
PDAYAQHEER ASTVAAA                                                   137

SEQ ID NO: 68           moltype = AA   length = 144
FEATURE                 Location/Qualifiers
source                  1..144
                        mol_type = protein
                        organism = Metarhizium album
SEQUENCE: 68
AGGLPGLDAV QSGYARSIIA KAKTAGVGRR GCAAAIATGL VESTLMMYAN SAVPESLRHH    60
HDRVGSDHDS IGLFQQRASV YRNIACDMDA GCSAGQFFAR IKGVSGWHTM ATGTLSQTVQ    120
QSSYPGRYGA QARAAAAICA AGGL                                           144

SEQ ID NO: 69           moltype = AA   length = 142
```

```
FEATURE                 Location/Qualifiers
source                  1..142
                        mol_type = protein
                        organism = Aschersonia aleyrodis
SEQUENCE: 69
NLPGLNAVQS RYARAIIAEA SNDGVGRQGC EAAIATGLVE SSIIMYANSK VPASLNYHHD    60
RVGSDHDSVG IFQQRASIYK DIACDMDAAC SAGQFFQEMR RIKGWQTMAV GTLCQKVQRS   120
AYPDRYNKRV AEARSICSAG GL                                           142

SEQ ID NO: 70           moltype = AA  length = 139
FEATURE                 Location/Qualifiers
source                  1..139
                        mol_type = protein
                        organism = Metarhizium album
SEQUENCE: 70
GLTELQSKYA RRITAQARKE ELGAQGCQAA IATALMESTL IMHANSAVPG SLAFHHDRLG    60
YDGDSVGLFQ QRASIYTDLG CSMNAACSAH QFFVEMRDVP DWESMDVGTL CQAVQRSQNP   120
ERYYEFIDLA ASVCAEAGL                                               139

SEQ ID NO: 71           moltype = AA  length = 139
FEATURE                 Location/Qualifiers
source                  1..139
                        mol_type = protein
                        organism = Cordyceps brongniartii
SEQUENCE: 71
PGLNHAQSRN AKAAIDQVRA EGLNRQACLA VISTALQESE LQIYANPIVP ASMNYPHDKV    60
GGDQDSIGMF QQRAKFYSDI ATDMSAAGST RLFLADMKGI AGWQTMEVSA LCQTVQKAEA   120
GNLYGQRISL AEQVCSAAG                                               139

SEQ ID NO: 72           moltype = AA  length = 139
FEATURE                 Location/Qualifiers
source                  1..139
                        mol_type = protein
                        organism = Metarhizium rileyi
SEQUENCE: 72
GLDEVQSKYA GRIIAQVKME NLGPKACQTA ITTSLMESTL IMHANERVPE SLTYEHERLG    60
YDGDSVGLFQ QRALFYTDIK CNMDAVCSAH QFLARMKEIP EWETIDVGTL AQKVQRSEQP   120
ERYHQFVDQS VSICNLGGL                                               139

SEQ ID NO: 73           moltype = AA  length = 139
FEATURE                 Location/Qualifiers
source                  1..139
                        mol_type = protein
                        organism = Cordyceps confragosa
SEQUENCE: 73
PGINEEQSRN AGAAIWQVRN YRLGRQACLA VISTALQESE LEVYANPRVP ESYKYPHNRE    60
GGDQDSVGMF QQRKAYYPDI AADMDPARST GQFLDAMLRV PGWQNMEISQ LDQAVQHAEA   120
GNLYGQRIPL ATRICNAAG                                               139

SEQ ID NO: 74           moltype = AA  length = 139
FEATURE                 Location/Qualifiers
source                  1..139
                        mol_type = protein
                        organism = Cordyceps confragosa
SEQUENCE: 74
PGLNNVQSRN AKAAIGEVRA EGLNRQACLA VISTALQESE LQIYANPRVP ASMNYPHDKV    60
GGDQDSVGMF QQRAQFYPNI ATDMSAAGST RQFLSVMKGI KGWQTMEISA LDQAVQRAQA   120
GNLYAKRIPL AKQVCSAAG                                               139

SEQ ID NO: 75           moltype = AA  length = 142
FEATURE                 Location/Qualifiers
source                  1..142
                        mol_type = protein
                        organism = Cordyceps confragosa
SEQUENCE: 75
GSYPGLDAVQ SRNAAAAIGE VRAEGLNRQA CLAVISTALQ ESTLHIYANP RVPASYNYPH    60
DLEGGDQDSV GMFQQRAQFY PDIGADMSAA GSTRQFLAVM KGIPGWQTME VSALDQAVQR   120
AEAGNLYAQR LPLANQVCSA AG                                           142

SEQ ID NO: 76           moltype = AA  length = 142
FEATURE                 Location/Qualifiers
source                  1..142
                        mol_type = protein
                        organism = Isaria fumosorosea
SEQUENCE: 76
GSYPGLDATQ SRNAAAAIGE VRAEGLGRQA CLAVISTALQ ESTLHIYANP VVPASMNYPH    60
DLVGGDQDSV GMFQQRPEWY PDIAADMSAA GSTRQFLAAM KQVAGWETME VSALDQAVQK   120
AEAGNLYAQR LPLANQVCSA AG                                           142
```

```
SEQ ID NO: 77            moltype = AA   length = 144
FEATURE                  Location/Qualifiers
source                   1..144
                         mol_type = protein
                         organism = Isaria fumosorosea
SEQUENCE: 77
AANLPGLNAV QTKYARAIIA QAKKDGVGAH GCQAGIATAM VESSIIMYAN NAVPESLKYP   60
HDRVGSDHDS VGLFQQRASI YKNVKCDMNA ACSAGQFYAE MKRVSGWKTM AVGTLCQKVQ  120
RSAYPDRYAK QVGLATNICK AGGL                                         144

SEQ ID NO: 78            moltype = AA   length = 141
FEATURE                  Location/Qualifiers
source                   1..141
                         mol_type = protein
                         organism = Isaria fumosorosea
SEQUENCE: 78
IAGLDETQSR HAQAIIDVVK TEGVGALGCQ AAIATALTES ELYMHANHAV PGSLDKPHDR   60
VGADQDSVGL FQQRAVFYTD VGCTMDAACS AGLFVKDLRA VAGWQGMETA ALCQAIQRSQ  120
IPDAYIKNVA KAVEVCGGSG L                                            141

SEQ ID NO: 79            moltype = AA   length = 143
FEATURE                  Location/Qualifiers
source                   1..143
                         mol_type = protein
                         organism = Purpureocillium lilacinum
SEQUENCE: 79
GNLPTLNAVQ SKNARAIIAQ TKKQGLGRQG CMAALATGLT ESQIKILANN KVPASLKYHY   60
DGKGSDHDSV GIFQQRAMYY KDIKCDMDAA CSASLFFKGM TAIKGWKTMD VAKLCQAVQR  120
SAVPTAYRKY TSQAKTICAA GGL                                          143

SEQ ID NO: 80            moltype = AA   length = 143
FEATURE                  Location/Qualifiers
source                   1..143
                         mol_type = protein
                         organism = Pochonia chlamydosporia
SEQUENCE: 80
GNLPTLNALQ TKHARAIIAQ TKKQGLGRQG CEAAIATGLT ESSLRILANR SVPKSLNYKY   60
DGIGSDHDSV GIFQQRAMYY KDIKCDMDAA CSASLFFKGM VAVKGWKTMD VAKLCQAVQR  120
SAVPTAYRKY TSAAKSICSA GGI                                          143

SEQ ID NO: 81            moltype = AA   length = 144
FEATURE                  Location/Qualifiers
source                   1..144
                         mol_type = protein
                         organism = Pochonia chlamydosporia
SEQUENCE: 81
AANLPGLNSL QSGYARAIIA KAKADGVGRH GCEAAIATGL VESSLIMYAN NAVPASLKYH   60
HDRVGSDHDS IGIFQQRASI YKNIACDMEA GCSAGQFIAE MKRISGWQTM AVGTLCQKVQ  120
RSAYPDRYAK QVPTATKVCA AGGL                                         144

SEQ ID NO: 82            moltype = AA   length = 143
FEATURE                  Location/Qualifiers
source                   1..143
                         mol_type = protein
                         organism = Pochonia chlamydosporia
SEQUENCE: 82
SGNLPGLNSV QTGHARAIIA QTKKQGLGRQ GCEAAIATGL TESGLRILAN NVVPASLKYP   60
HDGMGSDHDS VGIFQQRAMY YTDIGCDMDA ACSASSFFKG MTAIKGWQTM DVAKLCQAVQ  120
RSAVPDAYKK YVGAAASICA AGG                                          143

SEQ ID NO: 83            moltype = AA   length = 143
FEATURE                  Location/Qualifiers
source                   1..143
                         mol_type = protein
                         organism = Penicillium oxalicum
SEQUENCE: 83
GNLPGLSATQ SQHARDIIAE AKREGLGLQG CSAGIATALV ESSILIYANN AVPASLNYPH   60
DAVGSDHDSI GIFQQRAMYY PNIAADMDAA KSAAQFFQKM KSISGWQTMA IGTLCQKVQV  120
SAYPDRYAAR AADAQNICKA GGI                                          143

SEQ ID NO: 84            moltype = AA   length = 148
FEATURE                  Location/Qualifiers
source                   1..148
                         mol_type = protein
                         organism = Metarhizium anisopliae
SEQUENCE: 84
TGDLPPRTYS NLSGLQSKYA RGIMAQAKRE HLGSQGCRAG IATALVESTL IMHANMAVPA   60
SLAYDFDRLG KDADSIGLFQ QRASIYTNIK CSMDVACSAH QFFKEMKTVP QWKYMPIGQL  120
CQEVQHSENP ERYHDFIDQA TEICQAAG                                     148
```

```
SEQ ID NO: 85          moltype = AA  length = 143
FEATURE                Location/Qualifiers
source                 1..143
                       mol_type = protein
                       organism = Metarhizium anisopliae
SEQUENCE: 85
GNLPDLNALQ SKYARGIIAQ AKKDGVGAHG CQAGIATALT ESSLVMYANN AVPASLKYPH  60
DRVGSDHDSV GLFQQRASIY KDVKCDMDAA CSAGLFFTEM KRVKGWQTMA VGTLCQRVQR  120
SAYPDRYNKF VPTATKVCKA GGL                                         143

SEQ ID NO: 86          moltype = AA  length = 144
FEATURE                Location/Qualifiers
source                 1..144
                       mol_type = protein
                       organism = Penicillium roqueforti
SEQUENCE: 86
SSNLPGLSAT QTKHAKAIIA EAKKEGLGRQ GCLAGISTAL VESNILIYAN KKVPASLKYH  60
HDAVAEDYDS VGIFQQRAVY YPNIAADMDA AKSAAQFFKI MKKVSGWKKM NTGKLCQKVQ  120
GSAYPSRYQE RVPESKKICS AGGL                                        144

SEQ ID NO: 87          moltype = AA  length = 140
FEATURE                Location/Qualifiers
source                 1..140
                       mol_type = protein
                       organism = Talaromyces islandicus
SEQUENCE: 87
GNLPGLDSTQ SSHARAIIAE AKREKLGHQG CLAGIATALT ESSILIYANS AVPASLNYPH  60
DAVGSDHDSV GIFQQRAVYY PNIAADMDPA KSAAQFFAKM KGVSGWQTMN VGELCQKVQG  120
SAYPTRYQEH LSAAESICSA                                             140

SEQ ID NO: 88          moltype = AA  length = 144
FEATURE                Location/Qualifiers
source                 1..144
                       mol_type = protein
                       organism = Penicillium expansum
SEQUENCE: 88
SGNLPGLTST QSKHAKAIIA EAKKENLGRQ GCLAGIATGL VESNILVYAN KKVPDSLKYP  60
HDAVGSDNDS VGIFQQRAIY YPDIAADMDA AKSAAQFFKG IKNVNGWKTM EVGKLCQKVQ  120
GSAYPSRYAE RLDDAKKICV AGGL                                        144

SEQ ID NO: 89          moltype = AA  length = 142
FEATURE                Location/Qualifiers
source                 1..142
                       mol_type = protein
                       organism = Acremonium chrysogenum
SEQUENCE: 89
NLPGLDSTQT ANAQGILEQV GTDDVGLQGC LAGFATALVE SNIYIYANEA VPESLNYPYD  60
KMGSDHDSVG IFQQRAMFYP DIAANMDPAR SAGQFFDKMV SISGWETMDV GELCQAVQVS  120
AYPDRYAERV EEARAICNAG GI                                          142

SEQ ID NO: 90          moltype = AA  length = 139
FEATURE                Location/Qualifiers
source                 1..139
                       mol_type = protein
                       organism = Mycobacterium chelonae
SEQUENCE: 90
STKDRHALAT INEGKRLGIT PKGICIAIAV ELVETNLTMY ANSNVPASLG YPHEKVGSDH  60
DSTGLFQQRQ AWGPLSETMD PTLSARLFFL GGHSGQRGLT DFDYNSNSRT PGGWAQAVQV  120
SAFPYRYDER YTEAQQIYA                                              139

SEQ ID NO: 91          moltype = AA  length = 121
FEATURE                Location/Qualifiers
source                 1..121
                       mol_type = protein
                       organism = Mycobacterium sp.
SEQUENCE: 91
NGKAVIAAGL QMKVPEKGII IGLAVGMEES GLRNLANSNV PESLGIPHEG VGHDHKSVGI  60
MQQQPWWGSL RDLMTPGVAA QKFFAKLLKV GGWQNMAPTV AAQTVQGSAY PDAYAAFVTQ  120
A                                                                 121

SEQ ID NO: 92          moltype = AA  length = 142
FEATURE                Location/Qualifiers
source                 1..142
                       mol_type = protein
                       organism = Torrubiella hemipterigena
SEQUENCE: 92
GNLPTLNSVQ SRNANGIIAE VKRRNLGRQG CLAAITTGLT ESSIRILANN AVPSSLNYAH  60
DGLGSDHDSV GIFQQRAKYY TNIQCDMTAD CSAGLFLAKM AGISGWQTMD VATLCQKVQV  120
```

```
SAVPDAYKKY TSQAGTICSA AG                                                142

SEQ ID NO: 93           moltype = AA   length = 142
FEATURE                 Location/Qualifiers
source                  1..142
                        mol_type = protein
                        organism = Torrubiella hemipterigena
SEQUENCE: 93
NLPGLNAVQT KYANAIIAEA KKVGVGAHGC QAAIATGLVE SSIIMYANKG VPASLNYPHD         60
RVGSDHDSIG IFQQRASIYK NIKCDMDAAC SAGQFFTEMK KVKGWQTMAV GTLCQKVQRS        120
AYPDRYAKQV GLATKVCKAG GL                                                142

SEQ ID NO: 94           moltype = AA   length = 147
FEATURE                 Location/Qualifiers
source                  1..147
                        mol_type = protein
                        organism = Arthrobacter sp.
SEQUENCE: 94
LTAAQVKVAR AFIGVGKQLS ISDIGLQIAI MVGLQESGLR VLANSSVLAS MTFAHDGVGS         60
DHDSVGSAQQ RPSAGWGSVA DLMSPVYDAQ AFFGGTSGPN HGSPRGLLDI PGWKSMPKGE        120
AAQAVQVSAF PELYAQWEGK ASSIVAA                                           147

SEQ ID NO: 95           moltype = AA   length = 137
FEATURE                 Location/Qualifiers
source                  1..137
                        mol_type = protein
                        organism = Actinoplanes utahensis
SEQUENCE: 95
GLNQAQMSNA ATIVRLAQER DLPRRAMLIA VMTAFQESSL RNLANSSVPA SLDRPHQGVG         60
DDFDSVGLFQ QRPSQGWGTV AQLMDPRYAA DAFYDRLVEI PDWESLSLGD AAQAVQRSAV        120
PDAYADHEDR AIRIVDA                                                      137

SEQ ID NO: 96           moltype = AA   length = 137
FEATURE                 Location/Qualifiers
source                  1..137
                        mol_type = protein
                        organism = Metarhizium majus
SEQUENCE: 96
LTELQSKYAR GIIRQAKKEH LGSQGCMAGI ATALVESTLL MHANYAVPDS LVYEYDRLGH         60
DADSIGLFQQ RASIYPNIKC SMDVACSARQ FFEGMKRVPD WRYMDVGKLC QEVQRSENPE        120
RYHEFINQAK GICQQGG                                                      137

SEQ ID NO: 97           moltype = AA   length = 137
FEATURE                 Location/Qualifiers
source                  1..137
                        mol_type = protein
                        organism = Micromonospora carbonacea
SEQUENCE: 97
GLSQLQMDNA KTIVDVGRDM KLPRRGLVVA VATAMQESDL HNLASDVLPE SANYPHQGSG         60
SDHDSVGLFQ QRPSSGWGTV RDLMRPAYAA RVFYEALLEV PGWEEMSLTA AAQAVQISAF        120
PDAYAQHEER ATTVVAA                                                      137

SEQ ID NO: 98           moltype = AA   length = 131
FEATURE                 Location/Qualifiers
source                  1..131
                        mol_type = protein
                        organism = Mycobacterium immunogenum
SEQUENCE: 98
LDAGQMEVAR KIIEEGLRRG LSPEAIQIAL ATALTESGLR SLANSSVPDS MMLANDGVGH         60
DHDSVGPFQQ RQSWGATADL MDPSRSAGKF YDQLVKVSGW QDMSVAQAAQ AVQRSAFPDA        120
YAKYEAQASQ I                                                            131

SEQ ID NO: 99           moltype = AA   length = 139
FEATURE                 Location/Qualifiers
source                  1..139
                        mol_type = protein
                        organism = Hirsutella minnesotensis
SEQUENCE: 99
ASKVSGLDPV QSRNADAIIA QAKKDRVGEH GCTAALTTAL SQTGIKILAN KKVPDSVKYK         60
HDDLGTQGDS VGIFQQSVQK YKDIACVMKA DCSAALFFRD IKAVKGWEKM DVTKLLESTN        120
KAGTPAAFKK FEGQAAKIC                                                    139

SEQ ID NO: 100          moltype = AA   length = 141
FEATURE                 Location/Qualifiers
source                  1..141
                        mol_type = protein
                        organism = Hirsutella minnesotensis
SEQUENCE: 100
DLPGLNPTQE AHARAIIGAN NQGNYGRQGC LAAITTGLTE SKLRILANPK VPASLKYKHD         60
```

```
ATGTDHDSIG IFQQRASIYK NIACDMDAAC SAGQFFKEMK AISGWQTMDV PTLCQKVQRS    120
AFPARYREYL ASATAICQAA G                                              141

SEQ ID NO: 101          moltype = AA  length = 143
FEATURE                 Location/Qualifiers
source                  1..143
                        mol_type = protein
                        organism = Penicillium brasilianum
SEQUENCE: 101
GNLPGLSATQ SKHARDIIAE AKREDLGLHG CSAGIATALV ESNILIYANK DVPKSLNYPH     60
DAVGSDHDSV GIFQQRAMYY PDIAADMDAA KSAAQFFKKM KNISGWKSMA VGTLCQKVQG    120
SAYPTRYAER VSEAEKICNA GGI                                            143

SEQ ID NO: 102          moltype = AA  length = 143
FEATURE                 Location/Qualifiers
source                  1..143
                        mol_type = protein
                        organism = Tolypocladium ophioglossoides
SEQUENCE: 102
NLPDLNAVQS AHARSIIDEV KKVGVGMHGC EAAITTGLTE ESQSSLRILA NKNVPASLNY     60
AHDGLGSDHD SIGIFQQRAM YYKDIACDMK ADCSAGLFFN GMKDIKGWQT MDIATLCQKV    120
QRSAYPTAYQ KYTGTAAKVC KAG                                            143

SEQ ID NO: 103          moltype = AA  length = 143
FEATURE                 Location/Qualifiers
source                  1..143
                        mol_type = protein
                        organism = Madurella mycetomatis
SEQUENCE: 103
GNLPGLNSVQ SKHARAIIAQ AKKDKVGRHG CQAGIATAIV ESNILVYANR KVPASMKYPH     60
DAVGSDHDSV GIFQQRARYY PNIAANMDPA RSAGQFFAKM KKVKGWKTMA VGKLCQKVQV    120
SAYPDRYAKQ VSKAAKICAA GGL                                            143

SEQ ID NO: 104          moltype = AA  length = 144
FEATURE                 Location/Qualifiers
source                  1..144
                        mol_type = protein
                        organism = Aspergillus udagawae
SEQUENCE: 104
SGSLPGLNAK QSAHAHKVID EAKKEGLGRQ GCLAGIATAL VESNLLMYAN SKVPASLNYP     60
HDAVGHDYDS VGIFQQRAVY YPNIAADMDA ARSAAQFFAK MKNISGWKTM EVGKLCQKVQ    120
VSAYPDRYAQ RVPAAEKICA AGGL                                           144

SEQ ID NO: 105          moltype = AA  length = 138
FEATURE                 Location/Qualifiers
source                  1..138
                        mol_type = protein
                        organism = Nocardia farcinica
SEQUENCE: 105
SKKDEYALAI LAEGRRRGIT PRGIVIAFAT VYVECDFIMY ANEKVPESLR LPHERVGRDG     60
FSVGLFQQQI VRGAGGAYWW ADCATCMDPT LSAGLFFERL ARLDYNSNEH SPGWYAQAVQ    120
RSAYPHRYDE RMKDAQAL                                                  138

SEQ ID NO: 106          moltype = AA  length = 137
FEATURE                 Location/Qualifiers
source                  1..137
                        mol_type = protein
                        organism = Micromonospora sp.
SEQUENCE: 106
GLDQRQMDNA KVIVDVGRAM KMPRRALVIA VATAMQESNL YNLASDVLPE SYDYPHQGSG     60
SDHDSVGLFQ QRPSSGWGTV AQLMRPSYAA QAFYTALKEV PGWTELSLTA AAQAVQVSAY    120
PDAYAPHEER ATTVVAA                                                   137

SEQ ID NO: 107          moltype = AA  length = 137
FEATURE                 Location/Qualifiers
source                  1..137
                        mol_type = protein
                        organism = Micromonospora sp.
SEQUENCE: 107
GLDQAQMDNA KKIVQAGREM GVPRRGLVIA VATAMQESTL LNYASGVLPE SQSYPHQAIG     60
WDHDSVGLFQ QRPSSGWGTV RELMDPEYAT KAFLSALEEI PGWQDLPLTV AAQAVQVSAF    120
PDAYAQHEWR AAQVVGA                                                   137

SEQ ID NO: 108          moltype = AA  length = 144
FEATURE                 Location/Qualifiers
source                  1..144
                        mol_type = protein
                        organism = Penicillium murcianum
SEQUENCE: 108
```

```
SGNLPGLSST QSKHAKAIIG EAKKEDLGRQ GCLAGIATAL VESNILIYAN KDVPSSLNYP    60
HDAVGSDYDS VGIFQQRAKY YPDIAADMDA AKSAAQFFKG MKGVSGWKTM EVGKLCQKVQ   120
GSAYPTRYAE RVDEAKKICA AGGL                                         144

SEQ ID NO: 109           moltype = AA  length = 147
FEATURE                  Location/Qualifiers
source                   1..147
                         mol_type = protein
                         organism = Micromonospora sp.
SEQUENCE: 109
TGELPRFAEY GDTQIRNAAI IIKVGQDMGV PSRGWVIALA TAMQESALRN LANSGVPESL    60
ALPHEGVGAD HDSLGLFQQR PGWGTVAERM NPAYTARKFY EKLVKVRSWQ RRPLTVVAQQ   120
VQISAYPDAY AKHEELASTI VDALAGG                                      147

SEQ ID NO: 110           moltype = AA  length = 142
FEATURE                  Location/Qualifiers
source                   1..142
                         mol_type = protein
                         organism = Trichoderma gamsii
SEQUENCE: 110
NLPGLNAVQT KYANAIIAKA KAEGVGAHGC QAAIATAMVE SSIIMYANNG VPESLKYPHD    60
RVGSDHDRIG LFQQPASIYK NIKCDMDAAC SAGQFYTEMK KISGWKNMAI GTLAQKVQRS   120
AYPDRYAKQV GLATNVCKAG GL                                           142

SEQ ID NO: 111           moltype = AA  length = 151
FEATURE                  Location/Qualifiers
source                   1..151
                         mol_type = protein
                         organism = Arthrobacter sp.
SEQUENCE: 111
LTPRQESVAR TYIAVGQQLG IPRSGQIIAI MMALQESSLR MLANPSVPAS VQFPNDGVGR    60
DHDSIGSAQQ RPAAGWGTVE QLMDASYNAR AFYGGPSGPN RGSPRGLLDI PGWQGMDKGL   120
AAQAVQVSAF PELYARWERA ATAIVAALEG G                                 151

SEQ ID NO: 112           moltype = AA  length = 144
FEATURE                  Location/Qualifiers
source                   1..144
                         mol_type = protein
                         organism = Arthrobacter sp.
SEQUENCE: 112
LTSDQIAVAK GYISVGKQLG VPQEALIIAI MMALQESSLR VLANSNVPAS FQFSHDGVGS    60
DHDSLGTAQQ RPAAGWGSVE ELMDPDYNAR AFYGGPSGPN RGSPRGLLDV SGWQSMDKGQ   120
AAQAVQVSAF PELYARWESQ ATAI                                         144

SEQ ID NO: 113           moltype = AA  length = 153
FEATURE                  Location/Qualifiers
source                   1..153
                         mol_type = protein
                         organism = Microbacterium sp.
SEQUENCE: 113
GSTRTLTATE LGHAATILAV ARSLGVSERG QQIAMMTALQ ESGLKMYANS SVPASLDYPH    60
DAVGSDHDSV NFFQQRVSGW GSVKDLMDPT YAARAFFGGP DGPNEGSPRG LLDIPGWESM   120
SLGEAAQTVQ VSAFPDAYDK WEGAAQQIIS SVG                                153

SEQ ID NO: 114           moltype = AA  length = 144
FEATURE                  Location/Qualifiers
source                   1..144
                         mol_type = protein
                         organism = Arthrobacter sp.
SEQUENCE: 114
LTARQIAVAS DYISVGKQLG VPRDGQIIAI MMSLQESGLR VLANANVPES LNYPHDGVGS    60
DHDSLGSAQQ RPAAGWGSIA QLMDSMYNVQ AFYGGPAGPN RGSPPGLLDI RGWQSMSKGQ   120
AAQAVQVSAF PELYAHWEPQ ATAI                                         144

SEQ ID NO: 115           moltype = AA  length = 141
FEATURE                  Location/Qualifiers
source                   1..141
                         mol_type = protein
                         organism = Micromonospora halophytica
SEQUENCE: 115
LPGYGDNQLR NAAVIITVGQ EMKVPPRGWV VAVATAMQES RLLNLANRTV AQSRRIPNQG    60
VGADHDSVGL FQQRASWGTV EQRMTPEYAA RKFYEKLVQV PGWQTMPLTR AAQRVQISAF   120
PDAYAKHEDL AARIVDALAG G                                            141

SEQ ID NO: 116           moltype = AA  length = 137
FEATURE                  Location/Qualifiers
source                   1..137
                         mol_type = protein
                         organism = Micromonospora nigra
```

```
SEQUENCE: 116
GLTRAQMDNA EAIVRAGREM GVPRRALVIA VATAMQESTL YNVASGVLPE SQRHPHQGVG    60
WDHDSVGLFQ QRSSSGWGPV GRLMDPEFAT RQFLTALLRV PGWQRMRLTD AAQAVQVSAY   120
PGHYARHEGL ATEVVDA                                                 137

SEQ ID NO: 117          moltype = AA   length = 143
FEATURE                 Location/Qualifiers
source                  1..143
                        mol_type = protein
                        organism = Penicillium patulum
SEQUENCE: 117
GKLPGLSSTQ SKHAKDIIGE AKKEGLGRQG CLAGIATGLV ESNLLIYANK KVPASLKYPH    60
DAVGSDHDSV GIFQQRAMYY PDIAADMDAA KSAAQFFKEM KRVSGWKSMD VGKLCQKVQR   120
SAYPSRYADR VGDAKKICAA GGL                                          143

SEQ ID NO: 118          moltype = AA   length = 152
FEATURE                 Location/Qualifiers
source                  1..152
                        mol_type = protein
                        organism = Arthrobacter sp.
SEQUENCE: 118
VTARQMAVAG DYVSIGQQLG IPRDGQIIAI MMALQESSLR VLANVNVPAS LQYPHDGLGS    60
DHDSLGTAQQ RPAAGWGTVE QLMDPKYNVR AFYGGPSGPN RGSPPGLLDI RGWQSMNKGQ   120
AAQAVQVSAF PELYARWEAE ATAIVEALDG GM                                152

SEQ ID NO: 119          moltype = AA   length = 144
FEATURE                 Location/Qualifiers
source                  1..144
                        mol_type = protein
                        organism = Mycobacterium abscessus
SEQUENCE: 119
NAQVVVAVGE KMHIPPQGII VALATALQES GLKNYANDGT GQLRGDQQGI ASSLQLPHDA    60
VGRDHGSLGI MQQQYPWWGT IQELMTPAIA ARKFYEALLK VNNWQNLPVT VAAQTVQGSA   120
FPDAYAAQEP KARALYATYR GAGG                                         144

SEQ ID NO: 120          moltype = AA   length = 137
FEATURE                 Location/Qualifiers
source                  1..137
                        mol_type = protein
                        organism = Mycobacterium canariasense
SEQUENCE: 120
TKDQVASEFI AEGKRRGITE RGIVICIATG LVESNLTVYA NSKVPESLSL PHDAVGSDGK    60
SVGPLQQQVV WGNGGWWWGD AATCMDPTRS AGLFYDRLVK KPYQSATSDV AAGAIAQSIQ   120
GSAFPDRYAT RMAEARQ                                                 137

SEQ ID NO: 121          moltype = AA   length = 147
FEATURE                 Location/Qualifiers
source                  1..147
                        mol_type = protein
                        organism = Micromonospora rifamycinica
SEQUENCE: 121
SGNIPRLGSY GQTQMRNAAV IIKVGQDMRV PPRGWVIAVA TAMQESALRN LSNSTVAGSR    60
GIPNEGVGSD HDSVGLFQQR AGWGSVAQRM SPDYAARKFY EKLLKVDGWE RMPLTRAAQK   120
VQISAYPDAY AKHEDIASQI VNALAGG                                      147

SEQ ID NO: 122          moltype = AA   length = 137
FEATURE                 Location/Qualifiers
source                  1..137
                        mol_type = protein
                        organism = Micromonospora rifamycinica
SEQUENCE: 122
GLDRAQMNNA QKIVKAGRAM GVPRRALVIA VATAMQESNL YNYASGVLPE SQNYPHEAIG    60
WDHDSVGLFQ QRPSSGWGEV GQLMDPAFAT RAFLTALLAI PGWEDLPLTV AAQAVQISAY   120
PDLYAQHEWR ATEVVAA                                                 137

SEQ ID NO: 123          moltype = AA   length = 144
FEATURE                 Location/Qualifiers
source                  1..144
                        mol_type = protein
                        organism = Arthrobacter alpinus
SEQUENCE: 123
LSESQTKVAK TYIAVGRARG VPNGGIVIAL MMGFQESGMQ MLANASVPES LNFPHDGVGS    60
DHDSVGSAQQ RPSAGWGSVE ELMQPAYNAE AFYGGPQGPN RGSPRGLLDI PGWQGLDKGA   120
AAQAVQGSAF PERYAKWQPE AEAI                                         144

SEQ ID NO: 124          moltype = AA   length = 148
FEATURE                 Location/Qualifiers
source                  1..148
                        mol_type = protein
```

```
                    organism = Microbacterium hominis
SEQUENCE: 124
LGHTQLTHAA TIITTGSGIE GVGRQGVLIA LMAALTESTL RMLANAAHPA SLDLPHDGVG    60
GDHDSLGLFQ MRPTSGWGSV DQLMDPKYQA RAFFGGETGP NFPSPAGLLD IAGWQSADPG   120
AAAQAVERSA FPDRYQRYQP VAEAIISA                                     148

SEQ ID NO: 125          moltype = AA  length = 130
FEATURE                 Location/Qualifiers
source                  1..130
                        mol_type = protein
                        organism = Gordonia phage
SEQUENCE: 125
AITEQAKKMG VSKRGAIIGV ATGLVESGDP MKMWANNAVP ESLKFPHDEV GSDHDSIGLF    60
QQRQAGWGTV ADRMDPHRSA AMFFDALMKV PGWETMDMGA AAQAVQRSAF PGKYAERMPR   120
ATELVDKFGI                                                         130

SEQ ID NO: 126          moltype = AA  length = 147
FEATURE                 Location/Qualifiers
source                  1..147
                        mol_type = protein
                        organism = Micromonospora rosaria
SEQUENCE: 126
TGSMPRTFGY GERQMRNAAI IIKVGQDMKV PARGWVIAIA TAIQESGLKN YANSTVPESL    60
AIPHEAVGSD HDSVGLFQQR PGWGTVAQRM NPSYSARKFY EKLVKVPDWE KRSLTNAAQM   120
VQISAFPDAY AKHEETASRI VDLLAGG                                      147

SEQ ID NO: 127          moltype = AA  length = 131
FEATURE                 Location/Qualifiers
source                  1..131
                        mol_type = protein
                        organism = Tsukamurella pseudospumae
SEQUENCE: 127
TPDQVAAAFI VEGLRSGVSE RGIVICLATG LVESNLTVYA NPADPESLAE PHDAVGSDAN    60
SVGPLQQRAP WWGSSARERM NPTLSSRLFY RALRALPYDS PAHSPGWYAQ QVQRSAFPDR   120
YDRRITEAQA I                                                       131

SEQ ID NO: 128          moltype = AA  length = 137
FEATURE                 Location/Qualifiers
source                  1..137
                        mol_type = protein
                        organism = Micromonospora rosaria
SEQUENCE: 128
GLTQVQMDNA KVIVDVGADL KMPRRALVVA VATAMQESNL YNLASDVLPE SHQYTDQGSG    60
SDHDSVGLFQ QRPSSGWGTV RDLMRPAHAA QLFYEALRQI PGWQSLSIAA AAQAVQISAF   120
PDAYAQHEQR ASTVVTA                                                 137

SEQ ID NO: 129          moltype = AA  length = 142
FEATURE                 Location/Qualifiers
source                  1..142
                        mol_type = protein
                        organism = Tilletia walkeri
SEQUENCE: 129
GLISGLNAIQ TAHAYQIAKA VRAKGLPRQA CLAAITTGIT EANLLNYANS DVSASFNYQY    60
DAVSSDYDSV GVFQQRVTYY PDVGADMDPQ QAASQFLDKM VNINGWENTD VGTLCQDVQG   120
SAYPDRYNEN VGQAQDICTA MG                                           142

SEQ ID NO: 130          moltype = AA  length = 142
FEATURE                 Location/Qualifiers
source                  1..142
                        mol_type = protein
                        organism = Tilletia controversa
SEQUENCE: 130
GLLSGWNALQ TAHAYQIAKA VRAKGLPRQA CLAAICTGIT EANLLNYANS DVAESFNYQY    60
DAVSSDYDSV GVFQQRVTYY PNVAADMDPQ SAAAQFLDKM VNINGWETTD VGSLCQAVQG   120
SAYPDRYNEH VGQAQDICSA MG                                           142

SEQ ID NO: 131          moltype = AA  length = 145
FEATURE                 Location/Qualifiers
source                  1..145
                        mol_type = protein
                        organism = Pochonia chlamydosporia
SEQUENCE: 131
NLPGLNALQS KYANAIIAQA KKDGVGPHGL TNYPLYATLT LVQTSIIMYA NKGVPQSLNY    60
PHDRVGSDHD NIGLFQLRAS VYKNIACDMD AGCSAGLFLD AMRKIKGWER MAIGTLCQKV   120
QRTAYPDRYA KQVGLATNVC KAGGL                                        145

SEQ ID NO: 132          moltype = AA  length = 138
FEATURE                 Location/Qualifiers
source                  1..138
```

```
                              mol_type = protein
                              organism = Pochonia chlamydosporia
SEQUENCE: 132
LLEVQQKYAK LIIAQAKKEN VGRHGCQTGI ATALTESTLI MHANPVVPES LGYPHERLGY    60
DGDSVGLFQQ RAIYYTDIKC SMNAKCSAHQ FYEIMKKIPD WQNIPVGVLC QKVQISAIPE   120
AYNKFVEQAG SICAAAGM                                                 138

SEQ ID NO: 133          moltype = AA   length = 142
FEATURE                 Location/Qualifiers
source                  1..142
                        mol_type = protein
                        organism = Pochonia chlamydosporia
SEQUENCE: 133
NLPGLNDVQS ANARAVIDEN NKEKLGKQGC IAALTTGLTE SSLRILANNG VPASLNYKHD    60
GLGSDHDSIG IFQQRASIYT NIECDMGAAC SASQFFKGMT AVSGWETMDV ATLCQKVQRS   120
AFPDAYKKWV GTATDACAAA GV                                            142

SEQ ID NO: 134          moltype = AA   length = 141
FEATURE                 Location/Qualifiers
source                  1..141
                        mol_type = protein
                        organism = Purpureocillium lilacinum
SEQUENCE: 134
NLPGLNAKQS AHARAIIAET KKEKLGHQGC LAAITTGLTE SSLRVLANKK VPQSLKYKND    60
GLGSDHDSIG IFQQRAMYYK DIKCDMDAAC SASLFFKGMK AVKGWQKMDV ATLCQKVQRS   120
AVPSAYKKHV DAAGKICKAG G                                             141

SEQ ID NO: 135          moltype = AA   length = 144
FEATURE                 Location/Qualifiers
source                  1..144
                        mol_type = protein
                        organism = Paraphaeosphaeria sporulosa
SEQUENCE: 135
SGTLPGLNSV QTRNARAIIA RTKKDFAASQ QKRACYVAIT TAFQESGIRI LANSKYPASL    60
NYPHDGVGSD HDSVGIFQQR PSWGSTKDRM NADLSAHFFF NALKRVRGWQ SLAIGVAAQK   120
VQVSAFPDAY NKWVAKAEKV CNAG                                          144

SEQ ID NO: 136          moltype = AA   length = 139
FEATURE                 Location/Qualifiers
source                  1..139
                        mol_type = protein
                        organism = Cordyceps brongniartii
SEQUENCE: 136
PGLDAVQSRN AAAAIGQVRA EGLNRQACLA VISTTLQEST LHVYANPVVP ASINYPHDLV    60
GGDQDSTGMF QQRPEYYPDI AADMSAAGST RQFLAAMKQV SNWQTMEVSA LDQAVQRAEA   120
GNLYAQRLPL ASRVCSAAG                                                139

SEQ ID NO: 137          moltype = AA   length = 134
FEATURE                 Location/Qualifiers
source                  1..134
                        mol_type = protein
                        organism = Gordonia phage
SEQUENCE: 137
KYPFAITEQA KKMGLSKRAA IIGNATALVE VGDPMKMYAN TAVPESLKFP HDAVGSDHDS    60
IGLFQQRQAG WGTVADRMDP HRSAKMFYDA LVKVPGWETM DMGAAAQAVQ RSAFPGKYAG   120
RMARATELVD KFGI                                                     134

SEQ ID NO: 138          moltype = AA   length = 155
FEATURE                 Location/Qualifiers
source                  1..155
                        mol_type = protein
                        organism = Arthrobacter nicotinovorans
SEQUENCE: 138
SGSMPDGQAV GLSAGQIAVA QGYISVGKQL GVPREAMVIA IMMSLQETTL RMLANANVPA    60
SFQFPHDGVG SDHDSVGSAQ QRPAAGWGTV AELMDLTYNA RAFYGGPSGP NKGSPRGLLD   120
VPGWSAMSKG QAAQAVQVSA FPELYARWEQ QATAI                              155

SEQ ID NO: 139          moltype = AA   length = 132
FEATURE                 Location/Qualifiers
source                  1..132
                        mol_type = protein
                        organism = Mycobacterium conceptionense
SEQUENCE: 139
TNDAYAREII RAGRDLGITP RGIVIAFATV YVESNWIMWA NAAVPESLAI PHERVGSDGK    60
SVGLFQQQVV WGNGAWWWGS AADCMDPYKS ARLFFQRLAK RDYNNGDPGA HAQAIQQSAY   120
PDRYGQRMSE AQ                                                       132

SEQ ID NO: 140          moltype = AA   length = 137
FEATURE                 Location/Qualifiers
```

```
                       source          1..137
                                       mol_type = protein
                                       organism = Micromonospora narathiwatensis
SEQUENCE: 140
GLDQRQMDNA KVIVDAGRAM NLPRRALVVA VATAMQESNL YNLASDVLPE SYNYPHQGSG    60
SDHDSVGLFQ QRPSSGWGTV AELMQPAYAA RAFFAALAEV PGWADLSLTE AAQAVQVSAY   120
PDAYAQHEER ATTVVAA                                                 137

SEQ ID NO: 141         moltype = AA   length = 137
FEATURE                Location/Qualifiers
source                 1..137
                       mol_type = protein
                       organism = Micromonospora narathiwatensis
SEQUENCE: 141
GLDGDQMANA VSIVRAGQEM GVPQRGLVIA VATAMQESNL YNYASGVLPE SQNYPHQAIG    60
WDHDSVGLFQ QRPSSGWGAV RDLMQPAYAT KQFLSALLQI PGWQNMALTD AAQAVQVSAF   120
PWAYAQHEWR ATEVVDA                                                 137

SEQ ID NO: 142         moltype = AA   length = 137
FEATURE                Location/Qualifiers
source                 1..137
                       mol_type = protein
                       organism = Micromonospora auratinigra
SEQUENCE: 142
GLDQRQMDNA KAIVDVARAM KLPRRAMVIA VATAMQESDL YNLASDVLPE SFDYPHQGSG    60
SDHDSIGLFQ QRPSSGWGTV AQIMRPAYAA RAFLTALCEV PGWTGLSLTD AAQAVQVSAF   120
PDAYAQHEKR ASTVVAA                                                 137

SEQ ID NO: 143         moltype = AA   length = 136
FEATURE                Location/Qualifiers
source                 1..136
                       mol_type = protein
                       organism = Mycobacterium sp.
SEQUENCE: 143
TADQYAPAVL QAGRDLGITP KGVVIGFATV YVESNWTMYA NAKVPESMNI PHDAVGSDGL    60
SVGLFQQQVR DDGNGWWWGD AATCMDPYKS AQLFFSRLKR LDYNSEAQSP GSYAQAIQQS   120
AFPDRYDQRM GDAQSL                                                  136

SEQ ID NO: 144         moltype = AA   length = 137
FEATURE                Location/Qualifiers
source                 1..137
                       mol_type = protein
                       organism = Micromonospora sediminicola
SEQUENCE: 144
GLDQRQMDNA KAIVDVGREM RLPRRALVVA VATAMQESDL YNLASDVLPE SFDYPHQGSG    60
SDHDSIGLFQ QRPSSGWGTV AEIMRPAYAA RAFFTALAEV PGWEEMSVTA AAQAVQVSAF   120
PDAYAKHEQR AATVVAA                                                 137

SEQ ID NO: 145         moltype = AA   length = 153
FEATURE                Location/Qualifiers
source                 1..153
                       mol_type = protein
                       organism = Microbacterium sp.
SEQUENCE: 145
GSKRTLGPTE LNHAATILSI ARSLGVSVKG QQIAIMTALQ ESGLKMYANS SVPASLDYPH    60
DAVGSDHDSV NFFQQRVSGW GTVAELMDPT YATKAFFGGP EGPNQGSPRG LLDVPGWESM   120
PLGKAAQTVQ VSAYPDAYDK WETAAQQIIT AVG                               153

SEQ ID NO: 146         moltype = AA   length = 137
FEATURE                Location/Qualifiers
source                 1..137
                       mol_type = protein
                       organism = Micromonospora coriariae
SEQUENCE: 146
GLDQAQMDNA TAIVRAGQKM DVPRRALVIA VATAMQESNL YNYASGVLPE SQNYPHQAIG    60
WDHDSVGLFQ QRPSTGWGAV PDLMKPEYAT QQFLTALLEV PGWQDLPLTV AAQTVQVSAF   120
GWLYAQHEWR ATEVVDA                                                 137

SEQ ID NO: 147         moltype = AA   length = 137
FEATURE                Location/Qualifiers
source                 1..137
                       mol_type = protein
                       organism = Micromonospora citrea
SEQUENCE: 147
GLDNAQMENA EVIVRTGRKM GMPRRALVIA VATAMQESNL YNVASGVLPE SQNYPHQGIG    60
WDHDSVGLFQ QRSSSGWGEV GQLMDPAFAT RQFLSALAEV PGWQQMRLTD AAQAVQISAY   120
PEHYAKHEWR ATEVVEA                                                 137

SEQ ID NO: 148         moltype = AA   length = 137
```

```
FEATURE                 Location/Qualifiers
source                  1..137
                        mol_type = protein
                        organism = Micromonospora peucetia
SEQUENCE: 148
IPQYGERQLR NAARIIKVGQ EMKVSPRGWV IAVATALQES RLLNLANRTV SESETIPNEG    60
IGADHDSVGL FQQRASWGSV TQRMTPEYAA RKFYEKLVRV PGWETMPLSR AAQAVQISAF   120
PDAYAKHEDV AARIVSA                                                  137

SEQ ID NO: 149          moltype = AA   length = 147
FEATURE                 Location/Qualifiers
source                  1..147
                        mol_type = protein
                        organism = Micromonospora yangpuensis
SEQUENCE: 149
TGRMPRSAGY GERQLRNAAI IIKVGQDMKV PARGWVIAIA TAIQESGLKN YANSTVPESL    60
ALPHEAVGRD HDSVGLFQQR PGWGSVKQRM TPSYSARKFY EKLIQVPNWE KRSLTDAAQR   120
VQISAFPDAY AKHEETASRI VDALAGG                                       147

SEQ ID NO: 150          moltype = AA   length = 137
FEATURE                 Location/Qualifiers
source                  1..137
                        mol_type = protein
                        organism = Micromonospora rhizosphaerae
SEQUENCE: 150
GLDKAQMDNA EAIVKAGQEM GVPRRALVIA VATAMQESNL YNYASGVLPE SQNYPHQAIG    60
WDHDSVGLFQ QRPSSGWGSV PDLMKPEFAT RQFLTALVAV PGWQDMPLTL AAQTVQVSAF   120
PWAYAQHEWR ANEVVNA                                                  137

SEQ ID NO: 151          moltype = AA   length = 147
FEATURE                 Location/Qualifiers
source                  1..147
                        mol_type = protein
                        organism = Micromonospora echinaurantiaca
SEQUENCE: 151
TGKMPRMSEY GESQLRNAAR IVKVGQEMKV PPRGWVIAVA TAMQESGLRN LANRTVAQSR    60
DLPNEGVAD HDSVGLFQQR ANWGSVAQRM TPEYAARKFY EKLLKVPGWQ RMPLTTAAQK   120
VQISAFPDAY AKHEALAARI VDALAGG                                       147

SEQ ID NO: 152          moltype = AA   length = 137
FEATURE                 Location/Qualifiers
source                  1..137
                        mol_type = protein
                        organism = Micromonospora inositola
SEQUENCE: 152
GLDEDQMDNA KAIVRAGRDM GVPRRGLVIA VATAMQESNL YNYASAVLPE SQNYPHQAIG    60
WDHDSVGLFQ QRPSSGWGTV GDLMRPEYAT KQFLTALEQI PGWQDMALTD AAQAVQVSAF   120
PWAYAQHEWR ADEVVDA                                                  137

SEQ ID NO: 153          moltype = AA   length = 137
FEATURE                 Location/Qualifiers
source                  1..137
                        mol_type = protein
                        organism = Micromonospora inositola
SEQUENCE: 153
GLDQRQMDNA KVIVDVGRDM KLPRRALIVA IATAMQESNL YNLASDVLPE SYDYPHQGSG    60
ADHDSVGLFQ QRPSSGWGTV AELMRPAYAA RAFYAALAEV PGWADLSITQ AAQAVQVSAF   120
PDAYAQHEQR ATTVVDA                                                  137

SEQ ID NO: 154          moltype = AA   length = 137
FEATURE                 Location/Qualifiers
source                  1..137
                        mol_type = protein
                        organism = Micromonospora coxensis
SEQUENCE: 154
GLTQAQMDNA KVIVDVGVGM GVPRRGLVVA IATAMQESNL HNLASDVLPE SFDHPHQGSG    60
SDHDSVGLFQ QRPSSGWGTV AQLMRPAYAA RAFYTALLEV PGWQDMSVTA AAQAVQISAF   120
PDAYAKHEQR AGTVVAA                                                  137

SEQ ID NO: 155          moltype = AA   length = 126
FEATURE                 Location/Qualifiers
source                  1..126
                        mol_type = protein
                        organism = Micromonospora mirobrigensis
SEQUENCE: 155
GLDETQMDNA KAIVRSAKKM GVPRQAMVIA VATAMQESTL LNYASGVLPE SQDYPHQAIG    60
WDHDSVGLFQ QRPSSGWGTV EQLMDPEFAT QAFLSVLLQV PGWQDMPLTL AAQIVQVSAF   120
PDAYAQ                                                              126
```

-continued

```
SEQ ID NO: 156         moltype = AA   length = 137
FEATURE                Location/Qualifiers
source                 1..137
                       mol_type = protein
                       organism = Micromonospora viridifaciens
SEQUENCE: 156
GLDRAQMDNA TTIVRTGRDM GVPRRGLIIA VATAMQESNL YNYASGVLPE SQNYPHQAIG   60
WDHDSVGLFQ QRPSSGWGTV ADLMKPAYAT RQFLAALEQI PGWQNMALTD AAQAVQISAF  120
PWAYAQHEWR ATEVVDA                                                 137

SEQ ID NO: 157         moltype = AA   length = 139
FEATURE                Location/Qualifiers
source                 1..139
                       mol_type = protein
                       organism = Micromonospora haikouensis
SEQUENCE: 157
VPGVGEWTSA QTTHATVIVS VGRQRRVAPR GYVIALAVAM QESTLRNLAN STVPESLNIP   60
HDAVGSDHDS VGLFQQRPGW GSVRERMTPS YAARKFYEAL VDVDGWQRMR LTDAAQAVQR  120
SGTPEAYQKW EDDAEALAA                                               139

SEQ ID NO: 158         moltype = AA   length = 137
FEATURE                Location/Qualifiers
source                 1..137
                       mol_type = protein
                       organism = Micromonospora peucetia
SEQUENCE: 158
GLDKAQMKNA QAIVRTGREM EMPRRALVIA VATAMQESNL YNVASGVLPE SRNHPHQGIG   60
WDHDSVGLFQ QRSSSGWGEV GQLMDPEFAT RQFLAALAQV PGWQQMRLTD AAQAVQISAY  120
PEHYAKHEGR ATTVVGA                                                 137

SEQ ID NO: 159         moltype = AA   length = 137
FEATURE                Location/Qualifiers
source                 1..137
                       mol_type = protein
                       organism = Micromonospora citrea
SEQUENCE: 159
GLTQAQMDNA KVIVDVGADL KMPRRAMVVA VATAMQESNL YNLASDVLPE SRQYPHQGSG   60
SDHDSVGLFQ QRPSSGWGTV RELMRPAYAA RAFYEALREV PGWQEMSVAA AAQAVQVSAF  120
PDAYARHEER ATTIVAA                                                 137

SEQ ID NO: 160         moltype = AA   length = 137
FEATURE                Location/Qualifiers
source                 1..137
                       mol_type = protein
                       organism = Micromonospora saelicesensis
SEQUENCE: 160
GLDQAQMDNA KIIVDVGLEM KMPRRALVVA LSTAMQESNL YNLASDVLPE SAEYPNQGSG   60
SDHDSVGLFQ QRPSSGWGTV AQLMRPSYAA RAFYTALNEI PGWQDMSVTA AAQAVQISAY  120
PDAYAQHEDR ATTVAAA                                                 137

SEQ ID NO: 161         moltype = AA   length = 137
FEATURE                Location/Qualifiers
source                 1..137
                       mol_type = protein
                       organism = Micromonospora echinospora
SEQUENCE: 161
GLTQRQMDNA KAIVDVGVEL RMPRRALVVA IATAMQESDL HNLANDRIAE SARYPHQGSG   60
TDHDSVGLFQ QRPSSGWGSV RELMQPAYAA RVFYRALREV SGWEDMSVTA AAQAVQRSAY  120
PGAYAKHERR ATTVVDA                                                 137

SEQ ID NO: 162         moltype = AA   length = 137
FEATURE                Location/Qualifiers
source                 1..137
                       mol_type = protein
                       organism = Micromonospora purpureochromogenes
SEQUENCE: 162
GLDQAQMDNA KAIVKAGRKM GVPRQALIIA VATAMQESNL YNYASGVLPE SQNYPYQAIG   60
WDHDSVGLFQ QRPSSGWGEV RDLMDPEYAT QAFLSALLEI PGWQDLALTD AAQAVQVSAF  120
PWAYAQHEWR ATEVVEA                                                 137

SEQ ID NO: 163         moltype = AA   length = 143
FEATURE                Location/Qualifiers
source                 1..143
                       mol_type = protein
                       organism = Micromonospora echinofusca
SEQUENCE: 163
SANPPGSAAD ASWKPAQVGH AATIVRVGAE KDVPSKGWTV AVATAMQEST LRNLANSMVP   60
ESLGIPHEGV GRDHDSVGLF QQRPGWGTVV QRMTPDYAAG KFYDALVKVN GWEAMSLAEA  120
AQAVQVSRYP DAYAKWQSEA QRL                                          143
```

```
SEQ ID NO: 164          moltype = AA   length = 137
FEATURE                 Location/Qualifiers
source                  1..137
                        mol_type = protein
                        organism = Micromonospora echinaurantiaca
SEQUENCE: 164
GLTQAQMDNA KIIVDVGVDM KIPRRGLVVA IATAMQESNL YNYASGVLPE SQNYPHQAIG    60
WDHDSVGLFQ QRPSSGWGTV KDLMRPAYAA RAFYEALREI PGWQEMSVTA AAQAVQISAF   120
PDAYAQHEGR ATTVVAA                                                  137

SEQ ID NO: 165          moltype = AA   length = 131
FEATURE                 Location/Qualifiers
source                  1..131
                        mol_type = protein
                        organism = Micromonospora citrea
SEQUENCE: 165
SAQSTNAATI VAVGRQRQVP PRGFVIALAT AMQESTLRNL ANSTVPESLS LPHEGVGRDH    60
DSVGLFQQRP GWGSVRERMT PSYAAAKFYE ALVRVDGWQR MRLTDAAQAV QRSGLPEAYQ   120
KWEADAEQLA A                                                        131

SEQ ID NO: 166          moltype = AA   length = 137
FEATURE                 Location/Qualifiers
source                  1..137
                        mol_type = protein
                        organism = Micromonospora echinaurantiaca
SEQUENCE: 166
GLTEAQMENA EAIVRTGREM GVPRRALVIA VATAMQESNL YNYASGVLPE SQNYPHQAVG    60
WDHDSVGLFQ QRPSSGWGPV RRLMEPEFAT RQFLSALEQV PGWQRMRLTD AAQAVQISAY   120
PEHYAKHEWR ATKVVEA                                                  137

SEQ ID NO: 167          moltype = AA   length = 133
FEATURE                 Location/Qualifiers
source                  1..133
                        mol_type = protein
                        organism = Micromonospora echinaurantiaca
SEQUENCE: 167
GLSQRQMDNA KTIVDVGVRS RMPRRALVVA VATAMQESNL HNVANDQIAE SLRYPHQGTG    60
TDHDSVGLFQ QRPSSGWGSV RELMQPTYAA SAFYRALREV PGWQKLSVTA AAQAVQQSAY   120
PGAYAKHERR ATA                                                      133

SEQ ID NO: 168          moltype = AA   length = 137
FEATURE                 Location/Qualifiers
source                  1..137
                        mol_type = protein
                        organism = Micromonospora rhizosphaerae
SEQUENCE: 168
GLDQRQMDNA KVIVDVGREM KMPRRGLIIA VATAMQESNL YNYASGVLPE SQNYPYQAIG    60
WDHDSVGLFQ QRPSSGWGTV AELMRPAYAA RAFYSALNEV PGWQDLSLTQ AAQAVQVSAF   120
PDAYARHEER ATTVVDA                                                  137

SEQ ID NO: 169          moltype = AA   length = 141
FEATURE                 Location/Qualifiers
source                  1..141
                        mol_type = protein
                        organism = Micromonospora pallida
SEQUENCE: 169
GPVAGLTVAQ MNNAKKIVRA GRAMGVPRRA LVIAVATAMQ ESNLYNLASG VVPESQNHPN    60
QGVGWDHDSI GLFQQRASMG WGTVAQIMDP AYATRQFLTV LLTVPGWQQM RLTDAAQAVQ   120
VSGFPEAYAQ HESRATVIVN A                                             141

SEQ ID NO: 170          moltype = AA   length = 137
FEATURE                 Location/Qualifiers
source                  1..137
                        mol_type = protein
                        organism = Micromonospora krabiensis
SEQUENCE: 170
GLTRAQMKNA GAIVRTGREM KVPRRALVIA VATAMQESNL YNYASGVLPE SQNYPHQAIG    60
WDHDSVGLFQ QRPSSGWGSV GDLMRPEYAT RQFLTALEEV PGWQQMPLTD AAQAVQVSAF   120
GWLYAQHEWA ATEVVDA                                                  137

SEQ ID NO: 171          moltype = AA   length = 137
FEATURE                 Location/Qualifiers
source                  1..137
                        mol_type = protein
                        organism = Micromonospora krabiensis
SEQUENCE: 171
GLTQAQMDNA KVIVDVGRDL DVPKFGMIIA VATAMQESTL LNYASGVLPE SQDYPHQAIG    60
WDHDSVGLFQ QRPSSGWGTV AELMRPAFAA RAFYLALLEV PGWQDMSLTV AAQTVQVSAF   120
```

```
PDAYAQHEDR ATEVVEA                                                       137

SEQ ID NO: 172          moltype = AA   length = 143
FEATURE                 Location/Qualifiers
source                  1..143
                        mol_type = protein
                        organism = Mycobacterium phage
SEQUENCE: 172
EGRRARSGQG QLDHPVISEK GIVIALATGL VESNLTMYAN RADPDSLKYP HDAVGSDANS          60
VGVFQQRAPW WGTLADRMDV ARSAAMFYGS LARQRIVDNA GTPNEKRFDY NTDRVSPGTW         120
AQMVQKSAFP DRYDQRMAEA RKI                                                143

SEQ ID NO: 173          moltype = AA   length = 102
FEATURE                 Location/Qualifiers
source                  1..102
                        mol_type = protein
                        organism = Mycobacterium phage
SEQUENCE: 173
TIMVESNWIM YANNAVPESL NFPHDAIGSD HDSIGLFQQR PSWGTVAQRM NPRESAGMFL          60
KELAKLDWRN MDRGAACQAV QRSAFPGRYA AQEQAAVEMV RA                           102

SEQ ID NO: 174          moltype = AA   length = 142
FEATURE                 Location/Qualifiers
source                  1..142
                        mol_type = protein
                        organism = Pseudonocardia sp.
SEQUENCE: 174
LDEKQLANAA TIITVGTQAG VPAAGLKVAL MTALQESKLR MLANSTVPAS LDYPHEGVGS          60
DHDSVNMFQQ RPHWGKLADL MDARYAVRAF FGGPNGPNGG SPRGLLDIKG WDTMPPGQAA         120
QRVQVSAFPD AYDQWEGAAE TI                                                 142

SEQ ID NO: 175          moltype = AA   length = 148
FEATURE                 Location/Qualifiers
source                  1..148
                        mol_type = protein
                        organism = Microbacterium pygmaeum
SEQUENCE: 175
LRRAQLTHAA TIITVGSGID GVGRQGVLIA LMAALTESTL RMLANAAHPA SLDMPNDGVG          60
SDHDSLGLFQ MRPTSGWGTV AELMDARYQV RAFFGGPDGP NYPSPAGLLD IAGWQTADPG         120
TAAQAVERSA YPDRYQNYQP VAESIIAA                                           148

SEQ ID NO: 176          moltype = AA   length = 123
FEATURE                 Location/Qualifiers
source                  1..123
                        mol_type = protein
                        organism = Pseudonocardia sp.
SEQUENCE: 176
GFAGPQLANA AAIVSVGVEM GVSQRGQVIA VATAIQESKL LMYANSTVPA SLDLPHDRVG          60
SDHDSVGLFQ QRAPWGPLQV RMDARGSAKL FYARLLTVPG WQSMPLAQAA QAVQISAFPD         120
AYA                                                                      123

SEQ ID NO: 177          moltype = AA   length = 145
FEATURE                 Location/Qualifiers
source                  1..145
                        mol_type = protein
                        organism = Mycobacterium phage
SEQUENCE: 177
TQDGIAIGII AEGRRSRSGE GQLDHPVMSA KGIVIALAVA LVETNLKMYA NRSDPESLNF          60
PHDAVGSDAN SVGVFQQRAP WWGTVADRMD VARSAAMFYN SLYRQRVGGA DYNTDRVSPG         120
TWGQMVQQSA FPDRYDKRMA EARQI                                              145

SEQ ID NO: 178          moltype = AA   length = 147
FEATURE                 Location/Qualifiers
source                  1..147
                        mol_type = protein
                        organism = Micromonospora avicenniae
SEQUENCE: 178
SGKMPRLADY GDSQLRNAAR IIGTGQKMKV PPRGWVIAVA TAMQESRLRN LANRTVGESQ          60
GLPNEGVGAD HDSVGLFQQR ASWGTVRQRM TPEYAAKKFY EGLLDIPDWE QLPLTEAAQR         120
VQRSAFPDAY AKHEAVAAQI VDALAGG                                            147

SEQ ID NO: 179          moltype = AA   length = 127
FEATURE                 Location/Qualifiers
source                  1..127
                        mol_type = protein
                        organism = Mycobacterium abscessus
SEQUENCE: 179
SKDDYARAII AEGKRRGISP LGIQIGLATV YVESDFIMYA NEDDPESLNY PHEALSEDAN          60
STGLFQQRAP WWGTVADRMD ATRSAGLFFA ALAKLDYNNP ARSPGSYAQA VQKSAFPDRY         120
```

```
DKRFNDA                                                              127

SEQ ID NO: 180          moltype = AA   length = 140
FEATURE                 Location/Qualifiers
source                  1..140
                        mol_type = protein
                        organism = Mycobacterium abscessus
SEQUENCE: 180
AGTVGDLDGR QTQVAKDIVA EGLRRGIPFK GLVIGVATAL QESSLRELAN PSVPESMQIP    60
HDGVGKDHDS VGPFQQRQSW GATADLMNSR TSAGKFFAAL QKVAGWQNMS HTEAAQAVQR   120
SAFPSAYAKH VAHADRIVRA                                              140

SEQ ID NO: 181          moltype = AA   length = 121
FEATURE                 Location/Qualifiers
source                  1..121
                        mol_type = protein
                        organism = Mycobacterium abscessus
SEQUENCE: 181
NGKAVIATGL QMKIPEKGII VALATAMQES GLKNYANPNV PESMQIPHEA VGHDHASVGI    60
FQQQPWWGSI KDLMTPGVAA QKFYAALLKV GGWESMAPTQ AAQAVQRSAY PDAYADDVPA   120
A                                                                  121

SEQ ID NO: 182          moltype = AA   length = 137
FEATURE                 Location/Qualifiers
source                  1..137
                        mol_type = protein
                        organism = Mycobacterium abscessus
SEQUENCE: 182
GLTRTQMKNA EIIVRTGRGM GVPRRGMVIA VATAMQESNL YNLASGVIPE SQRHPHQGLG    60
WDHDSVGLFQ QRSSSGWGPV DRLMDPEFAT RQFLGALERV PGWQQMRLTD AAQAVQVSAY   120
PDYYAKHEWR ANEVVDA                                                 137

SEQ ID NO: 183          moltype = AA   length = 134
FEATURE                 Location/Qualifiers
source                  1..134
                        mol_type = protein
                        organism = Mycobacterium abscessus
SEQUENCE: 183
LNERQMEIAR TIVAEAQRRG LSPFAAKIAL ATGLTESGLR NLANSNVPAS LNILNDGVGK    60
DHDSTGVFQQ RQSWGATREL MTPMLAAGKF YDALVKVPGW EHMSLAAAAQ SVQRSAFPSA   120
YAKYEQQANQ VYQA                                                    134

SEQ ID NO: 184          moltype = AA   length = 127
FEATURE                 Location/Qualifiers
source                  1..127
                        mol_type = protein
                        organism = Mycobacterium abscessus
SEQUENCE: 184
SKDDYARAII AEGRRKGITP RGIQIGLATV YVESDFIMYA NEADPDSLNY PHEDLSEDEN    60
STGLFQQRAP WWGTVADRMD AARSAGLFFA ALAKLDYNNP SRSPGSYAQS VQQSAFPDRY   120
DQRFNDA                                                            127

SEQ ID NO: 185          moltype = AA   length = 130
FEATURE                 Location/Qualifiers
source                  1..130
                        mol_type = protein
                        mol_type = protein
                        organism = Mycobacterium abscessus
                        organism = Mycobacterium abscessus
SEQUENCE: 185
QMQVAKSIVA EGVRRHLPPK AMQIAIATAL QESGMRSLAN PNVPASMQIP HQGVGRDHDS    60
VGPFQQRQSW GATADLMNPA TSAGKFYDKL VRIPGWQEMP LTQAAQRVQV SAYPNAYAKH   120
TGPAGQIVAA                                                         130

SEQ ID NO: 186          moltype = AA   length = 135
FEATURE                 Location/Qualifiers
source                  1..135
                        mol_type = protein
                        organism = Mycobacterium abscessus
SEQUENCE: 186
SKEDGYARAI IAEGKRRGIS PRGIQIGLAT VFVEAALKMW ANEKVPESLE FPHDDVGYDG    60
YSVGLFQQQV VMGLNGQWWW ADCATCMNPT LSAGLFFDRL AKLPYNDTSR SPGSFAQDVQ   120
QSAYPDRYDK RFAEA                                                   135

SEQ ID NO: 187          moltype = AA   length = 127
FEATURE                 Location/Qualifiers
source                  1..127
                        mol_type = protein
                        organism = Pseudonocardia sp.
```

```
SEQUENCE: 187
IEGLGPEQVS NAGLIVATGV EMDVPRHGRV IALATAMQES SLKNLANSNV PQSLELPNQG    60
VGSDHDSVGL FQQREAGWGD VATRMDPRQS ARLFYNALLQ VPGWESLPVT RAAQLVQISA   120
FPDAYAK                                                            127

SEQ ID NO: 188          moltype = AA   length = 74
FEATURE                 Location/Qualifiers
source                  1..74
                        mol_type = protein
                        organism = Podospora anserina
SEQUENCE: 188
YPITGDVVNC RSGPGTSYSV VKQYTQGQDV TITCQTEGTN VNGVTIWDKT ADGNCYVSDY    60
YVQTGVNGYV TERC                                                     74

SEQ ID NO: 189          moltype = AA   length = 73
FEATURE                 Location/Qualifiers
source                  1..73
                        mol_type = protein
                        organism = Penicillium chrysogenum
SEQUENCE: 189
YPITGDGVNC RSGPGTSYSV VKSYKQGADV AITCQTAGTS VNGNEIWDKT EDGCYITDYY    60
IRTGSSSYVT KKC                                                      73

SEQ ID NO: 190          moltype = AA   length = 73
FEATURE                 Location/Qualifiers
source                  1..73
                        mol_type = protein
                        organism = Nectria haematococca
SEQUENCE: 190
YPVTSDNLNC RSGPGTAFAI KKSYKNGQDV TITCQTEGDN IEGNSIWDKT SDGCYVADKY    60
VKTGKDGYVK GKC                                                      73

SEQ ID NO: 191          moltype = AA   length = 61
FEATURE                 Location/Qualifiers
source                  1..61
                        mol_type = protein
                        organism = Metarhizium acridum
SEQUENCE: 191
YPITGTTVNC RAGPATDPAI VRAYKKDDKV SIARQTQGPD INGGTIWDKT ADGCYVSDYF    60
V                                                                   61

SEQ ID NO: 192          moltype = AA   length = 73
FEATURE                 Location/Qualifiers
source                  1..73
                        mol_type = protein
                        organism = Metarhizium robertsii
SEQUENCE: 192
FPVTADSLNC RAEPNTSSAV KKTYKKTDDV KISCQTEGPS INGNSIWDKT QDGCYVADYY    60
IKTGSSGYVT GKC                                                      73

SEQ ID NO: 193          moltype = AA   length = 73
FEATURE                 Location/Qualifiers
source                  1..73
                        mol_type = protein
                        organism = Metarhizium robertsii
SEQUENCE: 193
YAIEADGVNC RSGPSTSDKV VRTYNKGNDV KLECQTAGQA IHGDSLWDKT TDGCYVADYY    60
VKTGTTNMVT GQC                                                      73

SEQ ID NO: 194          moltype = AA   length = 73
FEATURE                 Location/Qualifiers
source                  1..73
                        mol_type = protein
                        organism = Fusarium oxysporum
SEQUENCE: 194
YPVTSDNLNC RSGPGTAFAI KKSYKKGQDV TITCQTQGDN VEGNSIWDKT SDGCYVADKY    60
VKTGKDGYVK GKC                                                      73

SEQ ID NO: 195          moltype = AA   length = 69
FEATURE                 Location/Qualifiers
source                  1..69
                        mol_type = protein
                        organism = Fusarium oxysporum
SEQUENCE: 195
DEGVRCRSGP TTSHAIQRQF TKGTDVTITC QIEGTNIEGN ALWDKTTFGC YVSDYYVATG    60
SSGYVTSKC                                                           69

SEQ ID NO: 196          moltype = AA   length = 73
FEATURE                 Location/Qualifiers
```

```
source                  1..73
                        mol_type = protein
                        organism = Thielavia terrestris
SEQUENCE: 196
YPVKADTLNC RSGPGTSYKV IKTYKKGTDL KITCQTPGTS VNGDNLWDKT SDGCYVADYY    60
VKTGTSGYVT AHC                                                      73

SEQ ID NO: 197          moltype = AA  length = 73
FEATURE                 Location/Qualifiers
source                  1..73
                        mol_type = protein
                        organism = Thielavia terrestris
SEQUENCE: 197
YPIKGDGVNC RTGPGTSYKV VKSYAKGVDV KITCQTHGES INGDTLWDKT SDGCYVADYY    60
VKTGTTNMVT GQC                                                      73

SEQ ID NO: 198          moltype = AA  length = 73
FEATURE                 Location/Qualifiers
source                  1..73
                        mol_type = protein
                        organism = Trichosporon asahii
SEQUENCE: 198
YPIKTDGVRC RSGPGTSYDI KKTYSAGDKV TLSCYKTGTS VEGNTYWDKT GDGCYVSDYY    60
VKTGSTTPVV SKC                                                      73

SEQ ID NO: 199          moltype = AA  length = 72
FEATURE                 Location/Qualifiers
source                  1..72
                        mol_type = protein
                        organism = Trichosporon asahii
SEQUENCE: 199
YPVKETLHCR SSPSTSGKIV KDYPKGTKIK LSCYSRGQSI GGNTIWDKTT DGCFVADYYV    60
TTGTTNPVVA AC                                                       72

SEQ ID NO: 200          moltype = AA  length = 73
FEATURE                 Location/Qualifiers
source                  1..73
                        mol_type = protein
                        organism = Fusarium oxysporum
SEQUENCE: 200
YPITGNNVNC REGPSTGYEV VKTYHKGDDV KLTCQTSGEG VLGNSLWDKT SDGCYVADYY    60
VKTGTSGMVT KDC                                                      73

SEQ ID NO: 201          moltype = AA  length = 73
FEATURE                 Location/Qualifiers
source                  1..73
                        mol_type = protein
                        organism = Fusarium oxysporum
SEQUENCE: 201
YPVTSDNLNC RSGPGTAFAI KKSYKKGQDV TITCQTQGDK VEGNSIWDKT SDGCYVADKY    60
VKTGKDGYVK GKC                                                      73

SEQ ID NO: 202          moltype = AA  length = 72
FEATURE                 Location/Qualifiers
source                  1..72
                        mol_type = protein
                        organism = Trichosporon asahii
SEQUENCE: 202
YPVKEGLNCR SEPNTGGGIV TSYAAGTQVT ITCATHGEAV NGHDVWDKTT DGCFVSDWYV    60
STGTAEFVAS EC                                                       72

SEQ ID NO: 203          moltype = AA  length = 73
FEATURE                 Location/Qualifiers
source                  1..73
                        mol_type = protein
                        organism = Trichosporon asahii
SEQUENCE: 203
YPIKTDGVRC RSGPGTSYDI KKTYSAGDKV TLSCYKTGTS VEGNTYWDKT GDGCYVSDYY    60
VKTGSTTPVV SKC                                                      73

SEQ ID NO: 204          moltype = AA  length = 73
FEATURE                 Location/Qualifiers
source                  1..73
                        mol_type = protein
                        organism = Fusarium oxysporum
SEQUENCE: 204
YPVTSDNLNC RSGPGTAFAI KKSYKKGQDV TINCQTQGDN VEGNSIWDKT SDGCYVADKY    60
VKTGKDGYVK GKC                                                      73
```

```
SEQ ID NO: 205          moltype = AA   length = 69
FEATURE                 Location/Qualifiers
source                  1..69
                        mol_type = protein
                        organism = Fusarium oxysporum
SEQUENCE: 205
DEGVRCRSGP TTSNAIQRQF AKGTDVAITC QTEGTHIKGN ALWDKTTFGC YVSDCYVATG    60
SSGYVTSKC                                                            69

SEQ ID NO: 206          moltype = AA   length = 73
FEATURE                 Location/Qualifiers
source                  1..73
                        mol_type = protein
                        organism = Fusarium oxysporum
SEQUENCE: 206
YPVTSDNLNC RSGPGTAFAI KKSYKKGQDV TITCQTQGDN VEGNSIWDKT SDGCYVADKY    60
VKTGKDGYVK GKC                                                       73

SEQ ID NO: 207          moltype = AA   length = 69
FEATURE                 Location/Qualifiers
source                  1..69
                        mol_type = protein
                        organism = Fusarium oxysporum
SEQUENCE: 207
DEGVRCRSGP TTSHAIQRQF TKGTDVTITC QIEGTNIEGN ALWDKTTFGC YVSDYYVATG    60
SSGYVTSKC                                                            69

SEQ ID NO: 208          moltype = AA   length = 73
FEATURE                 Location/Qualifiers
source                  1..73
                        mol_type = protein
                        organism = Fusarium oxysporum
SEQUENCE: 208
YPVTSDNLNC RSGPGTAFAI KKSYKKGQDV TITCQTQGDN VEGNSIWDKT SDGCYVADKY    60
VKTGKDGYVK GKC                                                       73

SEQ ID NO: 209          moltype = AA   length = 73
FEATURE                 Location/Qualifiers
source                  1..73
                        mol_type = protein
                        organism = Fusarium oxysporum
SEQUENCE: 209
YPVTSDNLNC RSGPGTAFAI KKSYKKGQDV TITCQTQGDK VEGNSIWDKT SDGCYVADKY    60
VKTGKDGYVK GKC                                                       73

SEQ ID NO: 210          moltype = AA   length = 69
FEATURE                 Location/Qualifiers
source                  1..69
                        mol_type = protein
                        organism = Fusarium oxysporum
SEQUENCE: 210
DEGVRCRSGP TTSNAIQRQF AKGTDVAITC QTEGTHIKGN VPWDKTTFGC YVSDYYVATG    60
SSGYVTSKC                                                            69

SEQ ID NO: 211          moltype = AA   length = 69
FEATURE                 Location/Qualifiers
source                  1..69
                        mol_type = protein
                        organism = Gibberella moniliformis
SEQUENCE: 211
DEGVRCRSGP TTSHAIQRQF TKGTDGTITY QTEGTNIEGN TLWDKTTFGC FVSDYYVATG    60
SSGYVTSKC                                                            69

SEQ ID NO: 212          moltype = AA   length = 73
FEATURE                 Location/Qualifiers
source                  1..73
                        mol_type = protein
                        organism = Fusarium oxysporum
SEQUENCE: 212
YPVTSDNLNC RSGPGTAFAI KKSYKKGQDV TITCQTQGDN VEGNSIWDKT SDGCYVADKY    60
VKTGKDGYVK DKC                                                       73

SEQ ID NO: 213          moltype = AA   length = 69
FEATURE                 Location/Qualifiers
source                  1..69
                        mol_type = protein
                        organism = Fusarium oxysporum
SEQUENCE: 213
DEGVRCRSGP TTSHAIQRQF TKGTDVTITC QIEGTNIEGN ALWDKTTFGC YVSDYYVATG    60
```

```
SSGYVTSKC                                                                 69

SEQ ID NO: 214           moltype = AA  length = 73
FEATURE                  Location/Qualifiers
source                   1..73
                         mol_type = protein
                         organism = Fusarium oxysporum
SEQUENCE: 214
YPVTSDNLNC RSGPGTAFAI KKSYKKGQDV TITCQTQGDN VEGNSIWDKT SDGCYVADKY          60
VKTGKDGYVK GKC                                                            73

SEQ ID NO: 215           moltype = AA  length = 69
FEATURE                  Location/Qualifiers
source                   1..69
                         mol_type = protein
                         organism = Fusarium oxysporum
SEQUENCE: 215
DEGVRCRSGP TTSHAIQRQF TKGTDVTITC QIEGTNIEGN ALWDKTTFGC YVSDYYVATG          60
SSGYVTSKC                                                                 69

SEQ ID NO: 216           moltype = AA  length = 73
FEATURE                  Location/Qualifiers
source                   1..73
                         mol_type = protein
                         organism = Penicillium oxalicum
SEQUENCE: 216
YPVKTDGLHC RSGPGTSYSI VKTYNTGTDL TITCQTPGPV INGDELWDKT SDGCYVSDYY          60
VKTGTSGYVA PHC                                                            73

SEQ ID NO: 217           moltype = AA  length = 73
FEATURE                  Location/Qualifiers
source                   1..73
                         mol_type = protein
                         organism = Penicillium oxalicum
SEQUENCE: 217
YPVKTDDLHC RSGPGTNYAV VKSYKIGTDL TITCQAPGTV VSGDELWDKT SDGCYVSDYY          60
VKTGTSGYVT KQC                                                            73

SEQ ID NO: 218           moltype = AA  length = 69
FEATURE                  Location/Qualifiers
source                   1..69
                         mol_type = protein
                         organism = Fusarium oxysporum
SEQUENCE: 218
DEGVRCRSGP TTSNAIQRQF AKGTDVAITC QTEGTHIKGN VPWDKTTFGC YISDYYVAKG          60
SSGYVTSKC                                                                 69

SEQ ID NO: 219           moltype = AA  length = 69
FEATURE                  Location/Qualifiers
source                   1..69
                         mol_type = protein
                         organism = Fusarium oxysporum
SEQUENCE: 219
DEGVRCRSGP TTSHAIQRQF TKGTDVTITC QIEGTNIEGN ALWDKTTFGC YLSDYYVATG          60
SSGYVTSKC                                                                 69

SEQ ID NO: 220           moltype = AA  length = 73
FEATURE                  Location/Qualifiers
source                   1..73
                         mol_type = protein
                         organism = Fusarium oxysporum
SEQUENCE: 220
YPVTSDNLNC RSGPGTGFAI KKSYKKGQDI TITCQTQGDN VEGNSIWDKT SNGCYVADKY          60
VKTGKDGYVK GKC                                                            73

SEQ ID NO: 221           moltype = AA  length = 69
FEATURE                  Location/Qualifiers
source                   1..69
                         mol_type = protein
                         organism = Gibberella fujikuroi
SEQUENCE: 221
DEGVRCRSGP TTSHAIQTHF VKGTDVTITC QTEGTYIGGS TLWDKTTFGC YVSDYYVATG          60
SSGYVTSKC                                                                 69

SEQ ID NO: 222           moltype = AA  length = 59
FEATURE                  Location/Qualifiers
source                   1..59
                         mol_type = protein
                         organism = Penicillium roqueforti
```

```
SEQUENCE: 222
YPVTGSVIDC HSGPGASHSV VKTYEERADI EIVCQATGTT VDGSDIWHQT VDDCYVSDF      59

SEQ ID NO: 223          moltype = AA  length = 74
FEATURE                 Location/Qualifiers
source                  1..74
                        mol_type = protein
                        organism = Pyronema omphalodes
SEQUENCE: 223
YPLVHTDTLN CRSSPSTSSS ITKTYKKSDD IKITCQTYGD TIKGNNIWDK TPDGCYVSDY      60
YVKTGKSGFV VGKC                                                       74

SEQ ID NO: 224          moltype = AA  length = 72
FEATURE                 Location/Qualifiers
source                  1..72
                        mol_type = protein
                        organism = Pyronema omphalodes
SEQUENCE: 224
YPAKETLRCR TSPSTSASIH KTYPAGADIK ITCQTTGTKV LTSNVWDKTS DGCYVSDYYV      60
STGHSGIFLS KC                                                         72

SEQ ID NO: 225          moltype = AA  length = 73
FEATURE                 Location/Qualifiers
source                  1..73
                        mol_type = protein
                        organism = Pseudogymnoascus pannorum
SEQUENCE: 225
FPITGNTVNC RSGPGTDFSI KQTYAKGEAV AITCQTSGTK INGNDIWDLT TDGCYVTDFY      60
VKTGSISYVL PKC                                                        73

SEQ ID NO: 226          moltype = AA  length = 68
FEATURE                 Location/Qualifiers
source                  1..68
                        mol_type = protein
                        organism = Fusarium oxysporum
SEQUENCE: 226
DKGVRCRSGP TTSHAIQRQF TKGTDVTITC QIEGTNIEGN ALWDKTTFGC YVSDYYVATG      60
SSGYVTLK                                                              68

SEQ ID NO: 227          moltype = AA  length = 68
FEATURE                 Location/Qualifiers
source                  1..68
                        mol_type = protein
                        organism = Fusarium oxysporum
SEQUENCE: 227
DKGVRCRSGP TTSHAIQRQF TKGTDVTITC QIEGTNIEGN ALWDKTTFGC YVSDYYVATG      60
SSGYVTLK                                                              68

SEQ ID NO: 228          moltype = AA  length = 73
FEATURE                 Location/Qualifiers
source                  1..73
                        mol_type = protein
                        organism = Acremonium chrysogenum
SEQUENCE: 228
YPITGNEVNC RSGPSTSSDI VTSYKKGDEV QVTCQIDGED IFGNTIWDQT EDGCYVADFY      60
VKTGSNAFVT EAC                                                        73

SEQ ID NO: 229          moltype = AA  length = 73
FEATURE                 Location/Qualifiers
source                  1..73
                        mol_type = protein
                        organism = Acremonium chrysogenum
SEQUENCE: 229
YPITADDVKC RAGPSTSHDI VTAFAEGHEV ELECQIVGEN IFGNSIWDKT TDGCYVSDYY      60
VRTGSDGMVV DNC                                                        73

SEQ ID NO: 230          moltype = AA  length = 73
FEATURE                 Location/Qualifiers
source                  1..73
                        mol_type = protein
                        organism = Acremonium chrysogenum
SEQUENCE: 230
YPVTADSLNC REGAGTDTAV VTTYTAGTDV EVVCQAEGEV IEGSSIWDQT QDGCYVSDVY      60
VDTGSDGYVA DKC                                                        73

SEQ ID NO: 231          moltype = AA  length = 73
FEATURE                 Location/Qualifiers
source                  1..73
                        mol_type = protein
```

```
                        organism = Metarhizium anisopliae
SEQUENCE: 231
YAIEADGVNC RSGPSTSDKV VRTYNKGNDV KLECQTAGQA IHGDSLWDKT TDGCYVADYY    60
VKTGTTNMVT GQC                                                      73

SEQ ID NO: 232          moltype = AA  length = 73
FEATURE                 Location/Qualifiers
source                  1..73
                        mol_type = protein
                        organism = Metarhizium anisopliae
SEQUENCE: 232
FPVTADSLNC RAEPNTSSAV KKTYKKTDDV KISCQTEGPS INGNSIWDKT QDGCYVADYY    60
IKTGSSGYVT GKC                                                      73

SEQ ID NO: 233          moltype = AA  length = 73
FEATURE                 Location/Qualifiers
source                  1..73
                        mol_type = protein
                        organism = Pseudogymnoascus pannorum
SEQUENCE: 233
YPITGTYVNC RTGPSTSFDI VRSYELGDEV DLTCQIAGET VTGDNLWDFT TDGCYVADYF    60
VKTGTFGMVV DEC                                                      73

SEQ ID NO: 234          moltype = AA  length = 73
FEATURE                 Location/Qualifiers
source                  1..73
                        mol_type = protein
                        organism = Pseudogymnoascus pannorum
SEQUENCE: 234
YPITGTYVNC RSGPSTSFDI VRSYELGDEV SLTCQIAGET VEGDYLWDLT TDGCYVADYF    60
VKTGTVGMVA EEC                                                      73

SEQ ID NO: 235          moltype = AA  length = 74
FEATURE                 Location/Qualifiers
source                  1..74
                        mol_type = protein
                        organism = Pseudogymnoascus pannorum
SEQUENCE: 235
YPISGDSVNC RSGPATSYKV IKTYAKGHDV KVTCQTVGET VKGDNLWDKT ADGCYVADYY    60
VKTGTTGRVV KTEC                                                     74

SEQ ID NO: 236          moltype = AA  length = 73
FEATURE                 Location/Qualifiers
source                  1..73
                        mol_type = protein
                        organism = Pseudogymnoascus pannorum
SEQUENCE: 236
VTSPTTVKCR SGPGTQYKIV KTYPASGREC YSCYESGTCI NGNCSWDYNY MDNCYISGYY    60
TGSACTTAAL GKC                                                      73

SEQ ID NO: 237          moltype = AA  length = 74
FEATURE                 Location/Qualifiers
source                  1..74
                        mol_type = protein
                        organism = Pseudogymnoascus pannorum
SEQUENCE: 237
YPISGTSVNC RSGPATSYKV IKTYKKGQDV KITCQTVGET VSGDNLWDKT SDGCYVADYY    60
VKTGTTGRVV KTEC                                                     74

SEQ ID NO: 238          moltype = AA  length = 73
FEATURE                 Location/Qualifiers
source                  1..73
                        mol_type = protein
                        organism = Pseudogymnoascus pannorum
SEQUENCE: 238
YPIKGSVVNC RAGPGTNFPI VKTFKKGDTV DITCQTPGTS ISGNSIWDLI PDNCFITDYY    60
VKTGTGKYIK PRC                                                      73

SEQ ID NO: 239          moltype = AA  length = 64
FEATURE                 Location/Qualifiers
source                  1..64
                        mol_type = protein
                        organism = Pseudogymnoascus pannorum
SEQUENCE: 239
VTNPTTVKCR SGPGTQYRIV KTYRAGDREC YSCYESGTCI NGNCSWDYNY MDNCYISGYY    60
TDSG                                                                64

SEQ ID NO: 240          moltype = AA  length = 73
FEATURE                 Location/Qualifiers
```

```
source                   1..73
                         mol_type = protein
                         organism = Pseudogymnoascus pannorum
SEQUENCE: 240
VTSPTTVKCR SGPGTQYKIV KTYPASGREC YSCYESGTCI NGNCSWDYNY MDNCYISGYY    60
TGSACTTAAL GKC                                                      73

SEQ ID NO: 241           moltype = AA  length = 73
FEATURE                  Location/Qualifiers
source                   1..73
                         mol_type = protein
                         organism = Pseudogymnoascus pannorum
SEQUENCE: 241
YPITGNTVNC RSGPGTDFPI KKTFAKGSIV SITCQTPGTK INGNEIWDLT SDGCFVSDFY    60
VKTGSITYVK PKC                                                      73

SEQ ID NO: 242           moltype = AA  length = 73
FEATURE                  Location/Qualifiers
source                   1..73
                         mol_type = protein
                         organism = Pseudogymnoascus pannorum
SEQUENCE: 242
YPITGTSVNC RSGPSTKFDV VRSYVLGDEV TLTCQIAGET VTGDYLWDLT TDGCYVADYF    60
VKTGTVGMVT EAC                                                      73

SEQ ID NO: 243           moltype = AA  length = 73
FEATURE                  Location/Qualifiers
source                   1..73
                         mol_type = protein
                         organism = Pseudogymnoascus pannorum
SEQUENCE: 243
YPITGTYVNC RSGPSTSYDI IRSYELGDEV DLTCQIAGET VTGDNLWDFT TDGCYVADYF    60
VKTGTFGMVV DEC                                                      73

SEQ ID NO: 244           moltype = AA  length = 74
FEATURE                  Location/Qualifiers
source                   1..74
                         mol_type = protein
                         organism = Pseudogymnoascus pannorum
SEQUENCE: 244
YPISGDSVNC RSGPATSYKV IKTYAKGHDV KVTCQTVGET VKGDNLWDKT ADGCYVADYY    60
VKTGTTGRVV KTEC                                                     74

SEQ ID NO: 245           moltype = AA  length = 73
FEATURE                  Location/Qualifiers
source                   1..73
                         mol_type = protein
                         organism = Pseudogymnoascus pannorum
SEQUENCE: 245
YPITGTYVNC RTGPSTSFDI VRSYELGDEV DLTCQIAGET VTGDNLWDFT TDGCYVADYF    60
VKTGTFGMVV DEC                                                      73

SEQ ID NO: 246           moltype = AA  length = 73
FEATURE                  Location/Qualifiers
source                   1..73
                         mol_type = protein
                         organism = Pseudogymnoascus pannorum
SEQUENCE: 246
YPITGTYVNC RSGPSTSFDI VRSYELGDEV SLTCQIAGET VEGDYLWDLT TDGCYVADYF    60
VKTGTVGMVA EEC                                                      73

SEQ ID NO: 247           moltype = AA  length = 72
FEATURE                  Location/Qualifiers
source                   1..72
                         mol_type = protein
                         organism = Pseudogymnoascus pannorum
SEQUENCE: 247
YPISGDSVNC RSGPATSYKV IKTYLKGHDV DLTCQTVGET VKGDSLWDKT TDGCYVADYY    60
VKTGTTGRVV KK                                                       72

SEQ ID NO: 248           moltype = AA  length = 73
FEATURE                  Location/Qualifiers
source                   1..73
                         mol_type = protein
                         organism = Pseudogymnoascus pannorum
SEQUENCE: 248
YPIKGSVVNC RSGPGTNFAI VKTFKKGDTV DITCQTPGTS ISGNSIWDLT PDNCFITDYY    60
VKTGTGKYIK PRC                                                      73
```

```
SEQ ID NO: 249          moltype = AA   length = 67
FEATURE                 Location/Qualifiers
source                  1..67
                        mol_type = protein
                        organism = Pseudogymnoascus pannorum
SEQUENCE: 249
CRSGPGTGYS VIATVKKGSY YSFGCYKTGT CVSGNCTWDR IFWDGKSCYV SGYYTDSACS    60
ASALGKC                                                              67

SEQ ID NO: 250          moltype = AA   length = 73
FEATURE                 Location/Qualifiers
source                  1..73
                        mol_type = protein
                        organism = Pseudogymnoascus pannorum
SEQUENCE: 250
YPITGTFVNC RSGPSTKFDV VRSYVLGDEV TLTCQIAGET VTGDYLWDLT TDGCYVADYF    60
VKTGTVGMVT EAC                                                       73

SEQ ID NO: 251          moltype = AA   length = 67
FEATURE                 Location/Qualifiers
source                  1..67
                        mol_type = protein
                        organism = Pseudogymnoascus pannorum
SEQUENCE: 251
CRSGPGTGYS VIATVKKGSY YSFGCYKTGT CVSGNCTWDR IFWDGKSCYV SGYYTDSACS    60
ASALGKC                                                              67

SEQ ID NO: 252          moltype = AA   length = 73
FEATURE                 Location/Qualifiers
source                  1..73
                        mol_type = protein
                        organism = Pseudogymnoascus pannorum
SEQUENCE: 252
YPITGTKVNC RTGPSTSFEI IRSYKLGDEV SLTCQIAGET VQGNYLWDLT TDGCYVADYF    60
VKTGSDGMVT EGC                                                       73

SEQ ID NO: 253          moltype = AA   length = 73
FEATURE                 Location/Qualifiers
source                  1..73
                        mol_type = protein
                        organism = Aspergillus clavatus
SEQUENCE: 253
YPITGDGVNC RSGPGTSYKV VKSYPKGHQV SIVCQATGTD VKGDSLWDKT SDGCYVADYY    60
VKTGTTGYVT KHC                                                       73

SEQ ID NO: 254          moltype = AA   length = 73
FEATURE                 Location/Qualifiers
source                  1..73
                        mol_type = protein
                        organism = Aspergillus clavatus
SEQUENCE: 254
YPITGDTVNC RSGPGTSHAV VKSYKKGEDV KIVCQAPGTD VKGESIWDKT SDGCYVADYY    60
VKTGTTGYVT KKC                                                       73

SEQ ID NO: 255          moltype = AA   length = 73
FEATURE                 Location/Qualifiers
source                  1..73
                        mol_type = protein
                        organism = Neosartorya fischeri
SEQUENCE: 255
YPITGNEVNC RAGPSTNDKV VKSYHKGDDV KLSCQTYGEN VQGNSIWDKT TDGCYVSDFY    60
VKTGSNSMVT KEC                                                       73

SEQ ID NO: 256          moltype = AA   length = 73
FEATURE                 Location/Qualifiers
source                  1..73
                        mol_type = protein
                        organism = Neosartorya fischeri
SEQUENCE: 256
YPITGDGVNC RSGPGTNHPV VKSYPKGHDV SIVCQAPGTD VKGDKLWDKT SDGCYVADYY    60
VKTGSTDYVT KHC                                                       73

SEQ ID NO: 257          moltype = AA   length = 73
FEATURE                 Location/Qualifiers
source                  1..73
                        mol_type = protein
                        organism = Neosartorya fischeri
SEQUENCE: 257
YPITGDGVNC RSGPGTNHPV VKSYPKGHDV SIVCQAPGTD VKGDKLWDKT SDGCYVADYY    60
```

```
VKTGSSDYVT KHC                                                               73

SEQ ID NO: 258           moltype = AA  length = 73
FEATURE                  Location/Qualifiers
source                   1..73
                         mol_type = protein
                         organism = Aspergillus terreus
SEQUENCE: 258
YPITGDGVNC RSGPGTSHAV VKSYPKGHEI SIVCQAAGTD VKGDNLWDKT SDGCYVADYY            60
VKTGSTGYVT KHC                                                               73

SEQ ID NO: 259           moltype = AA  length = 64
FEATURE                  Location/Qualifiers
source                   1..64
                         mol_type = protein
                         organism = Aspergillus terreus
SEQUENCE: 259
CRTGPSTNDG ITKTYKKGDD VKLSCQTYGE SIQGSTIWDK TTDGCYVADY YVKTGTSGMV            60
TGEC                                                                         64

SEQ ID NO: 260           moltype = AA  length = 73
FEATURE                  Location/Qualifiers
source                   1..73
                         mol_type = protein
                         organism = Aspergillus terreus
SEQUENCE: 260
YTITADGVNC RSGPGTSNKS VKTYAKGTDV KISCQQAGES IFGNSLWDKT SDGCYVSDYY            60
VKTGSTGYVT DKC                                                               73

SEQ ID NO: 261           moltype = AA  length = 73
FEATURE                  Location/Qualifiers
source                   1..73
                         mol_type = protein
                         organism = Chaetomium globosum
SEQUENCE: 261
YPITGSVVNC RSGPGTSYAV KKSYAKGADV KISCQTSGTS VNGNNIWDKT QDGCYVADYY            60
VKTGTNGYVT KKC                                                               73

SEQ ID NO: 262           moltype = AA  length = 73
FEATURE                  Location/Qualifiers
source                   1..73
                         mol_type = protein
                         organism = Chaetomium globosum
SEQUENCE: 262
YPITGSVVNC RSGPGTSYAV KKSYNKGADV TISCQTTGTS VNGNSIWDKT QDGCYVADYY            60
VKTGTNGYVT KKC                                                               73

SEQ ID NO: 263           moltype = AA  length = 73
FEATURE                  Location/Qualifiers
source                   1..73
                         mol_type = protein
                         organism = Chaetomium globosum
SEQUENCE: 263
YPITGNDVNC RSGPDTSYKS VKTYKKGADV KLTCQTYGES INGNAIWDKT SDGCYVSDYY            60
VKTGSNSMVT KEC                                                               73

SEQ ID NO: 264           moltype = AA  length = 73
FEATURE                  Location/Qualifiers
source                   1..73
                         mol_type = protein
                         organism = Neosartorya fumigata
SEQUENCE: 264
YPITGNGVNC RAGPSTNDKV IKSYAKGTDV KLSCQTYGEN INGNSIWDKT TDGCYVADYY            60
VKTGSNSMVT KEC                                                               73

SEQ ID NO: 265           moltype = AA  length = 73
FEATURE                  Location/Qualifiers
source                   1..73
                         mol_type = protein
                         organism = Neosartorya fumigata
SEQUENCE: 265
YPITGNGVNC RSGPGTNYPV VKSYPKGHEV SIVCQAPGTD IKGDKLWDKT SDGCYVADYY            60
VKTGTTGYVT KHC                                                               73

SEQ ID NO: 266           moltype = AA  length = 73
FEATURE                  Location/Qualifiers
source                   1..73
                         mol_type = protein
                         organism = Neosartorya fumigata
```

```
SEQUENCE: 266
YPITGDGVNC RSGPGTNYPV VKSYPKGHEV SIVCQAPGTD IKGDKLWDKT SDGCYVADYY     60
VKTGTTNYVA KHC                                                       73

SEQ ID NO: 267          moltype = AA   length = 73
FEATURE                 Location/Qualifiers
source                  1..73
                        mol_type = protein
                        organism = Penicillium chrysogenum
SEQUENCE: 267
YPITGDSVNC RSGPGTTHAV VKSYKKAQDV TVTCQTAGES IFGDNLWDKT SDGCYVADYY     60
VQTGTSNYVT TKC                                                       73

SEQ ID NO: 268          moltype = AA   length = 73
FEATURE                 Location/Qualifiers
source                  1..73
                        mol_type = protein
                        organism = Penicillium chrysogenum
SEQUENCE: 268
YPITSDQLNC RSGPSTSDSV VKTYKSGADV KVSCQTYGES INGNTIWDKT SDNCYVADYY     60
VKTGSDSMVT ESC                                                       73

SEQ ID NO: 269          moltype = AA   length = 73
FEATURE                 Location/Qualifiers
source                  1..73
                        mol_type = protein
                        organism = Nectria haematococca
SEQUENCE: 269
YPITGDDVRC RSGPGTSYAI KKTFKKGTNV KITCQTTGTN IKGNNIWDKV SEGCYVSDYY     60
VKTGSSGFVT KKC                                                       73

SEQ ID NO: 270          moltype = AA   length = 73
FEATURE                 Location/Qualifiers
source                  1..73
                        mol_type = protein
                        organism = Nectria haematococca
SEQUENCE: 270
YPITGDDVKC RSGPGTSYAV KKVLKKGTDV TITCQTEGTN ISGNTIWDKI SDGCYVSDYY     60
VKTGSNGYVK PKC                                                       73

SEQ ID NO: 271          moltype = AA   length = 73
FEATURE                 Location/Qualifiers
source                  1..73
                        mol_type = protein
                        organism = Hypocrea jecorina
SEQUENCE: 271
YPITGDVVNC RTGPGTSYAI KTSYKKSHDI SISCQTTGTS VNGNNIWDKT ADGCYVADYY     60
VKTGSSGFVT KKC                                                       73

SEQ ID NO: 272          moltype = AA   length = 73
FEATURE                 Location/Qualifiers
source                  1..73
                        mol_type = protein
                        organism = Thielavia terrestris
SEQUENCE: 272
YAITGDTVNC RSGPGTNYAV KKTYAKGHDV TLSCQTSGTT VNGNSIWDKT SDGCYVSDYY     60
VKTGSNSYVT KKC                                                       73

SEQ ID NO: 273          moltype = AA   length = 74
FEATURE                 Location/Qualifiers
source                  1..74
                        mol_type = protein
                        organism = Thielavia heterothallica
SEQUENCE: 273
YPVTANGGLS CRSGPGTSYP VKKTYKKGFD IKISCQTTGT SVNGYNIWDK TQDGCYVSDY     60
YVKTGKSGFV TTKC                                                      74

SEQ ID NO: 274          moltype = AA   length = 73
FEATURE                 Location/Qualifiers
source                  1..73
                        mol_type = protein
                        organism = Hypocrea jecorina
SEQUENCE: 274
YPITGDTVNC RSGPGTSFAI KKTYKKSQDV SVTCQTSGTS VNGNSIWDKT SDGCYVADYY     60
VKTGSSSYVT KKC                                                       73

SEQ ID NO: 275          moltype = AA   length = 73
FEATURE                 Location/Qualifiers
source                  1..73
```

```
                        mol_type = protein
                        organism = Chaetomium thermophilum
SEQUENCE: 275
YPITGEGVNC RSGPGTSYKV IKSYKKGTDV KISCQIKGES INGNNLWDKT QDGCYVSDYY    60
VKTGSNSMVT KQC                                                       73

SEQ ID NO: 276          moltype = AA   length = 73
FEATURE                 Location/Qualifiers
source                  1..73
                        mol_type = protein
                        organism = Chaetomium thermophilum
SEQUENCE: 276
YKITGNNVNC RSGPGTSYSV KKTYAKGTDV KITCQTTGTN INGNNIWDKT SDGCYVSDYY    60
VKTGTNGYVT TKC                                                       73

SEQ ID NO: 277          moltype = AA   length = 73
FEATURE                 Location/Qualifiers
source                  1..73
                        mol_type = protein
                        organism = Fusarium oxysporum
SEQUENCE: 277
YPITGNDVKC RSGPGTSYAV KKVLKKGTDV KITCQTEGTN ISGNTIWDKI SDGCYVSDYY    60
VKTGSSGYIK PKC                                                       73

SEQ ID NO: 278          moltype = AA   length = 73
FEATURE                 Location/Qualifiers
source                  1..73
                        mol_type = protein
                        organism = Thielavia heterothallica
SEQUENCE: 278
YPITGDDVNC RTGPGTSFKS VKTYPKGTDV KLSCQTYGEV IFGNSIWDKT QDGCYVSDYY    60
VKTGSNNMVT GEC                                                       73

SEQ ID NO: 279          moltype = AA   length = 74
FEATURE                 Location/Qualifiers
source                  1..74
                        mol_type = protein
                        organism = Thielavia heterothallica
SEQUENCE: 279
YPVTANGGLS CRSGPGTSYA VKKTYKKGFD VKISCQTTGT SVNGNNIWDK TQDGCYVADY    60
YVKTGKNGFV TSKC                                                      74

SEQ ID NO: 280          moltype = AA   length = 73
FEATURE                 Location/Qualifiers
source                  1..73
                        mol_type = protein
                        organism = Hypocrea virens
SEQUENCE: 280
YPITGEAVNC RTGPGTSFAI KKTYKKSQDV SVTCQTSGTS VNGNSIWDKT SDGCYVADYY    60
VKTGSSSYVT KKC                                                       73

SEQ ID NO: 281          moltype = AA   length = 73
FEATURE                 Location/Qualifiers
source                  1..73
                        mol_type = protein
                        organism = Metarhizium robertsii
SEQUENCE: 281
YPITGTTVNC RSGPSTHDKV IKTYNKGNDI KISCQVAGET VSGNNLWDKT QDGCFVSDYY    60
VKTGSNGMVT GQC                                                       73

SEQ ID NO: 282          moltype = AA   length = 73
FEATURE                 Location/Qualifiers
source                  1..73
                        mol_type = protein
                        organism = Fusarium oxysporum
SEQUENCE: 282
YPITGNDVKC RSGPGTSYAV KKVLKKGTDV KITCQTEGTN ISGNTIWDKI SDGCYVSDYY    60
VKTGSSGYIK PKC                                                       73

SEQ ID NO: 283          moltype = AA   length = 73
FEATURE                 Location/Qualifiers
source                  1..73
                        mol_type = protein
                        organism = Chaetomium thermophilum
SEQUENCE: 283
YAITGDNVNC RSGPGTSYAV KKVYKKGTDV KISCQTTGTN INGNNLWDKT SDGCYVSDYY    60
VKTGSNGYVT SKC                                                       73

SEQ ID NO: 284          moltype = AA   length = 73
```

```
FEATURE              Location/Qualifiers
source               1..73
                     mol_type = protein
                     organism = Thielavia terrestris
SEQUENCE: 284
YPITGNGVNC RSGPGTSHAV KKVYAKGTDI KVTCQTEGTS INGNSIWDKT SDGCYVADYY      60
VKTGSNSYVT KKC                                                        73

SEQ ID NO: 285       moltype = AA  length = 73
FEATURE              Location/Qualifiers
source               1..73
                     mol_type = protein
                     organism = Fusarium oxysporum
SEQUENCE: 285
YPITGNDVKC RSGPGTSYAV KKVLKKGTDV KITCQTEGTN ISGNTIWDKT SDGCYVSDYY      60
VKTGSSGYIK PKC                                                        73

SEQ ID NO: 286       moltype = AA  length = 73
FEATURE              Location/Qualifiers
source               1..73
                     mol_type = protein
                     organism = Fusarium oxysporum
SEQUENCE: 286
YPITGNDVKC RSGPGTSYAV KEVLKKGTDV KITCQTEGTN ISGNTIWDKI SDGCYVSDYY      60
VKTGSSGYIK PKC                                                        73

SEQ ID NO: 287       moltype = AA  length = 73
FEATURE              Location/Qualifiers
source               1..73
                     mol_type = protein
                     organism = Fusarium oxysporum
SEQUENCE: 287
FPITGNTVNC RSGPGTSYSV KRTYKKGQDV SITCQTYGTN VNGNSIWDKT SDGCYVADYY      60
VKTGSDEFVT KKC                                                        73

SEQ ID NO: 288       moltype = AA  length = 73
FEATURE              Location/Qualifiers
source               1..73
                     mol_type = protein
                     organism = Fusarium oxysporum
SEQUENCE: 288
YPITGNDVKC RSGPGTSYAV KKVLKKGTDV KITCQTEGTN ISGNTIWDKI SDGCYVSDYY      60
VKTGSNGYIK PKC                                                        73

SEQ ID NO: 289       moltype = AA  length = 73
FEATURE              Location/Qualifiers
source               1..73
                     mol_type = protein
                     organism = Fusarium oxysporum
SEQUENCE: 289
YPITGNDVKC RSGPGTSYAV KKVLKKGTDV KITCQTEGTN ISGNTIWDKI SDGCYVSDYY      60
VKTGSSGYIK PKC                                                        73

SEQ ID NO: 290       moltype = AA  length = 73
FEATURE              Location/Qualifiers
source               1..73
                     mol_type = protein
                     organism = Fusarium oxysporum
SEQUENCE: 290
YPITGNDVKC RSGPGTSYAV KKVLKKGTDV KITCQTEGTN ISGNTIWDKI SDGCYVSDYY      60
VKTGSSGYIK PKC                                                        73

SEQ ID NO: 291       moltype = AA  length = 73
FEATURE              Location/Qualifiers
source               1..73
                     mol_type = protein
                     organism = Fusarium oxysporum
SEQUENCE: 291
YPITGNDVKC RSGPGTSYAV KKVLKKGTDV KITCQTEGTN ISGNTIWDKI SDGCYVSDYY      60
VKTGSSGYIK PKC                                                        73

SEQ ID NO: 292       moltype = AA  length = 73
FEATURE              Location/Qualifiers
source               1..73
                     mol_type = protein
                     organism = Penicillium roqueforti
SEQUENCE: 292
YPITGDTVNC RSGPGTSHTV VKTYKKAHDV KITCQTTGDS ISGNNIWDKT SDGCYVADYY      60
VKTGSNSYVT AKC                                                        73
```

```
SEQ ID NO: 293          moltype = AA   length = 73
FEATURE                 Location/Qualifiers
source                  1..73
                        mol_type = protein
                        organism = Penicillium roqueforti
SEQUENCE: 293
YAITASVANC RTGPSTSNAV VTTYKKGADV KITCQTYGEN IQGNSIWDKT SDGCYVADYY    60
VKTGSNSMVT KDC                                                      73

SEQ ID NO: 294          moltype = AA   length = 73
FEATURE                 Location/Qualifiers
source                  1..73
                        mol_type = protein
                        organism = Trichoderma reesei
SEQUENCE: 294
YPITGDTVNC RSGPGTSFAI KKTYKKSQDV SVTCQTSGTS VNGNSIWDKT SDGCYVADYY    60
VKTGSSSYVT KKC                                                      73

SEQ ID NO: 295          moltype = AA   length = 73
FEATURE                 Location/Qualifiers
source                  1..73
                        mol_type = protein
                        organism = Metarhizium anisopliae
SEQUENCE: 295
YPITGTTVNC RSGPSTHDKV IKTYNKGNDI KISCQVAGEN VSGNNLWDKT RDGCYVSDYY    60
VKTGSNGMVT GQC                                                      73

SEQ ID NO: 296          moltype = AA   length = 73
FEATURE                 Location/Qualifiers
source                  1..73
                        mol_type = protein
                        organism = Pseudogymnoascus pannorum
SEQUENCE: 296
YPITGSTVNC RSGPGTSYAV KKTYKKGDAV TITCQKEGPV VSGNSIWDKT SDGCYVADYY    60
VKTGSNGYVK PKC                                                      73

SEQ ID NO: 297          moltype = AA   length = 72
FEATURE                 Location/Qualifiers
source                  1..72
                        mol_type = protein
                        organism = Pseudogymnoascus pannorum
SEQUENCE: 297
YPISGDSVNC RSGPATSYKV IKTYKKGHDV KITCQTVGET IKGGNLWDKT SDGCYVTDYY    60
VKTGTTGRVV KK                                                       72

SEQ ID NO: 298          moltype = AA   length = 72
FEATURE                 Location/Qualifiers
source                  1..72
                        mol_type = protein
                        organism = Pseudogymnoascus pannorum
SEQUENCE: 298
FPVTATVNCR SGPGTGFAVK KSYTKGHAVT ISCQTGGTSV QGNSIWDKTS DGCYVADYYV    60
KTGSSGYVKP KC                                                       72

SEQ ID NO: 299          moltype = AA   length = 73
FEATURE                 Location/Qualifiers
source                  1..73
                        mol_type = protein
                        organism = Pseudogymnoascus pannorum
SEQUENCE: 299
FPITGDTVNC RSGPGTSYAV KKSYNKGHSV TITCQTGGTS VKGNSIWDKT SDGCYVADYY    60
VKTGSSGYVK PKC                                                      73

SEQ ID NO: 300          moltype = AA   length = 73
FEATURE                 Location/Qualifiers
source                  1..73
                        mol_type = protein
                        organism = Pseudogymnoascus pannorum
SEQUENCE: 300
FPITGDSVNC RSGPGTSYAV KKSYAKGHSV TITCQTGGTS VNGNSIWDKT SDGCYVADYY    60
VKTGSSGYVK PKC                                                      73

SEQ ID NO: 301          moltype = AA   length = 73
FEATURE                 Location/Qualifiers
source                  1..73
                        mol_type = protein
                        organism = Pseudogymnoascus pannorum
SEQUENCE: 301
```

```
YPINAAGVNC RSGPGTSYAV KKSYAKDHAV TVTCQTAGTS VNGNSIWDKT SDGCYVADYY    60
VNTGSSGYVK PKC                                                      73

SEQ ID NO: 302          moltype = AA  length = 73
FEATURE                 Location/Qualifiers
source                  1..73
                        mol_type = protein
                        organism = Pseudogymnoascus pannorum
SEQUENCE: 302
YPINAAGVNC RSGPGTGYAV KKSYAKDHAV TVTCQTAGTT VNGNSIWDKT SDGCYVADYY    60
VNTGSSGYVK PKC                                                      73

SEQ ID NO: 303          moltype = AA  length = 73
FEATURE                 Location/Qualifiers
source                  1..73
                        mol_type = protein
                        organism = Pseudogymnoascus pannorum
SEQUENCE: 303
YPITGTTVNC RSGPGTSYAV KKTYKKGDAV TITCQKEGPV ISGNSIWDKT SDGCYVADYY    60
VKTGSNGYVK PKC                                                      73

SEQ ID NO: 304          moltype = AA  length = 73
FEATURE                 Location/Qualifiers
source                  1..73
                        mol_type = protein
                        organism = Pseudogymnoascus pannorum
SEQUENCE: 304
YPITGKTVNC RAGPGTSYPV KKTYSKGDTV TITCQTSGTK VNGNAIWDLT SDGCYLTDYY    60
VKTGTSKYIK PQC                                                      73

SEQ ID NO: 305          moltype = AA  length = 69
FEATURE                 Location/Qualifiers
source                  1..69
                        mol_type = protein
                        organism = Pseudogymnoascus pannorum
SEQUENCE: 305
YPISGTDVNC RSGPATSYKV VKTYKKGHDV KVTCQTVGET IKGDNLWDKT SDGCYVADYY    60
VKTGTTGRV                                                           69

SEQ ID NO: 306          moltype = AA  length = 73
FEATURE                 Location/Qualifiers
source                  1..73
                        mol_type = protein
                        organism = Pseudogymnoascus pannorum
SEQUENCE: 306
YPINTAGVNC RSGPGTSYAV KKSYAKDHAV TVTCQTAGTS VNGNAIWDKT SDGCYVADYY    60
VNTGSNGYVK PKC                                                      73

SEQ ID NO: 307          moltype = AA  length = 73
FEATURE                 Location/Qualifiers
source                  1..73
                        mol_type = protein
                        organism = Pseudogymnoascus pannorum
SEQUENCE: 307
YPINAAGVNC RSGPGTGYAV KKSYAKDHAV TVTCQTAGTS VNGNSIWDKT SDGCYVADYY    60
VNTGSSGYVK PKC                                                      73

SEQ ID NO: 308          moltype = AA  length = 74
FEATURE                 Location/Qualifiers
source                  1..74
                        mol_type = protein
                        organism = Pseudogymnoascus pannorum
SEQUENCE: 308
YPISGTSVNC RSGPATSYKV IKAYKKGQDV KITCQTVGET VSGDNLWDKT TDGCYVADYY    60
VKTGTTGRVV NAEC                                                     74

SEQ ID NO: 309          moltype = AA  length = 73
FEATURE                 Location/Qualifiers
source                  1..73
                        mol_type = protein
                        organism = Pseudogymnoascus pannorum
SEQUENCE: 309
FPITGDSVNC RSGPGTSYAV KKSYAKGHSV TITCQTGGTS VNGNSIWDKT SDGCYVADYY    60
VKTGSSGYVK PKC                                                      73

SEQ ID NO: 310          moltype = AA  length = 73
FEATURE                 Location/Qualifiers
source                  1..73
                        mol_type = protein
```

```
                        organism = Pseudogymnoascus pannorum
SEQUENCE: 310
FPITGDTVNC RSGPGTSYAV KKSYAKGHDV TITCQTGGTS VSGNSIWDKT SDGCYVADYY    60
VKTGSSGYVK PKC                                                      73

SEQ ID NO: 311          moltype = AA  length = 64
FEATURE                 Location/Qualifiers
source                  1..64
                        mol_type = protein
                        organism = Pseudogymnoascus pannorum
SEQUENCE: 311
YPITGKTVNC RAGPGTSYPV KKTYSKGDTV TITCQTSGTK VNGNAIWDLT SDGCYLTDYY    60
VKTG                                                                64

SEQ ID NO: 312          moltype = AA  length = 73
FEATURE                 Location/Qualifiers
source                  1..73
                        mol_type = protein
                        organism = Pseudogymnoascus pannorum
SEQUENCE: 312
FPITGDSVNC RSGPGTSYAV KKSYAKGHDV TITCQTGGTS VSGNSIWDKT SDGCYVADYY    60
VKTGSSGYVK PKC                                                      73

SEQ ID NO: 313          moltype = AA  length = 72
FEATURE                 Location/Qualifiers
source                  1..72
                        mol_type = protein
                        organism = Pseudogymnoascus pannorum
SEQUENCE: 313
FPVTETVNCR SGPGTSYGVK KSYTKGHAVT ISCQTGGTSV KGNSIWDKTS DGCYVADYYV    60
KTGSNGYVKP KC                                                       72

SEQ ID NO: 314          moltype = AA  length = 72
FEATURE                 Location/Qualifiers
source                  1..72
                        mol_type = protein
                        organism = Pseudogymnoascus pannorum
SEQUENCE: 314
FPVTATVNCR SGPGTGYAVK KSYTKGNAVT ISCQTGGTSV NGNSIWDKTS DGCYVADYYV    60
KTGSSGYVKP KC                                                       72

SEQ ID NO: 315          moltype = AA  length = 73
FEATURE                 Location/Qualifiers
source                  1..73
                        mol_type = protein
                        organism = Pseudogymnoascus pannorum
SEQUENCE: 315
YPINAAGVNC RSGPGTSYAV KKSYAKDHAV TVTCQTAGTS VNGNAIWDKT SDGCYVADYY    60
VNTGSNGYVK PKC                                                      73

SEQ ID NO: 316          moltype = AA  length = 73
FEATURE                 Location/Qualifiers
source                  1..73
                        mol_type = protein
                        organism = Pseudogymnoascus pannorum
SEQUENCE: 316
FPITGATVNC RSGPGTSYAV KKSYAKGHDV TITCQTGGTS VNGNSIWDKT SDGCYVADYY    60
VKTGSSGYVK PKC                                                      73

SEQ ID NO: 317          moltype = AA  length = 10
FEATURE                 Location/Qualifiers
source                  1..10
                        mol_type = protein
                        organism = Synthetic construct
VARIANT                 3
                        note = X=I or L
VARIANT                 6
                        note = X=A or G
VARIANT                 7
                        note = X=I or L
VARIANT                 8
                        note = X=T or V
SEQUENCE: 317
AGXATXXXES                                                          10

SEQ ID NO: 318          moltype = AA  length = 14
FEATURE                 Location/Qualifiers
source                  1..14
                        mol_type = protein
```

|  | organism = Synthetic construct | |
| --- | --- | --- |
| VARIANT | 2 | |
| | note = X=A or G | |
| VARIANT | 3 | |
| | note = X=Any amino Acid | |
| VARIANT | 7 | |
| | note = X=Any Amino Acid | |
| VARIANT | 10 | |
| | note = X=Any Amino Acid | |
| SEQUENCE: 318 | | |
| VXXLCQXVQX SAYP | | 14 |

| SEQ ID NO: 319 | moltype = length = |
| --- | --- |
| SEQUENCE: 319 | |
| 000 | |

| SEQ ID NO: 320 | moltype = DNA  length = 10767 |
| --- | --- |
| FEATURE | Location/Qualifiers |
| source | 1..10767 |
| | mol_type = other DNA |
| | organism = Synthetic construct |
| SEQUENCE: 320 | |

```
taggcgtatc acgaggccct tcgtctcgc gcgtttcggt gatgacggtg aaaacctctg   60
acacatgcag ctcccggaga cggtcacagc ttgtctgtaa gcgatgccg ggagcagaca   120
agcccgtcag ggcgcgtcag cgggtgttgg cgggtgtcgg ggctggctta actatgcggc  180
atcagagcag attgtactga gagtgcacca tatgcggtgt gaaataccgc acagatgcgt  240
aaggagaaaa taccgcatca ggcgccattc gccattcagg ctgcgcaact gttgggaagg  300
gcgatcggtg cgggcctctt cgctattacg ccagctggcg aaaggggat gtgctgcaag   360
gcgattaagt tgggtaacgc cagggttttc ccagtcacga cgttgtaaaa cgacggccag  420
tgaattggcc tccatggccg cggccgcgct ttgctaaaat tttggttgat ggaaggtatc  480
tggcgataaa ctccgacgac gtctagaagc aacaatctta tgcaaacgct cattggttct  540
tttcgaccgc aacatccatc atgaaactgg tattttgtct gtgtcagcag tctagaaccc  600
cttgccgggt attttagcat ttcatttttc tataaaaagg taccagcatg tatggatcgt  660
atcttccgta ccgtggttat taaatcccag cagaggccga taggcttaag aagtgaacat  720
ggcatggtta aggaagaagc cattactgag tatatatggc tagaataatc gctgggaaag  780
atttatgctt ccaagaggcg taggacggta taccatacag tacggtattt atgaacaatt  840
cgataatacc actccccaaa gcgggagata ggacacccgc ctcaggcacc aaccaccccc  900
tttttcaact gtcagtggtg cacgtttcca tcgagcataa gcttggtacc ctaaggatag  960
gccctaatct tatctcatg tgactgcatc gatgtgttg tcaaaatga ggcatgtgcg    1020
tcacccaca ggcggagaaa cgtgtggcta gtgcatgaca gtcccctcca tagattcaat  1080
ttaattttttc gcggcaattg tcgtgcagtt tgtatctaca tttcattcca tatatcaaga  1140
gttagtagtt ggacatcctg attatttgt ctaattactg aaaactcgaa gtactaacct   1200
actaataagc cagtttcaac cactaagtgc tcatttatac aatatttgca gaacccgacg  1260
ctaccctcc atcgccaaca tgtcttccaa gtcgcaattg acctacgcg cacgcgctag   1320
caagcacccc aatgcgctcg taagaagct cttcgaggtt gccgaggcca agaaaaccaa  1380
tgtcaccgtt tccgccgacg tgacaaccac caaagagctg ctggatttgg ctgaccgtat  1440
gcgcaccggg gttgaagttc ctattccgag ttcctattct tcaaatagta taggaacttc  1500
attagtttaa acgtacgatt ttgacatttg ctccattgtc gaggatggat ggaacgagcg  1560
gcgtgcgcca cgaaagtgag gctattgcct atcagctctt tgctacattc cggaaacaaa  1620
catcccttttt tgtgaattat ctacgcaact tagatgcgt gaacgcatct tcaaagtctt   1680
tcggcaggtc cggcacgact tttgcatcca gagaagcgcc tacatgtgta ttcgaccacc  1740
tcctagcgcg cttggatatg aggaaatatt actgagagtc gaaaacaagc tccaccgcac  1800
cagctcttct tggagtttta tattaaagaa tattcccagc tcgttgtatt attctttttc  1860
taccgtgcta atgtatcaag gactttggta cctattaacg ttattattcg tgtgctattc  1920
ccaaacataa ccctgtatat gtttcgaacg ccgttatgac ccatgtctta catactcatt  1980
aagtcattcc cttggataat ctcgactcag atgcggcggt tgatgtagga ggagaggtaa  2040
tcgaggacct cctgggagat gatgccgttc caggcgggt agcggatgga gccctcggcg   2100
gagcccttga gctgctcgat atgctgccac tcctcgatgg ggttggtctc atccttgagg  2160
gcgatcatct ccttggagat gggatcgtag gcgtagtagc gggagactag tgcgaagtaa  2220
tgatcgggga tggcggtgat ctgatggtgt taggtggtgc gggcgacgg gcgaggcgca  2280
ttatcggacc agttgccgac gacgttggtg agctcggtga ggcccttcat ggagaggaag  2340
gaggtcatga gatggcggcc gatatggac ttggggccgt tcttgatggc gaagatggag   2400
taggggggcgt tcttcttgag gccttgttg taggagcgga cgaggttatc cttgaggagc  2460
tggtactcct gcttgttgga ggaggagttg ccggtgcgct tgacgccgtt ctccagatgt  2520
tcggagttgc ggaggaactc atcgaggtag acgaggggat cgatgcgcc gcgggcgag   2580
aagaagtaga tatggcggga acgaggtc ttggtctcgg tgacgaggca ctggatgatg   2640
acgccgaggt acttgttctg gacgagcttg aaggacttgg gatcgacgtt cttgatatcg  2700
gagaagcggc cgcagttgat gaaggtggcg aggaagagga actggtagag ggtcttggtc  2760
ttggtgaagc gggaggtgta ctcgaaggag ttgaggatct tctcggtgat ctcccagatg  2820
gactcgccct cggagaggag ggccttgagc atcttcttgg aatggagtt gcccttatcg  2880
gcctcctcgg aggactcgaa ctggagctgg agggaggaga cgatatccgg tgatatcggac  2940
tgatgcttct ggccgtagta ggggatgatg gtgaactccc aggcgggat gagcttcttg   3000
agggaggcct ccaggatggt ggcttctgg tcttgtact tgaactggag ggacttgttg    3060
acgatatcga aggagaggga gttgagata atggtgttgt aggacatga ggtgagctc     3120
ttgatggcgc tgccgttatg ggtgatcatc cagcagaggt aggtgagctc ggcggcgcag  3180
agggcgatct tctcgccgga ggggcgctcg aagcgctcga cgaactggcg gacgaggacc  3240
ttgggggggg tcttgcagag gatatcgaac tgggcatgg tgctcagata ctacggctga   3300
tcgcgtagag gtactgagca aaacagatgt cagtaaggag aagagttgaa tgaatggaag  3360
aagagtagga aggaggtat ggggaaaga tatacgtact gatgcggacg aagagagaaa    3420
```

```
gaaggaaaaa agttgtggga ggggaaggag ggggaatcct tatatggagg ggcaagcgag   3480
aaggcgaatt agtgggcggg cttaagccct cgaccgccgc ccttatcatt ggacatggag   3540
gggtaatgcc cccaccacgc atgtgcggga ccgacgcaga atctgcacgg cggagtctct   3600
tccagactgt tgactttggg gcgatgactc ttgttgctgc ggccttttgg gtacaccaac   3660
ctcgttgatc ttgtttcctt ggttctcttt cgctcggaga cccgaccatg accccaccat   3720
cagtcactat cctgcctcgt cgataaaaat ttttcttcc ctctgattgt tacatagtat    3780
gtttccacct ttccggtgga tttcggacag tcaaactggg catcaacgca gtggtgggct   3840
gcttcgtttg ctgcgtgttg tacttgtttg catttgaacc ccgcggtcgt tcgagtcctt   3900
aattggtccg ctcccggtca cacccaagc agctgtggcc cggccgagtg gcgcctgtct    3960
ggtccacagt taattaaagg agagagttga acctggacgc cgcgcaaaaa gcaaagacgc   4020
gcctcgtggg cggtggatca atgatcggat ttagtggcag atggcatcac aggcggccaa   4080
tgaccaccgg gccaactggc cccgacattc cagcaatact gccaattga ctccaccatg    4140
catctcggct attattgaac tgggtttgat ggatggggac cctcttggaa ttgtcaaaga   4200
ttttgaagcg aagacgatct attggacggt agagatatac tcttgattta gtcgttggga   4260
ggccctgggg gaaagcaatg atggggaatg ttgctgctcc actgtggacc tcggctatgg   4320
aattacgtgc ttggatctaa gatgagctca tggctatgca ttgaatgaca gtgatatcag   4380
cagagcaagc agagaaggat ggaatgctaa ttttctagtg ctttgtgcaa gggtaaatca   4440
gggactgtct gtctggtctt ctacacgaag gaaagaccat ggctttcacg gtgtctgtat   4500
ttccggatat cctcaattcc gtcggtcgat tacaatcaca tgacttggct tccatttcac   4560
tactattatg cacacccact acatacatga tcatataacc aattgccctc atccccatcc   4620
tttaactata gcgaaatgga ttgattgtct accgccaggt gtcagtcacc ctctagatct   4680
cgagctcgct agagtcgacc tatggagtca ccacatttcc cagcaacttc cccacttcct   4740
ctgcaatcgc caacgtcctc tcttcactga gtctccgtcc gataacctgc actgcaaccg   4800
gtgccccatg gtacgcctcc ggatcatact cttcctgcac gagggcatca agctcactaa   4860
ccgccttgaa actctcattc ttcttatcga tgttcttatc cgcaaaggta accggaacaa   4920
ccacgctcgt gaaatccagc aaggttgatca cagaggcata cccatagtac cggaactggt   4980
catgccgtac cgcagcggta ggcgtaatcg gcgcgatgat ggcgtccagt tccttcccgg   5040
cctttttcttc agcctcccgc catttctcaa ggtactccat ctggtaattc cacttctgga   5100
gatgcgtgtc ccagagctcg ttcatgttaa cagctttgat gttcgggttc agtaggtctt   5160
tgatatttgg aatcgccggc tcgccggatg cactgatatc gccgcattacg tcggcgctga   5220
cgtcagccgc gtagatatgg gagatgagat cgtggccgaa atcgtgcttg tatgcgtcc    5280
acggggtcac ggtgtgaccg gctttggcga gtgcggcgac ggtggtttcc acgccgcgca   5340
ggataggagg gtgtggaagg acattgccgt cgaagttgta gtagccgata ttgagccccgc  5400
cgttcttgat cttggaggca ataatgtccg actcggactg gcgccagggc agggggataga  5460
ccttggagtc gtatttccat ggctcctgac cgaggacgga tttggtgaag aggcggaggt   5520
ctaacatact tcatcagtga ctgccggtct cgtatatagt ataaaaagca agaaaggagg   5580
acagtggagg cctggtatag agcaggaaaa gaaggaagag gcgaaggact caccctcaac   5640
agagtgcgta atcggcccga caacgctgtg caccgtctcc tgaccctcca tgctgttcgc   5700
catctttgca tacggcagcc gcccatgact cggccttaga ccgtacagga agttgaacgc   5760
ggccggcact cgaatcgagc caccgatatc cgttcctaca ccgatgacgc caccacgaat   5820
cccaacgatc gcaccctcac caccagaact gccgccgcac gaccagttct tgttgcgtgg   5880
gttgacggtg cgcccgatga tgttgttgac tgtctcgcag accatcaggg tctgcgggac   5940
agaggtcttg acgtagaaga cggcaccggc tttgcggagc atggttgtca gaaccgagtc   6000
cccttcgtcg tacttgttta gccatgagat gtagcccatt gatgtttcgt agccctggtg   6060
gcatatgtta gctgacaaaa agggacatct aacgactag gggcaacggt gtaccttgac    6120
tcgaagctgg tctttgagag agatggggag gccatggagt ggaccaacgg gtctcttgtg   6180
ctttgcgtag tattcatcga gttcccttgc ctgcgcgaga ggcgcgtcag ggaagaactc   6240
gtgggcgcag tttgtctgca cagaagccag cgtcagcttg atagtcccat aaggtggcgt   6300
tgttacatct ccctgagagg tagaggggac cctactaact gctgggcgat tgctgcccgt   6360
ttacagaatg ctagcgtaac ttccaccgag gtcaactctc cggccgccag cttggacaca   6420
agatctgcag cggaggcctc tgtgatcttc agttcggcct ctgaaaggat caccgattc    6480
tttgggaaat caataacgct gtcttccgca ggcagcgtct ggactttcca ttcatcaggg   6540
atggttttg cgaggcggc gcgcttatca gcggccagtt cttccaggga ttgaggcatg     6600
tgcatgcaat gtgtgtttat gtggaagtaa gatacgacga gtttgattga gaaaagacag   6660
ggtgattgtc aagttcagta tggaagaaag agtagaagaa gatcagacga cagggaagag   6720
cgatgacata aaaggtggaa gacggaagaa aaacgaacca aatcaatccc actctatgcc   6780
gggggttgga ctgcctgagg ccggcactgg tggggcttat cgataagttc tcgtcaccgg   6840
atgcaatgcg ctgtcaactg ctgacttggc cctgaacatc ctgtcctcta cagatccata   6900
ctatacaatg atcccagtta tagtgcggta aggtgcatat catatctcat tctcatgact   6960
cattcgactt ttttttagag aaagtacata cgtggaacat acactaaacg caacaggtcg   7020
cgacaacact ggtatacaaa acggtccccg gtgaatgacg ttattagtgt ctatccccca   7080
ctcacacccg aaaagaataa tagaaactaa cagaaaaagc ggcccgagga taagaggaac   7140
attcaaacag aaggggaatc ataaaaaccg aaaaatgcaa ggaaaagaga actcaaatca   7200
ataattttca taatactgtc gagagtaata cggaccagcg tctctcaggg acatgcgtcg   7260
gcgcaaggca tcatccaatc tctcatctaa cacatccagc attcgtgttc gatagtctaa   7320
ctgcttctct cggcgctcaa gtcttgcttc ccgatcatcg agttaattaa gaagttccta   7380
tactttctag agaataggaa ctcggaatag gaacttcaag gtaccgagct ctatcctcaa   7440
taccctatt tccacgattc cattgtcata tccaattccg tttctttttc ttgttttccc    7500
ctcatccaat cccgtccatc atttactcct ttttcttgtg aatgcaagtg gcactaagaa   7560
atccaacccc cagacaaatt ttcctactca ggaacacaaa aacctcgttt ctgctcctt    7620
ctcgtacttc attcctatcg tctcggaatt tcctcaacaa ccctttccga ctttgcgaca   7680
gcgtcgcgat tccagactta tgtgttctcg ttcctactgt cgttaccagt ctatttattc   7740
cgaaacctct gatcgctgaa tttcacacac aacacccccc cgttgatgct ggtggagaat   7800
ccgtagcgtc aagagttgaa ttcactccat gttgtaacga agtccacgaa ttgagacgat   7860
tgatgattac aaccccgcga tcgcctatcg acgattcgac gagatgccat tctcatcctc   7920
ctcatcctcc tccaccccg aggtgtctac caccccgctc gcagattact tctggatcgc    7980
aggtgtcgat ggcgcggaaa tcttagagac tttccaaaga ctcggcgacg aatcagggc    8040
aaacagtgcc accgctcctg gccccgctct tgcggacacg atcgaggaag atgcggacgc   8100
ggaggaggca cacgaccccc gtctggactc cctctctcga cccaattcca tggctggggg   8160
```

-continued

```
ccgcaattcc ttccagcggt tctcaatgcg ctcaggagac tccagtgagt ccagtgggaa   8220
tggtaccagc agcaaccgga gcagtctgac catcaagggt aatcagtcgc ccagagggtc   8280
gtcgtttcta gaagatttcg actttgacaa ggccctgttc aagtttgcaa acgagcggga   8340
gtcgttcctg tcggatctga gtctcagtgc cggagcaatc actccacct cccgtcctag    8400
gtccaggtta cgtacacaga agattgtctc cgaggaaagt ccctcccagc catccagctt   8460
gcttcgatca ggcattggta gtgtgcggcg tcatatggca ttcagagaca tgaatagtat   8520
gaaacggcag ccgtcagttg ctcgtcgcgg ccgcagcttg gcgtaatcat ggtcatagct   8580
gtttcctgtg tgaaattgtt atccgctcac aattccacac aacatacgag ccggaagcat   8640
aaagtgtaaa gcctggggtg cctaatgagt gagctaactc acattaattg cgttgcgctc   8700
actgcccgct ttccagtcgg gaaacctgtc gtgccagctg cattaatgaa tcggccaacg   8760
cgcggggaga gcggtttgc gtattgggcg ctcttccgct tcctcgctca ctgactcgct    8820
gcgctcggtc gttcggctgc ggcgagcggt atcagctcac tcaaaggcgg taatacggtt   8880
atccacagaa tcaggggata cgcaggaaa gaacatgtga gcaaaaggcc agcaaaaggc    8940
caggaaccgt aaaaaggccg cgttgctggc gtttttccat aggctccgcc ccctgacga    9000
gcatcacaaa aatcgacgct caagtcagag gtggcgaaac ccgacaggac tataaagata   9060
ccaggcgttt cccctggaa gctccctcgt gcgctctcct gttccgaccc tgccgcttac    9120
cggatacctg tccgcctttt tcccttcggg aagcgtggcg ctttctcata gctcacgctg   9180
taggtatctc agttcggtgt aggtcgttcg ctccaagctg ggctgtgtgc acgaacccc    9240
cgttcagccc gaccgctgcg ccttatccgg taactatcgt cttgagtcca acccggtaag   9300
acacgactta tcgccactgg cagcagccac tggtaacagg attagcagag cgaggtatgt   9360
aggcggtgct acagagttct tgaagtggtg gcctaactac ggctacacta agaacagt     9420
atttggtatc tgcgctctgc tgaagccagt taccttcgga aaaagagttg gtagctcttg   9480
atccggcaaa caaccaccg ctggtagcgg tggttttttt gtttgcaagc agcagattac    9540
gcgcagaaaa aaaggatctc aagaagatcc tttgatcttt tctacggggt ctgacgctca   9600
gtggaacgaa aactcacgtt aagggatttt ggtcatgaga ttatcaaaaa ggatcttcac   9660
ctagatcctt ttaaattaaa aatgaagttt taaatcaatc taaagtatat atgagtaaac   9720
ttggtctgac agttaccaat gcttaatcag tgaggcacct atctcagcga tctgtctatt   9780
tcgttcatcc atagttgcct gactccccgt cgtgtagata actacgatac gggagggctt   9840
accatctggc cccagtgctg caatgatacc gcgagaccca cgctcaccgg ctccagattt   9900
atcagcaata aaccagccag ccggaagggc cgagcgcaga agtggtcctg caactttatc   9960
cgcctccatc cagtctatta ttgttgccg ggaagctaga gtaagtagtt cgccagttaa    10020
tagtttcgc aacgttgttg ccattgctac aggcatcgtg gtgtcacgct cgtcgtttgg    10080
tatggcttca ttcagctccg gttcccaacg atcaaggcga gttacatgat ccccccatgtt 10140
gtgcaaaaaa gcggttagct ccttcggtcc tccgatcgtt gtcagaagta agttggccgc   10200
agtgttatca ctcatggtta tggcagcact gcataattct cttactgtca tgccatccgt   10260
aagatgcttt tctgtgactg gtgagtactc aaccaagtca ttctgagaat agtgtatgcg   10320
gcgaccgagt tgctcttgcc cggcgtcaat acgggataat accgcgccac atagcagaac   10380
tttaaaagtg ctcatcattg gaaaacgttc ttcggggcga aaactctcaa ggatcttacc   10440
gctgttgaga tccagttcga tgtaacccac tcgtgcaccc aactgatctt cagcatcttt   10500
tactttcacc agcgtttctg ggtgagcaaa aacaggaagg caaaatgccg caaaaaaggg   10560
aataagggcg acacggaaat gttgaatact catactcttc cttttcaat attattgaag    10620
catttatcag ggttattgtc tcatgagcgg atacatattt gaatgtattt agaaaaataa   10680
acaaataggg gttccgcgca catttccccg aaaagtgcca cctgacgtct aagaaaccat   10740
tattatcatg acattaacct ataaaaa                                       10767

SEQ ID NO: 321            moltype = DNA  length = 45
FEATURE                   Location/Qualifiers
source                    1..45
                          mol_type = other DNA
                          organism = Synthetic construct
SEQUENCE: 321
ctatatacac aactggggat ccaccatgca gctctccctc ctcgt                              45

SEQ ID NO: 322            moltype = DNA  length = 46
FEATURE                   Location/Qualifiers
source                    1..46
                          mol_type = other DNA
                          organism = Synthetic construct
SEQUENCE: 322
tagagtcgac ccagccgcgc cggccattac aacccaccag cctggc                             46

SEQ ID NO: 323            moltype = DNA  length = 27
FEATURE                   Location/Qualifiers
source                    1..27
                          mol_type = other DNA
                          organism = Synthetic construct
SEQUENCE: 323
gaattcgagc tcggtacctt gaagttc                                                  27

SEQ ID NO: 324            moltype = DNA  length = 31
FEATURE                   Location/Qualifiers
source                    1..31
                          mol_type = other DNA
                          organism = Synthetic construct
SEQUENCE: 324
ggtggatccc cagttgtgta tatagaggat t                                             31

SEQ ID NO: 325            moltype = DNA  length = 26
FEATURE                   Location/Qualifiers
```

```
source                   1..26
                         mol_type = other DNA
                         organism = Synthetic construct
SEQUENCE: 325
tgcgcggcgc ggctgggtcg actcta                                        26

SEQ ID NO: 326           moltype = DNA  length = 27
FEATURE                  Location/Qualifiers
source                   1..27
                         mol_type = other DNA
                         organism = Synthetic construct
SEQUENCE: 326
ttcacacagg aaacagctat gaccatg                                       27

SEQ ID NO: 327           moltype = DNA  length = 25
FEATURE                  Location/Qualifiers
source                   1..25
                         mol_type = other DNA
                         organism = Synthetic construct
SEQUENCE: 327
ctatatacac aactggggat ccacc                                         25

SEQ ID NO: 328           moltype = DNA  length = 26
FEATURE                  Location/Qualifiers
source                   1..26
                         mol_type = other DNA
                         organism = Synthetic construct
SEQUENCE: 328
tagagtcgac ccagccgcgc cggcca                                        26

SEQ ID NO: 329           moltype = AA  length = 146
FEATURE                  Location/Qualifiers
source                   1..146
                         mol_type = protein
                         organism = Ovatospora brasiliensis
SEQUENCE: 329
GGKGNLPGLN AKQSSHARAI VAQAKKDGVG LHGCEAGIAT ALVESGIKVY ANKKVPASLK    60
YPHDAVGSDH DSIGIFQQRA VYYPNIAADM DPARSAHQFF AKMKGVSGWK TMAVGKLCQK   120
VQVSAYPDRY AKRVSEATKI CKAAGI                                       146
```

POLYPEPTIDES HAVING LYZOZYME ACTIVITY, POLUNUCLEOTIDES ENCODING SAME AND USES AND COMPOSITIONS THEREOF

CROSS-REFERENCE TO RELATED APPLICATIONS

This application is a divisional of U.S. patent application Ser. No. 16/607,404, filed on Oct. 23, 2019, which is a 35 U.S.C. 371 national stage entry of International Application No. PCT/CN2018/086528, filed May 11, 2018, which claims priority to International Patent Application No. PCT/CN2017/084074, filed May 12, 2017. The contents of each of the aforementioned applications is fully incorporated herein by reference.

REFERENCE TO SEQUENCE LISTING

This application contains a Sequence Listing in computer readable form, which is incorporated herein by reference. The name of the file containing the Sequence Listing is SQ.XML, which contains 356,451 bytes and which was created on Nov. 10, 2023.

BACKGROUND

The present invention relates to novel LYS polypeptides having lysozyme activity, polynucleotides encoding the polypeptides, nucleic acid constructs, vectors, and host cells comprising the polynucleotides as well as methods of producing the polypeptides. The present invention also relates to compositions, specifically animal feed, comprising LYS polypeptides and the use of the LYS polypeptide in animal feed.

Lysozyme is an O-glycosyl hydrolase produced as a defensive mechanism against bacteria by many organisms. The enzyme causes the hydrolysis of bacterial cell walls by cleaving the glycosidic bonds of peptidoglycan; an important structural molecule in bacteria. After having their cell walls weakened by lysozyme action, bacterial cells lyse as a result of unbalanced osmotic pressure.

Lysozyme naturally occurs in many organisms such as viruses, plants, insects, birds, reptiles and mammals. In mammals, Lysozyme has been isolated from nasal secretions, saliva, tears, intestinal content, urine and milk. The enzyme cleaves the glycosidic bond between carbon number 1 of N-acetylmuramic acid and carbon number 4 of N-acetyl-D-glucosamine. In vivo, these two carbohydrates are polymerized to form the cell wall polysaccharide of many microorganisms.

Lysozyme has until now been classified into seven different glycoside hydrolase (GH) families (CAZy, www.cazy.org): GH18, GH19, hen egg-white lysozyme (GH22), goose egg-white lysozyme (GH23), bacteriophage T4 lysozyme (GH24), *Sphingomonas* flagellar protein (GH73) and *Chalaropsis* lysozymes (GH25).

Lysozyme extracted from hen egg white is the primary product available on the commercial market, but does not cleave N,6-O-diacetylmuramic acid in e.g. *Staphylococcus aureus* cell walls and is thus unable to lyse this important human pathogen among others (Masschalck B, Deckers D, Michiels CW (2002), "Lytic and nonlytic mechanism of inactivation of gram-positive bacteria by lysozyme under atmospheric and high hydrostatic pressure", *J Food Prot.* 65(12):1916-23).

Use of lysozyme has been suggested in animal feed (see for example WO 00/21381 and WO 04/026334), in cheese production (see for example WO 05/080559), food preservation (Hughey and Johnson (1987) *Appl Environ Microbiol* 53:2165), detergents (see for example U.S. Pat. No. 5,041, 236 and EP 0425016), in oral care (see for example U.S. Pat. No. 4,355,022, WO 04/017988 and WO 08/124764), cosmetology and dermatology, contraception, urology, and gynaecology (see for example WO 08/124764).

Antimicrobial growth promoters (AGP's) have traditionally been used for growth promotion in animals, and probably work by preventing low level infections by pathogens such as *Clostridium perfringens*. However, AGP's are increasingly being banned worldwide and therefore new solutions to promote animal growth but which are not AGP's are of interest.

SUMMARY

The inventors have discovered a completely novel class of polypeptides having lysozyme activity. As such, the invention relates to a composition comprising at least 0.01 mg of LYS polypeptide per kilogram of composition, wherein the polypeptide (a) has lysozyme activity and (b) comprises one or more LAD catalytic domains; wherein the LAD catalytic domain gives a domT score of at least 180 when queried using a Profile Hidden Markov Model (HMM) prepared using SEQ ID NOs: 46 to 187 and hmmbuild software program. Typically, the query is carried out using hmmscan software program by the Method of Determining the LAD Catalytic Domain by HMM.

The invention further relates to an isolated polypeptide having lysozyme activity, selected from the group consisting of:
  (a) a polypeptide having at least 95% sequence identity to the polypeptide of SEQ ID NO: 3;
  (b) a polypeptide having at least 94% sequence identity to the polypeptide of SEQ ID NO: 6;
  (c) a polypeptide having at least 80% sequence identity to the polypeptide of SEQ ID NO: 9;
  (d) a polypeptide having at least 80% sequence identity to the polypeptide of SEQ ID NO: 12;
  (e) a polypeptide having at least 87% sequence identity to the polypeptide of SEQ ID NO: 15;
  (f) a polypeptide having at least 81% sequence identity to the polypeptide of SEQ ID NO: 18;
  (g) a polypeptide having at least 80% sequence identity to the polypeptide of SEQ ID NO: 21;
  (h) a polypeptide having at least 80% sequence identity to the polypeptide of SEQ ID NO: 24;
  (i) a polypeptide having at least 87% sequence identity to the polypeptide of SEQ ID NO: 27;
  (j) a polypeptide having at least 96.2% sequence identity to the polypeptide of SEQ ID NO: 30;
  (k) a polypeptide having at least 80% sequence identity to the polypeptide of SEQ ID NO: 33;
  (l) a polypeptide having at least 80% sequence identity to the polypeptide of SEQ ID NO: 36;
  (m) a polypeptide having at least 81% sequence identity to the polypeptide of SEQ ID NO: 39;
  (n) a polypeptide having at least 80% sequence identity to the polypeptide of SEQ ID NO: 42;
  (o) a variant of the polypeptide of SEQ ID NO: 3, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10 or 11 positions;

(p) a variant of the polypeptide of SEQ ID NO: 6, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12 or 13 positions;

(q) a variant of the polypeptide selected from the group consisting of SEQ ID NO: 9 and SEQ ID NO: 36, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 or 44 positions;

(r) a variant of the polypeptide selected from the group consisting of SEQ ID NO: 12, SEQ ID NO: 21, SEQ ID NO: 24, SEQ ID NO: 33 and SEQ ID NO: 42, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;

(s) a variant of the polypeptide selected from the group consisting of SEQ ID NO: 15 and SEQ ID NO: 27, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions;

(t) a variant of the polypeptide selected from the group consisting of SEQ ID NO: 18 and SEQ ID NO: 39, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 or 42 positions;

(u) a variant of the polypeptide of SEQ ID NO: 30, wherein the variant has lysozyme activity and comprises one or more amino acid substitutions, and/or one or more amino acid deletions, and/or one or more amino acid insertions or any combination thereof in 1, 2, 3, 4, 5, 6, 7 or 8 positions;

(v) a polypeptide comprising the polypeptide of (a), (b), (c), (d), (e), (f), (g), (h), (i), (j), (k), (l), (m), (n), (o), (p), (q), (r), (s), (t) or (u) and a N-terminal and/or C-terminal His-tag and/or HQ-tag;

(w) a polypeptide comprising the polypeptide of (a), (b), (c), (d), (e), (f), (g), (h), (i), (j), (k), (l), (m), (n), (o), (p), (q), (r), (s), (t) or (u) and a N-terminal and/or C-terminal extension of up to 10 amino acids, e.g. 1, 2, 3, 4, 5, 6, 7, 8, 9 or 10 amino acids; and (x) a fragment of the polypeptide of (a), (b), (c), (d), (e), (f), (g), (h), (i), (j), (k), (l), (m), (n), (o), (p), (q), (r), (s), (t) or (u) having lysozyme activity and having at least 90% of the length of the mature polypeptide.

The invention also relates to animal feed additives or animal feed comprising the LYS polypeptide of the invention; use of the lysozyme of the LYS polypeptide in animal feed, in animal feed additives, in the preparation of a composition for use in animal feed, and for improving one or more performance parameters in an animal. The invention further relates to methods of improving performance parameters of an animal and for preparing an animal feed; isolated polynucleotides encoding the polypeptides of the invention, nucleic acid constructs, recombinant expression vectors, recombinant host cells and method of producing the LYS polypeptide of the invention. The invention is further directed to the use of composition of the invention in animal feed; in animal feed additives; in the preparation of a composition for use in animal feed; for improving the nutritional value of an animal feed; for increasing digestibility of the animal feed; and/or for improving one or more performance parameters in an animal.

Figure 1:
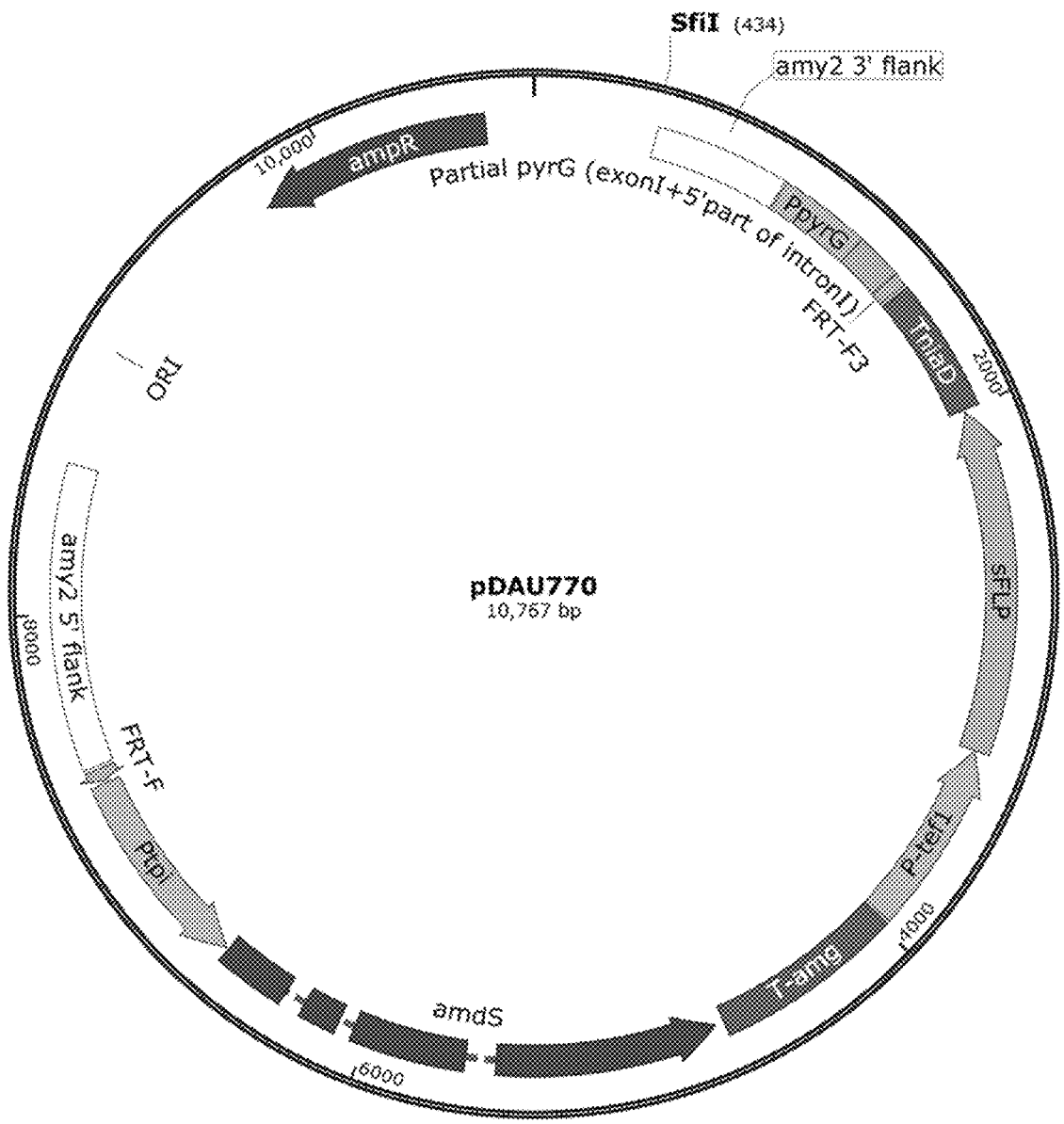
FIG. 1 represents the map of the different DNA features included on the plasmid pDAu770. The amy2 locus flanking regions (3' and 5') are indicated by white boxes. Promoter regions are indicated by green boxes for the promoter region of the pyrG, tefl and tpi gene. The purple boxes indicate the selection cassette (ampR for ampicillin resistance and amdS for acetamide selection). The terminator regions are indicated by blue boxes for the terminator region of the niaD and amg genes. The coding region of the FLPase (sFLP) and the first exon of the pyrG gene are indicated in orange. The 5' region of the pyrG intron is indicated in grey. The origin of replication of the plasmid is indicated by ORI.

Top panel represents the locus amy2 with the integration of the FLP landing pad composed of FRT-F and FRT-F3 the FLPase recognition site, as well as the amdS (acetamide) selection marker and the FLPase expression cassette. A split PyrG marker has been used and at the amy2 locus the 5' end of the pyrG marker is inserted.

Middle panel represents the transforming DNA, in particular the region that is integrated at the FLP landing pad by site specific recombination mediated by FLPase. The palsmid or PCR product must contain FRT-F and F3 sites as well as the remaining 3' part of the pyrG marker.

Bottom panel represents the resulting amy2 locus after site specific integration of the transforming DNA between the FRT sites. The amdS and FLP cassettes have been exchanged with the GOI expression cassette and the 3' part of the pyrG marker reconstituting a fully functional selection marker.

BRIEF DESCRIPTION OF THE SEQUENCE LISTING

SEQ ID NO: 1 is the cDNA sequence of a LYS polypeptide as isolated from *Penicillium simplicissimum*.

SEQ ID NO: 2 is the amino acid sequence as deduced from SEQ ID NO: 1.

SEQ ID NO: 3 is the amino acid sequence of the mature LYS polypeptide from *Penicillium simplicissimum*.

SEQ ID NO: 4 is the cDNA sequence of a LYS polypeptide as isolated from *Penicillium vasconiae*.

SEQ ID NO: 5 is the amino acid sequence as deduced from SEQ ID NO: 4.

SEQ ID NO: 6 is the amino acid sequence of the mature LYS polypeptide from *Penicillium vasconiae*.

SEQ ID NO: 7 is the cDNA sequence of a LYS polypeptide as isolated from *Talaromyces proteolyticus*.

SEQ ID NO: 8 is the amino acid sequence as deduced from SEQ ID NO: 7.

SEQ ID NO: 9 is the amino acid sequence of the mature LYS polypeptide from *Talaromyces proteolyticus*.

SEQ ID NO: 10 is the cDNA sequence of a LYS polypeptide as isolated from *Aspergillus* sp. XZ2668.

SEQ ID NO: 11 is the amino acid sequence as deduced from SEQ ID NO: 10.

SEQ ID NO: 12 is the amino acid sequence of the mature LYS polypeptide from *Aspergillus* sp. XZ2668.

SEQ ID NO: 13 is the cDNA sequence of a LYS polypeptide as isolated from *Penicillium antarcticum*.

SEQ ID NO: 14 is the amino acid sequence as deduced from SEQ ID NO: 13.

SEQ ID NO: 15 is the amino acid sequence of the mature LYS polypeptide from *Penicillium antarcticum*.

SEQ ID NO: 16 is the cDNA sequence of a LYS polypeptide as isolated from *Ovatospora brasiliensis*.

SEQ ID NO: 17 is the amino acid sequence as deduced from SEQ ID NO: 16.

SEQ ID NO: 18 is the amino acid sequence of the mature LYS polypeptide from *Ovatospora brasiliensis*.

SEQ ID NO: 19 is the cDNA sequence of a LYS polypeptide as isolated from *Penicillium wellingtonense*.

SEQ ID NO: 20 is the amino acid sequence as deduced from SEQ ID NO: 19.

SEQ ID NO: 21 is the amino acid sequence of the mature LYS polypeptide from *Penicillium wellingtonense*.

SEQ ID NO: 22 is the cDNA sequence of a LYS polypeptide as isolated from *Penicillium roseopurpureum*.

SEQ ID NO: 23 is the amino acid sequence as deduced from SEQ ID NO: 22.

SEQ ID NO: 24 is the amino acid sequence of the mature LYS polypeptide from *Penicillium roseopurpureum*.

SEQ ID NO: 25 is the cDNA sequence of a LYS polypeptide as isolated from *Penicillium virgatum*.

SEQ ID NO: 26 is the amino acid sequence as deduced from SEQ ID NO: 25.

SEQ ID NO: 27 is the amino acid sequence of the mature LYS polypeptide from *Penicillium virgatum*.

SEQ ID NO: 28 is the cDNA sequence of a LYS polypeptide as isolated from *Aspergillus niveus*.

SEQ ID NO: 29 is the amino acid sequence as deduced from SEQ ID NO: 28.

SEQ ID NO: 30 is the amino acid sequence of the mature LYS polypeptide from *Aspergillus niveus*.

SEQ ID NO: 31 is the cDNA sequence of a LYS polypeptide as isolated from *Chaetomium* sp. ZY369.

SEQ ID NO: 32 is the amino acid sequence as deduced from SEQ ID NO: 31.

SEQ ID NO: 33 is the amino acid sequence of the mature LYS polypeptide from *Chaetomium* sp. ZY369.

SEQ ID NO: 34 is the cDNA sequence of a LYS polypeptide as isolated from *Talaromyces atricola*.

SEQ ID NO: 35 is the amino acid sequence as deduced from SEQ ID NO: 34.

SEQ ID NO: 36 is the amino acid sequence of the mature LYS polypeptide from *Talaromyces atricola*.

SEQ ID NO: 37 is the cDNA sequence of a LYS polypeptide as isolated from *Trichocladium asperum*.

SEQ ID NO: 38 is the amino acid sequence as deduced from SEQ ID NO: 37.

SEQ ID NO: 39 is the amino acid sequence of the mature LYS polypeptide from *Trichocladium asperum*.

SEQ ID NO: 40 is the cDNA sequence of a LYS polypeptide as isolated from *Metarhizium carneum*.

SEQ ID NO: 41 is the amino acid sequence as deduced from SEQ ID NO: 40.

SEQ ID NO: 42 is the amino acid sequence of the mature LYS polypeptide from *Metarhizium carneum*.

SEQ ID NO: 43 is the cDNA sequence of a LYS polypeptide as isolated from *Thielavia terrestris*.

SEQ ID NO: 44 is the amino acid sequence as deduced from SEQ ID NO: 43.

SEQ ID NO: 45 is the amino acid sequence of the mature LYS polypeptide from *Thielavia terrestris*.

SEQ ID NO: 46 is the amino acid sequence of the LAD domain of SWISSPROT:A1C4L9 from *Aspergillus clavatus*.

SEQ ID NO: 47 is the amino acid sequence of the LAD domain of SWISSPROT:A4X6S9 from *Salinispora tropica*.

SEQ ID NO: 48 is the amino acid sequence of the LAD domain of SWISSPROT:A8M1H3 from *Salinispora arenicola*.

SEQ ID NO: 49 is the amino acid sequence of the LAD domain of SWISSPROT:Q3L9Z6 from *Rhodococcus erythropolis*.

SEQ ID NO: 50 is the amino acid sequence of the LAD domain of SWISSPROT:B5U576 from *Mycobacterium* phage Pacc40.

SEQ ID NO: 51 is the amino acid sequence of the LAD domain of SWISSPROT:B6GZX8 from *Penicillium rubens*.

SEQ ID NO: 52 is the amino acid sequence of the LAD domain of SWISSPROT:D1S6X5 from *Micromonospora aurantiaca*.

SEQ ID NO: 53 is the amino acid sequence of the LAD domain of SWISSPROT:D1S8J3 from *Micromonospora aurantiaca*.

SEQ ID NO: 54 is the amino acid sequence of the LAD domain of SWISSPROT:D1SH66 from *Micromonospora aurantiaca*.

SEQ ID NO: 55 is the amino acid sequence of the LAD domain of SWISSPROT:D5GBH0 from *Tuber melanosporum*.

SEQ ID NO: 56 is the amino acid sequence of the LAD domain of SWISSPROT:G9P583 from *Hypocrea atroviridis*.

SEQ ID NO: 57 is the amino acid sequence of the LAD domain of SWISSPROT:E9ED38 from *Metarhizium acridum*.

SEQ ID NO: 58 is the amino acid sequence of the LAD domain of SWISSPROT:E9FAK9 from *Metarhizium robertsii*.

SEQ ID NO: 59 is the amino acid sequence of the LAD domain of SWISSPROT:F4F8N8 from *Verrucosispora maris*.

SEQ ID NO: 60 is the amino acid sequence of the LAD domain of SWISSPROT:F4FI59 from *Verrucosispora maris*.

SEQ ID NO: 61 is the amino acid sequence of the LAD domain of SWISSPROT:J4USU4 from *Beauveria bassiana*.

SEQ ID NO: 62 is the amino acid sequence of the LAD domain of SWISSPROT:G2QV10 from *Thielavia terrestris*.

SEQ ID NO: 63 is the amino acid sequence of the LAD domain of SWISSPROT:A0A1C6W4S6 from *Micromonospora peucetia*.

SEQ ID NO: 64 is the amino acid sequence of the LAD domain of SWISSPROT:H8E7T0 from *Microbacterium laevaniformans*.

SEQ ID NO: 65 is the amino acid sequence of the LAD domain of SWISSPROT:I0PF45 from *Mycobacterium abscessus*.

SEQ ID NO: 66 is the amino acid sequence of the LAD domain of SWISSPROT:I0L0M9 from *Micromonospora lupini str Lupac*.

SEQ ID NO: 67 is the amino acid sequence of the LAD domain of SWISSPROT:I0L3A4 from *Micromonospora lupini str Lupac*.

SEQ ID NO: 68 is the amino acid sequence of the LAD domain of SWISSPROT:A0A0B2X541 from *Metarhizium album*.

SEQ ID NO: 69 is the amino acid sequence of the LAD domain of SWISSPROT:A0A168BML7 from *Aschersonia aleyrodis*.

SEQ ID NO: 70 is the amino acid sequence of the LAD domain of SWISSPROT:A0A0B2WV75 from *Metarhizium album*.

SEQ ID NO: 71 is the amino acid sequence of the LAD domain of SWISSPROT:A0A167BWW4 from *Cordyceps brongniartii*.

SEQ ID NO: 72 is the amino acid sequence of the LAD domain of SWISSPROT:A0A167ECQ5 from *Metarhizium rileyi*.

SEQ ID NO: 73 is the amino acid sequence of the LAD domain of SWISSPROT:A0A162JZ16 from *Cordyceps confragosa*.

SEQ ID NO: 74 is the amino acid sequence of the LAD domain of SWISSPROT:A0A168DNP6 from *Cordyceps confragosa*.

SEQ ID NO: 75 is the amino acid sequence of the LAD domain of SWISSPROT:A0A168DOL5 from *Cordyceps confragosa*.

SEQ ID NO: 76 is the amino acid sequence of the LAD domain of SWISSPROT:A0A168BQC6 from *Isaria fumosorosea*.

SEQ ID NO: 77 is the amino acid sequence of the LAD domain of SWISSPROT:A0A167XCS5 from *Isaria fumosorosea*.

SEQ ID NO: 78 is the amino acid sequence of the LAD domain of SWISSPROT:A0A167NNI6 from *Isaria fumosorosea*.

SEQ ID NO: 79 is the amino acid sequence of the LAD domain of SWISSPROT:A0A179H6H8 from *Purpureocillium lilacinum*.

SEQ ID NO: 80 is the amino acid sequence of the LAD domain of SWISSPROT:A0A179FH10 from *Pochonia chlamydosporia*.

SEQ ID NO: 81 is the amino acid sequence of the LAD domain of SWISSPROT:A0A179F665 from *Pochonia chlamydosporia*.

SEQ ID NO: 82 is the amino acid sequence of the LAD domain of SWISSPROT:A0A179F1Q1 from *Pochonia chlamydosporia*.

SEQ ID NO: 83 is the amino acid sequence of the LAD domain of SWISSPROT:S7ZNE7 from *Penicillium oxalicum*.

SEQ ID NO: 84 is the amino acid sequence of the LAD domain of SWISSPROT:A0A0D9PBV5 from *Metarhizium anisopliae*.

SEQ ID NO: 85 is the amino acid sequence of the LAD domain of SWISSPROT:A0A0D9NPP1 from *Metarhizium anisopliae*.

SEQ ID NO: 86 is the amino acid sequence of the LAD domain of SWISSPROT:W6QNL2 from *Penicillium roqueforti*.

SEQ ID NO: 87 is the amino acid sequence of the LAD domain of SWISSPROT:A0A0U1M0W5 from *Talaromyces islandicus*.

SEQ ID NO: 88 is the amino acid sequence of the LAD domain of SWISSPROT:A0A0A2I9P6 from *Penicillium expansum*.

SEQ ID NO: 89 is the amino acid sequence of the LAD domain of SWISSPROT:A0A086T4C8 from *Acremonium chrysogenum*.

SEQ ID NO: 90 is the amino acid sequence of the LAD domain of SWISSPROT:X8ERY9 from *Mycobacterium chelonae*.

SEQ ID NO: 91 is the amino acid sequence of the LAD domain of SWISSPROT:A0A081HTU5 from *Mycobacterium* sp TKK.

SEQ ID NO: 92 is the amino acid sequence of the LAD domain of SWISSPROT:A0A0A1TMJ0 from *Torrubiella hemipterigena*.

SEQ ID NO: 93 is the amino acid sequence of the LAD domain of SWISSPROT:A0A0A1TNZ8 from *Torrubiella hemipterigena*.

SEQ ID NO: 94 is the amino acid sequence of the LAD domain of SWISSPROT:A0A0A1D149 from *Arthrobacter* sp PAMC.

SEQ ID NO: 95 is the amino acid sequence of the LAD domain of SWISSPROT:A0A0A6UNI9 from *Actinoplanes utahensis*.

SEQ ID NO: 96 is the amino acid sequence of the LAD domain of SWISSPROT:A0A0B4I0X1 from *Metarhizium majus*.

SEQ ID NO: 97 is the amino acid sequence of the LAD domain of SWISSPROT:A0A0D0WU99 from *Micromonospora carbonacea*.

SEQ ID NO: 98 is the amino acid sequence of the LAD domain of SWISSPROT:A0A0D1LTE6 from *Mycobacterium immunogenum*.

SEQ ID NO: 99 is the amino acid sequence of the LAD domain of SWISSPROT:A0A0F8A5E8 from *Hirsutella minnesotensis*.

SEQ ID NO: 100 is the amino acid sequence of the LAD domain of SWISSPROT:A0A0F8A6I7 from *Hirsutella minnesotensis*.

SEQ ID NO: 101 is the amino acid sequence of the LAD domain of SWISSPROT:A0A0F7TVL0 from *Penicillium brasilianum*.

SEQ ID NO: 102 is the amino acid sequence of the LAD domain of SWISSPROT:A0A0L0N1U6 from *Tolypocladium ophioglossoides*.

SEQ ID NO: 103 is the amino acid sequence of the LAD domain of SWISSPROT:A0A0M0UGY1 from *Madurella mycetomatis*.

SEQ ID NO: 104 is the amino acid sequence of the LAD domain of SWISSPROT:A0A0K8L1J1 from *Aspergillus udagawae*.

SEQ ID NO: 105 is the amino acid sequence of the LAD domain of SWISSPROT:A0A0H5NX60 from *Nocardia farcinica*.

SEQ ID NO: 106 is the amino acid sequence of the LAD domain of SWISSPROT:A0A0M2RBW0 from *Micromonospora* sp HK10.

SEQ ID NO: 107 is the amino acid sequence of the LAD domain of SWISSPROT:A0A0M2RKI6 from *Micromonospora* sp HK10.

SEQ ID NO: 108 is the amino acid sequence of the LAD domain of SWISSPROT:A0A1F5LVD8 from *Penicillium murcianum*.

SEQ ID NO: 109 is the amino acid sequence of the LAD domain of SWISSPROT:A0A0M8XNG9 from *Micromonospora* sp.

SEQ ID NO: 110 is the amino acid sequence of the LAD domain of SWISSPROT:A0A0W7W0M4 from *Trichoderma gamsii*.

SEQ ID NO: 111 is the amino acid sequence of the LAD domain of SWISSPROT:A0A0Q9MHJ4 from *Arthrobacter* sp Soil761.

SEQ ID NO: 112 is the amino acid sequence of the LAD domain of SWISSPROT:A0A0Q9MU26 from *Arthrobacter* sp Soil736.

SEQ ID NO: 113 is the amino acid sequence of the LAD domain of SWISSPROT:A0A0P0DUT5 from *Microbacterium* sp No 7.

SEQ ID NO: 114 is the amino acid sequence of the LAD domain of SWISSPROT:A0A0Q9N9Z1 from *Arthrobacter* sp Soil762.

SEQ ID NO: 115 is the amino acid sequence of the LAD domain of SWISSPROT:A0A1C6RVB7 from *Micromonospora halophytica*.

SEQ ID NO: 116 is the amino acid sequence of the LAD domain of SWISSPROT:A0A1C6SUA9 from *Micromonospora nigra*.

SEQ ID NO: 117 is the amino acid sequence of the LAD domain of SWISSPROT:A0A135LMU8 from *Penicillium patulum*.

SEQ ID NO: 118 is the amino acid sequence of the LAD domain of SWISSPROT:A0A0S9BYR1 from *Arthrobacter* sp Leaf69.

SEQ ID NO: 119 is the amino acid sequence of the LAD domain of SWISSPROT:A0A0U0ZSQ6 from *Mycobacterium abscessus*.

SEQ ID NO: 120 is the amino acid sequence of the LAD domain of SWISSPROT:A0A100WIQ1 from *Mycobacterium canariasense*.

SEQ ID NO: 121 is the amino acid sequence of the LAD domain of SWISSPROT:A0A109IP50 from *Micromonospora rifamycinica*.

SEQ ID NO: 122 is the amino acid sequence of the LAD domain of SWISSPROT:A0A109IHN3 from *Micromonospora rifamycinica*.

SEQ ID NO: 123 is the amino acid sequence of the LAD domain of SWISSPROT:A0A0S2M353 from *Arthrobacter alpinus*.

SEQ ID NO: 124 is the amino acid sequence of the LAD domain of SWISSPROT:A0A134DEL4 from *Microbacterium hominis*.

SEQ ID NO: 125 is the amino acid sequence of the LAD domain of SWISSPROT:A0A142KAG2 from *Gordonia* phage Obliviate.

SEQ ID NO: 126 is the amino acid sequence of the LAD domain of SWISSPROT:A0A136PN50 from *Micromonospora rosaria*.

SEQ ID NO: 127 is the amino acid sequence of the LAD domain of SWISSPROT:A0A138A7X6 from *Tsukamurella pseudospumae*.

SEQ ID NO: 128 is the amino acid sequence of the LAD domain of SWISSPROT:A0A136PTZ6 from *Micromonospora rosaria*.

SEQ ID NO: 129 is the amino acid sequence of the LAD domain of SWISSPROT:A0A177U5Z0 from *Tilletia walkeri*.

SEQ ID NO: 130 is the amino acid sequence of the LAD domain of SWISSPROT:A0A177VGU0 from *Tilletia controversa*.

SEQ ID NO: 131 is the amino acid sequence of the LAD domain of SWISSPROT:A0A179G202 from *Pochonia chlamydosporia* 170.

SEQ ID NO: 132 is the amino acid sequence of the LAD domain of SWISSPROT:A0A179G1N9 from *Pochonia chlamydosporia* 170.

SEQ ID NO: 133 is the amino acid sequence of the LAD domain of SWISSPROT:A0A179FEB3 from *Pochonia chlamydosporia* 170.

SEQ ID NO: 134 is the amino acid sequence of the LAD domain of SWISSPROT:A0A179HTK7 from *Purpureocillium lilacinum*.

SEQ ID NO: 135 is the amino acid sequence of the LAD domain of SWISSPROT:A0A177C655 from *Paraphaeosphaeria sporulosa*.

SEQ ID NO: 136 is the amino acid sequence of the LAD domain of SWISSPROT:A0A167GE76 from *Cordyceps brongniartii* RCEF 3172.

SEQ ID NO: 137 is the amino acid sequence of the LAD domain of SWISSPROT:A0A160DID3 from *Gordonia* phage Utz.

SEQ ID NO: 138 is the amino acid sequence of the LAD domain of SWISSPROT:A0A175J866 from *Arthrobacter nicotinovorans*.

SEQ ID NO: 139 is the amino acid sequence of the LAD domain of SWISSPROT:A0A1A1X5E5 from *Mycobacterium conceptionense*.

SEQ ID NO: 140 is the amino acid sequence of the LAD domain of SWISSPROT:A0A1A8ZCI7 from *Micromonospora narathiwatensis*.

SEQ ID NO: 141 is the amino acid sequence of the LAD domain of SWISSPROT:A0A1A8Z6H4 from *Micromonospora narathiwatensis*.

SEQ ID NO: 142 is the amino acid sequence of the LAD domain of SWISSPROT:A0A1A8Z6S5 from *Micromonospora auratinigra*.

SEQ ID NO: 143 is the amino acid sequence of the LAD domain of SWISSPROT:A0A1A2MHG1 from *Mycobacterium* sp E1747.

SEQ ID NO: 144 is the amino acid sequence of the LAD domain of SWISSPROT:A0A1A9BD29 from *Micromonospora sediminicola*.

SEQ ID NO: 145 is the amino acid sequence of the LAD domain of SWISSPROT:A0A196L8B1 from *Microbacterium* sp H83.

SEQ ID NO: 146 is the amino acid sequence of the LAD domain of SWISSPROT:A0A1C4X8A3 from *Micromonospora coriariae*.

SEQ ID NO: 147 is the amino acid sequence of the LAD domain of SWISSPROT:A0A1C6U2J5 from *Micromonospora citrea*.

SEQ ID NO: 148 is the amino acid sequence of the LAD domain of SWISSPROT:A0A1C6V2H5 from *Micromonospora peucetia*.

SEQ ID NO: 149 is the amino acid sequence of the LAD domain of SWISSPROT:A0A1C6VFJ6 from *Micromonospora yangpuensis*.

SEQ ID NO: 150 is the amino acid sequence of the LAD domain of SWISSPROT:A0A1C6S481 from *Micromonospora rhizosphaerae*.

SEQ ID NO: 151 is the amino acid sequence of the LAD domain of SWISSPROT:A0A1C5K5N0 from *Micromonospora echinaurantiaca*.

SEQ ID NO: 152 is the amino acid sequence of the LAD domain of SWISSPROT:A0A1C5K0N2 from *Micromonospora inositola*.

SEQ ID NO: 153 is the amino acid sequence of the LAD domain of SWISSPROT:A0A1C5JUR0 from *Micromonospora inositola*.

SEQ ID NO: 154 is the amino acid sequence of the LAD domain of SWISSPROT:A0A1C5JX99 from *Micromonospora coxensis*.

SEQ ID NO: 155 is the amino acid sequence of the LAD domain of SWISSPROT:A0A1C4ZAM5 from *Micromonospora mirobrigensis*.

SEQ ID NO: 156 is the amino acid sequence of the LAD domain of SWISSPROT:A0A1C4Z5B4 from *Micromonospora viridifaciens*.

SEQ ID NO: 157 is the amino acid sequence of the LAD domain of SWISSPROT:A0A1C4YQ99 from *Micromonospora haikouensis*.

SEQ ID NO: 158 is the amino acid sequence of the LAD domain of SWISSPROT:A0A1C6W5T7 from *Micromonospora peucetia*.

SEQ ID NO: 159 is the amino acid sequence of the LAD domain of SWISSPROT:A0A1C6W1B9 from *Micromonospora citrea*.

SEQ ID NO: 160 is the amino acid sequence of the LAD domain of SWISSPROT:A0A1C5A7S5 from *Micromonospora saelicesensis*.

SEQ ID NO: 161 is the amino acid sequence of the LAD domain of SWISSPROT:A0A1C5A2Q7 from *Micromonospora echinospora*.

SEQ ID NO: 162 is the amino acid sequence of the LAD domain of SWISSPROT:A0A1C4ZJ35 from *Micromonospora purpureochromogenes*.

SEQ ID NO: 163 is the amino acid sequence of the LAD domain of SWISSPROT:A0A1C5G758 from *Micromonospora echinofusca*.

SEQ ID NO: 164 is the amino acid sequence of the LAD domain of SWISSPROT:A0A1C5HSB2 from *Micromonospora echinaurantiaca*.

SEQ ID NO: 165 is the amino acid sequence of the LAD domain of SWISSPROT:A0A1C6TPW2 from *Micromonospora citrea*.

SEQ ID NO: 166 is the amino acid sequence of the LAD domain of SWISSPROT:A0A1C5IVI4 from *Micromonospora echinaurantiaca*.

SEQ ID NO: 167 is the amino acid sequence of the LAD domain of SWISSPROT:A0A1C6SEC0 from *Micromonospora pallida*.

SEQ ID NO: 168 is the amino acid sequence of the LAD domain of SWISSPROT:A0A1C6SF84 from *Micromonospora rhizosphaerae*.

SEQ ID NO: 169 is the amino acid sequence of the LAD domain of SWISSPROT:A0A1C6SQT8 from *Micromonospora pallida*.

SEQ ID NO: 170 is the amino acid sequence of the LAD domain of SWISSPROT:A0A1C3N2H1 from *Micromonospora krabiensis*.

SEQ ID NO: 171 is the amino acid sequence of the LAD domain of SWISSPROT:A0A1C3N0X1 from *Micromonospora krabiensis*.

SEQ ID NO: 172 is the amino acid sequence of the LAD domain of SWISSPROT:A0A1C9EHM2 from *Mycobacterium* phage Tonenili.

SEQ ID NO: 173 is the amino acid sequence of the LAD domain of SWISSPROT:A0A1C9EHF6 from *Mycobacterium* phage Tonenili.

SEQ ID NO: 174 is the amino acid sequence of the LAD domain of SWISSPROT:A0A1E4IB54 from *Pseudonocardia* sp SCN 72-86.

SEQ ID NO: 175 is the amino acid sequence of the LAD domain of SWISSPROT:A0A1G8AK84 from *Microbacterium pygmaeum*.

SEQ ID NO: 176 is the amino acid sequence of the LAD domain of SWISSPROT:A0A1E4NTZ4 from *Pseudonocardia* sp SCN 73-27.

SEQ ID NO: 177 is the amino acid sequence of the LAD domain of SWISSPROT:A0A1J0MA43 from *Mycobacterium* phage Lukilu.

SEQ ID NO: 178 is the amino acid sequence of the LAD domain of SWISSPROT:A0A1N6R3C0 from *Micromonospora avicenniae*.

SEQ ID NO: 179 is the amino acid sequence of the LAD domain of SWISSPROT:A0A1N0VNN7 from *Mycobacterium abscessus* subsp *abscessus*.

SEQ ID NO: 180 is the amino acid sequence of the LAD domain of SWISSPROT:A0A1N4DHL3 from *Mycobacterium abscessus* subsp *abscessus*.

SEQ ID NO: 181 is the amino acid sequence of the LAD domain of SWISSPROT:A0A1N4RVY0 from *Mycobacterium abscessus* subsp *abscessus*.

SEQ ID NO: 182 is the amino acid sequence of the LAD domain of SWISSPROT:A0A1N6X5P6 from *Micromonospora avicenniae*.

SEQ ID NO: 183 is the amino acid sequence of the LAD domain of SWISSPROT:A0A1N2VK68 from *Mycobacterium abscessus* subsp *abscessus*.

SEQ ID NO: 184 is the amino acid sequence of the LAD domain of SWISSPROT:A0A1N1GK82 from *Mycobacterium abscessus* subsp *abscessus*.

SEQ ID NO: 185 is the amino acid sequence of the LAD domain of SWISSPROT:A0A1N1EP78 from *Mycobacterium abscessus* subsp *abscessus*.

SEQ ID NO: 186 is the amino acid sequence of the LAD domain of SWISSPROT:A0A1N1G9F3 from *Mycobacterium abscessus* subsp *abscessus*.

SEQ ID NO: 187 is the amino acid sequence of the LAD domain of SWISSPROT:A0A1Q8LJS1 from *Pseudonocardia* sp Ae717_Ps2.

SEQ ID NO: 188 is the amino acid sequence of the lysozyme enhancing domain of SWISSPROT:B2ASY2 from *Podospora anserina*.

SEQ ID NO: 189 is the amino acid sequence of the lysozyme enhancing domain of SWISSPROT:B6GZX8 from *Penicillium chrysogenum*.

SEQ ID NO: 190 is the amino acid sequence of the lysozyme enhancing domain of SWISSPROT:C7ZQ22 from *Nectria haematococca*.

SEQ ID NO: 191 is the amino acid sequence of the lysozyme enhancing domain of SWISSPROT:E9DSA6 from *Metarhizium acridum*.

SEQ ID NO: 192 is the amino acid sequence of the lysozyme enhancing domain of SWISSPROT:E9F1Z9 from *Metarhizium robertsii*.

SEQ ID NO: 193 is the amino acid sequence of the lysozyme enhancing domain of SWISSPROT:E9FC42 from *Metarhizium robertsii*.

SEQ ID NO: 194 is the amino acid sequence of the lysozyme enhancing domain of SWISSPROT:F9F2K5 from *Fusarium oxysporum*.

SEQ ID NO: 195 is the amino acid sequence of the lysozyme enhancing domain of SWISSPROT:F9GF09 from *Fusarium oxysporum*.

SEQ ID NO: 196 is the amino acid sequence of the lysozyme enhancing domain of SWISSPROT:G2QV10 from *Thielavia terrestris*.

SEQ ID NO: 197 is the amino acid sequence of the lysozyme enhancing domain of SWISSPROT:G2QV26 from *Thielavia terrestris*.

SEQ ID NO: 198 is the amino acid sequence of the lysozyme enhancing domain of SWISSPROT:J5TH48 from *Trichosporon asahii* var. *Asahii*.

SEQ ID NO: 199 is the amino acid sequence of the lysozyme enhancing domain of SWISSPROT:J4UH35 from *Trichosporon asahii* var. *Asahii*.

SEQ ID NO: 200 is the amino acid sequence of the lysozyme enhancing domain of SWISSPROT:J9NQ28 from *Fusarium oxysporum* f. sp. *Lycopersici*.

SEQ ID NO: 201 is the amino acid sequence of the lysozyme enhancing domain of SWISSPROT:J9NQW0 from *Fusarium oxysporum* f. sp. *Lycopersici*.

SEQ ID NO: 202 is the amino acid sequence of the lysozyme enhancing domain of SWISSPROT:K1VMN5 from *Trichosporon asahii* var. *Asahii*.

SEQ ID NO: 203 is the amino acid sequence of the lysozyme enhancing domain of SWISSPROT:K1WL46 from *Trichosporon asahii* var. *Asahii*.

SEQ ID NO: 204 is the amino acid sequence of the lysozyme enhancing domain of SWISSPROT:W9Z045 from *Fusarium oxysporum* f. sp. *Melonis*.

SEQ ID NO: 205 is the amino acid sequence of the lysozyme enhancing domain of SWISSPROT:X0A5V9 from *Fusarium oxysporum* f. sp. *Melonis*.

SEQ ID NO: 206 is the amino acid sequence of the lysozyme enhancing domain of SWISSPROT:N1S551 from *Fusarium oxysporum* f. sp. *Cubense*.

SEQ ID NO: 207 is the amino acid sequence of the lysozyme enhancing domain of SWISSPROT:N4UD22 from *Fusarium oxysporum* f. sp. *Cubense*.

SEQ ID NO: 208 is the amino acid sequence of the lysozyme enhancing domain of SWISSPROT:N4UT47 from *Fusarium oxysporum* f. sp. *Cubense*.

SEQ ID NO: 209 is the amino acid sequence of the lysozyme enhancing domain of SWISSPROT:W9KWW4 from *Fusarium oxysporum*.

SEQ ID NO: 210 is the amino acid sequence of the lysozyme enhancing domain of SWISSPROT:X0MM97 from *Fusarium oxysporum* f. sp. *Vasinfectum*.

SEQ ID NO: 211 is the amino acid sequence of the lysozyme enhancing domain of SWISSPROT:W7N5Q6 from *Gibberella moniliformis*.

SEQ ID NO: 212 is the amino acid sequence of the lysozyme enhancing domain of SWISSPROT:X0BE07 from *Fusarium oxysporum* f. sp. *Raphani*.

SEQ ID NO: 213 is the amino acid sequence of the lysozyme enhancing domain of SWISSPROT:X0BII8 from *Fusarium oxysporum*.

SEQ ID NO: 214 is the amino acid sequence of the lysozyme enhancing domain of SWISSPROT:W9NW59 from *Fusarium oxysporum* f. sp. *Pisi*.

SEQ ID NO: 215 is the amino acid sequence of the lysozyme enhancing domain of SWISSPROT:W9NXR4 from *Fusarium oxysporum* f. sp. *Pisi*.

SEQ ID NO: 216 is the amino acid sequence of the lysozyme enhancing domain of SWISSPROT:S7ZNE7 from *Penicillium oxalicum*.

SEQ ID NO: 217 is the amino acid sequence of the lysozyme enhancing domain of SWISSPROT:S7Z5Z6 from *Penicillium oxalicum*.

SEQ ID NO: 218 is the amino acid sequence of the lysozyme enhancing domain of SWISSPROT:W9LDD0 from *Fusarium oxysporum* f. sp. *Lycopersici*.

SEQ ID NO: 219 is the amino acid sequence of the lysozyme enhancing domain of SWISSPROT:W9HEM8 from *Fusarium oxysporum*.

SEQ ID NO: 220 is the amino acid sequence of the lysozyme enhancing domain of SWISSPROT:W9JDH4 from *Fusarium oxysporum*.

SEQ ID NO: 221 is the amino acid sequence of the lysozyme enhancing domain of SWISSPROT:S0EPI6 from *Gibberella fujikuroi*.

SEQ ID NO: 222 is the amino acid sequence of the lysozyme enhancing domain of SWISSPROT:W6QNL2 from *Penicillium roqueforti*.

SEQ ID NO: 223 is the amino acid sequence of the lysozyme enhancing domain of SWISSPROT:U4LJD9 from *Pyronema omphalodes*.

SEQ ID NO: 224 is the amino acid sequence of the lysozyme enhancing domain of SWISSPROT:U4LG64 from *Pyronema omphalodes*.

SEQ ID NO: 225 is the amino acid sequence of the lysozyme enhancing domain of SWISSPROT: A0A094AK50 from *Pseudogymnoascus pannorum*.

SEQ ID NO: 226 is the amino acid sequence of the lysozyme enhancing domain of SWISSPROT:W9JIH2 from *Fusarium oxysporum*.

SEQ ID NO: 227 is the amino acid sequence of the lysozyme enhancing domain of SWISSPROT:X0FW82 from *Fusarium oxysporum* f. sp. *radicis-lycopersici*.

SEQ ID NO: 228 is the amino acid sequence of the lysozyme enhancing domain of SWISSPROT: A0A086TBY7 from *Acremonium chrysogenum*.

SEQ ID NO: 229 is the amino acid sequence of the lysozyme enhancing domain of SWISSPROT:A0A086T755 from *Acremonium chrysogenum*.

SEQ ID NO: 230 is the amino acid sequence of the lysozyme enhancing domain of SWISSPROT: A0A086T4C8 from *Acremonium chrysogenum*.

SEQ ID NO: 231 is the amino acid sequence of the lysozyme enhancing domain of SWISSPROT: A0A086NNR4 from *Metarhizium anisopliae*.

SEQ ID NO: 232 is the amino acid sequence of the lysozyme enhancing domain of SWISSPROT: A0A086NFK5 from *Metarhizium anisopliae*.

SEQ ID NO: 233 is the amino acid sequence of the lysozyme enhancing domain of SWISSPROT: A0A094FY19 from *Pseudogymnoascus pannorum*.

SEQ ID NO: 234 is the amino acid sequence of the lysozyme enhancing domain of SWISSPROT: A0A094G1N0 from *Pseudogymnoascus pannorum*.

SEQ ID NO: 235 is the amino acid sequence of the lysozyme enhancing domain of SWISSPROT: A0A094GEA0 from *Pseudogymnoascus pannorum*.

SEQ ID NO: 236 is the amino acid sequence of the lysozyme enhancing domain of SWISSPROT: A0A094GJR5 from *Pseudogymnoascus pannorum*.

SEQ ID NO: 237 is the amino acid sequence of the lysozyme enhancing domain of SWISSPROT:A0A094G660 from *Pseudogymnoascus pannorum*.

SEQ ID NO: 238 is the amino acid sequence of the lysozyme enhancing domain of SWISSPROT: A0A093YBN4 from *Pseudogymnoascus pannorum*.

SEQ ID NO: 239 is the amino acid sequence of the lysozyme enhancing domain of SWISSPROT:A0A094FSZ5 from *Pseudogymnoascus pannorum*.

SEQ ID NO: 240 is the amino acid sequence of the lysozyme enhancing domain of SWISSPROT: A0A094FBW1 from *Pseudogymnoascus pannorum*.

SEQ ID NO: 241 is the amino acid sequence of the lysozyme enhancing domain of SWISSPROT: A0A094H0G2 from *Pseudogymnoascus pannorum*.

SEQ ID NO: 242 is the amino acid sequence of the lysozyme enhancing domain of SWISSPROT: A0A094H7M1 from *Pseudogymnoascus pannorum*.

SEQ ID NO: 243 is the amino acid sequence of the lysozyme enhancing domain of SWISSPROT: A0A093Y8W3 from *Pseudogymnoascus pannorum*.

SEQ ID NO: 244 is the amino acid sequence of the lysozyme enhancing domain of SWISSPROT: A0A094GYN9 from *Pseudogymnoascus pannorum*.

SEQ ID NO: 245 is the amino acid sequence of the lysozyme enhancing domain of SWISSPROT: A0A093XAD4 from *Pseudogymnoascus pannorum*.

SEQ ID NO: 246 is the amino acid sequence of the lysozyme enhancing domain of SWISSPROT:A0A094H7J6 from *Pseudogymnoascus pannorum*.

SEQ ID NO: 247 is the amino acid sequence of the lysozyme enhancing domain of SWISSPROT:A0A094E0I1 from *Pseudogymnoascus pannorum*.

SEQ ID NO: 248 is the amino acid sequence of the lysozyme enhancing domain of SWISSPROT: A0A094CC50 from *Pseudogymnoascus pannorum*.

SEQ ID NO: 249 is the amino acid sequence of the lysozyme enhancing domain of SWISSPROT:A0A094II95 from *Pseudogymnoascus pannorum*.

SEQ ID NO: 250 is the amino acid sequence of the lysozyme enhancing domain of SWISSPROT: A0A094IAA0 from *Pseudogymnoascus pannorum*.

SEQ ID NO: 251 is the amino acid sequence of the lysozyme enhancing domain of SWISSPROT:A0A094IBC0 from *Pseudogymnoascus pannorum*.

SEQ ID NO: 252 is the amino acid sequence of the lysozyme enhancing domain of SWISSPROT:A0A094E946 from *Pseudogymnoascus pannorum*.

SEQ ID NO: 253 is the amino acid sequence of the lysozyme enhancing domain of SWISSPROT: A0A094A3A0 from *Pseudogymnoascus pannorum*.

SEQ ID NO: 254 is the amino acid sequence of the lysozyme enhancing domain of SWISSPROT:A1C4L9 from *Aspergillus clavatus*.

SEQ ID NO: 255 is the amino acid sequence of the lysozyme enhancing domain of SWISSPROT:A1CBV9 from *Aspergillus clavatus*.

SEQ ID NO: 256 is the amino acid sequence of the lysozyme enhancing domain of SWISSPROT:A1DA80 from *Neosartorya fischeri*.

SEQ ID NO: 257 is the amino acid sequence of the lysozyme enhancing domain of SWISSPROT:A1DBW2 from *Neosartorya fischeri*.

SEQ ID NO: 258 is the amino acid sequence of the lysozyme enhancing domain of SWISSPROT:A1DDF2 from *Neosartorya fischeri*.

SEQ ID NO: 259 is the amino acid sequence of the lysozyme enhancing domain of SWISSPROT:Q0CED1 from *Aspergillus terreus*.

SEQ ID NO: 260 is the amino acid sequence of the lysozyme enhancing domain of SWISSPROT:Q0CED2 from *Aspergillus terreus*.

SEQ ID NO: 261 is the amino acid sequence of the lysozyme enhancing domain of SWISSPROT:Q0CV85 from *Aspergillus terreus*.

SEQ ID NO: 262 is the amino acid sequence of the lysozyme enhancing domain of SWISSPROT:Q2GND8 from *Chaetomium globosum*.

SEQ ID NO: 263 is the amino acid sequence of the lysozyme enhancing domain of SWISSPROT:Q2GND9 from *Chaetomium globosum*.

SEQ ID NO: 264 is the amino acid sequence of the lysozyme enhancing domain of SWISSPROT:Q2H6W7 from *Chaetomium globosum*.

SEQ ID NO: 265 is the amino acid sequence of the lysozyme enhancing domain of SWISSPROT:Q4WAY2 from *Neosartorya fumigata*.

SEQ ID NO: 266 is the amino acid sequence of the lysozyme enhancing domain of SWISSPROT:Q4WBR4 from *Neosartorya fumigata*.

SEQ ID NO: 267 is the amino acid sequence of the lysozyme enhancing domain of SWISSPROT:Q4WVY3 from *Neosartorya fumigata*.

SEQ ID NO: 268 is the amino acid sequence of the lysozyme enhancing domain of SWISSPROT:B6H9X5 from *Penicillium chrysogenum*.

SEQ ID NO: 269 is the amino acid sequence of the lysozyme enhancing domain of SWISSPROT:B6HR38 from *Penicillium chrysogenum*.

SEQ ID NO: 270 is the amino acid sequence of the lysozyme enhancing domain of SWISSPROT:C7Z8W0 from *Nectria haematococca*.

SEQ ID NO: 271 is the amino acid sequence of the lysozyme enhancing domain of SWISSPROT:C7ZQ20 from *Nectria haematococca*.

SEQ ID NO: 272 is the amino acid sequence of the lysozyme enhancing domain of SWISSPROT:G0RP87 from *Hypocrea jecorina*.

SEQ ID NO: 273 is the amino acid sequence of the lysozyme enhancing domain of SWISSPROT:G2RG69 from *Thielavia terrestris*.

SEQ ID NO: 274 is the amino acid sequence of the lysozyme enhancing domain of SWISSPROT:G2QNE9 from *Thielavia heterothallica*.

SEQ ID NO: 275 is the amino acid sequence of the lysozyme enhancing domain of SWISSPROT:G0RM22 from *Hypocrea jecorina*.

SEQ ID NO: 276 is the amino acid sequence of the lysozyme enhancing domain of SWISSPROT:G0SG36 from *Chaetomium thermophilum* var. *Thermophilum*.

SEQ ID NO: 277 is the amino acid sequence of the lysozyme enhancing domain of SWISSPROT:G0RZV3 from *Chaetomium thermophilum* var. *Thermophilum*.

SEQ ID NO: 278 is the amino acid sequence of the lysozyme enhancing domain of SWISSPROT:J9NQV9 from *Fusarium oxysporum* f. sp. *Lycopersici*.

SEQ ID NO: 279 is the amino acid sequence of the lysozyme enhancing domain of SWISSPROT:G2QD02 from *Thielavia heterothallica*.

SEQ ID NO: 280 is the amino acid sequence of the lysozyme enhancing domain of SWISSPROT:G2QNF0 from *Thielavia heterothallica*.

SEQ ID NO: 281 is the amino acid sequence of the lysozyme enhancing domain of SWISSPROT:G9MHR1 from *Hypocrea virens*.

SEQ ID NO: 282 is the amino acid sequence of the lysozyme enhancing domain of SWISSPROT:E9ELX9 from *Metarhizium robertsii*.

SEQ ID NO: 283 is the amino acid sequence of the lysozyme enhancing domain of SWISSPROT:F9F2K4 from *Fusarium oxysporum*.

SEQ ID NO: 284 is the amino acid sequence of the lysozyme enhancing domain of SWISSPROT:G0RZV2 from *Chaetomium thermophilum* var. *Thermophilum*.

SEQ ID NO: 285 is the amino acid sequence of the lysozyme enhancing domain of SWISSPROT:G2RG70 from *Thielavia terrestris*.

SEQ ID NO: 286 is the amino acid sequence of the lysozyme enhancing domain of SWISSPROT:W9Z992 from *Fusarium oxysporum* f. sp. *Melonis*.

SEQ ID NO: 287 is the amino acid sequence of the lysozyme enhancing domain of SWISSPROT:W9ZZW9 from *Fusarium oxysporum* f. sp. *Melonis*.

SEQ ID NO: 288 is the amino acid sequence of the lysozyme enhancing domain of SWISSPROT:W9ZAE8 from *Fusarium oxysporum* f. sp. *Melonis*.

SEQ ID NO: 289 is the amino acid sequence of the lysozyme enhancing domain of SWISSPROT:N1RWA4 from *Fusarium oxysporum* f. sp. *Cubense*.

SEQ ID NO: 290 is the amino acid sequence of the lysozyme enhancing domain of SWISSPROT:N4UKT7 from *Fusarium oxysporum* f. sp. *Cubense*.

SEQ ID NO: 291 is the amino acid sequence of the lysozyme enhancing domain of SWISSPROT:W9KX02 from *Fusarium oxysporum*.

SEQ ID NO: 292 is the amino acid sequence of the lysozyme enhancing domain of SWISSPROT:X0B4J3 from *Fusarium oxysporum* f. sp. *Raphani*.

SEQ ID NO: 293 is the amino acid sequence of the lysozyme enhancing domain of SWISSPROT:W6QE02 from *Penicillium roqueforti*.

SEQ ID NO: 294 is the amino acid sequence of the lysozyme enhancing domain of SWISSPROT:W6R4X8 from *Penicillium roqueforti*.

SEQ ID NO: 295 is the amino acid sequence of the lysozyme enhancing domain of SWISSPROT:A0A024S9B8 from *Trichoderma reesei*.

SEQ ID NO: 296 is the amino acid sequence of the lysozyme enhancing domain of SWISSPROT: A0A086NN36 from *Metarhizium anisopliae*.

SEQ ID NO: 297 is the amino acid sequence of the lysozyme enhancing domain of SWISSPROT: A0A094GA03 from *Pseudogymnoascus pannorum*.

SEQ ID NO: 298 is the amino acid sequence of the lysozyme enhancing domain of SWISSPROT: A0A094C8U1 from *Pseudogymnoascus pannorum*.

SEQ ID NO: 299 is the amino acid sequence of the lysozyme enhancing domain of SWISSPROT:A0A093Z6Z8 from *Pseudogymnoascus pannorum*.

SEQ ID NO: 300 is the amino acid sequence of the lysozyme enhancing domain of SWISSPROT: A0A094IML3 from *Pseudogymnoascus pannorum*.

SEQ ID NO: 301 is the amino acid sequence of the lysozyme enhancing domain of SWISSPROT: A0A094GY79 from *Pseudogymnoascus pannorum*.

SEQ ID NO: 302 is the amino acid sequence of the lysozyme enhancing domain of SWISSPROT: A0A093XPZ7 from *Pseudogymnoascus pannorum*.

SEQ ID NO: 303 is the amino acid sequence of the lysozyme enhancing domain of SWISSPROT: A0A093XAS9 from *Pseudogymnoascus pannorum*.

SEQ ID NO: 304 is the amino acid sequence of the lysozyme enhancing domain of SWISSPROT:A0A094I8J6 from *Pseudogymnoascus pannorum*.

SEQ ID NO: 305 is the amino acid sequence of the lysozyme enhancing domain of SWISSPROT: A0A094FTL0 from *Pseudogymnoascus pannorum*.

SEQ ID NO: 306 is the amino acid sequence of the lysozyme enhancing domain of SWISSPROT:A0A094AT39 from *Pseudogymnoascus pannorum*.

SEQ ID NO: 307 is the amino acid sequence of the lysozyme enhancing domain of SWISSPROT: A0A093XSP5 from *Pseudogymnoascus pannorum*.

SEQ ID NO: 308 is the amino acid sequence of the lysozyme enhancing domain of SWISSPROT: A0A094BAE6 from *Pseudogymnoascus pannorum*.

SEQ ID NO: 309 is the amino acid sequence of the lysozyme enhancing domain of SWISSPROT:A0A094IE25 from *Pseudogymnoascus pannorum*.

SEQ ID NO: 310 is the amino acid sequence of the lysozyme enhancing domain of SWISSPROT: A0A094HNM8 from *Pseudogymnoascus pannorum*.

SEQ ID NO: 311 is the amino acid sequence of the lysozyme enhancing domain of SWISSPROT:A0A094ETJ5 from *Pseudogymnoascus pannorum*.

SEQ ID NO: 312 is the amino acid sequence of the lysozyme enhancing domain of SWISSPROT:A0A094EPJ7 from *Pseudogymnoascus pannorum*.

SEQ ID NO: 313 is the amino acid sequence of the lysozyme enhancing domain of SWISSPROT: A0A094E9W0 from *Pseudogymnoascus pannorum*.

SEQ ID NO: 314 is the amino acid sequence of the lysozyme enhancing domain of SWISSPROT: A0A094BWD6 from *Pseudogymnoascus pannorum*.

SEQ ID NO: 315 is the amino acid sequence of the lysozyme enhancing domain of SWISSPROT: A0A094BTS1 from *Pseudogymnoascus pannorum*.

SEQ ID NO: 316 is the amino acid sequence of the lysozyme enhancing domain of SWISSPROT: A0A093ZTZ8 from *Pseudogymnoascus pannorum*.

SEQ ID NO: 317 is conserved motif I AG[I/L]AT[A/G][I/L][T/V]ES.

SEQ ID NO: 318 is conserved motif II V[G/A]XLCQXVQXSAYP.

SEQ ID NO: 319 is conserved motif III [CGY][YF][VIL][ASTP][DG]X[YF][VIT]X[TS][GAN].

SEQ ID NO: 320 is the synthetic DNA construct of plasmid pDAu770.

SEQ ID NO: 321 is the forward primer KKSC0972-F.

SEQ ID NO: 322 is the reverse primer KKSC0972-R.

SEQ ID NO: 323 is forward primer F1.

SEQ ID NO: 324 is reverse primer F1.

SEQ ID NO: 325 is forward primer F3.

SEQ ID NO: 326 is reverse primer F3.

SEQ ID NO: 327 Primer bind forward.

SEQ ID NO: 328 Primer bind reverse.

SEQ ID NO: 329 is the amino acid sequence of the truncated LYA polypeptide from *Ovatospora brasiliensis*.

Definitions

Animal: The term "animal" refers to any animal except humans. Examples of animals are monogastric animals, including but not limited to pigs or swine (including, but not limited to, piglets, growing pigs, and sows); poultry such as turkeys, ducks, quail, guinea fowl, geese, pigeons (including squabs) and chicken (including but not limited to broiler chickens (referred to herein as broiles), chicks, layer hens (referred to herein as layers)); horses (including but not limited to hotbloods, coldbloods and warm bloods) crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish).

Animal feed: The term "animal feed" refers to any compound, preparation, or mixture suitable for, or intended for intake by a monogastric animal. Animal feed for a monogastric animal typically comprises concentrates as well as vitamins, minerals, enzymes, direct fed microbial, amino acids and/or other feed ingredients (such as in a premix).

Antimicrobial activity: The term "antimicrobial activity" is defined herein as an activity that kills or inhibits the growth of microorganisms, such as, algae, archea, bacteria, fungi and/or protozoans. The antimicrobial activity can, for example, be bactericidal meaning the killing of bacteria or bacteriostatic meaning the prevention of bacterial growth. The antimicrobial activity can include catalyzing the hydrolysis of 1,4-beta-linkages between N-acetylmuramic acid and N-acetyl-D-glucosamine residues in a peptidoglycan and between N-acetyl-D-glucosamine residues in chitodextrins. Antimicrobial activity can also include the LYS polypeptide binding to the surface of the microorganism and inhibiting its growth. The antimicrobial effect can also include the use of the LYS polypeptides of the present invention for activation of bacterial autolysins, as an immunostimulator, by inhibiting or reducing bacterial toxins and by an opsonin effect.

Body Weight Gain: The term "body weight gain" means an increase in live weight of an animal during a given period of time e.g. the increase in weight from day 1 to day 21.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Concentrates: The term "concentrates" means feed with high protein and energy concentrations, such as fish meal, molasses, oligosaccharides, sorghum, seeds and grains (either whole or prepared by crushing, milling, etc. from e.g. corn, oats, rye, barley, wheat), oilseed press cake (e.g. from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

European Production Efficacy Factor (EPEF): The "European Production Efficacy Factor" is a way of comparing the performance of animals. This single-figure facilitates comparison of performance within and among farms and can be used to assess environmental, climatic and managerial variables. The EPEF is calculated as [(liveability (%)× Liveweight (kg))/(Age at depletion (days)×FCR)]×100, wherein livability is the percentage of animals alive at slaughter, Liveweight is the average weight of the animals at slaughter, age of depletion is the age of the animals at slaughter and FCR is the feed conversion ratio at slaughter.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feed Conversion Ratio (FCR): FCR is a measure of an animal's efficiency in converting feed mass into increases of the desired output. Animals raised for meat—such as swine, poultry and fish—the output is the mass gained by the animal. Specifically, FCR is calculated as feed intake divided by weight gain, all over a specified period. Improvement in FCR means reduction of the FCR value. A FCR improvement of 2% means that the FCR was reduced by 2%.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, brassica (e.g. kale, rapeseed (canola), rutabaga (swede), turnip), clover (e.g. alsike clover, red clover, subterranean clover, white clover), grass (e.g. Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves from soybeans, rapeseed and other legumes; and fractions from the refining of grains for animal or human consumption or from fuel production or other industries.

Fragment: The term "fragment" means a LYS polypeptide having one or more (e.g., several) amino acids absent from the amino and/or carboxyl terminus of a mature polypeptide or domain; wherein the fragment has lysozyme activity.

In one aspect, the fragment comprises at least 90% of the length of the mature polypeptide, such as at least 203 amino acids of SEQ ID NO: 2, at least 203 amino acids of SEQ ID NO: 3, at least 203 amino acids of SEQ ID NO: 5, at least 203 amino acids of SEQ ID NO: 6, at least 200 amino acids of SEQ ID NO: 8, at least 200 amino acids of SEQ ID NO: 9, at least 273 amino acids of SEQ ID NO: 11, at least 273 amino acids of SEQ ID NO: 12, at least 205 amino acids of SEQ ID NO: 14, at least 205 amino acids of SEQ ID NO: 15, at least 207 amino acids of SEQ ID NO: 17, at least 207 amino acids of SEQ ID NO: 18, at least 207 amino acids of SEQ ID NO: 20, at least 207 amino acids of SEQ ID NO: 21, at least 208 amino acids of SEQ ID NO: 23, at least 208 amino acids of SEQ ID NO: 24, at least 205 amino acids of SEQ ID NO: 26, at least 205 amino acids of SEQ ID NO: 27, at least 205 amino acids of SEQ ID NO: 29, at least 205 amino acids of SEQ ID NO: 30, at least 203 amino acids of SEQ ID NO: 32, at least 203 amino acids of SEQ ID NO: 33, at least 202 amino acids of SEQ ID NO: 35, at least 202 amino acids of SEQ ID NO: 36, at least 202 amino acids of SEQ ID NO: 38, at least 202 amino acids of SEQ ID NO: 39, at least 273 amino acids of SEQ ID NO: 41, at least 273 amino acids of SEQ ID NO: 42, at least 204 amino acids of SEQ ID NO: 44, or at least 204 amino acids of SEQ ID NO: 45.

In one aspect, the fragment comprises at least 92% of the length of the mature polypeptide, such as at least 207 amino acids of SEQ ID NO: 2, at least 207 amino acids of SEQ ID NO: 3, at least 207 amino acids of SEQ ID NO: 5, at least 207 amino acids of SEQ ID NO: 6, at least 205 amino acids of SEQ ID NO: 8, at least 205 amino acids of SEQ ID NO: 9, at least 279 amino acids of SEQ ID NO: 11, at least 279 amino acids of SEQ ID NO: 12, at least 209 amino acids of SEQ ID NO: 14, at least 209 amino acids of SEQ ID NO: 15, at least 211 amino acids of SEQ ID NO: 17, at least 211 amino acids of SEQ ID NO: 18, at least 211 amino acids of SEQ ID NO: 20, at least 211 amino acids of SEQ ID NO: 21, at least 213 amino acids of SEQ ID NO: 23, at least 213 amino acids of SEQ ID NO: 24, at least 209 amino acids of SEQ ID NO: 26, at least 209 amino acids of SEQ ID NO: 27, at least 209 amino acids of SEQ ID NO: 29, at least 209 amino acids of SEQ ID NO: 30, at least 207 amino acids of SEQ ID NO: 32, at least 207 amino acids of SEQ ID NO: 33, at least 207 amino acids of SEQ ID NO: 35, at least 207 amino acids of SEQ ID NO: 36, at least 207 amino acids of SEQ ID NO: 38, at least 207 amino acids of SEQ ID NO: 39, at least 279 amino acids of SEQ ID NO: 41, at least 279 amino acids of SEQ ID NO: 42, at least 208 amino acids of SEQ ID NO: 44, or at least 208 amino acids of SEQ ID NO: 45.

In one aspect, the fragment comprises at least 94% of the length of the mature polypeptide, such as at least 212 amino acids of SEQ ID NO: 2, at least 212 amino acids of SEQ ID NO: 3, at least 212 amino acids of SEQ ID NO: 5, at least 212 amino acids of SEQ ID NO: 6, at least 209 amino acids of SEQ ID NO: 8, at least 209 amino acids of SEQ ID NO: 9, at least 285 amino acids of SEQ ID NO: 11, at least 285 amino acids of SEQ ID NO: 12, at least 214 amino acids of SEQ ID NO: 14, at least 214 amino acids of SEQ ID NO: 15, at least 216 amino acids of SEQ ID NO: 17, at least 216 amino acids of SEQ ID NO: 18, at least 216 amino acids of SEQ ID NO: 20, at least 216 amino acids of SEQ ID NO: 21, at least 218 amino acids of SEQ ID NO: 23, at least 218 amino acids of SEQ ID NO: 24, at least 214 amino acids of SEQ ID NO: 26, at least 214 amino acids of SEQ ID NO: 27, at least 214 amino acids of SEQ ID NO: 29, at least 214 amino acids of SEQ ID NO: 30, at least 212 amino acids of SEQ ID NO: 32, at least 212 amino acids of SEQ ID NO: 33, at least 211 amino acids of SEQ ID NO: 35, at least 211 amino acids of SEQ ID NO: 36, at least 211 amino acids of SEQ ID NO: 38, at least 211 amino acids of SEQ ID NO: 39, at least 285 amino acids of SEQ ID NO: 41, at least 285 amino acids of SEQ ID NO: 42, at least 213 amino acids of SEQ ID NO: 44, or at least 213 amino acids of SEQ ID NO: 45.

In one aspect, the fragment comprises at least 96% of the length of the mature polypeptide, such as at least 216 amino acids of SEQ ID NO: 2, at least 216 amino acids of SEQ ID NO: 3, at least 216 amino acids of SEQ ID NO: 5, at least 216 amino acids of SEQ ID NO: 6, at least 214 amino acids of SEQ ID NO: 8, at least 214 amino acids of SEQ ID NO: 9, at least 291 amino acids of SEQ ID NO: 11, at least 291 amino acids of SEQ ID NO: 12, at least 218 amino acids of SEQ ID NO: 14, at least 218 amino acids of SEQ ID NO: 15, at least 220 amino acids of SEQ ID NO: 17, at least 220 amino acids of SEQ ID NO: 18, at least 220 amino acids of SEQ ID NO: 20, at least 220 amino acids of SEQ ID NO: 21, at least 222 amino acids of SEQ ID NO: 23, at least 222 amino acids of SEQ ID NO: 24, at least 218 amino acids of SEQ ID NO: 26, at least 218 amino acids of SEQ ID NO: 27, at least 218 amino acids of SEQ ID NO: 29, at least 218 amino acids of SEQ ID NO: 30, at least 216 amino acids of SEQ ID NO: 32, at least 216 amino acids of SEQ ID NO: 33, at least 216 amino acids of SEQ ID NO: 35, at least 216 amino acids of SEQ ID NO: 36, at least 216 amino acids of SEQ ID NO: 38, at least 216 amino acids of SEQ ID NO: 39, at least 291 amino acids of SEQ ID NO: 41, at least 291 amino acids of SEQ ID NO: 42, at least 217 amino acids of SEQ ID NO: 44, or at least 217 amino acids of SEQ ID NO: 45.

In one aspect, the fragment comprises at least 98% of the length of the mature polypeptide, such as at least 221 amino acids of SEQ ID NO: 2, at least 221 amino acids of SEQ ID NO: 3, at least 221 amino acids of SEQ ID NO: 5, at least 221 amino acids of SEQ ID NO: 6, at least 218 amino acids of SEQ ID NO: 8, at least 218 amino acids of SEQ ID NO: 9, at least 297 amino acids of SEQ ID NO: 11, at least 297 amino acids of SEQ ID NO: 12, at least 223 amino acids of SEQ ID NO: 14, at least 223 amino acids of SEQ ID NO: 15, at least 225 amino acids of SEQ ID NO: 17, at least 225 amino acids of SEQ ID NO: 18, at least 225 amino acids of SEQ ID NO: 20, at least 225 amino acids of SEQ ID NO: 21, at least 227 amino acids of SEQ ID NO: 23, at least 227 amino acids of SEQ ID NO: 24, at least 223 amino acids of SEQ ID NO: 26, at least 223 amino acids of SEQ ID NO: 27, at least 223 amino acids of SEQ ID NO: 29, at least 223 amino acids of SEQ ID NO: 30, at least 221 amino acids of SEQ ID NO: 32, at least 221 amino acids of SEQ ID NO: 33, at least 220 amino acids of SEQ ID NO: 35, at least 220 amino acids of SEQ ID NO: 36, at least 220 amino acids of SEQ ID NO: 38, at least 220 amino acids of SEQ ID NO: 39, at least 297 amino acids of SEQ ID NO: 41, at least 297 amino acids of SEQ ID NO: 42, at least 222 amino acids of SEQ ID NO: 44, or at least 222 amino acids of SEQ ID NO: 45.

In one aspect, the fragment comprises at least 99% of the length of the mature polypeptide, such as at least 223 amino acids of SEQ ID NO: 2, at least 223 amino acids of SEQ ID NO: 3, at least 223 amino acids of SEQ ID NO: 5, at least 223 amino acids of SEQ ID NO: 6, at least 220 amino acids of SEQ ID NO: 8, at least 220 amino acids of SEQ ID NO: 9, at least 300 amino acids of SEQ ID NO: 11, at least 300 amino acids of SEQ ID NO: 12, at least 225 amino acids of SEQ ID NO: 14, at least 225 amino acids of SEQ ID NO: 15, at least 227 amino acids of SEQ ID NO: 17, at least 227 amino acids of SEQ ID NO: 18, at least 227 amino acids of SEQ ID NO: 20, at least 227 amino acids of SEQ ID NO: 21, at least 229 amino acids of SEQ ID NO: 23, at least 229 amino acids of SEQ ID NO: 24, at least 225 amino acids of SEQ ID NO: 26, at least 225 amino acids of SEQ ID NO: 27, at least 225 amino acids of SEQ ID NO: 29, at least 225 amino acids of SEQ ID NO: 30, at least 223 amino acids of SEQ ID NO: 32, at least 223 amino acids of SEQ ID NO: 33, at least 222 amino acids of SEQ ID NO: 35, at least 222 amino acids of SEQ ID NO: 36, at least 222 amino acids of SEQ ID NO: 38, at least 222 amino acids of SEQ ID NO: 39, at least 300 amino acids of SEQ ID NO: 41, at least 300 amino acids of SEQ ID NO: 42, at least 224 amino acids of SEQ ID NO: 44, or at least 224 amino acids of SEQ ID NO: 45.

Fusion polypeptide: The term "fusion polypeptide" is a polypeptide in which one polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779). A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Hybrid polypeptide: The term "hybrid polypeptide" means a polypeptide comprising domains from two or more polypeptides, e.g., a binding domain from one polypeptide and a catalytic domain from another polypeptide. The domains may be fused at the N-terminus or the C-terminus.

Isolated: The term "isolated" means a substance in a form that does not occur in nature or in an environment in which the substance does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Lysozyme activity: The term "lysozyme activity" means the hydrolysis of the 1,4-beta-linkages between N-acetylmuramic acid and N-acetyl-D-glucosamine residues in a peptidoglycan, resulting in bacteriolysis. Lysozyme belongs to the enzyme class EC 3.2.1.17. Lysozyme activity is typically measured by the lytic action of the lysozyme on Micrococcus luteus ATCC 4698. In appropriate experimental conditions these changes are proportional to the amount of lysozyme in the medium (c.f. INS 1105 of the Combined Compendium of Food Additive Specifications of the Food and Agriculture Organisation of the UN (www.fao.org)). For the purpose of the present invention, lysozyme activity is determined according to the reducing-ends assay described in Example 1 ("Determination of Lysozyme Activity using reducing ends assay"). The polypeptide has lysozyme activity if it shows activity against Micrococcus luteus ATCC 4698.

In one aspect, the polypeptides of the present invention have at least 50%, e.g., preferably at least 60%, preferably at least 70%, more preferably at least 80%, more preferably at least 90%, even more preferably at least 95% or most preferably at least 100% of the lysozyme activity of SEQ ID NO: 12, preferably wherein lysozyme activity is determined as described in Example 1. In one aspect, the polypeptides of the present invention have at least 50%, e.g., preferably at least 60%, preferably at least 70%, more preferably at least 80%, more preferably at least 90%, even more preferably at least 95% or most preferably at least 100% of the lysozyme activity of SEQ ID NO: 12 wherein lysozyme activity is determined as follows: LYS polypeptide (50 μL of 0.7 μg/mL LYS polypeptide in phosphate buffer (5 mM citrate, 5 mM $K_2HPO_4$, 0.01% TritonX-100, pH 5.0)) is mixed with Micrococcus lysodeikticus solution (450 μL of 1% lyophilized Micrococcus lysodeikticus ATCC No. 4698 in milli-Q water) and incubated at 40° C. with shaking (500 rpm) for 45 min; the sample is centrifuged (4000 g, 5 min); supernatant (100 μL) is mixed with HCl (50 μL 3.2M) and incubated at 95° C. for 80 min; NaOH (50 μL, 3.5 M) is added and 150 μL of the sample is added to 4-hydroxybenzhydrazide in K—Na tartrate/NaOH buffer (75 μL of 50 g/L K—Na tartrate+20 g/L NaOH); the mixture is incubated at 95° C. for 10 min; and the optical density is measured at 405 nm.

Mature polypeptide: The term "mature polypeptide" means a polypeptide in its final form following translation and any post-translational modifications, such as N-terminal processing, C-terminal truncation, glycosylation, phosphorylation, etc.

In one aspect, the mature polypeptide is amino acids 1 to 226 of SEQ ID NO: 2 and amino acids −19 to −1 of SEQ ID NO: 2 are a signal peptide. In another aspect, the mature polypeptide is amino acids 1 to 226 of SEQ ID NO: 3. In one aspect, the mature polypeptide is amino acids 1 to 226 of SEQ ID NO: 5 and amino acids −19 to −1 of SEQ ID NO: 5 are a signal peptide. In another aspect, the mature polypeptide is amino acids 1 to 226 of SEQ ID NO: 6. In one aspect, the mature polypeptide is amino acids 1 to 223 of SEQ ID NO: 8 and amino acids −20 to −1 of SEQ ID NO: 8 are a signal peptide. In another aspect, the mature polypeptide is amino acids 1 to 223 of SEQ ID NO: 9. In one aspect, the mature polypeptide is amino acids 1 to 304 of SEQ ID NO: 11 and amino acids −20 to −1 of SEQ ID NO: 11 are a signal peptide. In another aspect, the mature polypeptide is amino acids 1 to 304 of SEQ ID NO: 12. In one aspect, the mature polypeptide is amino acids 1 to 228 of SEQ ID NO: 14 and amino acids −19 to −1 of SEQ ID NO: 14 are a signal peptide. In another aspect, the mature polypeptide is amino acids 1 to 228 of SEQ ID NO: 15. In one aspect, the mature polypeptide is amino acids 1 to 230 of SEQ ID NO: 17 and amino acids −20 to −1 of SEQ ID NO: 17 are a signal peptide. In another aspect, the mature polypeptide is amino acids 1 to 230 of SEQ ID NO: 18. In one aspect, the mature polypeptide is amino acids 1 to 230 of SEQ ID NO: 20 and amino acids −21 to −1 of SEQ ID NO: 20 are a signal peptide. In another aspect, the mature polypeptide is amino acids 1 to 230 of SEQ ID NO: 21. In one aspect, the mature polypeptide is amino acids 1 to 232 of SEQ ID NO: 23 and amino acids −22 to −1 of SEQ ID NO: 23 are a signal peptide. In another aspect, the mature polypeptide is amino acids 1 to 232 of SEQ ID NO: 24. In one aspect, the mature polypeptide is amino acids 1 to 228 of SEQ ID NO: 26 and amino acids −20 to −1 of SEQ ID NO: 26 are a signal peptide. In another aspect, the mature polypeptide is amino acids 1 to 228 of SEQ ID NO: 27. In one aspect, the mature polypeptide is amino acids 1 to 228 of SEQ ID NO: 29 and amino acids −20 to −1 of SEQ ID NO: 29 are a signal peptide. In another aspect, the mature polypeptide is amino acids 1 to 228 of SEQ ID NO: 30. In one aspect, the mature polypeptide is amino acids 1 to 226 of SEQ ID NO: 32 and amino acids −19 to −1 of SEQ ID NO: 32 are a signal peptide. In another aspect, the mature polypeptide is amino acids 1 to 226 of SEQ ID NO: 33. In one aspect, the mature polypeptide is amino acids 1 to 225 of SEQ ID NO: 35 and amino acids −20 to −1 of SEQ ID NO: 35 are a signal peptide. In another aspect, the mature polypeptide is amino acids 1 to 225 of SEQ ID NO: 36. In one aspect, the mature polypeptide is amino acids 1 to 225 of SEQ ID NO: 38 and amino acids −19 to −1 of SEQ ID NO: 38 are a signal peptide. In another aspect, the mature polypeptide is amino acids 1 to 225 of SEQ ID NO: 39. In one aspect, the mature polypeptide is amino acids 1 to 304 of SEQ ID NO: 41 and amino acids −19 to −1 of SEQ ID NO: 41 are a signal peptide. In another aspect, the mature polypeptide is amino acids 1 to 304 of SEQ ID NO: 42. In one aspect, the mature polypeptide is amino acids 1 to 227 of SEQ ID NO: 44 and amino acids −19 to −1 of SEQ ID NO: 44 are a signal peptide. In another aspect, the mature polypeptide is amino acids 1 to 227 of SEQ ID NO: 45.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having lysozyme activity.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Obtained or obtainable from: The term "obtained or obtainable from" means that the polypeptide may be found in an organism from a specific taxonomic rank. In one embodiment, the polypeptide is obtained or obtainable from the kingdom Fungi, wherein the term kingdom is the taxonomic rank. In a preferred embodiment, the polypeptide is obtained or obtainable from the phylum Ascomycota, wherein the term phylum is the taxonomic rank. In another preferred embodiment, the polypeptide is obtained or obtainable from the subphylum Pezizomycotina, wherein the term subphylum is the taxonomic rank.

If the taxonomic rank of a polypeptide is not known, it can easily be determined by a person skilled in the art by performing a BLASTP search of the polypeptide (using e.g. the National Center for Biotechnology Information (NCIB) website www.ncbi.nlm.nih.gov/) and comparing it to the closest homologues. An unknown polypeptide which is a fragment of a known polypeptide is considered to be of the same taxonomic species. An unknown natural polypeptide or artificial variant which comprises a substitution, deletion and/or insertion in up to 10 positions is considered to be from the same taxonomic species as the known polypeptide.

Operably linked: The term "operably linked" means a configuration in which a control sequence is placed at an appropriate position relative to the coding sequence of a polynucleotide such that the control sequence directs expression of the coding sequence.

Roughage: The term "roughage" means dry plant material with high levels of fiber, such as fiber, bran, husks from seeds and grains and crop residues (such as stover, copra, straw, chaff, sugar beet waste).

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labelled "longest identity" (obtained using the −nobrief option) is used as the percent identity and is calculated as follows: (Identical Residues×100)/(Length of Alignment−Total Number of Gaps in Alignment).

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labelled "longest identity" (obtained using the −nobrief option) is used as the percent identity and is calculated as follows: (Identical Deoxyribonucleotides×100)/(Length of Alignment−Total Number of Gaps in Alignment).

Subsequence: The term "subsequence" means a polynucleotide having one or more (e.g., several) nucleotides absent from the 5' and/or 3' end of a mature polypeptide coding sequence; wherein the subsequence encodes a fragment having lysozyme activity.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having lysozyme activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, or 3 amino acids adjacent to and immediately following the amino acid occupying the position.

In one aspect, the variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations.

In one aspect, the variant of the present invention has at least 50%, e.g., preferably at least 60%, preferably at least 70%, more preferably at least 80%, more preferably at least 90%, even more preferably at least 95% or most preferably at least 100% of the lysozyme activity of SEQ ID NO: 12, preferably wherein lysozyme activity is determined as described in Example 1. In one aspect, the variant of the present invention has at least 50%, e.g., preferably at least 60%, preferably at least 70%, more preferably at least 80%, more preferably at least 90%, even more preferably at least 95% or most preferably at least 100% of the lysozyme activity of SEQ ID NO: 12 wherein lysozyme activity is determined as follows: LYS polypeptide (50 µL of 0.7 µg/mL LYS polypeptide in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K—Na tartrate/NaOH buffer (75 µL of 50 g/L K—Na tartrate+20 g/L NaOH); the mixture is incubated at 95° C. for 10 min; and the optical density is measured at 405 nm.

In one aspect, the variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations and has at least 50%, e.g., preferably at least 60%, preferably at least 70%, more preferably at least 80%, more preferably at least 90%, even more preferably at least 95% or most preferably at least 100% of the lysozyme activity of SEQ ID NO: 12, preferably wherein lysozyme activity is determined as described in Example 1.

For purposes of the present invention, the nomenclature [E/Q] means that the amino acid at this position may be a glutamic acid (Glu, E) or a glutamine (Gln, Q). Likewise the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION

The inventors have discovered a completely novel class of polypeptides having lysozyme activity. Said polypeptides are structurally quite different from known lysozymes. As shown in the sequence identity matrix below, the polypeptides of the present invention all have a sequence identity less than 45% to the prior art sequences disclosed in WO2013/076259, suggesting that these novel polypeptides may have a different folding pattern to known lysozymes.

|  | GH class | SEQ3 | SEQ2 | SEQ4 | SEQ6 | SEQ8 | HEWL |
|---|---|---|---|---|---|---|---|
| SEQ ID NO: 3 of present invention | Not defined | 100 | 27 | 33.3 | 43.8 | 23.3 | 30.93 |
| SEQ ID NO: 2 of WO2013/076259 | GH23 | 27 | 100 | 27 | 33.3 | 32 | 21.3 |
| SEQ ID NO: 4 of WO2013/076259 | GH24 | 33.3 | 27 | 100 | 79 | 32.7 | 33.33 |
| SEQ ID NO: 6 of WO2013/076259 | GH25 | 43.8 | 33.3 | 79 | 100 | 34.1 | 44.78 |
| SEQ ID NO: 8 of WO2013/076259 | GH25 | 23.3 | 32 | 32.7 | 34.1 | 100 | 28.97 |
| Hen Egg White (Swissprot P00698) | GH22 | 30.9 | 21.3 | 33.3 | 44.8 | 29 | 100 |

The polypeptides of the present invention demonstrate typical lysozyme activity such as activity in the traditional OD drop assay against *Micrococcus lysodeikticus* (see example 14) or a reducing ends assay using *Micrococcus lysodeikticus* as substrate (see example 13).

The polypeptides of the invention having lysozyme activity are herein named LYS polypeptides and comprise one or more LAD (Lysozyme Active Domain) catalytic domains and optionally one or more lysozyme enhancing domains (LED).

Compositions Comprising Polypeptides Having Lysozyme Activity

In the first aspect, the invention relates to a composition comprising at least 0.01 mg of LYS polypeptide per kilogram of composition, wherein the polypeptide (a) has lysozyme activity and (b) comprises one or more LAD catalytic domains; wherein the LAD catalytic domain gives a domT score of at least 180 when queried using a Profile Hidden Markov Model (HMM) prepared using SEQ ID NOs: 46 to 187 and hmmbuild software program, and wherein the query is carried out using hmmscan software program by the Method of Determining the LAD Catalytic Domain by HMM.

In an embodiment, the polypeptide further comprises one or more lysozyme enhancing domains (LED). Thus, the invention further relates to a composition comprising at least 0.01 mg of LYS polypeptide per kilogram of composition, wherein:

(a) the LYS polypeptide has lysozyme activity;
(b) the LYS polypeptide comprises one or more LAD catalytic domains; wherein the LAD catalytic domain gives a domT score of at least 180 when queried using a Profile Hidden Markov Model (HMM) prepared using SEQ ID NOs: 46 to 187 and hmmbuild software program, and wherein the query is carried out using hmmscan software program by the Method of Determining the LAD Catalytic Domain by HMM;
(c) the polypeptide comprises one or more LED domains, wherein the LED gives a domT score of at least 100 when queried using a Profile Hidden Markov Model prepared using SEQ ID NOs: 188 to 316 and hmmbuild software program, and wherein the query is carried out using the hmmscan software program.

The theory behind Profile HMMs as described in Durbin et al. (Biological sequence analysis: probabilistic models of proteins and nucleic acids, Cambridge University Press, 1998) and Krogh et al. (1994 *J. Mol. Biol.* 235:1501-1531), both incorporated herein by reference, is characterization of a set of proteins based on the probability of each amino acid occurring at each position in the alignment of the proteins of the set.

Specifically, profile HMMs are statistical models of multiple sequence alignments, or even of single sequences. They capture position-specific information about how conserved each column of the alignment is, and which residues are likely. All profile methods are more or less statistical descriptions of the consensus of a multiple sequence alignment. They use position-specific scores for amino acids or nucleotides (residues) and position specific penalties for opening and extending an insertion or deletion. Traditional pairwise alignment (for example, BLAST, FASTA or the Smith/Waterman algorithm) uses position-independent scoring parameters. This property of profiles captures important information about the degree of conservation at various positions in the multiple alignment, and the varying degree to which gaps and insertions are permitted.

The advantage of using HMMs is that HMMs have a formal probabilistic basis. Probability theory is used to guide how all the scoring parameters should be set. One of the most important aspect is that HMMs have a consistent theory for setting position-specific gap and insertion scores. The methods are consistent and therefore highly automatable, allowing hundreds of profile HMMs to be applied to e.g. whole genome analysis. An example of a protein domain model database is Pfam (Sonnhammer et al., 1997, 'A comprehensive database of protein families based on seed alignments', Proteins, 28:405-420; Finn et al., 2010, 'The Pfam protein families database', Nucl. Acids Res., 38: D211-D222), which is a significant part of the Interpro protein domain annotation system. The construction and use of Pfam is tightly tied to the HMMER software package (see en.wikipedia.org/wiki/HMMER).

The LAD catalytic domain is defined in the following manner. SEQ ID NOs: 46 to 187, which are partial sequences of the Uniprot entries as explained in the 'overview of sequence listing' section herein, are aligned using the software program MUSCLE v3.8.31 with the default settings. Using this alignment, a hidden Markov model (HMM) is built for the LAD catalytic domain. The HMM is constructed using the software program 'hmmbuild' from the package HMMER 3.0 (March 2010) (http://hmmer.org/) and the software is invoked using the default settings.

A LAD catalytic domain is defined to match the above mentioned HMM using the software program 'hmmscan' from the package HMMER 3.0 (March 2010) (http://hmmer.org/) using the default settings if the domT score is at least 170. In a preferred embodiment, the domT score is at least 175, preferably at least 180, more preferably at least 185, even more preferably at least 190, even more preferably at least 195, or most preferably at least 200.

The HMM profile of the LAD catalytic domain as generated using SEQ ID NOs: 46 to 187 according to the procedure above is given in example 10. The HMM profile can be copied into a text file which is subsequently loaded into the software program 'hmmscan' so that other polypeptides can be tested to see whether said polypeptide comprises one or more LAD catalytic domains.

The Lysozyme Enhancing Domain (LED) is defined in the following manner. SEQ ID NOs: 188 to 316, which are partial sequences of the Uniprot entries as explained in the 'overview of sequence listing' section herein, are aligned using the software program MUSCLE v3.8.31 with the default settings. Using this alignment, a hidden Markov model (HMM) is built for the LED. The HMM is constructed using the software program 'hmmbuild' from the package HMMER 3.0 (March 2010) (http://hmmer.org/) and the software is invoked using the default settings.

A LED is defined to match the above mentioned HMM using the software program 'hmmscan' from the package HMMER 3.0 (March 2010) (http://hmmer.org/) using the default settings if the domT score is at least 100. In a preferred embodiment, the domT score is at least 103, preferably at least 106, more preferably at least 109, more preferably at least 112, more preferably at least 115, more preferably at least 118, even more preferably at least 121, or most preferably at least 124.

The HMM profile of the LED as generated using SEQ ID NOs: 188 to 316 according to the procedure above is given in example 11. The HMM profile can be copied into a text file which is subsequently loaded into the software program 'hmmscan' so that other polypeptides can be tested to see whether said polypeptide comprises one or more LED.

In an embodiment, the LAD catalytic domain gives a domT score of at least 175 and the LED gives a domT score of at least 100. In an embodiment, the LAD catalytic domain gives a domT score of at least 180 and the LED gives a domT score of at least 100. In an embodiment, the LAD catalytic domain gives a domT score of at least 185 and the LED gives a domT score of at least 100. In an embodiment, the LAD catalytic domain gives a domT score of at least 190 and the LED gives a domT score of at least 100. In an embodiment, the LAD catalytic domain gives a domT score of at least 195 and the LED gives a domT score of at least 100. In an embodiment, the LAD catalytic domain gives a domT score of at least 200 and the LED gives a domT score of at least 100.

In an embodiment, the LAD catalytic domain gives a domT score of at least 175 and the LED gives a domT score of at least 103. In an embodiment, the LAD catalytic domain gives a domT score of at least 180 and the LED gives a domT score of at least 103. In an embodiment, the LAD catalytic domain gives a domT score of at least 185 and the LED gives a domT score of at least 103. In an embodiment, the LAD catalytic domain gives a domT score of at least 190 and the LED gives a domT score of at least 103. In an embodiment, the LAD catalytic domain gives a domT score of at least 195 and the LED gives a domT score of at least 103. In an embodiment, the LAD catalytic domain gives a domT score of at least 200 and the LED gives a domT score of at least 103.

In an embodiment, the LAD catalytic domain gives a domT score of at least 175 and the LED gives a domT score of at least 106. In an embodiment, the LAD catalytic domain gives a domT score of at least 180 and the LED gives a domT score of at least 106. In an embodiment, the LAD catalytic domain gives a domT score of at least 185 and the LED gives a domT score of at least 106. In an embodiment, the LAD catalytic domain gives a domT score of at least 190 and the LED gives a domT score of at least 106. In an embodiment, the LAD catalytic domain gives a domT score of at least 195 and the LED gives a domT score of at least 106. In an embodiment, the LAD catalytic domain gives a domT score of at least 200 and the LED gives a domT score of at least 106.

In an embodiment, the LAD catalytic domain gives a domT score of at least 175 and the LED gives a domT score of at least 109. In an embodiment, the LAD catalytic domain gives a domT score of at least 180 and the LED gives a domT score of at least 109. In an embodiment, the LAD catalytic domain gives a domT score of at least 185 and the LED gives a domT score of at least 109. In an embodiment, the LAD catalytic domain gives a domT score of at least 190 and the LED gives a domT score of at least 109. In an embodiment, the LAD catalytic domain gives a domT score of at least 195 and the LED gives a domT score of at least 109. In an embodiment, the LAD catalytic domain gives a domT score of at least 200 and the LED gives a domT score of at least 109.

In an embodiment, the LAD catalytic domain gives a domT score of at least 175 and the LED gives a domT score of at least 112. In an embodiment, the LAD catalytic domain gives a domT score of at least 180 and the LED gives a domT score of at least 112. In an embodiment, the LAD catalytic domain gives a domT score of at least 185 and the LED gives a domT score of at least 112. In an embodiment, the LAD catalytic domain gives a domT score of at least 190 and the LED gives a domT score of at least 112. In an embodiment, the LAD catalytic domain gives a domT score of at least 195 and the LED gives a domT score of at least 112. In an embodiment, the LAD catalytic domain gives a domT score of at least 200 and the LED gives a domT score of at least 112.

In an embodiment, the LAD catalytic domain gives a domT score of at least 175 and the LED gives a domT score of at least 115. In an embodiment, the LAD catalytic domain gives a domT score of at least 180 and the LED gives a domT score of at least 115. In an embodiment, the LAD catalytic domain gives a domT score of at least 185 and the LED gives a domT score of at least 115. In an embodiment, the LAD catalytic domain gives a domT score of at least 190 and the LED gives a domT score of at least 115. In an embodiment, the LAD catalytic domain gives a domT score of at least 195 and the LED gives a domT score of at least 115. In an embodiment, the LAD catalytic domain gives a domT score of at least 200 and the LED gives a domT score of at least 115.

In an embodiment, the LAD catalytic domain gives a domT score of at least 175 and the LED gives a domT score of at least 118. In an embodiment, the LAD catalytic domain gives a domT score of at least 180 and the LED gives a domT score of at least 118. In an embodiment, the LAD catalytic domain gives a domT score of at least 185 and the LED gives a domT score of at least 118. In an embodiment, the LAD catalytic domain gives a domT score of at least 190 and the LED gives a domT score of at least 118. In an embodiment, the LAD catalytic domain gives a domT score of at least 195 and the LED gives a domT score of at least 118. In an embodiment, the LAD catalytic domain gives a domT score of at least 200 and the LED gives a domT score of at least 118.

In an embodiment, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN](SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment of the first aspect, the invention relates to a composition comprising one or more LYS polypeptides having lysozyme activity, wherein the polypeptide is dosed at least 0.01 mg of polypeptide per kilogram of composition and is selected from the group consisting of:
(a) a polypeptide having at least 80%, e.g., at least 85%, at least 90% or at least 95% sequence identity to the polypeptide of SEQ ID NO: 3;
(b) a polypeptide having at least 80%, e.g., at least 85%, at least 90% or at least 95% sequence identity to the polypeptide of SEQ ID NO: 6;
(c) a polypeptide having at least 80%, e.g., at least 85%, at least 90% or at least 95% sequence identity to the polypeptide of SEQ ID NO: 9;
(d) a polypeptide having at least 80%, e.g., at least 85%, at least 90% or at least 95% sequence identity to the polypeptide of SEQ ID NO: 12;
(e) a polypeptide having at least 80%, e.g., at least 85%, at least 90% or at least 95% sequence identity to the polypeptide of SEQ ID NO: 15;
(f) a polypeptide having at least 80%, e.g., at least 85%, at least 90% or at least 95% sequence identity to the polypeptide of SEQ ID NO: 18;
(g) a polypeptide having at least 80%, e.g., at least 85%, at least 90% or at least 95% sequence identity to the polypeptide of SEQ ID NO: 21;
(h) a polypeptide having at least 80%, e.g., at least 85%, at least 90% or at least 95% sequence identity to the polypeptide of SEQ ID NO: 24;
(i) a polypeptide having at least 80%, e.g., at least 85%, at least 90% or at least 95% sequence identity to the polypeptide of SEQ ID NO: 27;
(j) a polypeptide having at least 80%, e.g., at least 85%, at least 90% or at least 95% sequence identity to the polypeptide of SEQ ID NO: 30;
(k) a polypeptide having at least 80%, e.g., at least 85%, at least 90% or at least 95% sequence identity to the polypeptide of SEQ ID NO: 33;

(l) a polypeptide having at least 80%, e.g., at least 85%, at least 90% or at least 95% sequence identity to the polypeptide of SEQ ID NO: 36;

(m) a polypeptide having at least 80%, e.g., at least 85%, at least 90% or at least 95% sequence identity to the polypeptide of SEQ ID NO: 39;

(n) a polypeptide having at least 80%, e.g., at least 85%, at least 90% or at least 95% sequence identity to the polypeptide of SEQ ID NO: 42;

(o) a polypeptide having at least 80%, e.g., at least 85%, at least 90% or at least 95% sequence identity to the polypeptide of SEQ ID NO: 45;

(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;

(q) a polypeptide comprising the polypeptide of (a), (b), (c), (d), (e), (f), (g), (h), (i), (j), (k), (l), (m), (n), (o) or (p) and a N-terminal and/or C-terminal His-tag and/or HQ-tag;

(r) a polypeptide comprising the polypeptide of (a), (b), (c), (d), (e), (f), (g), (h), (i), (j), (k), (l), (m), (n), (o) or (p) and a N-terminal and/or C-terminal extension of up to 10 amino acids, e.g. 1, 2, 3, 4, 5, 6, 7, 8, 9 or 10 amino acids; and (s) a fragment of the polypeptide of (a), (b), (c), (d), (e), (f), (g), (h), (i), (j), (k), (l), (m), (n), (o) or (p) having lysozyme activity and having at least 90% of the length of the mature polypeptide.

In one embodiment of the first aspect, the invention relates to a composition comprising one or more LYS polypeptides having lysozyme activity, wherein the LYS polypeptide is dosed at least 0.01 mg of polypeptide per kilogram of composition and comprises a LAD catalytic domain that is selected from the group consisting of:

(a) a polypeptide having at least 80%, e.g., at least 85%, at least 90% or at least 95% sequence identity to amino acids 84 to 226 of SEQ ID NO: 3;

(b) a polypeptide having at least 80%, e.g., at least 85%, at least 90% or at least 95% sequence identity to amino acids 84 to 226 of SEQ ID NO: 6;

(c) a polypeptide having at least 80%, e.g., at least 85%, at least 90% or at least 95% sequence identity to amino acids 81 to 220 of SEQ ID NO: 9;

(d) a polypeptide having at least 80%, e.g., at least 85%, at least 90% or at least 95% sequence identity to amino acids 161 to 304 of SEQ ID NO: 12;

(e) a polypeptide having at least 80%, e.g., at least 85%, at least 90% or at least 95% sequence identity to amino acids 85 to 228 of SEQ ID NO: 15;

(f) a polypeptide having at least 80%, e.g., at least 85%, at least 90% or at least 95% sequence identity to amino acids 88 to 230 of SEQ ID NO: 18;

(g) a polypeptide having at least 80%, e.g., at least 85%, at least 90% or at least 95% sequence identity to amino acids 87 to 230 of SEQ ID NO: 21;

(h) a polypeptide having at least 80%, e.g., at least 85%, at least 90% or at least 95% sequence identity to amino acids 90 to 232 of SEQ ID NO: 24;

(i) a polypeptide having at least 80%, e.g., at least 85%, at least 90% or at least 95% sequence identity to amino acids 85 to 228 of SEQ ID NO: 27;

(j) a polypeptide having at least 80%, e.g., at least 85%, at least 90% or at least 95% sequence identity to amino acids 85 to 228 of SEQ ID NO: 30;

(k) a polypeptide having at least 80%, e.g., at least 85%, at least 90% or at least 95% sequence identity to amino acids 84 to 226 of SEQ ID NO: 33;

(l) a polypeptide having at least 80%, e.g., at least 85%, at least 90% or at least 95% sequence identity to amino acids 83 to 222 of SEQ ID NO: 36;

(m) a polypeptide having at least 80%, e.g., at least 85%, at least 90% or at least 95% sequence identity to amino acids 82 to 225 of SEQ ID NO: 39;

(n) a polypeptide having at least 80%, e.g., at least 85%, at least 90% or at least 95% sequence identity to amino acids 161 to 303 of SEQ ID NO: 42; and (o) a polypeptide having at least 80%, e.g., at least 85%, at least 90% or at least 95% sequence identity to amino acids 85 to 227 of SEQ ID NO: 45.

In one embodiment of the first aspect, the invention relates to a composition comprising one or more LYS polypeptides having lysozyme activity, wherein the LYS polypeptide is dosed at least 0.01 mg of polypeptide per kilogram of composition and comprises a LAD catalytic domain that is selected from the group consisting of:

(a) a polypeptide having at least 80%, e.g., at least 85%, at least 90% or at least 95% sequence identity to amino acids 84 to 226 of SEQ ID NO: 3;

(b) a polypeptide having at least 80%, e.g., at least 85%, at least 90% or at least 95% sequence identity to amino acids 84 to 226 of SEQ ID NO: 6;

(c) a polypeptide having at least 80%, e.g., at least 85%, at least 90% or at least 95% sequence identity to amino acids 81 to 220 of SEQ ID NO: 9;

(d) a polypeptide having at least 80%, e.g., at least 85%, at least 90% or at least 95% sequence identity to amino acids 161 to 304 of SEQ ID NO: 12;

(e) a polypeptide having at least 80%, e.g., at least 85%, at least 90% or at least 95% sequence identity to amino acids 85 to 228 of SEQ ID NO: 15;

(f) a polypeptide having at least 80%, e.g., at least 85%, at least 90% or at least 95% sequence identity to amino acids 88 to 230 of SEQ ID NO: 18;

(g) a polypeptide having at least 80%, e.g., at least 85%, at least 90% or at least 95% sequence identity to amino acids 87 to 230 of SEQ ID NO: 21;

(h) a polypeptide having at least 80%, e.g., at least 85%, at least 90% or at least 95% sequence identity to amino acids 90 to 232 of SEQ ID NO: 24;

(i) a polypeptide having at least 80%, e.g., at least 85%, at least 90% or at least 95% sequence identity to amino acids 85 to 228 of SEQ ID NO: 27;

(j) a polypeptide having at least 80%, e.g., at least 85%, at least 90% or at least 95% sequence identity to amino acids 85 to 228 of SEQ ID NO: 30;

(k) a polypeptide having at least 80%, e.g., at least 85%, at least 90% or at least 95% sequence identity to amino acids 84 to 226 of SEQ ID NO: 33;

(l) a polypeptide having at least 80%, e.g., at least 85%, at least 90% or at least 95% sequence identity to amino acids 83 to 222 of SEQ ID NO: 36;

(m) a polypeptide having at least 80%, e.g., at least 85%, at least 90% or at least 95% sequence identity to amino acids 82 to 225 of SEQ ID NO: 39;

(n) a polypeptide having at least 80%, e.g., at least 85%, at least 90% or at least 95% sequence identity to amino acids 161 to 303 of SEQ ID NO: 42; and (o) a polypeptide having at least 80%, e.g., at least 85%, at least 90% or at least 95% sequence identity to amino acids 85 to 227 of SEQ ID NO: 45;

and wherein the LYS polypeptide comprises a LED domain that is selected from the group consisting of:

(a) a polypeptide having at least 80%, e.g., at least 85%, at least 90% or at least 95% sequence identity to amino acids 1 to 73 of SEQ ID NO: 3;

(b) a polypeptide having at least 80%, e.g., at least 85%, at least 90% or at least 95% sequence identity to amino acids 1 to 73 of SEQ ID NO: 6;

(c) a polypeptide having at least 80%, e.g., at least 85%, at least 90% or at least 95% sequence identity to amino acids 1 to 73 of SEQ ID NO: 9;

(d) a polypeptide having at least 80%, e.g., at least 85%, at least 90% or at least 95% sequence identity to amino acids 1 to 72 of SEQ ID NO: 12;

(e) a polypeptide having at least 80%, e.g., at least 85%, at least 90% or at least 95% sequence identity to amino acids 1 to 73 of SEQ ID NO: 15;

(f) a polypeptide having at least 80%, e.g., at least 85%, at least 90% or at least 95% sequence identity to amino acids 1 to 73 of SEQ ID NO: 18;

(g) a polypeptide having at least 80%, e.g., at least 85%, at least 90% or at least 95% sequence identity to amino acids 1 to 73 of SEQ ID NO: 21;

(h) a polypeptide having at least 80%, e.g., at least 85%, at least 90% or at least 95% sequence identity to amino acids 1 to 73 of SEQ ID NO: 24;

(i) a polypeptide having at least 80%, e.g., at least 85%, at least 90% or at least 95% sequence identity to amino acids 1 to 73 of SEQ ID NO: 27;

(j) a polypeptide having at least 80%, e.g., at least 85%, at least 90% or at least 95% sequence identity to amino acids 1 to 73 of SEQ ID NO: 30;

(k) a polypeptide having at least 80%, e.g., at least 85%, at least 90% or at least 95% sequence identity to amino acids 1 to 73 of SEQ ID NO: 33;

(l) a polypeptide having at least 80%, e.g., at least 85%, at least 90% or at least 95% sequence identity to amino acids 1 to 73 of SEQ ID NO: 36;

(m) a polypeptide having at least 80%, e.g., at least 85%, at least 90% or at least 95% sequence identity to amino acids 1 to 72 of SEQ ID NO: 39;

(n) a polypeptide having at least 80%, e.g., at least 85%, at least 90% or at least 95% sequence identity to amino acids 1 to 73 of SEQ ID NO: 42;

(o) a polypeptide having at least 80%, e.g., at least 85%, at least 90% or at least 95% sequence identity to amino acids 1 to 73 of SEQ ID NO: 45;

(d) a polypeptide having at least 80%, e.g., at least 85%, at least 90% or at least 95% sequence identity to amino acids 96 to 167 of SEQ ID NO: 12; and (n) a polypeptide having at least 80%, e.g., at least 85%, at least 90% or at least 95% sequence identity to amino acids 96 to 168 of SEQ ID NO: 42.

In one embodiment to any part of the first aspect, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment to any part of the first aspect, the polypeptide is of fungal origin. In an embodiment, the polypeptide is obtained or obtainable from the taxonomic phylum Ascomycota, preferably the taxonomic subphylum Pezizomycotina.

In one embodiment to any part of the first aspect, the composition comprises at least 0.01 mg of polypeptide (enzyme protein) per kilogram of composition, such as at least 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g, 75 g or 100 g per kilogram of composition. In one embodiment, the composition comprises at most 250 g of polypeptide per kilogram of composition, such as at most 150 g, 100 g, 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition. In one embodiment, the composition comprises between 0.01 mg and 250 g of polypeptide (enzyme protein) per kilogram of composition, such as between 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g, 75 g or 100 g per kilogram of composition and 150 g, 100 g, 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition, or any combination thereof.

In one embodiment to any part of the first aspect, the composition comprises one or more formulating agents (such as those described herein), preferably a formulating agent selected from the list consisting of glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose, preferably selected from the list consisting of 1,2-propylene glycol, 1,3-propylene glycol, sodium sulfate, dextrin, cellulose, sodium thiosulfate, kaolin and calcium carbonate.

In one embodiment to any part of the first aspect, the composition comprises one or more additional enzymes. The one or more additional enzymes is preferably selected from the group consisting of acetyl xylan esterase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lipase, lysophospholipase, lysozyme, mannanase, alpha-mannosidase, beta-mannosidase, phytase, phospholipase A1, phospholipase A2, phospholipase C, phospholipase D, protease, pullulanase, pectinase, pectin lyase, xylanase, beta-xylosidase or any combination thereof.

In one embodiment to any part of the first aspect, the composition comprises one or more probiotics. The one or more probiotics is preferably selected from the group consisting of *Bacillus subtilis, Bacillus lichenformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium sp., Carnobacterium sp., Clostridium butyricum, Clostridium sp., Enterococcus faecium, Enterococcus sp., Lactobacillus sp., Lactobacillus acidophilus, Lactobacillus farciminus, Lactobacillus rhamnosus, Lactobacillus reuteri, Lactobacillus salivarius, Lactococcus lactis, Lactococcus sp., Leuconostoc sp., Megasphaera elsdenii, Megasphaera sp., Pediococsus acidilactici, Pediococcus sp., Propionibacterium thoenii, Propionibacterium sp.* and *Streptococcus sp.* or any combination thereof.

Granules Comprising Polypeptides Having Lysozyme Activity

In a second aspect, the invention relates to a granule comprising a LYS polypeptide, wherein the polypeptide (a) has lysozyme activity and (b) comprises one or more LAD catalytic domains; wherein the LAD catalytic domain gives a domT score of at least 180 when queried using a Profile Hidden Markov Model (HMM) prepared using SEQ ID NOs: 46 to 187 and hmmbuild software program, and wherein the query is carried out using hmmscan software program by the Method of Determining the LAD Catalytic Domain by HMM. In one embodiment, the granule comprises a core particle and one or more coatings. In a preferred embodiment, the coating comprises salt and/or wax and/or flour. Preferred formulations are disclosed in the formulation section below.

In an embodiment, the polypeptide further comprises one or more lysozyme enhancing domains (LED). Thus, the invention further relates to a granule comprising a LYS polypeptide, wherein:
  (a) the LYS polypeptide has lysozyme activity;
  (b) the LYS polypeptide comprises one or more LAD catalytic domains, wherein the LAD catalytic domain gives a domT score of at least 170 when queried using a Profile Hidden Markov Model prepared using SEQ ID NOs: 46 to 187 and hmmbuild software program, and wherein the query is carried out using hmmscan software program by the Method of Determining the LAD Catalytic Domain by HMM;
  (c) the polypeptide comprises one or more LED domains, wherein the LED gives a domT score of at least 100 when queried using a Profile Hidden Markov Model prepared using SEQ ID NOs: 188 to 316 and hmmbuild software program, and typically wherein the query is carried out using the hmmscan software program by the Method of Determining the Lysozyme Enhancing Domain by HMM.

In one embodiment, the granule comprises a core particle and one or more coatings. In a preferred embodiment, the coating comprises salt and/or wax and/or flour. Preferred formulations are disclosed in the formulation section below.

In an embodiment, the domT score of the LAD catalytic domain is at least 175, preferably at least 180, more preferably at least 185, even more preferably at least 190, even more preferably at least 195, or most preferably at least 200. In an embodiment, the domT score of the LED is at least 103, preferably at least 106, more preferably at least 109, more preferably at least 112, more preferably at least 115, more preferably at least 118, even more preferably at least 121, or most preferably at least 124. Preferred combinations of domT scores are as disclosed in the first aspect of the invention.

In an embodiment, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN](SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment of the second aspect, the invention relates to a granule comprising one or more LYS polypeptides having lysozyme activity, wherein the LYS polypeptide is selected from the group consisting of:
  (a) a polypeptide having at least 80%, e.g., at least 85%, at least 90% or at least 95% sequence identity to the polypeptide of SEQ ID NO: 3;
  (b) a polypeptide having at least 80%, e.g., at least 85%, at least 90% or at least 95% sequence identity to the polypeptide of SEQ ID NO: 6;
  (c) a polypeptide having at least 80%, e.g., at least 85%, at least 90% or at least 95% sequence identity to the polypeptide of SEQ ID NO: 9;
  (d) a polypeptide having at least 80%, e.g., at least 85%, at least 90% or at least 95% sequence identity to the polypeptide of SEQ ID NO: 12;
  (e) a polypeptide having at least 80%, e.g., at least 85%, at least 90% or at least 95% sequence identity to the polypeptide of SEQ ID NO: 15;
  (f) a polypeptide having at least 80%, e.g., at least 85%, at least 90% or at least 95% sequence identity to the polypeptide of SEQ ID NO: 18;
  (g) a polypeptide having at least 80%, e.g., at least 85%, at least 90% or at least 95% sequence identity to the polypeptide of SEQ ID NO: 21;
  (h) a polypeptide having at least 80%, e.g., at least 85%, at least 90% or at least 95% sequence identity to the polypeptide of SEQ ID NO: 24;
  (i) a polypeptide having at least 80%, e.g., at least 85%, at least 90% or at least 95% sequence identity to the polypeptide of SEQ ID NO: 27;
  (j) a polypeptide having at least 80%, e.g., at least 85%, at least 90% or at least 95% sequence identity to the polypeptide of SEQ ID NO: 30;

(k) a polypeptide having at least 80%, e.g., at least 85%, at least 90% or at least 95% sequence identity to the polypeptide of SEQ ID NO: 33;

(l) a polypeptide having at least 80%, e.g., at least 85%, at least 90% or at least 95% sequence identity to the polypeptide of SEQ ID NO: 36;

(m) a polypeptide having at least 80%, e.g., at least 85%, at least 90% or at least 95% sequence identity to the polypeptide of SEQ ID NO: 39;

(n) a polypeptide having at least 80%, e.g., at least 85%, at least 90% or at least 95% sequence identity to the polypeptide of SEQ ID NO: 42;

(o) a polypeptide having at least 80%, e.g., at least 85%, at least 90% or at least 95% sequence identity to the polypeptide of SEQ ID NO: 45;

(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;

(q) a polypeptide comprising the polypeptide of (a), (b), (c), (d), (e), (f), (g), (h), (i), (j), (k), (l), (m), (n), (o) or (p) and a N-terminal and/or C-terminal His-tag and/or HQ-tag;

(r) a polypeptide comprising the polypeptide of (a), (b), (c), (d), (e), (f), (g), (h), (i), (j), (k), (l), (m), (n), (o) or (p) and a N-terminal and/or C-terminal extension of up to 10 amino acids, e.g. 1, 2, 3, 4, 5, 6, 7, 8, 9 or 10 amino acids; and (s) a fragment of the polypeptide of (a), (b), (c), (d), (e), (f), (g), (h), (i), (j), (k), (l), (m), (n), (o) or (p) having lysozyme activity and having at least 90% of the length of the mature polypeptide.

In one embodiment, the granule comprises a core particle and one or more coatings. In a preferred embodiment, the coating comprises salt and/or wax and/or flour. Preferred formulations are disclosed in the formulation section below.

In one embodiment of the second aspect, the invention relates to a granule comprising one or more LYS polypeptides having lysozyme activity, wherein the LYS polypeptide comprises a LAD catalytic domain that is selected from the group consisting of:

(a) a polypeptide having at least 80%, e.g., at least 85%, at least 90% or at least 95% sequence identity to amino acids 84 to 226 of SEQ ID NO: 3;

(b) a polypeptide having at least 80%, e.g., at least 85%, at least 90% or at least 95% sequence identity to amino acids 84 to 226 of SEQ ID NO: 6;

(c) a polypeptide having at least 80%, e.g., at least 85%, at least 90% or at least 95% sequence identity to amino acids 81 to 220 of SEQ ID NO: 9;

(d) a polypeptide having at least 80%, e.g., at least 85%, at least 90% or at least 95% sequence identity to amino acids 161 to 304 of SEQ ID NO: 12;

(e) a polypeptide having at least 80%, e.g., at least 85%, at least 90% or at least 95% sequence identity to amino acids 85 to 228 of SEQ ID NO: 15;

(f) a polypeptide having at least 80%, e.g., at least 85%, at least 90% or at least 95% sequence identity to amino acids 88 to 230 of SEQ ID NO: 18;

(g) a polypeptide having at least 80%, e.g., at least 85%, at least 90% or at least 95% sequence identity to amino acids 87 to 230 of SEQ ID NO: 21;

(h) a polypeptide having at least 80%, e.g., at least 85%, at least 90% or at least 95% sequence identity to amino acids 90 to 232 of SEQ ID NO: 24;

(i) a polypeptide having at least 80%, e.g., at least 85%, at least 90% or at least 95% sequence identity to amino acids 85 to 228 of SEQ ID NO: 27;

(j) a polypeptide having at least 80%, e.g., at least 85%, at least 90% or at least 95% sequence identity to amino acids 85 to 228 of SEQ ID NO: 30;

(k) a polypeptide having at least 80%, e.g., at least 85%, at least 90% or at least 95% sequence identity to amino acids 84 to 226 of SEQ ID NO: 33;

(l) a polypeptide having at least 80%, e.g., at least 85%, at least 90% or at least 95% sequence identity to amino acids 83 to 222 of SEQ ID NO: 36;

(m) a polypeptide having at least 80%, e.g., at least 85%, at least 90% or at least 95% sequence identity to amino acids 82 to 225 of SEQ ID NO: 39;

(n) a polypeptide having at least 80%, e.g., at least 85%, at least 90% or at least 95% sequence identity to amino acids 161 to 303 of SEQ ID NO: 42; and (o) a polypeptide having at least 80%, e.g., at least 85%, at least 90% or at least 95% sequence identity to amino acids 85 to 227 of SEQ ID NO: 45.

In one embodiment of the second aspect, the invention relates to a granule comprising one or more LYS polypeptides having lysozyme activity, wherein the LYS polypeptide comprises a LAD catalytic domain that is selected from the group consisting of:

(a) a polypeptide having at least 80%, e.g., at least 85%, at least 90% or at least 95% sequence identity to amino acids 84 to 226 of SEQ ID NO: 3;

(b) a polypeptide having at least 80%, e.g., at least 85%, at least 90% or at least 95% sequence identity to amino acids 84 to 226 of SEQ ID NO: 6;

(c) a polypeptide having at least 80%, e.g., at least 85%, at least 90% or at least 95% sequence identity to amino acids 81 to 220 of SEQ ID NO: 9;

(d) a polypeptide having at least 80%, e.g., at least 85%, at least 90% or at least 95% sequence identity to amino acids 161 to 304 of SEQ ID NO: 12;

(e) a polypeptide having at least 80%, e.g., at least 85%, at least 90% or at least 95% sequence identity to amino acids 85 to 228 of SEQ ID NO: 15;

(f) a polypeptide having at least 80%, e.g., at least 85%, at least 90% or at least 95% sequence identity to amino acids 88 to 230 of SEQ ID NO: 18;

(g) a polypeptide having at least 80%, e.g., at least 85%, at least 90% or at least 95% sequence identity to amino acids 87 to 230 of SEQ ID NO: 21;

(h) a polypeptide having at least 80%, e.g., at least 85%, at least 90% or at least 95% sequence identity to amino acids 90 to 232 of SEQ ID NO: 24;

(i) a polypeptide having at least 80%, e.g., at least 85%, at least 90% or at least 95% sequence identity to amino acids 85 to 228 of SEQ ID NO: 27;

(j) a polypeptide having at least 80%, e.g., at least 85%, at least 90% or at least 95% sequence identity to amino acids 85 to 228 of SEQ ID NO: 30;

(k) a polypeptide having at least 80%, e.g., at least 85%, at least 90% or at least 95% sequence identity to amino acids 84 to 226 of SEQ ID NO: 33;

(l) a polypeptide having at least 80%, e.g., at least 85%, at least 90% or at least 95% sequence identity to amino acids 83 to 222 of SEQ ID NO: 36;

(m) a polypeptide having at least 80%, e.g., at least 85%, at least 90% or at least 95% sequence identity to amino acids 82 to 225 of SEQ ID NO: 39;

(n) a polypeptide having at least 80%, e.g., at least 85%, at least 90% or at least 95% sequence identity to amino acids 161 to 303 of SEQ ID NO: 42; and (o) a polypeptide having at least 80%, e.g., at least 85%, at least 90% or at least 95% sequence identity to amino acids 85 to 227 of SEQ ID NO: 45;

and wherein the LYS polypeptide comprises a LED domain that is selected from the group consisting of:

(a) a polypeptide having at least 80%, e.g., at least 85%, at least 90% or at least 95% sequence identity to amino acids 1 to 73 of SEQ ID NO: 3;

(b) a polypeptide having at least 80%, e.g., at least 85%, at least 90% or at least 95% sequence identity to amino acids 1 to 73 of SEQ ID NO: 6;

(c) a polypeptide having at least 80%, e.g., at least 85%, at least 90% or at least 95% sequence identity to amino acids 1 to 73 of SEQ ID NO: 9;

(d) a polypeptide having at least 80%, e.g., at least 85%, at least 90% or at least 95% sequence identity to amino acids 1 to 72 of SEQ ID NO: 12;

(e) a polypeptide having at least 80%, e.g., at least 85%, at least 90% or at least 95% sequence identity to amino acids 1 to 73 of SEQ ID NO: 15;

(f) a polypeptide having at least 80%, e.g., at least 85%, at least 90% or at least 95% sequence identity to amino acids 1 to 73 of SEQ ID NO: 18;

(g) a polypeptide having at least 80%, e.g., at least 85%, at least 90% or at least 95% sequence identity to amino acids 1 to 73 of SEQ ID NO: 21;

(h) a polypeptide having at least 80%, e.g., at least 85%, at least 90% or at least 95% sequence identity to amino acids 1 to 73 of SEQ ID NO: 24;

(i) a polypeptide having at least 80%, e.g., at least 85%, at least 90% or at least 95% sequence identity to amino acids 1 to 73 of SEQ ID NO: 27;

(j) a polypeptide having at least 80%, e.g., at least 85%, at least 90% or at least 95% sequence identity to amino acids 1 to 73 of SEQ ID NO: 30;

(k) a polypeptide having at least 80%, e.g., at least 85%, at least 90% or at least 95% sequence identity to amino acids 1 to 73 of SEQ ID NO: 33;

(l) a polypeptide having at least 80%, e.g., at least 85%, at least 90% or at least 95% sequence identity to amino acids 1 to 73 of SEQ ID NO: 36;

(m) a polypeptide having at least 80%, e.g., at least 85%, at least 90% or at least 95% sequence identity to amino acids 1 to 72 of SEQ ID NO: 39;

(n) a polypeptide having at least 80%, e.g., at least 85%, at least 90% or at least 95% sequence identity to amino acids 1 to 73 of SEQ ID NO: 42;

(o) a polypeptide having at least 80%, e.g., at least 85%, at least 90% or at least 95% sequence identity to amino acids 1 to 73 of SEQ ID NO: 45;

(d) a polypeptide having at least 80%, e.g., at least 85%, at least 90% or at least 95% sequence identity to amino acids 96 to 167 of SEQ ID NO: 12; and (n) a polypeptide having at least 80%, e.g., at least 85%, at least 90% or at least 95% sequence identity to amino acids 96 to 168 of SEQ ID NO: 42.

In one embodiment, the granule comprises a core particle and one or more coatings. In a preferred embodiment, the coating comprises salt and/or wax and/or flour. Preferred formulations are disclosed in the formulation section below.

In one embodiment to any part of the second aspect, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment to any part of the second aspect, the polypeptide is of fungal origin. In an embodiment, the polypeptide is obtained or obtainable from the taxonomic phylum Ascomycota, preferably the taxonomic subphylum Pezizomycotina.

In one embodiment to any part of the first aspect, the composition comprises at least 0.01 mg of polypeptide (enzyme protein) per kilogram of composition, such as at least 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g, 75 g or 100 g per kilogram of composition. In one embodiment, the composition comprises at most 250 g of polypeptide per kilogram of composition, such as at most 150 g, 100 g, 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition. In one embodiment, the composition comprises between 0.01 mg and 250 g of polypeptide (enzyme protein) per kilogram of composition, such as between 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g, 75 g or 100 g per kilogram of composition and 150 g, 100 g, 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition, or any combination thereof.

In one embodiment to any part of the second aspect, the granule comprises one or more formulating agents (such as those described herein), preferably a formulating agent selected from the list consisting of glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose, preferably selected from the list consisting of 1,2-propylene glycol, 1,3-propylene glycol, sodium sulfate, dextrin, cellulose, sodium thiosulfate, kaolin and calcium carbonate.

In one embodiment to any part of the second aspect, the granule comprises a core particle and one or more coatings. In a preferred embodiment, the coating comprises salt and/or wax and/or flour. Preferred formulations are disclosed in the formulation section below.

In one embodiment to any part of the second aspect, the granule comprises one or more additional enzymes. The one or more additional enzymes is preferably selected from the group consisting of acetyl xylan esterase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lipase, lysophospholipase, lysozyme, mannanase, alpha-mannosidase, beta-mannosidase, phytase, phospholipase A1, phospholipase A2, phospholipase C, phospholipase D, protease, pullulanase, pectinase, pectin lyase, xylanase, beta-xylosidase or any combination thereof.

In one embodiment to any part of the second aspect, the granule comprises one or more probiotics. The one or more probiotics is preferably selected from the group consisting of *Bacillus subtilis, Bacillus lichenformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp. and *Streptococcus* sp. or any combination thereof.

Liquid Formulations Comprising Polypeptides Having Lysozyme Activity

In a third aspect, the invention relates to liquid formulations, wherein the liquid formulation comprises:
(a) 0.01% to 25% w/w of LYS polypeptide wherein:
 (i) the LYS polypeptide has lysozyme activity;
 (ii) the LYS polypeptide comprises one or more LAD catalytic domains, wherein the LAD catalytic domain gives a domT score of at least 170 when queried using a Profile Hidden Markov Model prepared using SEQ ID NOs: 46 to 187 and hmmbuild software program, and wherein the query is carried out using hmmscan software program by the Method of Determining the LAD Catalytic Domain by HMM;
(b) 20% to 80% w/w of polyol;
(c) 0.01% to 2.0% w/w preservative; and
(d) water.

In an embodiment, the domT score of the LAD catalytic domain is at least 175, preferably at least 180, more preferably at least 185, even more preferably at least 190, even more preferably at least 195, or most preferably at least 200. In an embodiment, the domT score of the LED is at least 103, preferably at least 106, more preferably at least 109, more preferably at least 112, more preferably at least 115, more preferably at least 118, even more preferably at least 121, or most preferably at least 124. Preferred combinations of domT scores are as disclosed in the first aspect of the invention.

In an embodiment, the polypeptide further comprises one or more lysozyme enhancing domains (LED). Thus, the invention further relates to a liquid formulation, wherein the liquid formulation comprises:
(a) 0.01% to 25% w/w of LYS polypeptide wherein:
 (i) the LYS polypeptide has lysozyme activity;
 (ii) the LYS polypeptide comprises one or more LAD catalytic domains, wherein the LAD catalytic domain gives a domT score of at least 170 when queried using a Profile Hidden Markov Model prepared using SEQ ID NOs: 46 to 187 and hmmbuild software program, and wherein the query is carried out using hmmscan software program by the Method of Determining the LAD Catalytic Domain by HMM;
 (iii) the LYS polypeptide comprises one or more LED domains, wherein the LED gives a domT score of at least 100 when queried using a Profile Hidden Markov Model prepared using SEQ ID NOs: 188 to 316 and hmmbuild software program, and wherein the query is carried out using the hmmscan software program by the Method of Determining the Lysozyme Enhancing Domain by HMM;
(b) 20% to 80% w/w of polyol;
(c) 0.01% to 2.0% w/w preservative; and
(d) water.

In an embodiment, the domT score of the LAD catalytic domain is at least 175, preferably at least 180, more preferably at least 185, even more preferably at least 190, even more preferably at least 195, or most preferably at least 200. In an embodiment, the domT score of the LED is at least 103, preferably at least 106, more preferably at least 109, more preferably at least 112, more preferably at least 115, more preferably at least 118, even more preferably at least 121, or most preferably at least 124. Preferred combinations of domT scores are as disclosed in the first aspect of the invention.

In one embodiment of the third aspect, the invention relates to a liquid formulation comprising one or more LYS polypeptides having lysozyme activity, wherein the liquid formulation comprises:
(A) 0.01% to 25% w/w of LYS polypeptide wherein the LYS polypeptide is selected from the group consisting of:
 (a) a polypeptide having at least 80%, e.g., at least 85%, at least 90% or at least 95% sequence identity to the polypeptide of SEQ ID NO: 3;
 (b) a polypeptide having at least 80%, e.g., at least 85%, at least 90% or at least 95% sequence identity to the polypeptide of SEQ ID NO: 6;
 (c) a polypeptide having at least 80%, e.g., at least 85%, at least 90% or at least 95% sequence identity to the polypeptide of SEQ ID NO: 9;
 (d) a polypeptide having at least 80%, e.g., at least 85%, at least 90% or at least 95% sequence identity to the polypeptide of SEQ ID NO: 12;
 (e) a polypeptide having at least 80%, e.g., at least 85%, at least 90% or at least 95% sequence identity to the polypeptide of SEQ ID NO: 15;
 (f) a polypeptide having at least 80%, e.g., at least 85%, at least 90% or at least 95% sequence identity to the polypeptide of SEQ ID NO: 18;
 (g) a polypeptide having at least 80%, e.g., at least 85%, at least 90% or at least 95% sequence identity to the polypeptide of SEQ ID NO: 21;

(h) a polypeptide having at least 80%, e.g., at least 85%, at least 90% or at least 95% sequence identity to the polypeptide of SEQ ID NO: 24;
(i) a polypeptide having at least 80%, e.g., at least 85%, at least 90% or at least 95% sequence identity to the polypeptide of SEQ ID NO: 27;
(j) a polypeptide having at least 80%, e.g., at least 85%, at least 90% or at least 95% sequence identity to the polypeptide of SEQ ID NO: 30;
(k) a polypeptide having at least 80%, e.g., at least 85%, at least 90% or at least 95% sequence identity to the polypeptide of SEQ ID NO: 33;
(l) a polypeptide having at least 80%, e.g., at least 85%, at least 90% or at least 95% sequence identity to the polypeptide of SEQ ID NO: 36;
(m) a polypeptide having at least 80%, e.g., at least 85%, at least 90% or at least 95% sequence identity to the polypeptide of SEQ ID NO: 39;
(n) a polypeptide having at least 80%, e.g., at least 85%, at least 90% or at least 95% sequence identity to the polypeptide of SEQ ID NO: 42;
(o) a polypeptide having at least 80%, e.g., at least 85%, at least 90% or at least 95% sequence identity to the polypeptide of SEQ ID NO: 45;
(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;
(q) a polypeptide comprising the polypeptide of (a), (b), (c), (d), (e), (f), (g), (h), (i), (j), (k), (l), (m), (n), (o) or (p) and a N-terminal and/or C-terminal His-tag and/or HQ-tag;
(r) a polypeptide comprising the polypeptide of (a), (b), (c), (d), (e), (f), (g), (h), (i), j), (k), (l), (m), (n), (o) or (p) and a N-terminal and/or C-terminal extension of up to 10 amino acids, e.g. 1, 2, 3, 4, 5, 6, 7, 8, 9 or 10 amino acids; and
(s) a fragment of the polypeptide of (a), (b), (c), (d), (e), (f), (g), (h), (i), j), (k), (l), (m), (n), (o) or (p) having lysozyme activity and having at least 90% of the length of the mature polypeptide;
(B) 20% to 80% w/w of polyol;
(D) 0.01% to 2.0% w/w preservative; and
(D) water.

In one embodiment of the third aspect, the invention relates to a liquid formulation comprising one or more LYS polypeptides having lysozyme activity, wherein the liquid formulation comprises:
(A) 0.01% to 25% w/w of LYS polypeptide wherein the LYS polypeptide comprises a LAD catalytic domain that is selected from the group consisting of:
(a) a polypeptide having at least 80%, e.g., at least 85%, at least 90% or at least 95% sequence identity to amino acids 84 to 226 of SEQ ID NO: 3;
(b) a polypeptide having at least 80%, e.g., at least 85%, at least 90% or at least 95% sequence identity to amino acids 84 to 226 of SEQ ID NO: 6;
(c) a polypeptide having at least 80%, e.g., at least 85%, at least 90% or at least 95% sequence identity to amino acids 81 to 220 of SEQ ID NO: 9;
(d) a polypeptide having at least 80%, e.g., at least 85%, at least 90% or at least 95% sequence identity to amino acids 161 to 304 of SEQ ID NO: 12;
(e) a polypeptide having at least 80%, e.g., at least 85%, at least 90% or at least 95% sequence identity to amino acids 85 to 228 of SEQ ID NO: 15;
(f) a polypeptide having at least 80%, e.g., at least 85%, at least 90% or at least 95% sequence identity to amino acids 88 to 230 of SEQ ID NO: 18;
(g) a polypeptide having at least 80%, e.g., at least 85%, at least 90% or at least 95% sequence identity to amino acids 87 to 230 of SEQ ID NO: 21;
(h) a polypeptide having at least 80%, e.g., at least 85%, at least 90% or at least 95% sequence identity to amino acids 90 to 232 of SEQ ID NO: 24;
(i) a polypeptide having at least 80%, e.g., at least 85%, at least 90% or at least 95% sequence identity to amino acids 85 to 228 of SEQ ID NO: 27;
(j) a polypeptide having at least 80%, e.g., at least 85%, at least 90% or at least 95% sequence identity to amino acids 85 to 228 of SEQ ID NO: 30;
(k) a polypeptide having at least 80%, e.g., at least 85%, at least 90% or at least 95% sequence identity to amino acids 84 to 226 of SEQ ID NO: 33;
(l) a polypeptide having at least 80%, e.g., at least 85%, at least 90% or at least 95% sequence identity to amino acids 83 to 222 of SEQ ID NO: 36;
(m) a polypeptide having at least 80%, e.g., at least 85%, at least 90% or at least 95% sequence identity to amino acids 82 to 225 of SEQ ID NO: 39;
(n) a polypeptide having at least 80%, e.g., at least 85%, at least 90% or at least 95% sequence identity to amino acids 161 to 303 of SEQ ID NO: 42; and
(o) a polypeptide having at least 80%, e.g., at least 85%, at least 90% or at least 95% sequence identity to amino acids 85 to 227 of SEQ ID NO: 45;
(B) 20% to 80% w/w of polyol;
(C) 0.01% to 2.0% w/w preservative; and
(D) water.

In one embodiment of the third aspect, the invention relates to a liquid formulation comprising one or more LYS polypeptides having lysozyme activity, wherein the liquid formulation comprises:
(A) 0.01% to 25% w/w of LYS polypeptide wherein the LYS polypeptide comprises a LAD catalytic domain that is selected from the group consisting of:
(a) a polypeptide having at least 80%, e.g., at least 85%, at least 90% or at least 95% sequence identity to amino acids 84 to 226 of SEQ ID NO: 3;
(b) a polypeptide having at least 80%, e.g., at least 85%, at least 90% or at least 95% sequence identity to amino acids 84 to 226 of SEQ ID NO: 6;
(c) a polypeptide having at least 80%, e.g., at least 85%, at least 90% or at least 95% sequence identity to amino acids 81 to 220 of SEQ ID NO: 9;
(d) a polypeptide having at least 80%, e.g., at least 85%, at least 90% or at least 95% sequence identity to amino acids 161 to 304 of SEQ ID NO: 12;
(e) a polypeptide having at least 80%, e.g., at least 85%, at least 90% or at least 95% sequence identity to amino acids 85 to 228 of SEQ ID NO: 15;
(f) a polypeptide having at least 80%, e.g., at least 85%, at least 90% or at least 95% sequence identity to amino acids 88 to 230 of SEQ ID NO: 18;

(g) a polypeptide having at least 80%, e.g., at least 85%, at least 90% or at least 95% sequence identity to amino acids 87 to 230 of SEQ ID NO: 21;
(h) a polypeptide having at least 80%, e.g., at least 85%, at least 90% or at least 95% sequence identity to amino acids 90 to 232 of SEQ ID NO: 24;
(i) a polypeptide having at least 80%, e.g., at least 85%, at least 90% or at least 95% sequence identity to amino acids 85 to 228 of SEQ ID NO: 27;
(j) a polypeptide having at least 80%, e.g., at least 85%, at least 90% or at least 95% sequence identity to amino acids 85 to 228 of SEQ ID NO: 30;
(k) a polypeptide having at least 80%, e.g., at least 85%, at least 90% or at least 95% sequence identity to amino acids 84 to 226 of SEQ ID NO: 33;
(l) a polypeptide having at least 80%, e.g., at least 85%, at least 90% or at least 95% sequence identity to amino acids 83 to 222 of SEQ ID NO: 36;
(m) a polypeptide having at least 80%, e.g., at least 85%, at least 90% or at least 95% sequence identity to amino acids 82 to 225 of SEQ ID NO: 39;
(n) a polypeptide having at least 80%, e.g., at least 85%, at least 90% or at least 95% sequence identity to amino acids 161 to 303 of SEQ ID NO: 42; and
(o) a polypeptide having at least 80%, e.g., at least 85%, at least 90% or at least 95% sequence identity to amino acids 85 to 227 of SEQ ID NO: 45;
(B) the LYS polypeptide comprises a LED domain selected from the group consisting of:
(a) a polypeptide having at least 80%, e.g., at least 85%, at least 90% or at least 95% sequence identity to amino acids 1 to 73 of SEQ ID NO: 3;
(b) a polypeptide having at least 80%, e.g., at least 85%, at least 90% or at least 95% sequence identity to amino acids 1 to 73 of SEQ ID NO: 6;
(c) a polypeptide having at least 80%, e.g., at least 85%, at least 90% or at least 95% sequence identity to amino acids 1 to 73 of SEQ ID NO: 9;
(d) a polypeptide having at least 80%, e.g., at least 85%, at least 90% or at least 95% sequence identity to amino acids 1 to 72 of SEQ ID NO: 12;
(e) a polypeptide having at least 80%, e.g., at least 85%, at least 90% or at least 95% sequence identity to amino acids 1 to 73 of SEQ ID NO: 15;
(f) a polypeptide having at least 80%, e.g., at least 85%, at least 90% or at least 95% sequence identity to amino acids 1 to 73 of SEQ ID NO: 18;
(g) a polypeptide having at least 80%, e.g., at least 85%, at least 90% or at least 95% sequence identity to amino acids 1 to 73 of SEQ ID NO: 21;
(h) a polypeptide having at least 80%, e.g., at least 85%, at least 90% or at least 95% sequence identity to amino acids 1 to 73 of SEQ ID NO: 24;
(i) a polypeptide having at least 80%, e.g., at least 85%, at least 90% or at least 95% sequence identity to amino acids 1 to 73 of SEQ ID NO: 27;
(j) a polypeptide having at least 80%, e.g., at least 85%, at least 90% or at least 95% sequence identity to amino acids 1 to 73 of SEQ ID NO: 30;
(k) a polypeptide having at least 80%, e.g., at least 85%, at least 90% or at least 95% sequence identity to amino acids 1 to 73 of SEQ ID NO: 33;
(l) a polypeptide having at least 80%, e.g., at least 85%, at least 90% or at least 95% sequence identity to amino acids 1 to 73 of SEQ ID NO: 36;
(m) a polypeptide having at least 80%, e.g., at least 85%, at least 90% or at least 95% sequence identity to amino acids 1 to 72 of SEQ ID NO: 39;
(n) a polypeptide having at least 80%, e.g., at least 85%, at least 90% or at least 95% sequence identity to amino acids 1 to 73 of SEQ ID NO: 42;
(o) a polypeptide having at least 80%, e.g., at least 85%, at least 90% or at least 95% sequence identity to amino acids 1 to 73 of SEQ ID NO: 45;
(d) a polypeptide having at least 80%, e.g., at least 85%, at least 90% or at least 95% sequence identity to amino acids 96 to 167 of SEQ ID NO: 12; and
(n) a polypeptide having at least 80%, e.g., at least 85%, at least 90% or at least 95% sequence identity to amino acids 96 to 168 of SEQ ID NO: 42;
(C) 20% to 80% w/w of polyol;
(D) 0.01% to 2.0% w/w preservative; and
(E) water.

In one embodiment to any part of the third aspect, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment to any part of the third aspect, the polypeptide is of fungal origin. In an embodiment, the polypeptide is obtained or obtainable from the taxonomic phylum Ascomycota, preferably the taxonomic subphylum Pezizomycotina.

In one embodiment to any part of the third aspect, the liquid formulation comprises one or more formulating agents (such as those described herein), preferably a formulating agent selected from the list consisting of glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, PVA, acetate and phosphate, preferably selected from the list consisting of 1,2-propylene glycol, 1,3-propylene glycol, sodium sulfate, dextrin, cellulose, sodium thiosulfate, kaolin and calcium carbonate.

In one embodiment to any part of the third aspect, the liquid formulation comprises one or more polyols, preferably a polyol selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600, more preferably selected from the group consisting of glycerol, sorbitol and propylene glycol (MPG) or any combination thereof.

In one embodiment to any part of the third aspect, the liquid formulation comprises 20%-80% polyol (i.e. total amount of polyol), preferably 25%-75% polyol, more preferably 30%-70% polyol, more preferably 35%-65% polyol or most preferably 40%-60% polyol. In one embodiment to any part of the third aspect, the liquid formulation comprises 20%-80% polyol, preferably 25%-75% polyol, more preferably 30%-70% polyol, more preferably 35%-65% polyol or most preferably 40%-60% polyol wherein the polyol is selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600. In one embodiment to any part of the third aspect, the liquid formulation comprises 20%-80% polyol (i.e. total amount of polyol), preferably 25%-75% polyol, more preferably 30%-70% polyol, more preferably 35%-65% polyol or most preferably 40%-60% polyol wherein the polyol is selected from the group consisting of glycerol, sorbitol and propylene glycol (MPG).

In one embodiment to any part of the third aspect, the preservative is selected from the group consisting of sodium sorbate, potassium sorbate, sodium benzoate and potassium benzoate or any combination thereof. In one embodiment, the liquid formulation comprises 0.02% to 1.5% w/w preservative, more preferably 0.05% to 1.0% w/w preservative or most preferably 0.1% to 0.5% w/w preservative. In one embodiment, the liquid formulation comprises 0.01% to 2.0% w/w preservative (i.e. total amount of preservative), preferably 0.02% to 1.5% w/w preservative, more preferably 0.05% to 1.0% w/w preservative or most preferably 0.1% to 0.5% w/w preservative wherein the preservative is selected from the group consisting of sodium sorbate, potassium sorbate, sodium benzoate and potassium benzoate or any combination thereof.

In one embodiment to any part of the third aspect, the liquid formulation comprises 0.05% to 20% w/w LYS polypeptide, more preferably 0.2% to 15% w/w LYS polypeptide, more preferably 0.5% to 15% w/w LYS polypeptide or most preferably 1.0% to 10% w/w LYS polypeptide.

In one embodiment to any part of the third aspect, the liquid formulation comprises one or more additional enzymes. The one or more additional enzymes is preferably selected from the group consisting of acetyl xylan esterase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lipase, lysophospholipase, lysozyme, mannanase, alpha-mannosidase, beta-mannosidase, phytase, phospholipase A1, phospholipase A2, phospholipase C, phospholipase D, protease, pullulanase, pectinase, pectin lyase, xylanase, beta-xylosidase or any combination thereof.

In one embodiment to any part of the third aspect, the liquid formulation comprises one or more probiotics. The one or more probiotics is preferably selected from the group consisting of *Bacillus subtilis, Bacillus lichenformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius,* Lacto3coccus *lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp. and *Streptococcus* sp. or any combination thereof.

Polypeptides Having Lysozyme Activity

In a fourth aspect, the invention relates to polypeptides having lysozyme activity having at least 95%, e.g., at least 96%, at least 97%, at least 98%, at least 99%, or 100% sequence identity to the mature polypeptide of SEQ ID NO: 2. In one embodiment, the polypeptides differ by up to 11 amino acids, e.g., 1, 2, 3, 4, 5, 6, 7, 8, 9, 10, or 11 amino acids from the mature polypeptide of SEQ ID NO: 2.

In a continuation of the fourth aspect, the invention relates to polypeptides having lysozyme activity having at least 95%, e.g., at least 96%, at least 97%, at least 98%, at least 99%, or 100% sequence identity to SEQ ID NO: 3. In one embodiment, the polypeptides differ by up to 11 amino acids, e.g., 1, 2, 3, 4, 5, 6, 7, 8, 9, 10, or 11 amino acids from SEQ ID NO: 3.

In one embodiment, the invention relates to polypeptides having lysozyme activity and having a sequence identity to SEQ ID NO: 3 of at least 95% and wherein the polypeptide has at least 50%, such as at least 75%, at least 90%, at least 95% or at least 100% of the lysozyme activity of SEQ ID NO: 3. In one embodiment, lysozyme activity is determined as described in example 1.

In one embodiment, the polypeptide comprises or consists of the mature polypeptide of SEQ ID NO: 2. In one embodiment, the polypeptide preferably comprises or consists of the amino acid sequence of SEQ ID NO: 3; comprises the amino acid sequence of SEQ ID NO: 3 and a N-terminal and/or C-terminal His-tag and/or HQ-tag; comprises the amino acid sequence of SEQ ID NO: 3 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 3. In one embodiment, the polypeptide comprises or consists of amino acids 1 to 226 of SEQ ID NO: 3. In one embodiment, the polypeptide has been isolated.

In a continuation of the fourth aspect, the invention relates to polypeptides having lysozyme activity encoded by a polynucleotide having a sequence identity to the mature polypeptide coding sequence of SEQ ID NO: 1 of at least 95%, e.g., at least 96%, at least 97%, at least 98%, at least 99%, or 100%. In a further embodiment, the polypeptide has been isolated.

In a continuation of the fourth aspect, the invention relates to variants of SEQ ID NO: 3 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 3 is not more than 11, e.g. 1, 2, 3, 4, 5, 6, 7, 8, 9, 10, or 11. In an embodiment, the number of positions comprising one or more amino acid substitutions, and/or one or more amino acid deletions, and/or one or more amino acid insertions or any combination thereof in SEQ ID NO: 3 is not more than 10, e.g., 1, 2, 3, 4, 5, 6, 7, 8, 9 or 10. In one embodiment, the number of substitutions and/or deletions and/or insertions in SEQ ID NO: 3 is not more than 10, e.g. 1, 2, 3, 4, 5, 6, 7, 8, 9, or 10. In a further embodiment, the number of substitutions, preferably conservative substitutions, in SEQ ID NO: 3 is not more than 10, e.g. 1, 2, 3, 4, 5, 6, 7, 8, 9, or 10.

In an embodiment of the fourth aspect, the variant has at least 50%, such as at least 75%, at least 90%, at least 95% or at least 100% of the lysozyme activity of SEQ ID NO: 3. In one embodiment, lysozyme activity is determined as described in example 1.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. Other examples of conservative substitutions are G to A; A to G, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for lysozyme activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, Nature *Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide or a fusion polypeptide.

In a fifth aspect, the invention relates to polypeptides having lysozyme activity having at least 94%, e.g., at least 95%, at least 96%, at least 97%, at least 98%, at least 99%, or 100% sequence identity to the mature polypeptide of SEQ ID NO: 5. In one embodiment, the polypeptides differ by up to 13 amino acids, e.g., 1, 2, 3, 4, 5, 6, 7, 8, 9, 10, 11, 12, or 13 amino acids from the mature polypeptide of SEQ ID NO: 5.

In a continuation of the fifth aspect, the invention relates to polypeptides having lysozyme activity having at least 94%, e.g., at least 95%, at least 96%, at least 97%, at least 98%, at least 99%, or 100% sequence identity to SEQ ID NO: 6. In one embodiment, the polypeptides differ by up to 13 amino acids, e.g., 1, 2, 3, 4, 5, 6, 7, 8, 9, 10, 11, 12, or 13 amino acids from SEQ ID NO: 6.

In one embodiment, the invention relates to polypeptides having lysozyme activity and having a sequence identity to SEQ ID NO: 6 of at least 94% and wherein the polypeptide has at least 50%, such as at least 75%, at least 90%, at least 95% or at least 100% of the lysozyme activity of SEQ ID NO: 6. In one embodiment, the invention relates to polypeptides having lysozyme activity and having a sequence identity to SEQ ID NO: 6 of at least 95% and wherein the polypeptide has at least 50%, such as at least 75%, at least 90%, at least 95% or at least 100% of the lysozyme activity of SEQ ID NO: 6. In one embodiment, lysozyme activity is determined as described in example 1.

In one embodiment, the polypeptide comprises or consists of the mature polypeptide of SEQ ID NO: 5. In one embodiment, the polypeptide preferably comprises or consists of the amino acid sequence of SEQ ID NO: 6; comprises the amino acid sequence of SEQ ID NO: 6 and a N-terminal and/or C-terminal His-tag and/or HQ-tag; comprises the amino acid sequence of SEQ ID NO: 6 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 6. In one embodiment, the polypeptide comprises or consists of amino acids 1 to 226 of SEQ ID NO: 6. In one embodiment, the polypeptide has been isolated.

In a continuation of the fifth aspect, the invention relates to polypeptides having lysozyme activity encoded by a polynucleotide having a sequence identity to the mature polypeptide coding sequence of SEQ ID NO: 4 of at least 94%, e.g., at least 95%, at least 96%, at least 97%, at least 98%, at least 99%, or 100%. In a further embodiment, the polypeptide has been isolated.

In a continuation of the fifth aspect, the invention relates to variants of SEQ ID NO: 6 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 6 is not more than 13, e.g. 1, 2, 3, 4, 5, 6, 7, 8, 9, 10, 11, 12, or 13. In an embodiment, the number of positions comprising one or more amino acid substitutions, and/or one or more amino acid deletions, and/or one or more amino acid insertions or any combination thereof in SEQ ID NO: 6 is not more than 10, e.g., 1, 2, 3, 4, 5, 6, 7, 8, 9 or 10. In one embodiment, the number of substitutions and/or deletions and/or insertions in SEQ ID NO: 6 is not more than 10, e.g. 1, 2, 3, 4, 5, 6, 7, 8, 9, or 10. In a further embodiment, the number of substitutions, preferably conservative substitutions, in SEQ ID NO: 6 is not more than 10, e.g. 1, 2, 3, 4, 5, 6, 7, 8, 9, or 10. Examples of amino acid changes and conservative substitutions are described in the fourth aspect of the invention.

In an embodiment of the fifth aspect, the variant has at least 50%, such as at least 75%, at least 90%, at least 95% or at least 100% of the lysozyme activity of SEQ ID NO: 6. In one embodiment, lysozyme activity is determined as described in example 1.

In a sixth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 8. In one embodiment, the polypeptides differ by up to 44 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 amino acids from the mature polypeptide of SEQ ID NO: 8.

In a continuation of the sixth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9. In one embodiment, the polypeptides differ by up to 44 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 amino acids from SEQ ID NO: 9.

In one embodiment, the invention relates to polypeptides having lysozyme activity and having a sequence identity to SEQ ID NO: 9 of at least 80% and wherein the polypeptide has at least 50%, such as at least 75%, at least 90%, at least 95% or at least 100% of the lysozyme activity of SEQ ID NO: 9. In one embodiment, the invention relates to polypeptides having lysozyme activity and having a sequence identity to SEQ ID NO: 9 of at least 85% and wherein the polypeptide has at least 50%, such as at least 75%, at least 90%, at least 95% or at least 100% of the lysozyme activity of SEQ ID NO: 9. In one embodiment, the invention relates to polypeptides having lysozyme activity and having a sequence identity to SEQ ID NO: 9 of at least 90% and wherein the polypeptide has at least 50%, such as at least 75%, at least 90%, at least 95% or at least 100% of the lysozyme activity of SEQ ID NO: 9. In one embodiment, the invention relates to polypeptides having lysozyme activity and having a sequence identity to SEQ ID NO: 9 of at least 95% and wherein the polypeptide has at least 50%, such as at least 75%, at least 90%, at least 95% or at least 100% of the lysozyme activity of SEQ ID NO: 9. In one embodiment, lysozyme activity is determined as described in example 1.

In one embodiment, the polypeptide comprises or consists of the mature polypeptide of SEQ ID NO: 8. In one embodiment, the polypeptide preferably comprises or consists of the amino acid sequence of SEQ ID NO: 9; comprises the amino acid sequence of SEQ ID NO: 9 and a N-terminal and/or C-terminal His-tag and/or HQ-tag; comprises the amino acid sequence of SEQ ID NO: 9 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 9. In one embodiment, the polypeptide comprises or consists of amino acids 1 to 223 of SEQ ID NO: 9. In one embodiment, the polypeptide has been isolated.

In a continuation of the sixth aspect, the invention relates to polypeptides having lysozyme activity encoded by a polynucleotide having a sequence identity to the mature polypeptide coding sequence of SEQ ID NO: 7 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the sixth aspect, the invention relates to variants of SEQ ID NO: 9 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 9 is not more than 44, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44. In an embodiment, the number of positions comprising one or more amino acid substitutions, and/or one or more amino acid deletions, and/or one or more amino acid insertions or any combination thereof in SEQ ID NO: 9 is not more than 10, e.g., 1, 2, 3, 4, 5, 6, 7, 8, 9 or 10. In one embodiment, the number of substitutions and/or deletions and/or insertions in SEQ ID NO: 9 is not more than 10, e.g. 1, 2, 3, 4, 5, 6, 7, 8, 9, or 10. In a further embodiment, the number of substitutions, preferably conservative substitutions, in SEQ ID NO: 9 is not more than 10, e.g. 1, 2, 3, 4, 5, 6, 7, 8, 9, or 10. Examples of amino acid changes and conservative substitutions are described in the fourth aspect of the invention.

In an embodiment of the sixth aspect, the variant has at least 50%, such as at least 75%, at least 90%, at least 95% or at least 100% of the lysozyme activity of SEQ ID NO: 9. In one embodiment, lysozyme activity is determined as described in example 1.

In a seventh aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 11. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids from the mature polypeptide of SEQ ID NO: 11.

In a continuation of the seventh aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids from SEQ ID NO: 12.

In one embodiment, the invention relates to polypeptides having lysozyme activity and having a sequence identity to SEQ ID NO: 12 of at least 80% and wherein the polypeptide has at least 50%, such as at least 75%, at least 90%, at least 95% or at least 100% of the lysozyme activity of SEQ ID NO: 12. In one embodiment, the invention relates to polypeptides having lysozyme activity and having a sequence identity to SEQ ID NO: 12 of at least 85% and wherein the polypeptide has at least 50%, such as at least 75%, at least 90%, at least 95% or at least 100% of the lysozyme activity of SEQ ID NO: 12. In one embodiment, the invention relates to polypeptides having lysozyme activity and having a sequence identity to SEQ ID NO: 12 of at least 90% and wherein the polypeptide has at least 50%, such as at least 75%, at least 90%, at least 95% or at least 100% of the lysozyme activity of SEQ ID NO: 12. In one embodiment, the invention relates to polypeptides having lysozyme activity and having a sequence identity to SEQ ID NO: 12 of at least 95% and wherein the polypeptide has at least 50%, such as at least 75%, at least 90%, at least 95% or at least 100% of the lysozyme activity of SEQ ID NO: 12. In one embodiment, lysozyme activity is determined as described in example 1.

In one embodiment, the polypeptide comprises or consists of the mature polypeptide of SEQ ID NO: 11. In one embodiment, the polypeptide preferably comprises or consists of the amino acid sequence of SEQ ID NO: 12; comprises the amino acid sequence of SEQ ID NO: 12 and a N-terminal and/or C-terminal His-tag and/or HQ-tag; comprises the amino acid sequence of SEQ ID NO: 12 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 12. In one embodiment, the polypeptide comprises or consists of amino acids 1 to 304 of SEQ ID NO: 12. In one embodiment, the polypeptide has been isolated.

In a continuation of the seventh aspect, the invention relates to polypeptides having lysozyme activity encoded by a polynucleotide having a sequence identity to the mature polypeptide coding sequence of SEQ ID NO: 10 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the seventh aspect, the invention relates to variants of SEQ ID NO: 12 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 12 is not more than 50, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In an embodiment, the number of positions comprising one or more amino acid substitutions, and/or one or more amino acid deletions, and/or one or more amino acid insertions or any combination thereof in SEQ ID NO: 12 is not more than 10, e.g., 1, 2, 3, 4, 5, 6, 7, 8, 9 or 10. In one embodiment, the number of substitutions and/or deletions and/or insertions in SEQ ID NO: 12 is not more than 10, e.g. 1, 2, 3, 4, 5, 6, 7, 8, 9, or 10. In a further embodiment, the number of substitutions, preferably conservative substitutions, in SEQ ID NO: 12 is not more than 10, e.g. 1, 2, 3, 4, 5, 6, 7, 8, 9, or 10. Examples of amino acid changes and conservative substitutions are described in the fourth aspect of the invention.

In an embodiment of the seventh aspect, the variant has at least 50%, such as at least 75%, at least 90%, at least 95% or at least 100% of the lysozyme activity of SEQ ID NO: 12. In one embodiment, lysozyme activity is determined as described in example 1.

In a eighth aspect, the invention relates to polypeptides having lysozyme activity having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 14. In one embodiment, the polypeptides differ by up to 29 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, or 29 amino acids from the mature polypeptide of SEQ ID NO: 14.

In a continuation of the eighth aspect, the invention relates to polypeptides having lysozyme activity having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15. In one embodiment, the polypeptides differ by up to 29 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, or 29 amino acids from SEQ ID NO: 15.

In one embodiment, the invention relates to polypeptides having lysozyme activity and having a sequence identity to SEQ ID NO: 15 of at least 87% and wherein the polypeptide has at least 50%, such as at least 75%, at least 90%, at least 95% or at least 100% of the lysozyme activity of SEQ ID NO: 15. In one embodiment, the invention relates to polypeptides having lysozyme activity and having a sequence identity to SEQ ID NO: 15 of at least 90% and wherein the polypeptide has at least 50%, such as at least 75%, at least 90%, at least 95% or at least 100% of the lysozyme activity of SEQ ID NO: 15. In one embodiment, the invention relates to polypeptides having lysozyme activity and having a sequence identity to SEQ ID NO: 15 of at least 95% and wherein the polypeptide has at least 50%, such as at least 75%, at least 90%, at least 95% or at least 100% of the lysozyme activity of SEQ ID NO: 15. In one embodiment, lysozyme activity is determined as described in example 1.

In one embodiment, the polypeptide comprises or consists of the mature polypeptide of SEQ ID NO: 14. In one embodiment, the polypeptide preferably comprises or consists of the amino acid sequence of SEQ ID NO: 15; comprises the amino acid sequence of SEQ ID NO: 15 and a N-terminal and/or C-terminal His-tag and/or HQ-tag; comprises the amino acid sequence of SEQ ID NO: 15 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 15. In one embodiment, the polypeptide comprises or consists of amino acids 1 to 228 of SEQ ID NO: 15. In one embodiment, the polypeptide has been isolated.

In a continuation of the eighth aspect, the invention relates to polypeptides having lysozyme activity encoded by a polynucleotide having a sequence identity to the mature polypeptide coding sequence of SEQ ID NO: 13 of at least 87%, e.g., at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the eighth aspect, the invention relates to variants of SEQ ID NO: 15 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 15 is not more than 29, e.g. 1, 2, 3, 4, 5, 6, 7, 8, 9, 10, 11, 12, 13, 14, 15, 16, 17, 18, 19, 20, 21, 22, 23, 24, 25, 26, 27, 28, or 29. In an embodiment, the number of positions comprising one or more amino acid substitutions, and/or one or more amino acid deletions, and/or one or more amino acid insertions or any combination thereof in SEQ ID NO: 15 is not more than 10, e.g., 1, 2, 3, 4, 5, 6, 7, 8, 9 or 10. In one embodiment, the number of substitutions and/or deletions and/or insertions in SEQ ID NO: 15 is not more than 10, e.g. 1, 2, 3, 4, 5, 6, 7, 8, 9, or 10. In a further embodiment, the number of substitutions, preferably conservative substitutions, in SEQ ID NO: 15 is not more than 10, e.g. 1, 2, 3, 4, 5, 6, 7, 8, 9, or 10. Examples of amino acid changes and conservative substitutions are described in the fourth aspect of the invention.

In an embodiment of the eighth aspect, the variant has at least 50%, such as at least 75%, at least 90%, at least 95% or at least 100% of the lysozyme activity of SEQ ID NO: 15. In one embodiment, lysozyme activity is determined as described in example 1.

In a ninth aspect, the invention relates to polypeptides having lysozyme activity having at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 17. In one embodiment, the polypeptides differ by up to 43 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43 amino acids from the mature polypeptide of SEQ ID NO: 17.

In a continuation of the ninth aspect, the invention relates to polypeptides having lysozyme activity having at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18. In one embodiment, the polypeptides differ by up to 43 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43 amino acids from SEQ ID NO: 18.

In a continuation of the ninth aspect, the invention relates to polypeptides having lysozyme activity having at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18. In one embodiment, the polypeptides differ by up to 28 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27 or 28 amino acids from SEQ ID NO: 239.

In one embodiment, the invention relates to polypeptides having lysozyme activity and having a sequence identity to SEQ ID NO: 18 of at least 81% and wherein the polypeptide has at least 50%, such as at least 75%, at least 90%, at least 95% or at least 100% of the lysozyme activity of SEQ ID NO: 18. In one embodiment, the invention relates to polypeptides having lysozyme activity and having a sequence identity to SEQ ID NO: 18 of at least 85% and wherein the polypeptide has at least 50%, such as at least 75%, at least 90%, at least 95% or at least 100% of the lysozyme activity of SEQ ID NO: 18. In one embodiment, the invention relates to polypeptides having lysozyme activity and having a sequence identity to SEQ ID NO: 18 of at least 90% and wherein the polypeptide has at least 50%, such as at least 75%, at least 90%, at least 95% or at least 100% of the lysozyme activity of SEQ ID NO: 18. In one embodiment, the invention relates to polypeptides having lysozyme activity and having a sequence identity to SEQ ID NO: 18 of at least 95% and wherein the polypeptide has at least 50%, such as at least 75%, at least 90%, at least 95% or at least 100% of the lysozyme activity of SEQ ID NO: 18. In one embodiment, lysozyme activity is determined as described in example 1.

In one embodiment, the polypeptide comprises or consists of the mature polypeptide of SEQ ID NO: 17. In one embodiment, the polypeptide comprises or consists of the mature polypeptide of SEQ ID NO: 239. In one embodiment, the polypeptide preferably comprises or consists of the amino acid sequence of SEQ ID NO: 18; comprises the amino acid sequence of SEQ ID NO: 18 and a N-terminal and/or C-terminal His-tag and/or HQ-tag; comprises the amino acid sequence of SEQ ID NO: 18 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 18. In one embodiment, the polypeptide comprises or consists of amino acids 1 to 230 of SEQ ID NO: 18. In one embodiment, the polypeptide comprises or consists of amino acids 1 to 146 of SEQ ID NO: 18. In one embodiment, the polypeptide has been isolated.

In a continuation of the ninth aspect, the invention relates to polypeptides having lysozyme activity encoded by a polynucleotide having a sequence identity to the mature polypeptide coding sequence of SEQ ID NO: 16 of at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the ninth aspect, the invention relates to variants of SEQ ID NO: 18 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 18 is not more than 43, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43. In an embodiment, the number of positions comprising one or more amino acid substitutions, and/or one or more amino acid deletions, and/or one or more amino acid insertions or any combination thereof in SEQ ID NO: 18 is not more than 10, e.g., 1, 2, 3, 4, 5, 6, 7, 8, 9 or 10. In one embodiment, the number of substitutions and/or deletions and/or insertions in SEQ ID NO: 18 is not more than 10, e.g. 1, 2, 3, 4, 5, 6, 7, 8, 9, or 10. In a further embodiment, the number of substitutions, preferably conservative substitutions, in SEQ ID NO: 18 is not more than 10, e.g. 1, 2, 3, 4, 5, 6, 7, 8, 9, or 10. Examples of amino acid changes and conservative substitutions are described in the fourth aspect of the invention.

In an embodiment of the ninth aspect, the variant has at least 50%, such as at least 75%, at least 90%, at least 95% or at least 100% of the lysozyme activity of SEQ ID NO: 18. In one embodiment, lysozyme activity is determined as described in example 1.

In a tenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 20. In one embodiment, the polypeptides differ by up to 45 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 amino acids from the mature polypeptide of SEQ ID NO: 20.

In a continuation of the tenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21. In one embodiment, the polypeptides differ by up to 45 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 amino acids from SEQ ID NO: 21.

In one embodiment, the invention relates to polypeptides having lysozyme activity and having a sequence identity to SEQ ID NO: 21 of at least 80% and wherein the polypeptide has at least 50%, such as at least 75%, at least 90%, at least 95% or at least 100% of the lysozyme activity of SEQ ID NO: 21. In one embodiment, the invention relates to polypeptides having lysozyme activity and having a sequence identity to SEQ ID NO: 21 of at least 85% and wherein the polypeptide has at least 50%, such as at least 75%, at least 90%, at least 95% or at least 100% of the lysozyme activity of SEQ ID NO: 21. In one embodiment, the invention relates to polypeptides having lysozyme activity and having a sequence identity to SEQ ID NO: 21 of at least 90% and wherein the polypeptide has at least 50%, such as at least 75%, at least 90%, at least 95% or at least 100% of the lysozyme activity of SEQ ID NO: 21. In one embodiment, the invention relates to polypeptides having lysozyme activity and having a sequence identity to SEQ ID NO: 21 of at least 95% and wherein the polypeptide has at least 50%, such as at least 75%, at least 90%, at least 95% or at least 100% of the lysozyme activity of SEQ ID NO: 21. In one embodiment, lysozyme activity is determined as described in example 1.

In one embodiment, the polypeptide comprises or consists of the mature polypeptide of SEQ ID NO: 20. In one embodiment, the polypeptide preferably comprises or consists of the amino acid sequence of SEQ ID NO: 21; comprises the amino acid sequence of SEQ ID NO: 21 and a N-terminal and/or C-terminal His-tag and/or HQ-tag; comprises the amino acid sequence of SEQ ID NO: 21 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 21. In one embodiment, the polypeptide comprises or consists of amino acids 1 to 230 of SEQ ID NO: 21. In one embodiment, the polypeptide has been isolated.

In a continuation of the tenth aspect, the invention relates to polypeptides having lysozyme activity encoded by a polynucleotide having a sequence identity to the mature polypeptide coding sequence of SEQ ID NO: 19 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the tenth aspect, the invention relates to variants of SEQ ID NO: 21 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 21 is not more than 45, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45. In an embodiment, the number of positions comprising one or more amino acid substitutions, and/or one or more amino acid deletions, and/or one or more amino acid insertions or any combination thereof in SEQ ID NO: 21 is not more than 10, e.g., 1, 2, 3, 4, 5, 6, 7, 8, 9 or 10. In one embodiment, the number of substitutions and/or deletions and/or insertions in SEQ ID NO: 21 is not more than 10, e.g. 1, 2, 3, 4, 5, 6, 7, 8, 9, or 10. In a further embodiment, the number of substitutions, preferably conservative substitutions, in SEQ ID NO: 21 is not more than 10, e.g. 1, 2, 3, 4, 5, 6, 7, 8, 9, or 10. Examples of amino acid changes and conservative substitutions are described in the fourth aspect of the invention.

In an embodiment of the tenth aspect, the variant has at least 50%, such as at least 75%, at least 90%, at least 95% or at least 100% of the lysozyme activity of SEQ ID NO: 21. In one embodiment, lysozyme activity is determined as described in example 1.

In a eleventh aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptides of SEQ ID NO: 23. In one embodiment, the polypeptides differ by up to 46 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46 amino acids from the mature polypeptide of SEQ ID NO: 23.

In a continuation of the eleventh aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 24. In one embodiment, the polypeptides differ by up to 46 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46 amino acids from SEQ ID NO: 24.

In one embodiment, the invention relates to polypeptides having lysozyme activity and having a sequence identity to SEQ ID NO: 24 of at least 80% and wherein the polypeptide has at least 50%, such as at least 75%, at least 90%, at least 95% or at least 100% of the lysozyme activity of SEQ ID NO: 24. In one embodiment, the invention relates to polypeptides having lysozyme activity and having a sequence identity to SEQ ID NO: 24 of at least 85% and wherein the polypeptide has at least 50%, such as at least 75%, at least 90%, at least 95% or at least 100% of the lysozyme activity of SEQ ID NO: 24. In one embodiment, the invention relates to polypeptides having lysozyme activity and having a sequence identity to SEQ ID NO: 24 of at least 90% and wherein the polypeptide has at least 50%, such as at least 75%, at least 90%, at least 95% or at least 100% of the lysozyme activity of SEQ ID NO: 24. In one embodiment, the invention relates to polypeptides having lysozyme activity and having a sequence identity to SEQ ID NO: 24 of at least 95% and wherein the polypeptide has at least 50%, such as at least 75%, at least 90%, at least 95% or at least 100% of the lysozyme activity of SEQ ID NO: 24. In one embodiment, lysozyme activity is determined as described in example 1.

In one embodiment, the polypeptide comprises or consists of the mature polypeptide of SEQ ID NO: 23. In one embodiment, the polypeptide preferably comprises or consists of the amino acid sequence of SEQ ID NO: 24; comprises the amino acid sequence of SEQ ID NO: 24 and a N-terminal and/or C-terminal His-tag and/or HQ-tag; comprises the amino acid sequence of SEQ ID NO: 24 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 24. In one embodiment, the polypeptide comprises or consists of amino acids 1 to 232 of SEQ ID NO: 24. In one embodiment, the polypeptide has been isolated.

In a continuation of the eleventh aspect, the invention relates to polypeptides having lysozyme activity encoded by a polynucleotide having a sequence identity to the mature polypeptide coding sequence of SEQ ID NO: 22 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the eleventh aspect, the invention relates to variants of SEQ ID NO: 24 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 24 is not more than 46, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46. In an embodiment, the number of positions comprising one or more amino acid substitutions, and/or one or more amino acid deletions, and/or one or more amino acid insertions or any combination thereof in SEQ ID NO: 24 is not more than 10, e.g., 1, 2, 3, 4, 5, 6, 7, 8, 9 or 10. In one embodiment, the number of substitutions and/or deletions and/or insertions in SEQ ID NO: 24 is not more than 10, e.g. 1, 2, 3, 4, 5, 6, 7, 8, 9, or 10. In a further embodiment, the number of substitutions, preferably conservative substitutions, in SEQ ID NO: 24 is not more than 10, e.g. 1, 2, 3, 4, 5, 6, 7, 8, 9, or 10. Examples of amino acid changes and conservative substitutions are described in the fourth aspect of the invention.

In an embodiment of the eleventh aspect, the variant has at least 50%, such as at least 75%, at least 90%, at least 95% or at least 100% of the lysozyme activity of SEQ ID NO: 24. In one embodiment, lysozyme activity is determined as described in example 1.

In a twelfth aspect, the invention relates to polypeptides having lysozyme activity having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 26. In one embodiment, the polypeptides differ by up to 29 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, or 29 amino acids from the mature polypeptide of SEQ ID NO: 26.

In a continuation of the twelfth aspect, the invention relates to polypeptides having lysozyme activity having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27. In one embodiment, the polypeptides differ by up to 29 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, or 29 amino acids from SEQ ID NO: 27.

In one embodiment, the invention relates to polypeptides having lysozyme activity and having a sequence identity to SEQ ID NO: 27 of at least 87% and wherein the polypeptide has at least 50%, such as at least 75%, at least 90%, at least 95% or at least 100% of the lysozyme activity of SEQ ID NO: 27. In one embodiment, the invention relates to polypeptides having lysozyme activity and having a sequence identity to SEQ ID NO: 27 of at least 90% and wherein the polypeptide has at least 50%, such as at least 75%, at least 90%, at least 95% or at least 100% of the lysozyme activity of SEQ ID NO: 27. In one embodiment, the invention relates to polypeptides having lysozyme activity and having a sequence identity to SEQ ID NO: 27 of at least 95% and wherein the polypeptide has at least 50%, such as at least 75%, at least 90%, at least 95% or at least 100% of the lysozyme activity of SEQ ID NO: 27. In one embodiment, lysozyme activity is determined as described in example 1.

In one embodiment, the polypeptide comprises or consists of the mature polypeptide of SEQ ID NO: 26. In one embodiment, the polypeptide preferably comprises or consists of the amino acid sequence of SEQ ID NO: 27; comprises the amino acid sequence of SEQ ID NO: 27 and a N-terminal and/or C-terminal His-tag and/or HQ-tag; comprises the amino acid sequence of SEQ ID NO: 27 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 27. In one embodiment, the polypeptide comprises or consists of amino acids 1 to 228 of SEQ ID NO: 27. In one embodiment, the polypeptide has been isolated.

In a continuation of the twelfth aspect, the invention relates to polypeptides having lysozyme activity encoded by a polynucleotide having a sequence identity to the mature polypeptide coding sequence of SEQ ID NO: 25 of at least 87%, e.g., at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the twelfth aspect, the invention relates to variants of SEQ ID NO: 27 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 27 is not more than 29, e.g. 1, 2, 3, 4, 5, 6, 7, 8, 9, 10, 11, 12, 13, 14, 15, 16, 17, 18, 19, 20, 21, 22, 23, 24, 25, 26, 27, 28, or 29. In an embodiment, the number of positions comprising one or more amino acid substitutions, and/or one or more amino acid deletions, and/or one or more amino acid insertions or any combination thereof in SEQ ID NO: 27 is not more than 10, e.g., 1, 2, 3, 4, 5, 6, 7, 8, 9 or 10. In one embodiment, the number of substitutions and/or deletions and/or insertions in SEQ ID NO: 27 is not more than 10, e.g. 1, 2, 3, 4, 5, 6, 7, 8, 9, or 10. In a further embodiment, the number of substitutions, preferably conservative substitutions, in SEQ ID NO: 27 is not more than 10, e.g. 1, 2, 3, 4, 5, 6, 7, 8, 9, or 10. Examples of amino acid changes and conservative substitutions are described in the fourth aspect of the invention.

In an embodiment of the twelfth aspect, the variant has at least 50%, such as at least 75%, at least 90%, at least 95% or at least 100% of the lysozyme activity of SEQ ID NO: 27. In one embodiment, lysozyme activity is determined as described in example 1.

In a thirteenth aspect, the invention relates to polypeptides having lysozyme activity having at least 96%, e.g., at least 97%, at least 98%, at least 99%, or 100% sequence identity to the mature polypeptide of SEQ ID NO: 29. In one embodiment, the polypeptides differ by up to 8 amino acids, e.g., 1, 2, 3, 4, 5, 6, 7, or 8 amino acids from the mature polypeptide of SEQ ID NO: 29.

In a continuation of the thirteenth aspect, the invention relates to polypeptides having lysozyme activity having at least 96%, e.g., at least 97%, at least 98%, at least 99%, or 100% sequence identity to SEQ ID NO: 30. In one embodiment, the polypeptides differ by up to 8 amino acids, e.g., 1, 2, 3, 4, 5, 6, 7, or 8 amino acids from SEQ ID NO: 30.

In one embodiment, the invention relates to polypeptides having lysozyme activity and having a sequence identity to SEQ ID NO: 30 of at least 96% and wherein the polypeptide has at least 50%, such as at least 75%, at least 90%, at least 95% or at least 100% of the lysozyme activity of SEQ ID NO: 30. In one embodiment, lysozyme activity is determined as described in example 1.

In one embodiment, the polypeptide comprises or consists of the mature polypeptide of SEQ ID NO: 29. In one embodiment, the polypeptide preferably comprises or consists of the amino acid sequence of SEQ ID NO: 30; comprises the amino acid sequence of SEQ ID NO: 30 and a N-terminal and/or C-terminal His-tag and/or HQ-tag; comprises the amino acid sequence of SEQ ID NO: 30 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 30. In one embodiment, the polypeptide comprises or consists of amino acids 1 to 228 of SEQ ID NO: 30. In one embodiment, the polypeptide has been isolated.

In a continuation of the thirteenth aspect, the invention relates to polypeptides having lysozyme activity encoded by a polynucleotide having a sequence identity to the mature polypeptide coding sequence of SEQ ID NO: 28 of at least 96%, e.g., at least 97%, at least 98%, at least 99%, or 100%. In a further embodiment, the polypeptide has been isolated.

In a continuation of the thirteenth aspect, the invention relates to variants of SEQ ID NO: 30 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 30 is not more than 8, e.g. 1, 2, 3, 4, 5, 6, 7, or 8. In one embodiment, the number of substitutions and/or deletions and/or insertions in SEQ ID NO: 30 is not more than 8, e.g. 1, 2, 3, 4, 5, 6, 7, or 8. In a further embodiment, the number of substitutions, preferably conservative substitutions, in SEQ ID NO: 30 is not more than 8, e.g. 1, 2, 3, 4, 5, 6, 7, or 8. Examples of amino acid changes and conservative substitutions are described in the fourth aspect of the invention.

In an embodiment of the thirteenth aspect, the variant has at least 50%, such as at least 75%, at least 90%, at least 95% or at least 100% of the lysozyme activity of SEQ ID NO: 30. In one embodiment, lysozyme activity is determined as described in example 1.

In a fourteenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 32. In one embodiment, the polypeptides differ by up to 45 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 amino acids from the mature polypeptide of SEQ ID NO: 32.

In a continuation of the fourteenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 33. In one embodiment, the polypeptides differ by up to 45 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 amino acids from SEQ ID NO: 33.

In one embodiment, the invention relates to polypeptides having lysozyme activity and having a sequence identity to SEQ ID NO: 33 of at least 80% and wherein the polypeptide has at least 50%, such as at least 75%, at least 90%, at least 95% or at least 100% of the lysozyme activity of SEQ ID NO: 33. In one embodiment, the invention relates to polypeptides having lysozyme activity and having a sequence identity to SEQ ID NO: 33 of at least 85% and wherein the polypeptide has at least 50%, such as at least 75%, at least 90%, at least 95% or at least 100% of the lysozyme activity of SEQ ID NO: 33. In one embodiment, the invention relates to polypeptides having lysozyme activity and having a sequence identity to SEQ ID NO: 33 of at least 90% and wherein the polypeptide has at least 50%, such as at least 75%, at least 90%, at least 95% or at least 100% of the lysozyme activity of SEQ ID NO: 33. In one embodiment, the invention relates to polypeptides having lysozyme activity and having a sequence identity to SEQ ID NO: 33 of at least 95% and wherein the polypeptide has at least 50%, such as at least 75%, at least 90%, at least 95% or at least 100% of the lysozyme activity of SEQ ID NO: 33. In one embodiment, lysozyme activity is determined as described in example 1.

In one embodiment, the polypeptide comprises or consists of the mature polypeptide of SEQ ID NO: 32. In one embodiment, the polypeptide preferably comprises or consists of the amino acid sequence of SEQ ID NO: 33; comprises the amino acid sequence of SEQ ID NO: 33 and a N-terminal and/or C-terminal His-tag and/or HQ-tag; comprises the amino acid sequence of SEQ ID NO: 33 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 33. In one embodiment, the polypeptide comprises or consists of amino acids 1 to 226 of SEQ ID NO: 33. In one embodiment, the polypeptide has been isolated.

In a continuation of the fourteenth aspect, the invention relates to polypeptides having lysozyme activity encoded by a polynucleotide having a sequence identity to the mature polypeptide coding sequence of SEQ ID NO: 31 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the fourteenth aspect, the invention relates to variants of SEQ ID NO: 33 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 33 is not more than 45, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45. In an embodiment, the number of positions comprising one or more amino acid substitutions, and/or one or more amino acid deletions, and/or one or more amino acid insertions or any combination thereof in SEQ ID NO: 33 is not more than 10, e.g., 1, 2, 3, 4, 5, 6, 7, 8, 9 or 10. In one embodiment, the number of substitutions and/or deletions and/or insertions in SEQ ID NO: 33 is not more than 10, e.g. 1, 2, 3, 4, 5, 6, 7, 8, 9, or 10. In a further embodiment, the number of substitutions, preferably conservative substitutions, in SEQ ID NO: 33 is not more than 10, e.g. 1, 2, 3, 4, 5, 6, 7, 8, 9, or 10. Examples of amino acid changes and conservative substitutions are described in the fourth aspect of the invention.

In an embodiment of the fourteenth aspect, the variant has at least 50%, such as at least 75%, at least 90%, at least 95% or at least 100% of the lysozyme activity of SEQ ID NO: 33. In one embodiment, lysozyme activity is determined as described in example 1.

In a fifteenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 35. In one embodiment, the polypeptides differ by up to 44 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 amino acids from the mature polypeptide of SEQ ID NO: 35.

In a continuation of the fifteenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 36. In one embodiment, the polypeptides differ by up to 44 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 amino acids from SEQ ID NO: 36.

In one embodiment, the invention relates to polypeptides having lysozyme activity and having a sequence identity to SEQ ID NO: 36 of at least 80% and wherein the polypeptide has at least 50%, such as at least 75%, at least 90%, at least 95% or at least 100% of the lysozyme activity of SEQ ID NO: 36. In one embodiment, the invention relates to polypeptides having lysozyme activity and having a sequence identity to SEQ ID NO: 36 of at least 85% and wherein the polypeptide has at least 50%, such as at least 75%, at least 90%, at least 95% or at least 100% of the lysozyme activity of SEQ ID NO: 36. In one embodiment, the invention relates to polypeptides having lysozyme activity and having a sequence identity to SEQ ID NO: 36 of at least 90% and wherein the polypeptide has at least 50%, such as at least 75%, at least 90%, at least 95% or at least 100% of the lysozyme activity of SEQ ID NO: 36. In one embodiment, the invention relates to polypeptides having lysozyme activity and having a sequence identity to SEQ ID NO: 36 of at least 95% and wherein the polypeptide has at least 50%, such as at least 75%, at least 90%, at least 95% or at least 100% of the lysozyme activity of SEQ ID NO: 36. In one embodiment, lysozyme activity is determined as described in example 1.

In one embodiment, the polypeptide comprises or consists of the mature polypeptide of SEQ ID NO: 35. In one embodiment, the polypeptide preferably comprises or consists of the amino acid sequence of SEQ ID NO: 36; comprises the amino acid sequence of SEQ ID NO: 36 and a N-terminal and/or C-terminal His-tag and/or HQ-tag; comprises the amino acid sequence of SEQ ID NO: 36 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 36. In one embodiment, the polypeptide comprises or consists of amino acids 1 to 225 of SEQ ID NO: 36. In one embodiment, the polypeptide has been isolated.

In a continuation of the fifteenth aspect, the invention relates to polypeptides having lysozyme activity encoded by a polynucleotide having a sequence identity to the mature polypeptide coding sequence of SEQ ID NO: 34 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the fifteenth aspect, the invention relates to variants of SEQ ID NO: 36 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 36 is not more than 44, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44. In an embodiment, the number of positions comprising one or more amino acid substitutions, and/or one or more amino acid deletions, and/or one or more amino acid insertions or any combination thereof in SEQ ID NO: 36 is not more than 10, e.g., 1, 2, 3, 4, 5, 6, 7, 8, 9 or 10. In one embodiment, the number of substitutions and/or deletions and/or insertions in SEQ ID NO: 36 is not more than 10, e.g. 1, 2, 3, 4, 5, 6, 7, 8, 9, or 10. In a further embodiment, the number of substitutions, preferably conservative substitutions, in SEQ ID NO: 36 is not more than 10, e.g. 1, 2, 3, 4, 5, 6, 7, 8, 9, or 10. Examples of amino acid changes and conservative substitutions are described in the fourth aspect of the invention.

In an embodiment of the fifteenth aspect, the variant has at least 50%, such as at least 75%, at least 90%, at least 95% or at least 100% of the lysozyme activity of SEQ ID NO: 36. In one embodiment, lysozyme activity is determined as described in example 1.

In a sixteenth aspect, the invention relates to polypeptides having lysozyme activity having at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 38. In one embodiment, the polypeptides differ by up to 42 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 amino acids from the mature polypeptide of SEQ ID NO: 38.

In a continuation of the sixteenth aspect, the invention relates to polypeptides having lysozyme activity having at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 39. In one embodiment, the polypeptides differ by up to 42 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 amino acids from SEQ ID NO: 39.

In one embodiment, the invention relates to polypeptides having lysozyme activity and having a sequence identity to SEQ ID NO: 39 of at least 81% and wherein the polypeptide has at least 50%, such as at least 75%, at least 90%, at least 95% or at least 100% of the lysozyme activity of SEQ ID NO: 39. In one embodiment, the invention relates to polypeptides having lysozyme activity and having a sequence identity to SEQ ID NO: 39 of at least 85% and wherein the polypeptide has at least 50%, such as at least 75%, at least 90%, at least 95% or at least 100% of the lysozyme activity of SEQ ID NO: 39. In one embodiment, the invention relates to polypeptides having lysozyme activity and having a sequence identity to SEQ ID NO: 39 of at least 90% and wherein the polypeptide has at least 50%, such as at least 75%, at least 90%, at least 95% or at least 100% of the lysozyme activity of SEQ ID NO: 39. In one embodiment, the invention relates to polypeptides having lysozyme activity and having a sequence identity to SEQ ID NO: 39 of at least 95% and wherein the polypeptide has at least 50%, such as at least 75%, at least 90%, at least 95% or at least 100% of the lysozyme activity of SEQ ID NO: 39. In one embodiment, lysozyme activity is determined as described in example 1.

In one embodiment, the polypeptide comprises or consists of the mature polypeptide of SEQ ID NO: 38. In one embodiment, the polypeptide preferably comprises or consists of the amino acid sequence of SEQ ID NO: 39; comprises the amino acid sequence of SEQ ID NO: 39 and a N-terminal and/or C-terminal His-tag and/or HQ-tag; comprises the amino acid sequence of SEQ ID NO: 39 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 39. In one embodiment, the polypeptide comprises or consists of amino acids 1 to 225 of SEQ ID NO: 39. In one embodiment, the polypeptide has been isolated.

In a continuation of the sixteenth aspect, the invention relates to polypeptides having lysozyme activity encoded by a polynucleotide having a sequence identity to the mature polypeptide coding sequence of SEQ ID NO: 37 of at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the sixteenth aspect, the invention relates to variants of SEQ ID NO: 39 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 39 is not more than 42, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42. In an embodiment, the number of positions comprising one or more amino acid substitutions, and/or one or more amino acid deletions, and/or one or more amino acid insertions or any combination thereof in SEQ ID NO: 39 is not more than 10, e.g., 1, 2, 3, 4, 5, 6, 7, 8, 9 or 10. In one embodiment, the number of substitutions and/or deletions and/or insertions in SEQ ID NO: 39 is not more than 10, e.g. 1, 2, 3, 4, 5, 6, 7, 8, 9, or 10. In a further embodiment, the number of substitutions, preferably conservative substitutions, in SEQ ID NO: 39 is not more than 10, e.g. 1, 2, 3, 4, 5, 6, 7, 8, 9, or 10. Examples of amino acid changes and conservative substitutions are described in the fourth aspect of the invention.

In an embodiment of the sixteenth aspect, the variant has at least 50%, such as at least 75%, at least 90%, at least 95% or at least 100% of the lysozyme activity of SEQ ID NO: 39. In one embodiment, lysozyme activity is determined as described in example 1.

In a seventeenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 41. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids from the mature polypeptide of SEQ ID NO: 41.

In a continuation of the seventeenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 42. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids from SEQ ID NO: 42.

In one embodiment, the invention relates to polypeptides having lysozyme activity and having a sequence identity to SEQ ID NO: 42 of at least 80% and wherein the polypeptide has at least 50%, such as at least 75%, at least 90%, at least 95% or at least 100% of the lysozyme activity of SEQ ID NO: 42. In one embodiment, the invention relates to polypeptides having lysozyme activity and having a sequence identity to SEQ ID NO: 42 of at least 85% and wherein the polypeptide has at least 50%, such as at least 75%, at least 90%, at least 95% or at least 100% of the lysozyme activity of SEQ ID NO: 42. In one embodiment, the invention relates to polypeptides having lysozyme activity and having a sequence identity to SEQ ID NO: 42 of at least 90% and wherein the polypeptide has at least 50%, such as at least 75%, at least 90%, at least 95% or at least 100% of the lysozyme activity of SEQ ID NO: 42. In one embodiment, the invention relates to polypeptides having lysozyme activity and having a sequence identity to SEQ ID NO: 42 of at least 95% and wherein the polypeptide has at least 50%, such as at least 75%, at least 90%, at least 95% or at least 100% of the lysozyme activity of SEQ ID NO: 42. In one embodiment, lysozyme activity is determined as described in example 1.

In one embodiment, the polypeptide comprises or consists of the mature polypeptide of SEQ ID NO: 41. In one embodiment, the polypeptide preferably comprises or consists of the amino acid sequence of SEQ ID NO: 42; comprises the amino acid sequence of SEQ ID NO: 42 and a N-terminal and/or C-terminal His-tag and/or HQ-tag; comprises the amino acid sequence of SEQ ID NO: 42 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 42. In one embodiment, the polypeptide comprises or consists of amino acids 1 to 304 of SEQ ID NO: 42. In one embodiment, the polypeptide has been isolated.

In a continuation of the seventeenth aspect, the invention relates to polypeptides having lysozyme activity encoded by a polynucleotide having a sequence identity to the mature polypeptide coding sequence of SEQ ID NO: 40 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the seventeenth aspect, the invention relates to variants of SEQ ID NO: 42 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 42 is not more than 50, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In an embodiment, the number of positions comprising one or more amino acid substitutions, and/or one or more amino acid deletions, and/or one or more amino acid insertions or any combination thereof in SEQ ID NO: 42 is not more than 10, e.g., 1, 2, 3, 4, 5, 6, 7, 8, 9 or 10. In one embodiment, the number of substitutions and/or deletions and/or insertions in SEQ ID NO: 42 is not more than 10, e.g. 1, 2, 3, 4, 5, 6, 7, 8, 9, or 10. In a further embodiment, the number of substitutions, preferably conservative substitutions, in SEQ ID NO: 42 is not more than 10, e.g. 1, 2, 3, 4, 5, 6, 7, 8, 9, or 10. Examples of amino acid changes and conservative substitutions are described in the fourth aspect of the invention.

In an embodiment of the seventeenth aspect, the variant has at least 50%, such as at least 75%, at least 90%, at least 95% or at least 100% of the lysozyme activity of SEQ ID NO: 42. In one embodiment, lysozyme activity is determined as described in example 1.

In an eighteenth aspect, the invention relates to polypeptides having lysozyme activity having at least 100%, e.g., or 100% sequence identity to the mature polypeptide of SEQ ID NO: 44. In one embodiment, the polypeptides differ by up to 0 amino acids, e.g., or 1 amino acids from the mature polypeptide of SEQ ID NO: 44.

In a continuation of the eighteenth aspect, the invention relates to polypeptides having lysozyme activity having at least 100%, e.g., or 100% sequence identity to SEQ ID NO: 45. In one embodiment, the polypeptides differ by up to 0 amino acids, e.g., or 1 amino acids from SEQ ID NO: 45.

In one embodiment, the invention relates to polypeptides having lysozyme activity and having a sequence identity to SEQ ID NO: 45 of at least 100% and wherein the polypeptide has at least 50%, such as at least 75%, at least 90%, at least 95% or at least 100% of the lysozyme activity of SEQ ID NO: 45. In one embodiment, lysozyme activity is determined as described in example 1.

In one embodiment, the polypeptide comprises or consists of the mature polypeptide of SEQ ID NO: 44. In one embodiment, the polypeptide preferably comprises or consists of the amino acid sequence of SEQ ID NO: 45; comprises the amino acid sequence of SEQ ID NO: 45 and a N-terminal and/or C-terminal His-tag and/or HQ-tag; comprises the amino acid sequence of SEQ ID NO: 45 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 45. In one embodiment, the polypeptide comprises or consists of amino acids 1 to 227 of SEQ ID NO: 45. In one embodiment, the polypeptide has been isolated.

In a continuation of the eighteenth aspect, the invention relates to polypeptides having lysozyme activity encoded by a polynucleotide having a sequence identity to the mature polypeptide coding sequence of SEQ ID NO: 43 of at least 100%, e.g., or 100%. In a further embodiment, the polypeptide has been isolated.

In a continuation of the eighteenth aspect, the invention relates to variants of SEQ ID NO: 45 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 45 is not more than 0, e.g. or 1. In one embodiment, the number of substitutions and/or deletions and/or insertions in SEQ ID NO: 45 is not more than 0, e.g. or 1. In a further embodiment, the number of substitutions, preferably conservative substitutions, in SEQ ID NO: 45 is not more than 0, e.g. or 1. Examples of amino acid changes and conservative substitutions are described in the fourth aspect of the invention.

In an embodiment of the eighteenth aspect, the variant has at least 50%, such as at least 75%, at least 90%, at least 95% or at least 100% of the lysozyme activity of SEQ ID NO: 45. In one embodiment, lysozyme activity is determined as described in example 1.

Taxonoimic and Structural Families

In an embodiment, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN](SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment, the polypeptide having lysozyme activity is obtained or is obtainable from the taxonomic phylum Ascomycota, preferably the taxonomic subphylum Pezizomycotina and is preferably is selected from the group selected from SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45.

In one embodiment, the polypeptide having lysozyme activity is obtained or is obtainable from the taxonomic class Eurotiomycetes, preferably the taxonomic order Eurotiales and is more preferably selected from the group consisting of SEQ ID NO: 3, SEQ ID NO: 6, SEQ ID NO:9, SEQ ID NO: 12, SEQ ID NO: 15, SEQ ID NO: 21, SEQ ID NO: 24, SEQ ID NO: 27, SEQ ID NO: 30 and SEQ ID NO: 36.

In one embodiment, the polypeptide having lysozyme activity is obtained or is obtainable from the taxonomic order Eurotiales, preferably the taxonomic family Aspergillaceae and is more preferably selected from the group consisting of SEQ ID NO: 3, SEQ ID NO: 6, SEQ ID NO: 12, SEQ ID NO: 15, SEQ ID NO: 21, SEQ ID NO: 24, SEQ ID NO: 27 and SEQ ID NO: 30.

In one embodiment, the polypeptide having lysozyme activity is obtained or is obtainable from the taxonomic order Eurotiales, preferably the taxonomic family Trichocomaceae and is more preferably selected from the group consisting of SEQ ID NO: 9 and SEQ ID NO: 36.

In one embodiment, the polypeptide having lysozyme activity is obtained or is obtainable from the taxonomic class Sordariomycetes and is preferably selected from the group selected from SEQ ID NO: 18, SEQ ID NO: 33, SEQ ID NO: 39, SEQ ID NO: 42 and SEQ ID NO: 45.

In one embodiment, the polypeptide having lysozyme activity is obtained or is obtainable from the taxonomic order Sordariales, preferably the taxonomic family Chaetomiaceae and is more preferably selected from the group consisting of SEQ ID NO: 18, SEQ ID NO: 33, SEQ ID NO: 39 and SEQ ID NO: 45.

In one embodiment, the polypeptide having lysozyme activity is obtained or is obtainable from the taxonomic order Hypocreales, preferably the taxonomic family Clavicipitaceae and is more preferably selected from the group consisting of SEQ ID NO: 42.

Sources of Polypeptides Having Lysozyme Activity

A polypeptide having lysozyme activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Penicillium*, or from the species *Penicillium simplicissimum, Penicillium vasconiae, Penicillium antarcticum, Penicillium wellingtonense, Penicillium roseopurpureum* or *Penicillium virgatum*.

The polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Aspergillus*, or from the species *Aspergillus* sp. XZ2668 or *Aspergillus niveus*.

The polypeptide may be a fungal polypeptide. In one aspect, the polypeptide is a polypeptide having lysozyme activity from a fungus of the class Eurotiomycetes, such as from the order Eurotiales, or from the family Trichocomaceae, or from the genus *Talaromyces*, or from the species *Talaromyces proteolyticus* or *Talaromyces atricola*.

The polypeptide may be a fungal polypeptide. In one aspect, the polypeptide is a polypeptide having lysozyme activity from a fungus of the class Sordariomycetes, such as from the order Hypocreales, or from the family Clavicipitaceae, or from the genus *Metarhizium*, or from the species *Metarhizium carneum*.

The polypeptide may be a fungal polypeptide. In one aspect, the polypeptide is a polypeptide having lysozyme activity from a fungus of the class Sordariomycetes, such as from the order Sordariales, or from the family Chaetomiaceae, or from the genus *Ovatospora*, or from the species *Ovatospora brasiliensis*.

The polypeptide may be a fungal polypeptide. In one aspect, the polypeptide is a polypeptide having lysozyme activity from a fungus of the class Sordariomycetes, such as from the order Sordariales, or from the family Chaetomiaceae, or from the genus *Chaetomium*, or from the species *Chaetomium* sp. ZY369.

The polypeptide may be a fungal polypeptide. In one aspect, the polypeptide is a polypeptide having lysozyme activity from a fungus of the class Sordariomycetes, such as from the order Sordariales, or from the family Chaetomiaceae, or from the genus *Trichocladium*, or from the species *Trichocladium asperum*.

The polypeptide may be a fungal polypeptide. In one aspect, the polypeptide is a polypeptide having lysozyme activity from a fungus of the class Sordariomycetes, such as from the order Sordariales, or from the family Chaetomiaceae, or from the genus *Thielavia*, or from the species *Thielavia terrestris*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In an embodiment, the polynucleotide encoding the polypeptide of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Trichophaea* or a strain of *Trichoderma*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide.

The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus lichenformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMB1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

In some embodiments, the polypeptide is heterologous to the recombinant host cell.

In some embodiments, at least one of the one or more control sequences is heterologous to the polynucleotide encoding the polypeptide.

In some embodiments, the recombinant host cell comprises at least two copies, e.g., three, four, or five, of the polynucleotide of the present invention.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology*, *Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide.

In one aspect, the cell is a *Penicillium simplicissimum* cell. In one aspect, the cell is a *Penicillium vasconiae* cell.

In one aspect, the cell is a *Talaromyces proteolyticus* cell. In one aspect, the cell is an *Aspergillus* sp. XZ2668 cell. In one aspect, the cell is a *Penicillium antarcticum* cell. In one aspect, the cell is a *Ovatospora brasiliensis* cell. In one aspect, the cell is a *Penicillium wellingtonense* cell. In one aspect, the cell is a *Penicillium roseopurpureum* cell. In one aspect, the cell is a *Penicillium virgatum* cell. In one aspect, the cell is an *Aspergillus niveus* cell. In one aspect, the cell is a *Chaetomium* sp. ZY369 cell. In one aspect, the cell is a *Talaromyces atricola* cell. In one aspect, the cell is a *Trichocladium asperum* cell. In one aspect, the cell is a *Metarhizium carneum* cell. In one aspect, the cell is a *Thielavia terrestris* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the fermentation medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In some embodiments, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In some embodiments, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid (s), and optionally further contains killed cells and/or cell debris. In some embodiments, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in the polypeptide of the invention. The term "enriched" indicates that the lysozyme activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10.

In a preferred embodiment, the composition comprises one or more LYS polypeptides having lysozyme activity selected from the list consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45.

In an embodiment, the composition comprises the polypeptide of the invention and one or more formulating agents, as described below.

The compositions may further comprise multiple enzymatic activities, such as one or more (e.g., several) enzymes selected from the group consisting of phytase, xylanase, galactanase, alpha-galactosidase, beta-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

The compositions may further comprise one or more probiotics. In an embodiment, the probiotic is selected from the group consisting of Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium sp., Carnobacterium sp., Clostridium butyricum, Clostridium sp., Enterococcus faecium, Enterococcus sp., Lactobacillus sp., Lactobacillus acidophilus, Lactobacillus farciminus, Lactobacillus rhamnosus, Lactobacillus reuteri, Lactobacillus salivarius, Lactococcus lactis, Lactococcus sp., Leuconostoc sp., Megasphaera elsdenii, Megasphaera sp., Pediococcus acidilactici, Pediococcus sp., Propionibacterium thoenii, Propionibacterium sp. and Streptococcus sp. or any combination thereof.

In an embodiment, the composition comprises one or more formulating agents as disclosed herein, preferably one or more of the compounds selected from the list consisting of glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate, kaolin and cellulose.

In an embodiment, the composition comprises one or more components selected from the list consisting of vitamins, minerals and amino acids.

The enzyme of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate (e.g. as disclosed in WO2000/70034). The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In one embodiment, the composition is a solid composition, such as a spray dried composition, comprising the LYS polypeptide of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose.

In a preferred embodiment, the formulating agent is selected from one or more of the following compounds: sodium sulfate, dextrin, cellulose, sodium thiosulfate, magnesium sulfate and calcium carbonate.

The present invention also relates to enzyme granules/particles comprising the LYS polypeptide of the invention optionally combined with one or more additional enzymes. The granule is composed of a core, and optionally one or more coatings (outer layers) surrounding the core.

Typically the granule/particle size, measured as equivalent spherical diameter (volume based average particle size), of the granule is 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) spray dried products, wherein a liquid enzyme-containing solution is atomized in a spray drying tower to form small droplets which during their way down the drying tower dry to form an enzyme-containing particulate material;

b) layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606;

c) absorbed core particles, wherein rather than coating the enzyme as a layer around the core, the enzyme is absorbed onto and/or into the surface of the core. Such a process is described in WO 97/39116.

d) extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme;

e) prilled products, wherein an enzyme-containing powder is suspended in molten wax and the suspension is sprayed, e.g., through a rotating disk atomiser, into a cooling chamber where the droplets quickly solidify (Michael S. Showell (editor); *Powdered detergents*; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique;

f) mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons);

h) fluid bed granulation, which involves suspending particulates in an air stream and spraying a liquid onto the fluidized particles via nozzles. Particles hit by spray droplets get wetted and become tacky. The tacky particles collide with other particles and adhere to them and form a granule;

i) the cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

In one embodiment, the core comprises a material selected from the group consisting of salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals and clay minerals (also known as hydrous aluminium phyllosilicates). In one embodiment, the core comprises a clay mineral such as kaolinite or kaolin.

The core may include an inert particle with the enzyme absorbed into it, or applied onto the surface, e.g., by fluid bed coating.

The core may have a diameter of 20-2000 µm, particularly 50-1500 µm, 100-1500 µm or 250-1200 µm.

The core may be surrounded by at least one coating, e.g., to improve the storage stability, to reduce dust formation during handling, or for coloring the granule. The optional coating(s) may include a salt and/or wax and/or flour coating, or other suitable coating materials.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In some embodiments the thickness of the coating is below 100 µm, such as below 60 µm, or below 40 µm.

The coating should encapsulate the core unit by forming a substantially continuous layer. A substantially continuous layer is to be understood as a coating having few or no holes, so that the core unit is encapsulated or enclosed with few or no uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

The salt may be added from a salt solution where the salt is completely dissolved or from a salt suspension wherein the fine particles are less than 50 µm, such as less than 10 µm or less than 5 m.

The salt coating may comprise a single salt or a mixture of two or more salts. The salt may be water soluble, in particular having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, sorbate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO1997/05245, WO1998/54980, WO1998/55599, WO2000/70034, WO2006/034710, WO2008/017661, WO2008/017659, WO2000/020569, WO2001/004279, WO1997/05245, WO2000/01793, WO2003/059086, WO2003/059087, WO2007/031483, WO2007/031485, WO2007/044968, WO2013/192043, WO2014/014647 and WO2015/197719 or polymer coating such as described in WO 2001/00042.

Specific examples of suitable salts are NaCl (CH20° C.=76%), Na2CO3 (CH20° C.=92%), NaNO3 (CH20° C.=73%), Na2HPO4 (CH20° C.=95%), Na3PO4 (CH25° C.=92%), NH4Cl (CH20° C.=79.5%), (NH4)2HPO4 (CH20° C.=93.0%), NH4H2PO4 (CH20° C.=93.1%), (NH4)2SO4 (CH20° C.=81.1%), KCl (CH20° C.=85%), K2HPO4 (CH20° C.=92%), KH2PO4 (CH20° C.=96.5%), KNO3 (CH20° C.=93.5%), Na2SO4 (CH20° C.=93%), K2SO4 (CH20° C.=98%), KHSO4 (CH20° C.=86%), MgSO4 (CH20° C.=90%), ZnSO4 (CH20° C.=90%) and sodium citrate (CH25° C.=86%). Other examples include NaH2PO4, (NH4)H2PO4, CuSO4, Mg(NO3)2, magnesium acetate, calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, sodium acetate, sodium benzoate, sodium citrate, sodium sulfate, zinc acetate, zinc benzoate, zinc carbonate, zinc chloride, zinc citrate and zinc sorbate.

The salt may be in anhydrous form, or it may be a hydrated salt, i.e. a crystalline salt hydrate with bound water(s) of crystallization, such as described in WO 99/32595. Specific examples include anhydrous sodium sulfate (Na2SO4), anhydrous magnesium sulfate (MgSO4), magnesium sulfate heptahydrate (MgSO4.7H2O), zinc sulfate heptahydrate (ZnSO4.7H20), sodium phosphate dibasic heptahydrate (Na2HPO4.7H2O), magnesium nitrate hexahydrate (Mg(NO3)2(6H2O)), sodium citrate dihydrate and magnesium acetate tetrahydrate.

Preferably the salt is applied as a solution of the salt, e.g., using a fluid bed.

A wax coating may comprise at least 60% by weight of a wax, e.g., at least 65%, at least 70%, at least 75%, at least 80%, at least 85%, at least 90%, at least 95% or at least 99% by weight.

Specific examples of waxes are polyethylene glycols; polypropylenes; Carnauba wax; Candelilla wax; bees wax; hydrogenated plant oil or animal tallow such as polyethylene glycol (PEG), methyl hydroxy-propyl cellulose (MHPC), polyvinyl alcohol (PVA), hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; microcrystalline wax; paraffin's; and fatty acids, such as hydrogenated linear long chained fatty acids and derivatives thereof. A preferred wax is palm oil or hydrogenated palm oil.

The granule may comprise a core comprising the LYS polypeptide of the invention, one or more salt coatings and one or more wax coatings. Examples of enzyme granules with multiple coatings are shown in WO1993/07263, WO1997/23606 and WO2016/149636.

Non-dusting granulates may be produced, e.g., as disclosed in U.S. Pat. Nos. 4,106,991 and 4,661,452 and may optionally be coated by methods known in the art. The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granulate may further comprise one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

Thus, in a further aspect, the present invention provides a granule, which comprises:
(a) a core comprising a LYS polypeptide having lysozyme activity according to the invention, and
(b) a coating consisting of one or more layer(s) surrounding the core.

In one embodiment, the coating comprises a salt coating as described herein. In one embodiment, the coating comprises a wax coating as described herein. In one embodiment, the coating comprises a salt coating followed by a wax coating as described herein.

Animal Feed Additives

The present invention also relates to animal feed additives comprising one or more LYS polypeptides having lysozyme activity. Thus, in one embodiment, the invention relates to an animal feed additive comprising a LYS polypeptide, wherein:
(a) the polypeptide has lysozyme activity;
(b) the polypeptide comprises one or more LAD catalytic domains; and
(c) the LAD catalytic domain gives a domT score of at least 170 when queried using a Profile Hidden Markov Model prepared using SEQ ID NOs: 46 to 187 and hmmbuild software program, and wherein the query is carried out using hmmscan software program by the Method of Determining the Lysozyme Enhancing Domain by HMM.

In an embodiment, the polypeptide further comprises one or more lysozyme enhancing domains, wherein the lysozyme enhancing domain gives a domT score of at least 100 when queried using a Profile Hidden Markov Model prepared using SEQ ID NOs: 188 to 316 and hmmbuild software program, and wherein the query is carried out using the hmmscan software program.

In an embodiment, the domT score of the LAD catalytic domain is at least 175, preferably at least 180, more preferably at least 185, even more preferably at least 190, even more preferably at least 195, or most preferably at least 200. In an embodiment, the domT score of the LED is at least 103, preferably at least 106, more preferably at least 109, more preferably at least 112, more preferably at least 115, more preferably at least 118, even more preferably at least 121, or most preferably at least 124. Preferred combinations of domT scores are as disclosed in the first aspect of the invention.

In an embodiment, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN](SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In another aspect, the invention relates to animal feed additives comprising one or more LYS polypeptides having lysozyme activity, wherein the polypeptide is selected from the group consisting of:
(a) a polypeptide having at least 80%, such as at least 85%, at least 90% or at least 95% sequence identity to the polypeptide of SEQ ID NO: 3;
(b) a polypeptide having at least 84%, such as at least 85%, at least 90% or at least 95% sequence identity to the polypeptide of SEQ ID NO: 6;
(c) a polypeptide having at least 80%, such as at least 85%, at least 90% or at least 95% sequence identity to the polypeptide of SEQ ID NO: 9;
(d) a polypeptide having at least 80%, such as at least 85%, at least 90% or at least 95% sequence identity to the polypeptide of SEQ ID NO: 12;
(e) a polypeptide having at least 80%, such as at least 85%, at least 90% or at least 95% sequence identity to the polypeptide of SEQ ID NO: 15;
(f) a polypeptide having at least 80%, such as at least 85%, at least 90% or at least 95% sequence identity to the polypeptide of SEQ ID NO: 18;
(g) a polypeptide having at least 80%, such as at least 85%, at least 90% or at least 95% sequence identity to the polypeptide of SEQ ID NO: 21;
(h) a polypeptide having at least 80%, such as at least 85%, at least 90% or at least 95% sequence identity to the polypeptide of SEQ ID NO: 24;
(i) a polypeptide having at least 80%, such as at least 85%, at least 90% or at least 95% sequence identity to the polypeptide of SEQ ID NO: 27;
(j) a polypeptide having at least 84%, such as at least 85%, at least 90% or at least 95% sequence identity to the polypeptide of SEQ ID NO: 30;
(k) a polypeptide having at least 80%, such as at least 85%, at least 90% or at least 95% sequence identity to the polypeptide of SEQ ID NO: 33;
(l) a polypeptide having at least 80%, such as at least 85%, at least 90% or at least 95% sequence identity to the polypeptide of SEQ ID NO: 36;
(m) a polypeptide having at least 84%, such as at least 85%, at least 90% or at least 95% sequence identity to the polypeptide of SEQ ID NO: 39;

(n) a polypeptide having at least 80%, such as at least 85%, at least 90% or at least 95% sequence identity to the polypeptide of SEQ ID NO: 42;
(o) a polypeptide having at least 80%, such as at least 85%, at least 90% or at least 95% sequence identity to the polypeptide of SEQ ID NO: 45;
(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;
(q) a polypeptide comprising the polypeptide of (a), (b), (c), (d), (e), (f), (g), (h), (i), (j), (k), (l), (m), (n), (o) or (p) and a N-terminal and/or C-terminal His-tag and/or HQ-tag;
(r) a polypeptide comprising the polypeptide of (a), (b), (c), (d), (e), (f), (g), (h), (i), (j), (k), (l), (m), (n), (o) or (p) and a N-terminal and/or C-terminal extension of up to 10 amino acids, e.g. 1, 2, 3, 4, 5, 6, 7, 8, 9 or 10 amino acids; and
(s) a fragment of the polypeptide of (a), (b), (c), (d), (e), (f), (g), (h), (i), (j), (k), (l), (m), (n), (o) or (p) having lysozyme activity and having at least 90% of the length of the mature polypeptide.

In an embodiment, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN](SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment, the polypeptide is of fungal origin. In an embodiment, the polypeptide is obtained or obtainable from the taxonomic phylum Ascomycota, preferably the taxonomic subphylum Pezizomycotina.

In an embodiment, the amount of enzyme in the animal feed additive is between 0.001% and 10% by weight of the composition.

In an embodiment, the animal feed additive comprises one or more formulating agents, preferably as described herein above.

In an embodiment, the animal feed additive comprises one or more additional enzymes, preferably as described herein below.

In an embodiment, the animal feed additive comprises one or more probiotics, preferably as described herein below.

In an embodiment, the animal feed additive comprises one or more vitamins, preferably as described herein below.

In an embodiment, the animal feed additive comprises one or more minerals, preferably as described herein below.

In an embodiment, the animal feed additive comprises one or more amino acids, preferably as described herein below.

In an embodiment, the animal feed additive comprises one or more prebiotics, preferably as described herein below.

In an embodiment, the animal feed additive comprises one or more organic acids, preferably as described herein below.

In an embodiment, the animal feed additive comprises one or more phytogenics, preferably as described herein below.

Animal Feed

The present invention also relates to animal feed compositions comprising one or more lysozymes of the invention. In one embodiment, the invention relates to an animal feed comprising the granule as described herein and plant based material. In one embodiment, the invention relates to an animal feed comprising the animal feed additive as described herein and plant based material.

Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one polypeptide having lysozyme activity as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington DC).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g. beet, sugar beet, spinach or quinoa. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) lysozyme/enzyme preparation may also be added before or during the feed ingredient step. Typically a liquid lysozyme/enzyme preparation comprises the polypeptide having lysozyme activity of the invention optionally with a polyol, such as glycerol, ethylene glycol or propylene glycol, and is added after the pelleting step, such as by spraying the liquid formulation onto the pellets. The enzyme may also be incorporated in a feed additive or premix.

Alternatively, the polypeptide having lysozyme activity can be prepared by freezing a mixture of liquid enzyme solution with a bulking agent such as ground soybean meal, and then lyophilizing the mixture.

The final enzyme concentration in the diet is within the range of 0.01-200 mg enzyme protein per kg diet, preferably between 0.05-100 mg/kg diet, more preferably 0.1-50 mg, even more preferably 0.2-20 mg enzyme protein per kg animal diet.

It is at present contemplated that the enzyme is administered in one or more of the following amounts (dosage ranges): 0.01-200; 0.05-100; 0.1-50; 0.2-20; 0.1-1; 0.2-2; 0.5-5; or 1-10; —all these ranges being in mg LYS polypeptide protein per kg feed (ppm).

For determining mg LYS polypeptide protein per kg feed, the LYS polypeptide is purified from the feed composition, and the specific activity of the purified LYS polypeptide is determined using a relevant assay (see under lysozyme activity). The lysozyme activity of the feed composition as such is also determined using the same assay, and on the basis of these two determinations, the dosage in mg lysozyme protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The same principles apply for determining mg LYS polypeptide protein in feed additives. Of course, if a sample is available of the LYS polypeptide used for preparing the feed additive or the feed, the specific activity is determined from this sample (no need to purify the LYS polypeptide from the feed composition or the additive).

Thus in a further aspect, the present invention also relates to an animal feed comprising one or more LYS polypeptides having lysozyme activity and plant based material. In another aspect, the present invention also relates to an animal feed comprising the animal feed additive of the invention (as described herein above) and plant based material.

In one embodiment, the invention relates to an animal feed comprising plant based material and a LYS polypeptide, wherein the polypeptide (a) has lysozyme activity and (b) comprises one or more LAD catalytic domains; wherein the LAD catalytic domain gives a domT score of at least 180 when queried using a Profile Hidden Markov Model (HMM) prepared using SEQ ID NOs: 46 to 187 and hmmbuild software program, and wherein the query is carried out using hmmscan software program by the Method of Determining the LAD Catalytic Domain by HMM.

In an embodiment, the polypeptide further comprises one or more lysozyme enhancing domains, wherein the lysozyme enhancing domain gives a domT score of at least 100 when queried using a Profile Hidden Markov Model prepared using SEQ ID NOs: 188 to 316 and hmmbuild software program, and wherein the query is carried out using the hmmscan software program by the Method of Determining the Lysozyme.

In an embodiment, the domT score of the LAD catalytic domain is at least 175, preferably at least 180, more preferably at least 185, even more preferably at least 190, even more preferably at least 195, or most preferably at least 200. In an embodiment, the domT score of the LED is at least 103, preferably at least 106, more preferably at least 109, more preferably at least 112, more preferably at least 115, more preferably at least 118, even more preferably at least 121, or most preferably at least 124. Preferred combinations of domT scores are as disclosed in the first aspect of the invention.

In an embodiment, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN](SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In another aspect, the invention relates to an animal feed comprising plant based material and one or more LYS polypeptides having lysozyme activity, wherein the polypeptide is selected from the group consisting of:

(a) a polypeptide having at least 80%, such as at least 85%, at least 90% or at least 95% sequence identity to the polypeptide of SEQ ID NO: 3;

(b) a polypeptide having at least 84%, such as at least 85%, at least 90% or at least 95% sequence identity to the polypeptide of SEQ ID NO: 6;

(c) a polypeptide having at least 80%, such as at least 85%, at least 90% or at least 95% sequence identity to the polypeptide of SEQ ID NO: 9;

(d) a polypeptide having at least 80%, such as at least 85%, at least 90% or at least 95% sequence identity to the polypeptide of SEQ ID NO: 12;

(e) a polypeptide having at least 80%, such as at least 85%, at least 90% or at least 95% sequence identity to the polypeptide of SEQ ID NO: 15;

(f) a polypeptide having at least 80%, such as at least 85%, at least 90% or at least 95% sequence identity to the polypeptide of SEQ ID NO: 18;

(g) a polypeptide having at least 80%, such as at least 85%, at least 90% or at least 95% sequence identity to the polypeptide of SEQ ID NO: 21;

(h) a polypeptide having at least 80%, such as at least 85%, at least 90% or at least 95% sequence identity to the polypeptide of SEQ ID NO: 24;

(i) a polypeptide having at least 80%, such as at least 85%, at least 90% or at least 95% sequence identity to the polypeptide of SEQ ID NO: 27;

(j) a polypeptide having at least 84%, such as at least 85%, at least 90% or at least 95% sequence identity to the polypeptide of SEQ ID NO: 30;

(k) a polypeptide having at least 80%, such as at least 85%, at least 90% or at least 95% sequence identity to the polypeptide of SEQ ID NO: 33;

(l) a polypeptide having at least 80%, such as at least 85%, at least 90% or at least 95% sequence identity to the polypeptide of SEQ ID NO: 36;

(m) a polypeptide having at least 84%, such as at least 85%, at least 90% or at least 95% sequence identity to the polypeptide of SEQ ID NO: 39;

(n) a polypeptide having at least 80%, such as at least 85%, at least 90% or at least 95% sequence identity to the polypeptide of SEQ ID NO: 42;

(o) a polypeptide having at least 80%, such as at least 85%, at least 90% or at least 95% sequence identity to the polypeptide of SEQ ID NO: 45;

(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;

(q) a polypeptide comprising the polypeptide of (a), (b), (c), (d), (e), (f), (g), (h), (i), (j), (k), (l), (m), (n), (o) or (p) and a N-terminal and/or C-terminal His-tag and/or HQ-tag;

(r) a polypeptide comprising the polypeptide of (a), (b), (c), (d), (e), (f), (g), (h), (i), j), (k), (l), (m), (n), (o) or (p) and a N-terminal and/or C-terminal extension of up to 10 amino acids, e.g. 1, 2, 3, 4, 5, 6, 7, 8, 9 or 10 amino acids; and (s) a fragment of the polypeptide of (a), (b), (c), (d), (e), (f), (g), (h), (i), j), (k), (l), (m), (n), (o) or (p) having lysozyme activity and having at least 90% of the length of the mature polypeptide.

In an embodiment, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN](SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment, the polypeptide is of fungal origin. In an embodiment, the polypeptide is obtained or obtainable from the taxonomic phylum Ascomycota, preferably the taxonomic subphylum Pezizomycotina.

In an embodiment, the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

In a further embodiment, the animal feed has been pelleted.

In another embodiment, the compositions described herein optionally include one or more enzymes. Enzymes can be classified on the basis of the handbook Enzyme Nomenclature from NC-IUBMB, 1992), see also the ENZYME site www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase, lysozyme and galactosidase is described in Henrissat et al, "The carbohydrate-active enzymes database (CAZy) in 2013", *Nucl. Acids Res*. (1 Jan. 2014) 42 (D1): D490-D495; see also www.cazy.org.

Thus the composition of the invention may also comprise at least one other enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); arabinofuranosidase (EC 3.2.1.55); beta-xylosidase (EC 3.2.1.37); acetyl xylan esterase (EC 3.1.1.72); feruloyl esterase (EC 3.1.1.73); cellulase (EC 3.2.1.4); cellobiohydrolases (EC 3.2.1.91); beta-glucosidase (EC 3.2.1.21); pullulanase (EC 3.2.1.41), alpha-mannosidase (EC 3.2.1.24), mannanase (EC 3.2.1.25) and beta-glucanase (EC 3.2.1.4 or EC 3.2.1.6), or any mixture thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Natuphos™ E (BASF), Finase® and Quantum® Blue (AB Enzymes), OptiPhos® (Huvepharma), AveMix® Phytase (Aveve Biochem), Phyzyme® XP (Verenium/DuPont) and Axtra® PHY (DuPont). Other preferred phytases include those described in e.g. WO 98/28408, WO 00/43503, and WO 03/066847.

In a particular embodiment, the composition of the invention comprises a xylanase (EC 3.2.1.8). Examples of commercially available xylanases include Ronozyme® WX (DSM Nutritional Products), Econase® XT and Barley (AB Vista), Xylathin® (Verenium), Hostazym® X (Huvepharma), Axtra® XB (Xylanase/beta-glucanase, DuPont) and Axtra® XAP (Xylanase/amylase/protease, DuPont), AveMix® XG 10 (xylanase/glucanase) and AveMix® 02 CS (xylanase/glucanase/pectinase, Aveve Biochem), and Naturgrain (BASF).

In a particular embodiment, the composition of the invention comprises a protease (EC 3.4). Examples of commercially available proteases include Ronozyme® ProAct (DSM Nutritional Products).

In a particular embodiment, the composition of the invention comprises an alpha-amylase (EC 3.2.1.1). Examples of commercially available alpha-amylases include Ronozyme® A and RONOZYME® RumiStar™ (DSM Nutritional Products).

In one embodiment, the composition of the invention comprises a multicomponent enzyme product, such as FRA® Octazyme (Framelco), Ronozyme® G2, Ronozyme® VP and Ronozyme® MultiGrain (DSM Nutritional Products), Rovabio® Excel or Rovabio® Advance (Adisseo).

Eubiotics are compounds which are designed to give a healthy balance of the micro-flora in the gastrointestinal tract. Eubiotics cover a number of different feed additives, such as probiotics, prebiotics, phytogenics (essential oils) and organic acids which are described in more detail below.

In an embodiment, the animal feed composition further comprises one or more additional probiotic. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus spp, and Pediococcus spp, Lactobacillus spp, Bifidobacterium spp, Lactobacillus acidophilus, Pediocosus acidilactici, Lactococcus lactis, Bifidobacterium bifidum, Propionibacterium thoenii, Lactobacillus farciminus, Lactobacillus rhamnosus, Clostridium butyricum, Bifidobacterium animalis ssp. animalis, Lactobacillus reuteri, Lactobacillus salivarius ssp. salivarius, Megasphaera elsdenii, Propionibacteria sp*.

In a more preferred embodiment, composition, animal feed additive or animal feed further comprises a bacterium from one or more of the following strains of *Bacillus subtilis:* 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, DSM 32315, NRRL B-50136, NRRL B-50605, NRRL B-50606, NRRL B-50622 and PTA-7547.

In a more preferred embodiment, composition, animal feed additive or animal feed further comprises a bacterium from one or more of the following strains of *Bacillus pumilus*: NRRL B-50016, ATCC 700385, NRRL B-50885 or NRRL B-50886.

In a more preferred embodiment, composition, animal feed additive or animal feed further comprises a bacterium from one or more of the following strains of *Bacillus lichenformis*: NRRL B 50015, NRRL B-50621 or NRRL B-50623.

In a more preferred embodiment, composition, animal feed additive or animal feed further comprises a bacterium from one or more of the following strains of *Bacillus amyloliquefaciens*: DSM 29869, DSM 29869, NRRL B 50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1\times10^4$ and $1\times10^{14}$ CFU/kg of dry matter, preferably between $1\times10^6$ and $1\times10^{12}$ CFU/kg of dry matter, and more preferably between $1\times10^7$ and $1\times10^{11}$ CFU/kg of dry matter. In a more preferred embodiment the bacterial count of each of the bacterial strains in the animal feed composition is between $1\times10^8$ and $1\times10^{10}$ CFU/kg of dry matter.

The bacterial count of each of the bacterial strains in the animal feed composition is between $1\times10^5$ and $1\times10^{15}$ CFU/animal/day, preferably between $1\times10^7$ and $1\times10^{13}$ CFU/animal/day, and more preferably between $1\times10^8$ and $1\times10^{12}$ CFU/animal/day. In a more preferred embodiment the bacterial count of each of the bacterial strains in the animal feed composition is between $1\times10^9$ and $1\times10^{11}$ CFU/animal/day. In one embodiment, the amount of probiotics is 0.001% to 10% by weight of the composition.

In another embodiment, the one or more bacterial strains are present in the form of a stable spore.

Examples of commercial products are Cylactin® (DSM Nutritional Products), Alterion (Adisseo), Enviva PRO (DuPont Animal Nutrition), Syncra® (mix enzyme+probiotic, DuPont Animal Nutrition), Ecobiol® and Fecinor® (Norel/Evonik) and GutCare® PY1 (Evonik).

Prebiotics are substances that induce the growth or activity of microorganisms (e.g., bacteria and fungi) that contribute to the well-being of their host. Prebiotics are typically non-digestible fiber compounds that pass undigested through the upper part of the gastrointestinal tract and stimulate the growth or activity of advantageous bacteria that colonize the large bowel by acting as substrate for them. Normally, prebiotics increase the number or activity of bifidobacteria and lactic acid bacteria in the GI tract.

Yeast derivatives (inactivated whole yeasts or yeast cell walls) can also be considered as prebiotics. They often comprise mannan-oligosaccharids, yeast beta-glucans or protein contents and are normally derived from the cell wall of the yeast, *Saccharomyces cerevisiae*.

In one embodiment, the amount of prebiotics is 0.001% to 10% by weight of the composition. Examples of yeast products are Yang® and Agrimos (Lallemand Animal Nutrition).

Phytogenics are a group of natural growth promoters or non-antibiotic growth promoters used as feed additives, derived from herbs, spices or other plants. Phytogenics can be single substances prepared from essential oils/extracts, essential oils/extracts, single plants and mixture of plants (herbal products) or mixture of essential oils/extracts/plants (specialized products).

Examples of phytogenics are rosemary, sage, oregano, thyme, clove, and lemongrass. Examples of essential oils are thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and curcuma extract.

In one embodiment, the amount of phytogeneics is 0.001% to 10% by weight of the composition. Examples of commercial products are Crina® (DSM Nutritional Products); Cinergy™, Biacid™ ProHacid™ Classic and Pro-Hacid™ Advance™ (all Promivi/Cargill) and Envivo EO (DuPont Animal Nutrition).

Organic acids (C1-C7) are widely distributed in nature as normal constituents of plants or animal tissues. They are also formed through microbial fermentation of carbohydrates mainly in the large intestine. They are often used in swine and poultry production as a replacement of antibiotic growth promoters since they have a preventive effect on the intestinal problems like necrotic enteritis in chickens and *Escherichia coli* infection in young pigs. Organic acids can be sold as mono component or mixtures of typically 2 or 3 different organic acids. Examples of organic acids are propionic acid, formic acid, citric acid, lactic acid, sorbic acid, malic acid, acetic acid, fumaric acid, benzoic acid, butyric acid and tartaric acid or their salt (typically sodium or potassium salt such as potassium diformate or sodium butyrate).

In one embodiment, the amount of organic acid is 0.001% to 10% by weight of the composition. Examples of commercial products are VevoVitall® (DSM Nutritional Products), Amasil®, Luprisil®, Lupro-Grain®, Lupro-Cid®, Lupro-Mix® (BASF), n-Butyric Acid AF (OXEA) and Adimix Precision (Nutriad).

The incorporation of the composition of feed additives as exemplified herein above to animal feeds, for example poultry feeds, is in practice carried out using a concentrate or a premix. A premix designates a preferably uniform mixture of one or more microingredients with diluent and/or carrier. Premixes are used to facilitate uniform dispersion of micro-ingredients in a larger mix. A premix according to the invention can be added to feed ingredients or to the drinking water as solids (for example as water soluble powder) or liquids.

The composition of the invention may further comprise one or more amino acids. Examples of amino acids which are used in animal feed are lysine, alanine, beta-alanine, threonine, methionine and tryptophan. In one embodiment, the amount of amino acid is 0.001% to 10% by weight of the composition.

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin C, vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, iodine, selenium and zinc.

Non-limiting examples of macro minerals include calcium, magnesium, phosphorus, potassium and sodium.

In one embodiment, the amount of vitamins is 0.001% to 10% by weight of the composition. In one embodiment, the amount of minerals is 0.001% to 10% by weight of the composition.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
|---|---|---|
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Other Feed Ingredients

The composition of the invention may further comprise colouring agents, stabilisers, growth improving additives and aroma compounds/flavourings, polyunsaturated fatty acids (PUFAs); reactive oxygen generating species, antioxidants, anti-microbial peptides, anti-fungal polypeptides and mycotoxin management compounds.

Examples of colouring agents are carotenoids such as beta-carotene, astaxanthin, and lutein.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a synthetase.

Antioxidants can be used to limit the number of reactive oxygen species which can be generated such that the level of reactive oxygen species is in balance with antioxidants.

Mycotoxins, such as deoxynivalenol, aflatoxin, zearalenone and fumonisin can be found in animal feed and can result in negative animal performance or illness. Compounds which can manage the levels of mycotoxin, such as via deactivation of the mycotoxin or via binding of the mycotoxin, can be added to the feed to ameliorate these negative effects. Examples of mycotoxin management compounds are Vitafix®, Vitafix Ultra (Nuscience), Mycofix®, Mycofix® Secure, FUMzyme®, Biomin® BBSH, Biomin® MTV (Biomin), Mold-Nil®, Toxy-Nil® and Unike® Plus (Nutriad).

Uses

A LYS polypeptide of the invention may also be used in animal feed, wherein the term "animal" refers to all animals except humans. Examples of animals are mono-gastric animals, e.g. pigs or swine (including, but not limited to, piglets, growing pigs, and sows); poultry (including but not limited to poultry, turkey, duck, quail, guinea fowl, goose, pigeon, squab, chicken, broiler, layer, pullet and chick); fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

In the use according to the invention the LYS polypeptide can be fed to the animal before, after, or simultaneously with the diet. The latter is preferred.

In a particular embodiment, the LYS polypeptide, in the form in which it is added to the feed, or when being included in a feed additive, is well-defined. Well-defined means that the LYS polypeptide preparation is at least 50% pure as determined by Size-exclusion chromatography (see Example 12 of WO 01/58275). In other particular embodiments the LYS polypeptide preparation is at least 60, 70, 80, 85, 88, 90, 92, 94, or at least 95% pure as determined by this method.

A well-defined LYS polypeptide preparation is advantageous. For instance, it is much easier to dose correctly to the feed a LYS polypeptide that is essentially free from interfering or contaminating other lysozymes. The term dose correctly refers in particular to the objective of obtaining consistent and constant results, and the capability of optimizing dosage based upon the desired effect.

For the use in animal feed, however, the LYS polypeptide need not be pure; it may e.g. include other enzymes, in which case it could be termed a LYS polypeptide preparation.

The LYS polypeptide preparation can be (a) added directly to the feed, or (b) it can be used in the production of one or more intermediate compositions such as feed additives or premixes that is subsequently added to the feed (or used in a treatment process). The degree of purity described above refers to the purity of the original LYS polypeptide preparation, whether used according to (a) or (b) above.

Methods of Improving Animal Performance

In an embodiment, the present invention also relates to a method of improving the performance of an animal comprising administering to the animal the animal feed or the animal feed additive of the invention.

In a preferred embodiment, the method of improving the performance of an animal comprises administering to the animal the animal feed or the animal feed additive comprising the LYS polypeptide of the invention. In one embodiment, the LYS polypeptide is selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45.

In an embodiment, the present invention also relates to the use of the animal feed or an animal feed additive of the invention for improving the performance of an animal. In another embodiment, the invention relates to the use of one or more lysozymes of the invention for improving the performance of an animal.

In one embodiment, 'improving the performance of an animal' means that there is an increase in body weight gain. In another embodiment, 'improving the performance of an animal' means that there is an improved feed conversion ratio. In a further embodiment, 'improving the performance of an animal' means that there is an increased feed efficiency. In a further embodiment, 'improving the performance of an animal' means that there is an increase in body weight gain and/or an improved feed conversion ratio and/or an increased feed efficiency.

In an embodiment, the animal feed comprises plant based material selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

Methods of Preparing an Animal Feed

In an embodiment, the present invention provides a method for preparing an animal feed comprising adding one or more LYS polypeptide of the invention to one or more animal feed ingredients. Animal feed ingredients include, but are not limited to concentrates (as defined herein), forage (as defined herein), enzymes, probiotic, vitamins, minerals and amino acids.

In a preferred embodiment, the method of preparing an animal feed comprises mixing plant based material with the LYS polypeptide of the invention. In one embodiment, the LYS polypeptide is selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45.

In an embodiment, the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

Preferred Embodiments

Herein follows a list of preferred embodiments of the invention.

1. A composition comprising at least 0.01 mg of LYS polypeptide per kilogram of composition, wherein the polypeptide (a) has lysozyme activity and (b) comprises one or more LAD catalytic domains; wherein the LAD catalytic domain gives a domT score of at least 180 when queried using a Profile Hidden Markov Model (HMM) prepared using SEQ ID NOs: 46 to 187 and hmmbuild software program, suitably wherein the query is carried out using hmmscan software program by the Method of Determining the LAD Catalytic Domain by HMM.

2. The composition of item 1, wherein the polypeptide further comprises one or more lysozyme enhancing domains, wherein the lysozyme enhancing domain gives a domT score of at least 100 when queried using a Profile Hidden Markov Model prepared using SEQ ID NOs: 188 to 316 and hmmbuild software program, and wherein the query is carried out using the hmmscan software program by the Method of Determining the Lysozyme Enhancing Domain.

3. The composition of any of items 1 to 2, wherein
   (a) the LAD catalytic domain comprises one or more motif I: AG[I/L]AT[A/G][I/L][T/V]ES (SEQ ID NO: 317) and/or one or more motif II V[G/A]XLCQXVQX-SAYP (SEQ ID NO: 318); and/or
   (b) the lysozyme enhancing domain comprises one or more motif III: [CGY][YF][VIL][ASTP][DG]X[YF][VIT]X[TS][GAN] (SEQ ID NO: 319).

4. A composition comprising one or more LYS polypeptides having lysozyme activity, wherein the polypeptide is dosed at least 0.01 mg of polypeptide per kilogram of composition and is selected from the group consisting of:
   (a) a polypeptide having at least 80% sequence identity to the polypeptide of SEQ ID NO: 3;
   (b) a polypeptide having at least 80% sequence identity to the polypeptide of SEQ ID NO: 6;
   (c) a polypeptide having at least 80% sequence identity to the polypeptide of SEQ ID NO: 9;
   (d) a polypeptide having at least 80% sequence identity to the polypeptide of SEQ ID NO: 12;

(e) a polypeptide having at least 80% sequence identity to the polypeptide of SEQ ID NO: 15;
(f) a polypeptide having at least 80% sequence identity to the polypeptide of SEQ ID NO: 18;
(g) a polypeptide having at least 80% sequence identity to the polypeptide of SEQ ID NO: 21;
(h) a polypeptide having at least 80% sequence identity to the polypeptide of SEQ ID NO: 24;
(i) a polypeptide having at least 80% sequence identity to the polypeptide of SEQ ID NO: 27;
(j) a polypeptide having at least 80% sequence identity to the polypeptide of SEQ ID NO: 30;
(k) a polypeptide having at least 80% sequence identity to the polypeptide of SEQ ID NO: 33;
(l) a polypeptide having at least 80% sequence identity to the polypeptide of SEQ ID NO: 36;
(m) a polypeptide having at least 80% sequence identity to the polypeptide of SEQ ID NO: 39;
(n) a polypeptide having at least 80% sequence identity to the polypeptide of SEQ ID NO: 42;
(o) a polypeptide having at least 80% sequence identity to the polypeptide of SEQ ID NO: 45;
(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;
(q) a polypeptide comprising the polypeptide of (a), (b), (c), (d), (e), (f), (g), (h), (i), j), (k), (l), (m), (n), (o) or (p) and a N-terminal and/or C-terminal His-tag and/or HQ-tag;
(r) a polypeptide comprising the polypeptide of (a), (b), (c), (d), (e), (f), (g), (h), (i), j), (k), (l), (m), (n), (o) or (p) and a N-terminal and/or C-terminal extension of up to 10 amino acids, e.g. 1, 2, 3, 4, 5, 6, 7, 8, 9 or 10 amino acids; and
(s) a fragment of the polypeptide of (a), (b), (c), (d), (e), (f), (g), (h), (i), (j), (k), (l), (m), (n), (o) or (p) having lysozyme activity and having at least 90% of the length of the mature polypeptide.

5. The composition of item 4, wherein the polypeptide is selected from the group consisting of:
(a) a polypeptide having at least 85% sequence identity to the polypeptide of SEQ ID NO: 3;
(b) a polypeptide having at least 85% sequence identity to the polypeptide of SEQ ID NO: 6;
(c) a polypeptide having at least 85% sequence identity to the polypeptide of SEQ ID NO: 9;
(d) a polypeptide having at least 85% sequence identity to the polypeptide of SEQ ID NO: 12;
(e) a polypeptide having at least 85% sequence identity to the polypeptide of SEQ ID NO: 15;
(f) a polypeptide having at least 85% sequence identity to the polypeptide of SEQ ID NO: 18;
(g) a polypeptide having at least 85% sequence identity to the polypeptide of SEQ ID NO: 21;
(h) a polypeptide having at least 85% sequence identity to the polypeptide of SEQ ID NO: 24;
(i) a polypeptide having at least 85% sequence identity to the polypeptide of SEQ ID NO: 27;
(j) a polypeptide having at least 85% sequence identity to the polypeptide of SEQ ID NO: 30;
(k) a polypeptide having at least 85% sequence identity to the polypeptide of SEQ ID NO: 33;
(l) a polypeptide having at least 85% sequence identity to the polypeptide of SEQ ID NO: 36;
(m) a polypeptide having at least 85% sequence identity to the polypeptide of SEQ ID NO: 39;
(n) a polypeptide having at least 85% sequence identity to the polypeptide of SEQ ID NO: 42;
(o) a polypeptide having at least 85% sequence identity to the polypeptide of SEQ ID NO: 45; and
(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 positions.

6. The composition of item 4, wherein the polypeptide is selected from the group consisting of:
(a) a polypeptide having at least 90% sequence identity to the polypeptide of SEQ ID NO: 3;
(b) a polypeptide having at least 90% sequence identity to the polypeptide of SEQ ID NO: 6;
(c) a polypeptide having at least 90% sequence identity to the polypeptide of SEQ ID NO: 9;
(d) a polypeptide having at least 90% sequence identity to the polypeptide of SEQ ID NO: 12;
(e) a polypeptide having at least 90% sequence identity to the polypeptide of SEQ ID NO: 15;
(f) a polypeptide having at least 90% sequence identity to the polypeptide of SEQ ID NO: 18;
(g) a polypeptide having at least 90% sequence identity to the polypeptide of SEQ ID NO: 21;
(h) a polypeptide having at least 90% sequence identity to the polypeptide of SEQ ID NO: 24;
(i) a polypeptide having at least 90% sequence identity to the polypeptide of SEQ ID NO: 27;
(j) a polypeptide having at least 90% sequence identity to the polypeptide of SEQ ID NO: 30;
(k) a polypeptide having at least 90% sequence identity to the polypeptide of SEQ ID NO: 33;
(l) a polypeptide having at least 90% sequence identity to the polypeptide of SEQ ID NO: 36;
(m) a polypeptide having at least 90% sequence identity to the polypeptide of SEQ ID NO: 39;
(n) a polypeptide having at least 90% sequence identity to the polypeptide of SEQ ID NO: 42;
(o) a polypeptide having at least 90% sequence identity to the polypeptide of SEQ ID NO: 45; and
(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21 or 22 positions.

The composition of item 4, wherein the polypeptide is selected from the group consisting of:
(a) a polypeptide having at least 95% sequence identity to the polypeptide of SEQ ID NO: 3;
(b) a polypeptide having at least 95% sequence identity to the polypeptide of SEQ ID NO: 6;
(c) a polypeptide having at least 95% sequence identity to the polypeptide of SEQ ID NO: 9;
(d) a polypeptide having at least 95% sequence identity to the polypeptide of SEQ ID NO: 12;
(e) a polypeptide having at least 95% sequence identity to the polypeptide of SEQ ID NO: 15;
(f) a polypeptide having at least 95% sequence identity to the polypeptide of SEQ ID NO: 18;
(g) a polypeptide having at least 95% sequence identity to the polypeptide of SEQ ID NO: 21;
(h) a polypeptide having at least 95% sequence identity to the polypeptide of SEQ ID NO: 24;
(i) a polypeptide having at least 95% sequence identity to the polypeptide of SEQ ID NO: 27;
j) a polypeptide having at least 95% sequence identity to the polypeptide of SEQ ID NO: 30;
(k) a polypeptide having at least 95% sequence identity to the polypeptide of SEQ ID NO: 33;
(l) a polypeptide having at least 95% sequence identity to the polypeptide of SEQ ID NO: 36;
(m) a polypeptide having at least 95% sequence identity to the polypeptide of SEQ ID NO: 39;
(n) a polypeptide having at least 95% sequence identity to the polypeptide of SEQ ID NO: 42;
(o) a polypeptide having at least 95% sequence identity to the polypeptide of SEQ ID NO: 45; and
(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10 or 11 positions.

8. The composition of any of items 4 to 7, wherein the LYS polypeptide comprises one or more motifs selected from the group consisting of (a) motif I:
(SEQ ID NO: 317)
AG[I/L]AT[A/G][I/L][T/V]ES;

(b) motif II
(SEQ ID NO: 318)
V[G/A]XLCQXVQXSAYP;
and (c) motif III:
(SEQ ID NO: 319)
[CGY][YF][VIL][ASTP][DG]X[YF][VIT]X[TS][GAN].

9. The composition of any of items 1 to 8, wherein the polypeptide is of fungal origin.
10. The composition of any of items 1 to 9, wherein the polypeptide is obtained or obtainable from the taxonomic phylum Ascomycota, preferably the taxonomic subphylum Pezizomycotina.
11. The composition of any of items 1 to 10, wherein the polypeptide comprises or consists of amino acids 1 to 226 of SEQ ID NO: 2, amino acids 1 to 226 of SEQ ID NO: 3, amino acids 1 to 226 of SEQ ID NO: 5, amino acids 1 to 226 of SEQ ID NO: 6, amino acids 1 to 223 of SEQ ID NO: 8, amino acids 1 to 223 of SEQ ID NO: 9, amino acids 1 to 304 of SEQ ID NO: 11, amino acids 1 to 304 of SEQ ID NO: 12, amino acids 1 to 228 of SEQ ID NO: 14, amino acids 1 to 228 of SEQ ID NO: 15, amino acids 1 to 230 of SEQ ID NO: 17, amino acids 1 to 230 of SEQ ID NO: 18, amino acids 1 to 230 of SEQ ID NO: 20, amino acids 1 to 230 of SEQ ID NO: 21, amino acids 1 to 232 of SEQ ID NO: 23, amino acids 1 to 232 of SEQ ID NO: 24, amino acids 1 to 228 of SEQ ID NO: 26, amino acids 1 to 228 of SEQ ID NO: 27, amino acids 1 to 228 of SEQ ID NO: 29, amino acids 1 to 228 of SEQ ID NO: 30, amino acids 1 to 226 of SEQ ID NO: 32, amino acids 1 to 226 of SEQ ID NO: 33, amino acids 1 to 225 of SEQ ID NO: 35, amino acids 1 to 225 of SEQ ID NO: 36, amino acids 1 to 225 of SEQ ID NO: 38, amino acids 1 to 225 of SEQ ID NO: 39, amino acids 1 to 304 of SEQ ID NO: 41, amino acids 1 to 304 of SEQ ID NO: 42, amino acids 1 to 227 of SEQ ID NO: 44, or amino acids 1 to 227 of SEQ ID NO: 45.
12. The composition of any of items 1 to 11 further comprising one or more formulating agents.
13. The composition of item 12, wherein the one or more formulating agent is selected from the group consisting of glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose or any combination thereof.
14. The composition of any of items 1 to 13 further comprising one or more additional enzymes.
15. The composition of item 14 wherein the one or more additional enzymes is selected from the group consisting of acetyl xylan esterase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lipase, lysophospholipase, lysozyme, mannanase, alpha-mannosidase, beta-mannosidase, phytase, phospholipase A1, phospholipase A2, phospholipase C, phospholipase D, protease, pullulanase, pectinase, pectin lyase, xylanase, beta-xylosidase, or any combination thereof.
16. The composition of any of items 1 to 15 further comprising one or more microbes.
17. The composition of item 16, wherein the one or more microbes is selected from the group consisting of *Bacillus subtilis, Bacillus lichenformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminis, Lactobacillus rhamnosus, Lactobacillus reuteri, Lactobacillus salivarius, Lactococ-*

*cus lactis*, *Lactococcus* sp., *Leuconostoc* sp., *Megasphaera elsdenii*, *Megasphaera* sp., *Pediococsus acidilactici*, *Pediococcus* sp., *Propionibacterium thoenii*, *Propionibacterium* sp. and *Streptococcus* sp. or any combination thereof.

18. The composition of any of items 1 to 17 further comprising one or more components selected from the list consisting of:
one or more vitamins;
one or more minerals;
one or more amino acids;
one or more phytogenics;
one or more prebiotics;
one or more organic acids; and
one or more other feed ingredients.

19. A granule comprising the composition of any of items 1 to 18.

20. The granule of item 19 wherein the granule is coated.

21. The granule of item 20 wherein the coating comprises a salt and/or wax and/or a flour.

22. An animal feed additive comprising the composition of any of items 1 to 18 or the granule of any of items 19 to 21.

23. An animal feed comprising plant based material and the composition of any of items 1 to 18, the granule of any of items 19 to 21 or the animal feed additive of item 22.

24. The animal feed of item 23, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

25. A pelleted animal feed comprising plant based material and the composition of any of items 1 to 18, the granule of any of items 19 to 21 or the animal feed additive of item 22.

26. The pelleted animal feed of item 25, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

27. A liquid formulation comprising the composition of any of items 1 to 18.

28. The liquid formulation of item 27, wherein the LYS polypeptide is dosed between 0.01% to 25% w/w of liquid formulation, preferably 0.05% to 20% w/w LYS polypeptide, more preferably 0.2% to 15% w/w LYS polypeptide, more preferably 0.5% to 15% w/w LYS polypeptide or most preferably 1.0% to 10% w/w LYS polypeptide.

29. The liquid formulation of any of items 27 to 28, wherein the formulation further comprises 20% to 80% w/w of polyol.

30. The liquid formulation of item 29, wherein the polyol is selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600 or any combination thereof.

31. The liquid formulation of any of items 27 to 30, wherein the formulation further comprises 0.01% to 2.0% w/w preservative.

32. The liquid formulation of item 31, wherein the preservative is selected from the group consisting of sodium sorbate, potassium sorbate, sodium benzoate and potassium benzoate or any combination thereof.

33. The liquid formulation of any of items 27 to 32 further comprising one or more components selected from the list consisting of:
one or more enzymes;
one or more microbes;
one or more vitamins;
one or more minerals;
one or more amino acids;
one or more phytogenics;
one or more prebiotics;
one or more organic acids; and
one or more other feed ingredients.

34. A method of preparing an animal feed comprising applying the liquid formulation of any of items 27 to 33 onto plant based material.

35. The method of item 34, wherein the liquid formulation is applied via a spray.

36. The method of any of items 34 to 35, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

37. The method of any of items 34 to 36, wherein the plant based material is in pelleted form.

38. A pelleted animal feed prepared using the method of any of items 34 to 37.

39. A method of improving one or more performance parameters of an animal comprising administering to one or more animals the composition of any of items 1 to 18, the granule of any of items 19 to 21, the animal feed additive of item 22, the animal feed of any of items 23 to 24, the pelleted animal feed of any of items 25 to 26 or 38 or the liquid formulation of any of items 27 to 33.

40. The method of item 39 wherein the performance parameter is selected from the list consisting of body weight gain (BWG), European Production Efficiency Factor (EPEF) and Feed Conversion Ratio (FCR) or any combination thereof.

41. A method of preparing an animal feed, comprising mixing the composition of any of items 1 to 18, the granule of any of items 19 to 21, the animal feed additive of item 22, the animal feed of any of items 23 to 24, the pelleted animal feed of any of items 25 to 26 or 38 or the liquid formulation of any of items 27 to 33 with plant based material.

42. The method of item 41, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

43. Use of composition of any of items 1 to 18, the granule of any of items 19 to 21, the animal feed additive of item 22, the animal feed of any of items 23 to 24, the pelleted animal feed of any of items 25 to 26 or 38 or the liquid formulation of any of items 27 to 33:
   in animal feed;
   in animal feed additives;
   in the preparation of a composition for use in animal feed;
   for improving the nutritional value of an animal feed;
   for increasing digestibility of the animal feed; and/or
   for improving one or more performance parameters in an animal.

44. An isolated polypeptide having lysozyme activity, selected from the group consisting of:
   (a) a polypeptide having at least 95%, e.g., at least 96%, at least 97%, at least 98%, at least 99%, or 100% sequence identity to the polypeptide of SEQ ID NO: 3;
   (b) a polypeptide having at least 94%, e.g., at least 95%, at least 96%, at least 97%, at least 98%, at least 99%, or 100% sequence identity to the polypeptide of SEQ ID NO: 6;
   (c) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 9;
   (d) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 12;
   (e) a polypeptide having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 15;
   (f) a polypeptide having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 18;
   (g) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 21;
   (h) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 24;
   (i) a polypeptide having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 27;
   (j) a polypeptide having at least 96.2%, e.g., at least 97%, at least 97.5%, at least 98%, at least 98.5%, at least 99%, or 100% sequence identity to the polypeptide of SEQ ID NO: 30;
   (k) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 33;
   (l) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 36;
   (m) a polypeptide having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 39;
   (n) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 42;
   (o) a variant of the polypeptide of SEQ ID NO: 3, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10 or 11 positions;
   (p) a variant of the polypeptide of SEQ ID NO: 6, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12 or 13 positions;
   (q) a variant of the polypeptide selected from the group consisting of SEQ ID NO: 9 and SEQ ID NO: 36, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 or 44 positions;
   (r) a variant of the polypeptide selected from the group consisting of SEQ ID NO: 12, SEQ ID NO: 21, SEQ ID NO: 24, SEQ ID NO: 33 and SEQ ID NO: 42, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;

(s) a variant of the polypeptide selected from the group consisting of SEQ ID NO: 15 and SEQ ID NO: 27, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions;
(t) a variant of the polypeptide selected from the group consisting of SEQ ID NO: 18 and SEQ ID NO: 39, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 or 42 positions;
(u) a variant of the polypeptide of SEQ ID NO: 30, wherein the variant has lysozyme activity and comprises one or more amino acid substitutions, and/or one or more amino acid deletions, and/or one or more amino acid insertions or any combination thereof in 1, 2, 3, 4, 5, 6, 7 or 8 positions;
(v) a polypeptide comprising the polypeptide of (a), (b), (c), (d), (e), (f), (g), (h), (i), (j), (k), (l), (m), (n), (o), (p), (q), (r), (s), (t) or (u) and a N-terminal and/or C-terminal His-tag and/or HQ-tag;
(w) a polypeptide comprising the polypeptide of (a), (b), (c), (d), (e), (f), (g), (h), (i), (j), (k), (l), (m), (n), (o), (p), (q), (r), (s), (t) or (u) and a N-terminal and/or C-terminal extension of up to 10 amino acids, e.g. 1, 2, 3, 4, 5, 6, 7, 8, 9 or 10 amino acids; and
(x) a fragment of the polypeptide of (a), (b), (c), (d), (e), (f), (g), (h), (i), (j), (k), (l), (m), (n), (o), (p), (q), (r), (s), (t) or (u) having lysozyme activity and having at least 90% of the length of the mature polypeptide.

45. The polypeptide according to item 44, wherein the polypeptide comprises or consists of amino acids 1 to 316 of SEQ ID NO: 2, amino acids 1 to 316 of SEQ ID NO: 3, amino acids 1 to 322 of SEQ ID NO: 4, amino acids 1 to 318 of SEQ ID NO: 6, amino acids 1 to 318 of SEQ ID NO: 7, amino acids 1 to 326 of SEQ ID NO: 8, amino acids 1 to 316 of SEQ ID NO: 10, amino acids 1 to 316 of SEQ ID NO: 11, amino acids 1 to 324 of SEQ ID NO: 12, amino acids 1 to 316 of SEQ ID NO: 14, amino acids 1 to 316 of SEQ ID NO: 15, amino acids 1 to 324 of SEQ ID NO: 16, amino acids 1 to 316 of SEQ ID NO: 18, amino acids 1 to 316 of SEQ ID NO: 19, amino acids 1 to 324 of SEQ ID NO: 20, amino acids 1 to 316 of SEQ ID NO: 22, amino acids 1 to 316 of SEQ ID NO: 23, amino acids 1 to 324 of SEQ ID NO: 24, amino acids 1 to 516 of SEQ ID NO: 26, amino acids 1 to 516 of SEQ ID NO: 27, amino acids 1 to 524 of SEQ ID NO: 28, amino acids 1 to 317 of SEQ ID NO: 30, amino acids 1 to 317 of SEQ ID NO: 31, amino acids 1 to 325 of SEQ ID NO: 32, amino acids 1 to 316 of SEQ ID NO: 34, amino acids 1 to 316 of SEQ ID NO: 35, amino acids 1 to 324 of SEQ ID NO: 36, amino acids 1 to 316 of SEQ ID NO: 38, amino acids 1 to 316 of SEQ ID NO: 39 or amino acids 1 to 324 of SEQ ID NO: 40.

46. A polynucleotide encoding the polypeptide of any of items 44 to 45.

47. A nucleic acid construct or expression vector comprising the polynucleotide of item 46 operably linked to one or more control sequences that direct the production of the polypeptide in an expression host.

48. A recombinant host cell comprising the polynucleotide of item 46 operably linked to one or more control sequences that direct the production of the polypeptide.

49. The recombinant host cell of item 48, wherein the host is a filamentous fungus, such as *Aspergillus*, *Trichoderma* or *Fusarium*, or a yeast, such as *Pichia* or *Saccharomyces*.

50. The recombinant host cell of item 49, wherein the host is an *Aspergillus*, such as *Aspergillus awamori*, *Aspergillus foetidus*, *Aspergillus japonicus*, *Aspergillus nidulans*, *Aspergillus niger* or *Aspergillus oryzae*.

51. The recombinant host cell of item 49, wherein the host is a *Trichoderma*, such as *Trichoderma harzianum*, *Trichoderma koningii*, *Trichoderma longibrachiatum*, *Trichoderma reesei* or *Trichoderma viride*.

52. The recombinant host cell of item 48, wherein the host is a *Bacillus* such as *Bacillus alkalophilus*, *Bacillus amyloliquefaciens*, *Bacillus brevis*, *Bacillus circulans*, *Bacillus clausii*, *Bacillus coagulans*, *Bacillus firmus*, *Geobacillus stearothermophilus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis*.

53. A method of producing the polypeptide of any of items 44 to 45, comprising:
(a) cultivating a cell, which in its wild-type form produces the polypeptide, under conditions conductive for production of the polypeptide; and
(b) recovering the polypeptide.

54. A method of producing the polypeptide of any of items 44 to 45, comprising:
(a) cultivating the recombinant host cell of any of items 48 to 52 under conditions conducive for production of the polypeptide; and
(b) recovering the polypeptide.

55. A transgenic plant, plant part or plant cell transformed with a polynucleotide encoding the polypeptide of any of items 44 to 45.

56. A whole broth formulation or cell culture composition comprising a polypeptide of any of items 44 to 45.

The present invention is further described by the following examples that should not be construed as limiting the scope of the invention.

EXAMPLES

Strains

*Escherichia coli* Top-10 strain purchased from Invitrogen (Life Technologies, Carlsbad, CA, USA) was used to propagate our expression vectors encoding for LYS polypeptides.

*Aspergillus oryzae* strain MT3568 was used for heterologous expression of the LYS polypeptide encoding sequences. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene.

The fungal strain NN044175 was isolated from soil samples collected from China, in 1998 by the dilution plate method with PDA medium, pH7, 25 C. It was then purified by transferring a single conidium onto a PDA agar plate. The strain NN044175 was identified as *Penicillium simplicissimum*, based on both morphological characteristics and ITS rDNA sequence.

The fungal strain NN053742 was isolated from a soil sample collected from Hubei province, China, in 2011 by the dilution plate method with PDA medium, at pH3, 25 C. It was then purified by transferring a single conidium onto a PDA agar plate. The strain NN053742 was identified as *Penicillium vasconiae*, based on both morphological characteristics and ITS rDNA sequence.

The fungal strain NN058285 was isolated from soil samples collected from Guizhou Province, China, in 2014 by the dilution plate method with PDA medium pH3. It was then purified by transferring a single conidium onto a PDA agar plate. The strain NN058285 was identified as *Talaromyces proteolyticus*, based on both morphological characteristics and ITS rDNA sequence.

The fungal strain NN053333 was isolated from soil samples collected from Hunan province, China, in 2010 by the dilution plate method with PDA medium, pH7, 25 C. It was then purified by transferring a single conidium onto a PDA agar plate. The strain NN053333 was identified as *Aspergillus* sp. XZ2668, based on both morphological characteristics and ITS rDNA sequence.

The fungal strain NN058605 was from CBS with access number as CBS100492. The strain NN058605 was identified as *Penicillium antarcticum*, based on both morphological characteristics and ITS rDNA sequence.

The fungal strain NN047528 was isolated from soil samples collected from China, in 1998 by the dilution plate method with YG medium, pH7, 37 C. It was then purified by transferring a single conidium onto a PDA agar plate. The strain NN047528 was identified as *Ovatospora brasiliensis*, based on both morphological characteristics and ITS rDNA sequence.

The fungal strain NN054749 was isolated from soil samples collected from Tibet, China, in 2012 by the dilution plate method with PDA medium, pH7, 1° C. It was then purified by transferring a single conidium onto a PDA agar plate. The strain NN054749 was identified as *Penicillium wellingtonense*, based on both morphological characteristics and ITS rDNA sequence.

The fungal strain NN054129 was isolated from soil samples collected from Gotland, Sweden in 2011 by the dilution plate method with Water agar, 24C. It was then purified by transferring a single conidium onto a PDA agar plate. The strain NN054129 was identified as *Penicillium roseopurpureum*, based on both morphological characteristics and ITS rDNA sequence.

The fungal strain NN058650 was isolated from soil samples collected from Guizhou Province, China, in 2014 by the dilution plate method with PDA medium pH3. It was then purified by transferring a single conidium onto a PDA agar plate. The strain NN058650 was identified as *Penicillium virgatum*, based on both morphological characteristics and ITS rDNA sequence.

The fungal strain NN046949 was isolated from soil samples collected from China, in 1998 by the dilution plate method with YG medium, pH7, 37 C. It was then purified by transferring a single conidium onto a PDA agar plate. The strain NN046949 was identified as *Aspergillus niveus*, based on both morphological characteristics and ITS rDNA sequence.

The fungal strain NN057921 was obtained through a collaboration with Professor Cai Lei in Institute of Microbiology, CAS, in 2014. The strain was collected from China. It was identified as *Chaetomium* sp. ZY369, based on both morphological characteristics and ITS rDNA sequence.

The fungal strain NN058427 was isolated from soil samples collected from Guizhou Province, China, in 2014 by the dilution plate method with PDA medium pH3, 25 C. It was then purified by transferring a single conidium onto a PDA agar plate. The strain N NN058427 was identified as *Talaromyces atricola*, based on both morphological characteristics and ITS rDNA sequence.

The fungal strain NN053773 was obtained through a collaboration with Institute of Microbiology, CAS, in 2011. The strain was collected from China and isolated by the dilution plate method with PDA medium pH7, 10C. It was then purified by transferring a single conidium onto a PDA agar plate. The strain NN053773 was identified as *Trichocladium asperum*, based on both morphological characteristics and ITS rDNA sequence.

The fungal strain NN058086 was isolated from soil samples collected from Guizhou Province, China, in 2014 by the dilution plate method with PDA medium pH3, 25 C. It was then purified by transferring a single conidium onto a PDA agar plate. The strain NN058086 was identified as *Metarhizium carneum*, based on both morphological characteristics and ITS rDNA sequence.

Strain *Thielavia terrestris* strain NRRL 8126 was purchased ATCC, and inoculated onto a PDA plate and incubated for 7 days at 37° C. in the darkness. Mycelia and spores from the plate were inoculated into 500 ml shake flasks containing 100 mls of YPG medium. The flasks were incubated for 6 days at 37° C. with shaking at 150 rpm.

Media and Solutions

DAP4C-1 medium was composed of 0.5 g yeast extract, 10 g maltose, 20 g dextrose, 11 g magnesium sulphate heptahydrate, 1 g dipotassium phosphate, 2 g citric acid monohydrate, 5.2 g potassium phosphate tribasic monohydrate, 1 mL Dowfax 63N10 (antifoaming agent), 2.5 g calcium carbonate, supplemented with 1 mL KU6 metal solution, and deionised water to 1000 mL.

KU6 metal solution was composed of 6.8 g $ZnCl_2$, 2.5 g $CuSO_4 \cdot 5H_2O$, 0.13 g $NiCl_2$, 13.9 g $FeSO_4 \cdot 7H_2O$, 8.45 g $MnSO_4 \cdot H_2O$, 3 g $C_6H_8O_7 \cdot H_2O$, and deionised water to 1000 mL.

YP 2% glucose medium was composed of 10 g yeast extract, 20 g Bacto-peptone, 20 g glucose, and deionised water to 1000 mL.

LB plates were composed of 10 g of Bacto-tryptone, 5 g of yeast extract, 10 g of sodium chloride, 15 g of Bacto-agar, and deionised water to 1000 mL.

LB medium was composed of 10 g of Bacto-tryptone, 5 g of yeast extract, and 10 g of sodium chloride, and deionised water to 1000 mL.

COVE-Sucrose-T plates were composed of 342 g of sucrose, 20 g of agar powder, 20 mL of COVE salt solution, and deionised water to 1000 mL. The medium was sterilized by autoclaving at 15 psi for 15 minutes (Bacteriological Analytical Manual, 8th Edition, Revision A, 1998). The medium was cooled to 60° C. and 10 mM acetamide, Triton X-100 (50 µL/500 mL) were added.

COVE-N-Agar tubes were composed of 218 g Sorbitol, 10 g Dextrose, 2.02 g $KNO_3$, 25 g agar, 50 mL Cove salt solution, and deionised water up to 1000 mL.

COVE salt solution was composed of 26 g of $MgSO_4 \cdot 7H_2O$, 26 g of KCL, 26 g of $KH_2PO_4$, 50 mL of COVE trace metal solution, and deionised water to 1000 mL.

COVE trace metal solution was composed of 0.04 g of $Na_2B_4O_7 \cdot 10H_2O$, 0.4 g of $CuSO_4 \cdot 5H_2O$, 1.2 g of $FeSO_4 \cdot 7H_2O$, 0.7 g of $MnSO_4 \cdot H_2O$, 0.8 g of $Na_2MoO_4 \cdot 2H_2O$, 10 g of $ZnSO_4 \cdot 7H_2O$, and deionised water to 1000 mL. YPM medium contained 1% of Yeast extract, 2% of Peptone and 2% of Maltose.

Example 1: Determination of Lysozyme Activity Using Reducing Ends Assay

The LYS polypeptide was diluted in phosphate buffer (5 mM citrate, 5 mM $K_2HPO_4$, 0.01% TritonX-100, pH 5.0) to 50 µg/mL in polypropylene tubes. The diluted LYS polypeptide was further diluted in a 96-well polypropylene microtiter plate to a concentration of 5.0 or 0.7 µg/mL in phosphate buffer (5 mM citrate, 5 mM $K_2HPO_4$, 0.01% TritonX-100, pH 5.0). In a polypropylene deepwell plate 50 µL of the LYS polypeptide dilution was mixed with 450 µL 1% *Micrococcus lysodeikticus* solution (lyophilized *Micrococcus lysodeikticus* ATCC No. 4698 (Sigma M3770) in milli-Q water) and incubated at 40° C. with shaking (500 rpm) for 45 min. After incubation the deepwell plate was centrifuged (4000 g, 5 min) to pellet insoluble material and 100 µL of the supernatant was mixed with 50 µL 3.2M HCl in a 96-well PCR plate and incubated at 95° C. for 80 min. 50 µL of 3.5 M NaOH was added to each well of the PCR plate, and 150 µL of each sample was transferred to a new PCR plate containing 75 µL/well 4-hydroxybenzhydrazide solution in K—Na tartrate/NaOH buffer (50 g/L K—Na tartrate+20 g/L NaOH). The plate was incubated at 95° C. for 10 min before 100 µL/sample was transferred to a clear flat-bottomed microtiter plate for optical density (OD) measurement at 405 nm. OD measurements were performed on three times diluted samples (50 µL sample diluted in 100 µL in Milli-Q water).

Example 2: Determination of Lysozyme Activity Using OD Drop Assay

Freeze-dried *Micrococcus lysodeikticus* ATCC No. 4698 (Sigma) was washed and suspended in 60 mM $KH_2PO_4$ buffer at pH6.0 with final concentration of 1% (w/v) as substrate stock. The concentration of the strain was adjusted by adding citric acid-$Na_2HPO_4$ buffer until OD450 reach approximately 1.

Citric acid-$Na_2HPO_4$ pH4 buffer were prepared by adding 61.45 ml 0.1M citric acid and 38.55 ml 0.2M Na2HPO$_4$ for pH4. 20 µL enzyme at 50 µg/mL and 200 µL of diluted bacterial strain solution in citric acid-$Na_2HPO_4$ buffer at pH4 were added to a 96 well plate, mixed and the OD450 was read. Then the plate was incubated at 37° C., 300 rpm for 1 hour and the OD450 was read. The OD difference between the 1 hour time point to the initial read showed the OD drop activity for the LYS polypeptide. Blank was set by adding 20 ul MQ water or the corresponding buffer, and each sample was measured in triplicate.

Example 3: Genomic DNA Extraction

*Penicillium simplicissimum* strain NN044175 was inoculated onto a PDA plate and incubated for 7 days at 25° C. in the darkness. Several mycelia-PDA plugs were inoculated into 500 ml shake flasks containing 100 ml of YPG medium. The flasks were incubated for 9 days at 25° C. with shaking at 160 rpm.

*Penicillium vasconiae* strain NN053742 was inoculated onto a PDA plate and incubated for 7 days at 25° C. in the darkness. Several mycelia-PDA plugs were inoculated into 500 ml shake flasks containing 100 ml of YPG medium. The flasks were incubated for 3 days at 25° C. with shaking at 160 rpm.

*Talaromyces proteolyticus* strain NN058285 was inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

*Aspergillus* sp. strain NN053333 was inoculated onto a PDA plate and incubated for 7 days at 25° C. in the darkness. Several mycelia-PDA plugs were inoculated into 500 ml shake flasks containing 100 ml of YPG medium. The flasks were incubated for 5 days at 25° C. with shaking at 160 rpm.

*Penicillium antarcticum* strain NN058605 was inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

*Ovatospora brasiliensis* strain NN047528 was inoculated onto a PDA plate and incubated for 7 days at 37° C. in the darkness. Several mycelia-PDA plugs were inoculated into 500 ml shake flasks containing 100 ml of YPG medium. The flasks were incubated for 2 days at 37° C. with shaking at 160 rpm.

*Penicillium wellingtonense* strain NN054749 was inoculated onto a PDA plate and incubated for 7 days at 25° C. in the darkness. Several mycelia-PDA plugs were inoculated into 500 ml shake flasks containing 100 ml of YPG medium. The flasks were incubated for 11 days at 25° C. with shaking at 160 rpm.

*Penicillium roseopurpureum* strain NN054129 was inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

*Penicillium virgatum* strain NN058650 was inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

*Aspergillus niveus* strain NN046949 was inoculated onto a PDA plate and incubated for 7 days at 25° C. in the darkness. Several mycelia-PDA plugs were inoculated into 500 ml shake flasks containing 100 ml of YPG medium. The flasks were incubated for 3 days at 25° C. with shaking at 160 rpm.

*Chaetomium* sp. strain NN057921 were inoculated onto a PDA plate and incubated for 7 days at 37° C. in the darkness. Several mycelia-PDA plugs were inoculated into 500 ml shake flasks containing 100 ml of YPG medium. The flasks were incubated for 8 days at 37° C. with shaking at 160 rpm.

The mycelia of *Penicillium antarcticum* strain NN058605 were collected by filtration through MIRACLOTH® (Calbiochem, La Jolla, CA, USA) and frozen under liquid nitrogen. Frozen mycelia were ground, by a mortar and a pestle, to a fine powder, and genomic DNA was isolated using MP Fast DNA spin kit for soil (MP Biomedicals, Santa Ana, California, USA) following the manufacturer's instruction.

*Talaromyces atricola* strain NN058427 was inoculated onto a PDA plate and incubated for 7 days at 25° C. in the darkness. Several mycelia-PDA plugs were inoculated into 500 ml shake flasks containing 100 ml of YPG medium. The flasks were incubated for 3 days at 25° C. with shaking at 160 rpm.

*Trichocladium asperum* strain NN053773 was inoculated onto a PDA plate and incubated for 7 days at 15° C. in the darkness. Several mycelia-PDA plugs were inoculated into 500 ml shake flasks containing 100 ml of YPG medium. The flasks were incubated for 4 days at 15° C. with shaking at 160 rpm.

*Metarhizium carneum* strain NN058086 was inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

The mycelia of *Thielavia terrestris* were collected by filtration through MIRACLOTH® (Calbiochem, La Jolla, CA, USA) and frozen under liquid nitrogen. Frozen mycelia were ground, by a mortar and a pestle, to a fine powder, and genomic DNA was isolated using DNeasy® Plant Maxi Kit (24) (QIAGEN GmbH, Hilden, Germany) following the manufacturer's instructions.

The mycelia of all the other strains were collected by filtration through MIRACLOTH® and frozen under liquid nitrogen. Frozen mycelia were ground, by a mortar and a pestle, to a fine powder, and genomic DNA was isolated using DNeasy® Plant Maxi Kit (24) (QIAGEN GmbH, Hilden, Germany) following the manufacturer's instruction.

Example 4: Genome Sequencing, Assembly and Annotation

The extracted genomic DNA samples of *Penicillium simplicissimum* strain NN044175 were delivered to Exiqon A/S (Denmark) for genome sequencing using an ILLU-MINA® MiSeq System (Illumina, Inc., San Diego, CA, USA). The raw reads were assembled at Novozymes Denmark using program Idba (Peng, Yu et al., 2010, *Research in Computational Molecular Biology*, 6044:426-440. Springer Berlin Heidelberg).

The extracted genomic DNA samples of *Talaromyces proteolyticus* strain NN058285, *Penicillium antarcticum* strain NN058605, *Penicillium roseopurpureum* strain NN054129, *Penicillium virgatum* strain NN058650, *Aspergillus niveus* strain NN046949, *Metarhizium carneum* strain NN058086 were delivered to Exiqon A/S for genome sequencing using an ILLUMINA® MiSeq System. The raw reads were assembled at Novozymes Denmark using program Spades (Anton Bankevich et al., 2012, *Journal of Computational Biology*, 19(5): 455-477).

The extracted genomic DNA samples of *Penicillium vasconiae* strain NN053742, *Ovatospora brasiliensis* strain NN047528, *Trichocladium asperum* strain NN053773 were delivered to Fasteris (Switzerland) for genome sequencing using an ILLUMINA® HiSeq 2000 System (Illumina, Inc., San Diego, CA, USA). The raw reads were assembled at Novozymes Denmark using program Idba.

The extracted genomic DNA samples of *Aspergillus* sp. strain NN053333, *Chaetomium* sp. strain NN057921 and *Talaromyces atricola* strain NN058427 were delivered to Novozymes Davis (USA) for genome sequencing using an ILLUMINA® MiSeq System. The raw reads were assembled at Novozymes Denmark using program Spades.

The extracted genomic DNA samples of *Penicillium wellingtonense* strain NN054749 were delivered to Novozymes Davis for genome sequencing using an ILLU-MINA® MiSeq System. The raw reads were assembled at Novozymes Denmark using program Idba.

The assembled sequences were analyzed using standard bioinformatics methods for gene identification and function prediction. GeneMark-ES fungal version (Ter-Hovhannisyan V et al., 2008, *Genome Research* 18(12): 1979-1990) was used for gene prediction. Blastall version 2.2.10 (Altschul et al., 1990, *Journal of Molecular Biology*. 215(3): 403-410, ftp://ftp.ncbi.nlm.nih.gov/blast/executables/release/2.2.10/) and HMMER version 2.1.1 (National Center for *Biotechnology* Information (NCBI), Bethesda, MD, USA) were used to predict function based on structural homology. The NZ5 family was identified directly by analysis of the Blast results. The Agene program (Munch and Krogh, 2006, *BMC Bioinformatics* 7: 263) and SignalP program (Nielsen et al., 1997, *Protein Engineering* 10: 1-6) were used to identify start codons. SignalP program was further used to predict signal peptides. Pepstats (Rice et al., 2000, *Trends in Genetics*. 16(6): 276-277) was used to predict isoelectric points and molecular weights.

Example 5: Cloning, Expression and Fermentation of Fungal NZ5 Genes (SEQ ID NO: 1, 4, 7, 10, 13, 16, 19, 22, 25, 28, 31, 34, 37 and 40)

Fourteen fungal LYS wild type genes, LYS_Pesi (SEQ ID NO: 1), LYS_Pv (SEQ ID NO:4), LYS_Tapr (SEQ ID NO:7), LYS_Asp2668 (SEQ ID NO:10), LYS_Pean (SEQ ID NO:13), LYS_chbr (SEQ ID NO:16), LYS_Pewe (SEQ ID NO:19), LYS_Pr (SEQ ID NO:22), LYS_Pevir (SEQ ID NO:25), LYS_asni (SEQ ID NO:28), LYS_ch369 (SEQ ID NO: 31), LYS_Taat (SEQ ID NO:34), LYS_Tras (SEQ ID NO: 37), LYS_Meca2 (SEQ ID NO:40) were cloned from *Penicillium simplicissimum* strain NN044175, *Penicillium vasconiae* strain NN053742, *Talaromyces proteolyticus* strain NN058285, *Aspergillus* sp. strain NN053333, *Penicillium antarcticum* strain NN058605, *Ovatospora brasiliensis* strain NN047528, *Penicillium wellingtonense* strain NN054749, *Penicillium roseopurpureum* strain NN054129, *Penicillium virgatum* strain NN058650, *Aspergillus niveus* strain NN046949, *Chaetomium* sp. strain NN057921, *Talaromyces atricola* strain NN058427, *Trichocladium asperum* strain NN053773, *Metarhizium carneum* strain NN058086 respectively.

The fungal LYS genes were cloned into an *Aspergillus oryzae* expression vector pCaHj505 as described in WO2013029496. The transcription of the LYS coding sequence with the native secretion signal was under the control of an *Aspergillus oryzae* alpha-amylase gene promoter.

The final expression plasmids, p505-LYS_Pesi, p505-LYS_Pv, p505-LYS_Tapr, p505-LYS_Asp2668, p505-LYS_Pean, p505-LYS_chbr, p505-LYS_Pewe, p505-LYS_Pr, p505-LYS_Pevir, p505-LYS_asni, p505-LYS_ch369, p505-LYS_Taat, p505-LYS_Tras and p505-LYS_Meca2, were individually transformed into an *Aspergillus oryzae* expression host. The LYS genes were integrated by homologous recombination into the *Aspergillus oryzae* host genome upon transformation. Four transformants of each transformation were selected from the selective media agar plate and inoculated to 3 ml of YPM or Dap4C medium in 24-well plate and incubated at 30° C., 150 rpm. After 3 days incubation, 20 µl of supernatant from each transformant were analyzed on NuPAGE Novex 4-12% Bis-Tris Gel w/MES according to the manufacturer's instructions. The resulting gel was stained with Instant Blue. SDS-PAGE profiles of the cultures showed that all genes were expressed with 1 protein band detected at approximately 28 kDa, 25 kDa, 25 kDa, 35 kDa, 25 kDa, 25 kDa, 25 kDa, 25 kDa, 25 kDa, 25 kDa, 25 kDa, 25 kDa, 25 kDa, 30 kDa. The recombinant *Aspergillus oryzae* strains with the strongest protein band were selected for shaking flask culturing. The recombinant strains were inoculated on slant made of slant medium and incubated at 37 C for 6-7 days. When strains were well grown to fully sporulated, they were inoculated to 2 L shaking flasks each containing 400 ml of YPM or DAP4C, 5-6 flasks for each strain. Flasks were shaking at 80 rpm, 30C. Cultures were harvested on day 3 or day 4 and filtered using a 0.22 m DURAPORE Membrane and were purified as described in example 9.

Figure 2:
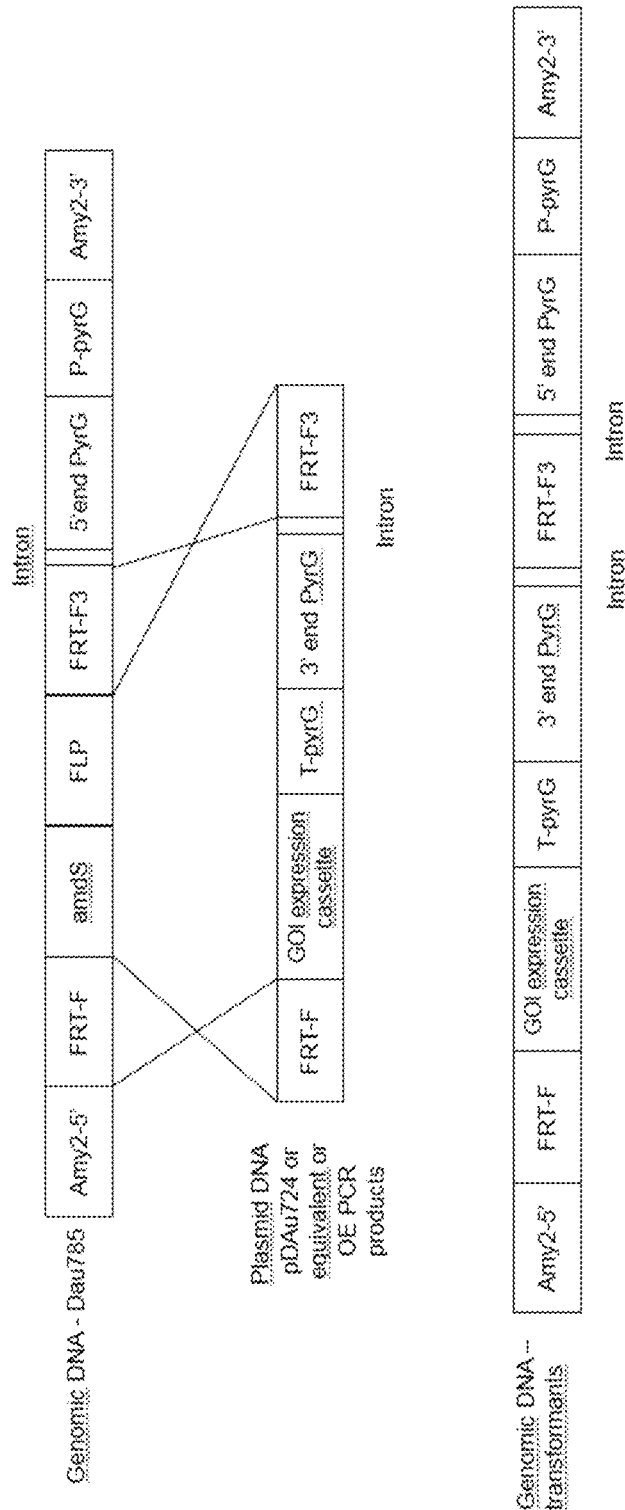
FIG. 2 is the schematic representation of transformation of the host strain DAu785 by the transforming DNA (either plasmid pDAu724 or derivatives or OverlapExtension PCR products.

Example 6: Construction of the Improved Split-Marker *Aspergillus oryzae* Host An improved *Aspergillus oryzae* host/vector system comparable to the one described in example 5 disclosed in WO 2016026938A1 was constructed. The improvement was made to reduce the size of the transforming DNA by moving the FLPase expression cassette located on PART-II of the plasmid pDAu724 (see page 34 in WO2016/026938, FIG. 7 and SEQ ID NO:30) to the integration locus amy2 in the genome of the host strain. The cloning of the FLPase expression cassette into pDAu703 (WO2016/026938 page 32 and FIG. 6 and SEQ ID:29) in done by amplification of the FLPase expression cassette from pDAu724 and cloning in between FRT-F3 and the amdS selection marker of pDAu703 to give the plasmid pDAu770 (FIG. 1, SEQ ID NO: 320). The same protocol as described in WO2016/026938 page 33 was used to transform the linearized plasmid pDAu770 into protoplasts of *A. oryzae* strain Jal1338 (disclosed in WO2012/160097). Transformants were selected on AmdS selection plates to obtain strain DAu785. The resulting recombinant host strain DAu785 has a modified amy2 locus comparable to the one in DAU716 (WO2016/026938) with the addition of the FLPase expression cassette (FIG. 2, top panel). The host strain DAu785 is now constitutively expressing the FLPase site specific recombinase allowing the integration at the FRT sites of the transforming DNA in this case the PCR fragments obtained by Overlap Extension PCR reaction (FIG. 2, middle and bottom panels) and described in Example 7.

Example 7: Overlap Extension PCR Cloning (SEQ ID NO: 43)

A PCR amplification of SEQ ID NO: 43 encoding the LYS polypeptide was carried out using Phusion High-Fidelity DNA polymerase (New England Biolabs, BioNordika Denmark A/S, Herlev, Denmark) in a 50 μL volume reaction and the primers disclosed in table 2.

TABLE 2

PCR primers

| Primer* | Primer SEQ ID NO: | Sequence |
|---|---|---|
| KKSC0972-F | 321 | 5'-CTATATACACAACTGGGGATCCACC ATGCAGCTCTCCCTCCTCGT |
| KKSC0972-R | 322 | 5'-TAGAGTCGACCCAGCCGCGCCGGCCA TTACAACCCACCAGCCTGGC |

*-F—forward primer; -R—reverse primer; Bold letters represent coding sequence.

The PCR reaction mix consisted of 10 μL Phusion reaction buffer HF (5×); 1 μL of PCR nucleotide Mix (10 mM); 2 μL forward cloning primers (2.5 mM); 2 μL reverse cloning primers (2.5 mM); 1 μL Phusion High-Fidelity DNA Polymerase #M0530L (2000U/mL); and PCR grade water up to 50 μL. PCR reaction was incubated on a thermocycler T100 (Biorad, Hercules, California, USA) using the following program: initial denaturation of 2 min at 98° C. followed by 30 cycles of 10 sec at 98° C., 2 min at 72° C. and ending up by a final elongation of 10 min at 72° C. The PCR amplicon was purified using AMPure XP beads system kit (Agencourt, Beverly, Massachusetts, USA) adapted on a Biomek FXp Liquid handler (Beckman Coulter, Brea, California, USA).

pDAu724 plasmid was used as DNA template to amplify two PCR products (F1 and F3) in reactions composed of 10 μL of KAPA polymerase buffer 5×, 1 μL 10 mM KAPA PCR Nucleotide Mix, 1 μL of 10 μM of the appropriate forward primers (SEQ ID NO: 323 for F1 and SEQ ID NO: 325 for F3, table 3), 1 μL of 10 μM of the appropriate reverse primers (SEQ ID NO: 324 for F1 and SEQ ID NO: 326 for F3, table 3), 1 to 10 ng of pDAu724 plasmid, 1 μL of KAPA Biosystems polymerase KK2502 (1 unit) and PCR-grade water up to 50 μL.

PCR amplification reactions were carried out on a DYAD® Dual-Block Thermal Cycler (MJ Research Inc., Waltham, MA, USA) programmed for 2 min. at 98° C. and followed by 35 cycles of 10 sec. at 98° C. and 2 min. at 72° C. and one final cycle of 10 min. at 72° C.

Five μl of the PCR reaction were analyzed by 1% agarose gel electrophoresis using TAE buffer where DNA bands of the appropriate size were observed. The remaining PCR reactions were purified using an ILLUSTRA™ GFX™ PCR DNA and Gel Band Purification Kit according to the manufacturer's instructions.

TABLE 3

PCR primers

| Primer | Primer SEQ ID NO: | Sequence |
|---|---|---|
| Forward primer F1 | 323 | GAATTCGAGCTCGGTACCTTGAAGTTC |
| Reverse primer F1 | 324 | GGTGGATCCCCAGTTGTGTATATAGAGGATT |
| Forward primer F3 | 325 | TGCGCGGCGCGGCTGGGTCGACTCTA |
| Reverse primer F3 | 326 | TTCACACAGGAAACAGCTATGACCATG |

Overlap Extension PCR reaction for cloning the LYS polypeptide gene amplified from *Thielavia terrestris* gDNA was composed of 10 μL KAPA polymerase buffer (5×), 1 μL 10 mM KAPA PCR Nucleotide Mix, 50 ng of PCR fragment F1 and equimolar amounts of PCR fragment F3 and LYS polypeptide gene encoding for SEQ ID NO: 45, 1 μl KAPA Biosystems polymerase KK2502 (1 unit) and PCR-grade water up to 48 μL. Reaction was incubated on a DYAD® Dual-Block Thermal Cycler (MJ Research Inc., Waltham, MA, USA) using a program composed of 2 min. at 98° C.; followed by 5 cycles each composed of 10 sec. at 98° C., 30 sec. at 68° C., and 5 min. at 72° C. and completed by a final extension of 8 min. at 72° C.

During the OE PCR reaction, annealing between fragment F1 and the LYS polypeptide gene encoding for SEQ ID NO: 45 was ensured by the overlap in SEQ ID NO: 327 included in the forward cloning primer (KKSC0972-F) and annealing between fragment F3 and the LYS polypeptide gene encoding for SEQ ID NO: 45 was ensured by the overlapping SEQ ID NO: 328 included in the reverse cloning primer (KKSC0972-R).

One μL of 10 mM primer SEQ1 and 1 μL of 10 mM primer SEQ4 were added to the OE PCR reaction and the reaction was incubated a second time on a DYAD® Dual-Block Thermal Cycler (MJ Research Inc., Waltham, MA, USA) using a program composed of 2 min at 98° C.; followed by 25 cycles each composed of 10 sec. at 98° C., and 4 min. at 72° C. and completed by a final extension of 10 min. at 72° C.

Five μl of the PCR reaction was analysed by 1% agarose gel electrophoresis using TAE buffer where an DNA band of the appropriate size was observed. The remaining PCR reaction was up-concentrated to 20 μL by heating the tube at 60° C. 10 μL of this reaction was used for *Aspergillus oryzae* DAu785 protoplasts transformation.

```
Primer bind forward SEQ ID NO: 327:
CTATATACACAACTGGGGATCCACC

Primer bind reverse SEQ ID NO: 328:
TAGAGTCGACCCAGCCGCGCCGGCCA
```

Example 8: Preparation of *Aspergillus* Protoplasts

Protoplasts of *Aspergillus oryzae* MT3568 were prepared according to WO 95/002043. One hundred μl of protoplasts were mixed with OE PCR fragment KKSC0972 and 250 μL of 60% PEG 4000 (Applichem, Darmstadt, Germany) (polyethylene glycol, molecular weight 4,000), 10 mM $CaCl_2$, and 10 mM Tris-HCl pH 7.5 and gently mixed. The mixtures were incubated at 37° C. for 30 minutes and the protoplasts were spread onto COVE plates for selection. After incubation for 4-7 days at 37° C. spores of four transformants were inoculated into 0.2 mL of YP+2% glucose or DAP4C-1 medium in 96 well microtiter plates. After 4 days cultivation at 30° C., the culture broths were analysed by SDS-PAGE to identify transformants producing the highest amounts of LYS polypeptide.

Spores of the best transformant from the transformation were spread onto COVE plates containing 0.01% TRITON® X-100 in order to isolate single colonies. The spreading was repeated twice in total on COVE plates containing 10 mM sodium nitrate. Spores were then inoculated into 500 mL shake flasks containing 100 mL of YP+2% glucose and incubated for 4 days at 30° C. with shaking at 100 rpm. Culture broths were harvested by filtration using a 0.2 μm filter device and purified as described in Example 9.

Example 9: Purification of LYS Polypeptides

Activity Detection for Purification Procedure

Freeze-dried bacterial strains *Micrococcus lysodeikticus* ATCC No. 4698 (Sigma) and *Exiguobacterium* sp. (isolated from soil) were separately washed and suspended in 60 mM $KH_2PO_4$ buffer at pH6.0 with final concentration of 1% (w/v) as substrate stock. Before activity detection, the concentration of substrate was diluted into 0.035% which correlates to OD450 about 0.7 by 60 mM KH2PO4 buffer at pH6.0 or pH 4.0. 10 ul of polypeptide sample (or 5 ul of sample with 5 ul of MQ water if containing high concentration of salt) and 190 ul of 0.035% substrate were added into 96-well plate, and then read OD450. The plate was incubated for 30 or 60 minutes, 300 rpm at room temperature or 37° C. in the thermomixer. The plate was shaked 10 seconds and read OD450 again. The OD drop showed lysozyme activity. Blank is added 10 μl of 60 mM $KH_2PO_4$ at pH 6.0 or pH4.0 buffer, and each sample was measured in duplicate if necessary.

Purification of SEQ ID NO: 3

The culture supernatant was firstly precipitated with ammonium sulfate (80% saturation), then dialyzed with 20 mM NaAc at pH4.5. The solution was filtered with 0.45 um filter and then loaded into SP Fast Flow column (GE Healthcare) equilibrated with 20 mM NaAc at pH4.5. A gradient increase of NaCl concentration was applied as elution buffer from zero to 1M, and then the elution fractions and flow-through fraction were collected to detect lysozyme activity. The fractions with lysozyme activity were analyzed by SDS-PAGE, and then concentrated for further evaluation. The protein concentration was determined by Qubit® Protein Assay Kit (Invitrogen, cat Q33212).

Purification of SEQ ID NO: 6 The culture supernatant was firstly precipitated with ammonium sulfate (80% saturation), then the precipitation was added water to adjust conductance to about 140 mS/cm. The solution was filtered with 0.45 um filter and then loaded into HIC High Performance column (GE Healthcare) equilibrated with 20 mM PBS at pH8.0 with 1.2M $(NH_4)_2SO_4$ added. A gradient decrease of $(NH_4)_2SO_4$ concentration was applied as elution buffer from 1.2M to zero, and then elution fractions and flow-through fraction were collected to detect lysozyme activity.

The flow-through and Fractions from 1 to 15 were collected and conductance was adjusted to 180 mS/cm, then reloaded into HIC column equilibrated with 20 mM PBS at pH8.0 with 1.8M $(NH_4)_2SO_4$ added. A gradient decrease of $(NH_4)_2SO_4$ concentration was applied as elution buffer from 1.8M to zero, and then elution fractions and flow-through fraction were collected to detect lysozyme activity. The fractions with lysozyme activity were analyzed by SDS-PAGE, pooled together, and diafiltrated with 20 mM PBS at pH6.0. The protein concentration was determined by Qubit® Protein Assay Kit (Invitrogen, cat Q33212).

Purification of SEQ ID NO: 9

The culture supernatant was firstly precipitated with ammonium sulfate (80% saturation), then the precipitation was added water to adjust conductance to about 170 mS/cm. The solution was filtered with 0.45 um filter and then loaded into HIC High Performance column (GE Healthcare) equilibrated with 20 mM PBS at pH7.0 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, pooled together, and diafiltrated with 20 mM PBS at pH6.0. The protein concentration was determined by Qubit® Protein Assay Kit (Invitrogen, cat Q33212).

Purification of SEQ ID NO: 12

The culture supernatant was firstly precipitated with ammonium sulfate (80% saturation), then the precipitation was added water to adjust conductance to about 185 mS/cm. The solution was filtered with 0.45 um filter and then loaded into HIC High Performance column (GE Healthcare) equilibrated with 20 mM PBS at pH6.0 with 1.8M $(NH_4)_2SO_4$ added. A gradient decrease of $(NH_4)_2SO_4$ concentration was applied as elution buffer from 1.8M to zero, and then elution fractions and flow-through fraction were collected to detect lysozyme activity. The fractions with lysozyme activity were analyzed by SDS-PAGE, pooled together, and diafiltrated with 20 mM Bis-Tris at pH6.0.

The sample was loaded into a Mono Q column (GE Healthcare) equilibrated with 20 mM Bis-Tris at pH6.0. A gradient increase of NaCl concentration was applied as elution buffer from zero to 1M, and then the elution fractions and flow-through fraction were collected to detect lysozyme activity. The fractions with lysozyme activity were analyzed by SDS-PAGE, and then concentrated for further evaluation.

The protein concentration was determined by Qubit® Protein Assay Kit (Invitrogen, cat Q33212).

Purification of SEQ ID NO: 15

The culture supernatant was firstly precipitated with ammonium sulfate (80% saturation), then the precipitation was added water to adjust conductance to about 170 mS/cm. The solution was filtered with 0.45 um filter and then loaded into Phenyl Fast Flow column (GE Healthcare) equilibrated with 20 mM PBS at pH6.0 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity.

The flow-through and Fractions with lysozyme activity were collected and conductance was adjusted to 190 mS/cm, then reloaded into HIC column equilibrated with 20 mM PBS at pH6.0 with 1.5M $(NH_4)_2SO_4$ added again. A gradient decrease of $(NH_4)_2SO_4$ concentration was applied as elution loaded into Capto SP column (GE Healthcare) equilibrated with 20 mM PBS at pH6.5. A gradient increase of NaCl concentration was applied as elution buffer from zero to 1M, and then the elution fractions and flow-through fraction were collected to detect lysozyme activity. The fractions with lysozyme activity were analyzed by SDS-PAGE, and then concentrated for further evaluation. The protein concentration was determined by Qubit® Protein Assay Kit (Invitrogen, cat Q33212).

Analysis by N-terminal sequencing (Applied Biosystems Precise Amino Acid Sequencer Model 494) and intact molecular weight (MAXIS II electrospray mass spectrometer (Bruker Daltonik GmbH, Bremen, DE)) showed that the N-terminal LED domain had been cleaved off leaving the LAD catalytic domain and that the molecule had a heterogeneous N-terminal (see table 4). The major product corresponded to residues 85-230 which is disclosed as SEQ ID NO: 329.

TABLE 4

N-terminal and intact molecular weigh determination

| Applied Biosystems N-terminal sequence | Residues of SEQ ID NO: 18 | Intact Molecular Weight | | |
|---|---|---|---|---|
| | | M.Wt Calculated | M.Wt. Observed | ID |
| GNLPGLN | 88-230 | 15167.31 Da | 15167.92 Da | OK |
| GKGNLPG | 86-230 | 15352.54 Da | 15353.04 Da | OK |
| GGKGNLP | 85-230 | 15409.59 Da | 15410.06 Da | OK | buffer from 1.5M to zero, and then elution fractions and flow-through fraction were collected to detect lysozyme activity. The fractions with lysozyme activity were analyzed by SDS-PAGE, pooled together, and diafiltrated with 20 mM PBS at pH6.0. The protein concentration was determined by Qubit® Protein Assay Kit (Invitrogen, cat Q33212).

Purification of SEQ ID NO: 18

The culture supernatant from the expression of LYS_chbr (SEQ ID NO:16) was firstly precipitated with ammonium sulfate (80% saturation), then the precipitation was added water to adjust conductance to about 170 mS/cm. The solution was filtered with 0.45 um filter and then loaded into Phenyl Sepharose High Performance column (GE Healthcare) equilibrated with 20 mM PBS at pH6.0 with 1.8M $(NH_4)_2SO_4$ added. A gradient decrease of $(NH_4)_2SO_4$ concentration was applied as elution buffer from 1.8M to zero, and then elution fractions and flow-through fraction were collected to detect lysozyme activity. The fractions with lysozyme activity were analyzed by SDS-PAGE, and fractions were pooled together, and diafiltrated with 20 mM PBS at pH6.0. The protein concentration was determined by Qubit® Protein Assay Kit (Invitrogen, cat Q33212).

Analysis by intact molecular weight (MAXIS II electrospray mass spectrometer (Bruker Daltonik GmbH, Bremen, DE)) showed that the major product corresponded to amino acids 1 to 230 of SEQ ID NO: 18 (detected mass 24128.35 Da, predicted mass 24128.21 Da) with a minor product corresponded to amino acids 4 to 230 of SEQ ID NO: 18 (detected mass 23768.79 Da, predicted mass 23768.16 Da).

Purification of SEQ ID NO: 329

The culture supernatant from the expression of LYS_chbr (SEQ ID NO:16) was firstly precipitated with ammonium sulfate (80% saturation), then dialyzed with 20 mM PBS at pH6.5. The solution was filtered with 0.45 um filter and then Purification of SEQ ID NO: 21

The culture supernatant was firstly precipitated with ammonium sulfate (80% saturation), then the precipitation was added water to adjust conductance to about 140 mS/cm. The solution was filtered with 0.45 um filter and then loaded into Phenyl Fast Flow column (GE Healthcare) equilibrated with 20 mM NaAc at pH4.5 with 2M NaCl added. A gradient decrease of NaCl concentration was applied as elution buffer from 2M to zero, and then elution fractions and flow-through fraction were collected to detect lysozyme activity.

The flow-through and Fractions with lysozyme activity were collected and conductance was adjusted to 180 mS/cm, then reloaded into HIC column equilibrated with 20 mM NaAc at pH4.5 with 4M NaCl added again. A gradient decrease of NaCl concentration was applied as elution buffer from 4M to zero, and then elution fractions and flow-through fraction were collected to detect lysozyme activity. The fractions with lysozyme activity and unbound sample were analyzed by SDS-PAGE, pooled together, and concentrated. The protein concentration was determined by Qubit® Protein Assay Kit (Invitrogen, cat Q33212).

Purification of SEQ ID NO: 24

The culture supernatant was firstly precipitated with ammonium sulfate (80% saturation), then the precipitation was added water to adjust conductance to about 170 mS/cm. The solution was filtered with 0.45 um filter and then loaded into HIC High Performance column (GE Healthcare) equilibrated with 20 mM PBS at pH6.0 with 4M NaCl added. A gradient decrease of NaCl concentration was applied as elution buffer from 4M to zero, and then elution fractions and flow-through fraction were collected to detect lysozyme activity.

The flow-through and unbound sample with lysozyme activity were collected and conductance was adjusted to 190 mS/cm, then reloaded into HIC column equilibrated with 20 mM PBS at pH6.0 with 1.8M $(NH_4)_2SO_4$ added again. A gradient decrease of $(NH_4)_2SO_4$ concentration was applied as elution buffer from 1.8M to zero, and then elution fractions and flow-through fraction were collected to detect lysozyme activity. The fractions with lysozyme activity were analyzed by SDS-PAGE, pooled together, and diafiltrated with 20 mM PBS at pH6.0. The protein concentration was determined by Qubit® Protein Assay Kit (Invitrogen, cat Q33212).

Purification of SEQ ID NO: 27

The culture supernatant was firstly precipitated with ammonium sulfate (80% saturation), then dialyzed with 20 mM NaAc at pH5.5. The solution was filtered with 0.45 um filter and then loaded into Capto SP column (GE Healthcare) equilibrated with 20 mM NaAc at pH5.5. A gradient increase of NaCl concentration was applied as elution buffer from zero to 1M, and then the elution fractions and flow-through fraction were collected to detect lysozyme activity. The fractions with lysozyme activity were analyzed by SDS-PAGE. The fractions with lysozyme activity were pooled and concentrated, but degradation of sample was found.

The conductance of sample was adjusted to 200 mS/cm, then reloaded into Phenyl High Performance column equilibrated with 20 mM PBS at pH6.0 with 2.0M $(NH_4)_2SO_4$ added again. A gradient decrease of $(NH_4)_2SO_4$ concentration was applied as elution buffer from 2.0M to zero, and then elution fractions and flow-through fraction were collected to detect lysozyme activity. The fractions with lysozyme activity were analyzed by SDS-PAGE, pooled together, and diafiltrated with 20 mM PBS at pH6.0. The protein concentration was determined by Qubit® Protein Assay Kit (Invitrogen, cat Q33212).

Purification of SEQ ID NO: 30

The culture supernatant was firstly precipitated with ammonium sulfate (80% saturation), then dialyzed with 20 mM NaAc at pH4.5. The solution was filtered with 0.45 um filter and then loaded into Capto SP column (GE Healthcare) equilibrated with 20 mM NaAc at pH4.5. A gradient increase of NaCl concentration was applied as elution buffer from zero to 1M, and then the elution fractions and flow-through fraction were collected to detect lysozyme activity. The fractions with lysozyme activity were analyzed by SDS-PAGE, and then concentrated for further evaluation. The protein concentration was determined by Qubit® Protein Assay Kit (Invitrogen, cat Q33212).

Purification of SEQ ID NO: 33

The culture supernatant of 033×73 was firstly precipitated with ammonium sulfate (80% saturation), then dialyzed with 20 mM NaAc at pH4.5. The solution was filtered with 0.45 um filter and then loaded into Capto SP column (GE Healthcare) equilibrated with 20 mM NaAc at pH4.5. A gradient increase of NaCl concentration was applied as elution buffer from zero to 1M, and then the elution fractions and flow-through fraction were collected to detect lysozyme activity. The fractions with lysozyme activity were analyzed by SDS-PAGE, and then concentrated for further evaluation. The protein concentration was determined by Qubit® Protein Assay Kit (Invitrogen, cat Q33212).

Purification of SEQ ID NO: 36

The culture supernatant was firstly precipitated with ammonium sulfate (80% saturation), then dialyzed with 20 mM PBS at pH7.0. The solution was filtered with 0.45 um filter and then loaded into Capto Q column (GE Healthcare) equilibrated with 20 mM PBS at pH7.0. A gradient increase of NaCl concentration was applied as elution buffer from zero to 1M, and then the elution fractions and flow-through fraction were collected to detect lysozyme activity. The fractions with lysozyme activity were analyzed by SDS-PAGE. The flow-through fraction with lysozyme activity was picked up for further purification.

The pH of flow-through fraction was adjusted to pH4.5, then reloaded into Capto SP column equilibrated with 20 mM NaAC at pH4.5. A gradient increase of NaCl concentration was applied as elution buffer from zero to 1M, and then the elution fractions and flow-through fraction were collected to detect lysozyme activity. The fractions with lysozyme activity were analyzed by SDS-PAGE, and pooled together. The protein concentration was determined by Qubit® Protein Assay Kit (Invitrogen, cat Q33212).

Purification of SEQ ID NO: 39

The culture supernatant was firstly precipitated with ammonium sulfate (80% saturation), then the precipitation was added water to adjust conductance to about 170 mS/cm. The solution was filtered with 0.45 um filter and then loaded into Phenyl Sepharose 6 Fast Flow column (GE Healthcare) equilibrated with 20 mM PBS at pH6.0 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The lysozyme activity still was found in flow-through fraction and fractions 1 to 12, and they were pooled together for further purification.

The conductance of samples with lysozyme activity was adjusted to 190 mS/cm, then reloaded into Phenyl Sepharose High Performance column equilibrated with 20 mM PBS at pH6.0 with 1.8M $(NH_4)_2SO_4$ added again. A gradient decrease of $(NH_4)_2SO_4$ concentration was applied as elution buffer from 1.8M to zero, and then elution fractions and flow-through fraction were collected to detect lysozyme activity. The fractions with lysozyme activity were analyzed by SDS-PAGE, pooled together, and diafiltrated with 20 mM PBS at pH6.0. The protein concentration was determined by Qubit® Protein Assay Kit (Invitrogen, cat Q33212).

Purification of SEQ ID NO: 42

The culture supernatant was firstly precipitated with ammonium sulfate (80% saturation), then the precipitation was added water to adjust conductance to about 170 mS/cm. The solution was filtered with 0.45 um filter and then loaded into Phenyl Sepharose High Performance column (GE Healthcare) equilibrated with 20 mM PBS at pH6.0 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, but with two bands found. The fractions with lysozyme activity were pooled together for further purification.

The conductance of the fractions was adjusted to 140 mS/cm, then reloaded into Phenyl Sepharose High Performance column equilibrated with 20 mM PBS at pH6.0 with 1.2M $(NH_4)_2SO_4$ added again. A gradient decrease of $(NH_4)_2SO_4$ concentration was applied as elution buffer from 1.2M to zero, and then elution fractions and flow-through fraction were collected to detect lysozyme activity. The fractions with lysozyme activity were analyzed by SDS-PAGE. Fractions 29 to 37 have lower molecular weight, were pooled together, and diafiltrated with 20 mM PBS at pH6.0. Fraction 43 to 45 have higher molecular weight, were pooled together, and diafiltrated with 20 mM PBS at pH6.0. The protein concentration was determined by Qubit® Protein Assay Kit (Invitrogen, cat Q33212).

Analysis by N-terminal sequencing (Applied Biosystems Precise Amino Acid Sequencer Model 494) showed that the product began with the N-terminal sequence YPIKDNN, corresponmding to amino acids 1 to 7 of SEQ ID NO: 42.

Analysis by intact molecular weight (MAXIS II electrospray mass spectrometer (Bruker Daltonik GmbH, Bremen, DE)) showed that the major product corresponded to amino acids 1 to 304 of SEQ ID NO: 42 (detected mass 31755.59 Da, predicted mass 31754.97 Da). There was also a small amount of a secondary product corresponding to amino acids 76 to 304 of SEQ ID NO: 42 (detected mass 23617.23 Da, predicted mass 23617.15 Da) due to the first LED domain being cleaved off the N-terminal.

Purification of SEQ ID NO: 45

The fermentation supernatant with the lysozyme was filtered through a Fast PES Bottle top filter with a 0.22 m cut-off. 250 ml filtered fermentation samples was diluted with 250 ml MilliQ water and pH was adjusted to 4.5. The lysozyme containing solution was purified by chromatography on Capto S, approximately 30 ml in a XK16 column, using as buffer A 50 mM Na-acetate pH 4.5, and as buffer B 50 mM Na-acetate+2 M NaCl pH 4.5 using a 0-100% gradient over ca. 10CV. The fractions from the column were pooled based on the chromatogram (absorption at 280 and 254 nm) and SDS-PAGE analysis.

The molecular weight was estimated to 25 kDa from SDS-PAGE and the purity was >90%.

Example 10: Method of Determining the LAD Catalytic Domain by HMM

SEQ ID NOs: 46 to 187 were aligned using the software program MUSCLE v3.8.31 with the default settings. Using this alignment, the HMM was constructed using the software program 'hmmbuild' from the package HMMER 3.0 (March 2010) (hmmer.org/) and the software was invoked using the default settings by the command: hmmscan3 --tblout output.dat model.hmm sequences.fasta. The LAD catalytic domain HMM profile thereby generated for subsequent loading into the software program 'hmmscan' is given below.

```
HMMER3/b [3.0 | March 2010]
NAME LAD catalytic domain
LENG 136
ALPH amino
RF no
CS no
MAP yes
DATE Fri Apr. 21 12:03:08 2017
NSEQ 142
EFFN 1.547058
CKSUM 201442427
STATS LOCAL MSV -10.1515 0.71110
STATS LOCAL VITERBI -10.6276 0.71110
STATS LOCAL FORWARD -4.1803 0.71110
HMM      A        C        D        E        F        G        H        I        K        L        M        N        P
         Q        R        S        T        V        W        Y
         m->m     m->i     m->d     i->m     i->i     d->m     d->d
COMPO  2.28000  4.46955  2.96306  2.70047  3.44014  2.89264  3.73492  2.95902  2.72837
       2.64684  3.53697  3.08243  3.38858  2.79348  2.98339  2.54635  2.85094  2.67860  4.50931  3.45344
       2.68610  4.42256  2.77533  2.73152  3.46377  2.40496  3.72526  3.29372  2.67763
       2.69331  4.24673  2.90332  2.73683  3.18173  2.89805  2.37875  2.77520  2.98532  4.58508  3.61512
       0.86176  1.29948  1.18774  1.49367  0.25431  0.00000     *
 1     2.70450  4.96091  2.44483  2.25748  4.38595  1.70411  3.76708  3.83155  2.65982
       3.40989  4.23378  2.69810  3.83638  2.89968  3.15311  2.53822  2.77031  3.44613  5.62694  4.24971
      17 - -
       2.68618  4.42225  2.77519  2.73123  3.46354  2.40513  3.72494  3.29354  2.67741
       2.69355  4.24690  2.90347  2.73739  3.18146  2.89801  2.37887  2.77519  2.98518  4.58477  3.61503
       0.02516  4.09093  4.81328  0.61958  0.77255  0.70021  0.68613
 2     2.95798  4.37838  4.41979  3.85216  2.84679  4.06442  4.15724  2.49260  3.70306
       1.06749  3.04032  4.02131  4.37743  3.87638  3.84752  3.36755  3.18313  2.46409  3.85059  2.85522
      18 - -
       2.68618  4.42225  2.77519  2.73123  3.46354  2.40513  3.72494  3.29354  2.67741
       2.69355  4.24690  2.90347  2.73739  3.18146  2.89801  2.37887  2.77519  2.98518  4.58477  3.61503
       0.02269  4.19301  4.91535  0.61958  0.77255  0.78684  0.60749
 3     2.64712  5.07695  2.31050  2.33245  4.40298  2.91636  3.64509  3.86596  2.37831
       3.34917  4.16311  2.30868  3.81995  2.76486  2.86800  2.40011  2.43728  3.46575  5.56134  4.16658
      19 - -
       2.68618  4.42225  2.77519  2.73123  3.46354  2.40513  3.72494  3.29354  2.67741
       2.69355  4.24690  2.90347  2.73739  3.18146  2.89801  2.37887  2.77519  2.98518  4.58477  3.61503
       0.02259  4.19722  4.91957  0.61958  0.77255  0.69335  0.69294
 4     2.14335  5.06169  2.79203  2.15230  4.37029  3.13800  3.41689  3.83159  2.36004
       3.35168  4.11530  2.86703  3.32033  2.51530  2.75969  2.34749  2.87496  3.40178  5.51777  4.12854
      20 - -
       2.68618  4.42225  2.77519  2.73123  3.46354  2.40513  3.72494  3.29354  2.67741
       2.69355  4.24690  2.90347  2.73739  3.18146  2.89801  2.37887  2.77519  2.98518  4.58477  3.61503
       0.02150  4.24624  4.96858  0.61958  0.77255  0.57423  0.82813
 5     2.32752  4.64440  3.12310  2.59357  3.83630  3.40168  3.74641  3.18648  2.50736
       2.57706  3.73330  3.10307  3.85311  2.95065  2.73902  2.58368  2.21457  2.53579  5.18615  3.89627
      21 - -
       2.68618  4.42225  2.77519  2.73123  3.46354  2.40513  3.72494  3.29354  2.67741
       2.69355  4.24690  2.90347  2.73739  3.18146  2.89801  2.37887  2.77519  2.98518  4.58477  3.61503
       0.01979  4.32837  5.05072  0.61958  0.77255  0.64493  0.74380
 6     2.80872  5.24372  2.92193  2.38964  4.59162  3.53977  3.72591  4.02013  2.14929
       3.51532  4.32009  2.91909  3.77704  1.36571  2.64059  2.86001  3.11361  3.64412  5.64559  4.31503
```

-continued

```
22 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01973 4.33131 5.05366 0.61958 0.77255 0.64820 0.74021
7 2.62542 4.63457 2.55319 2.60028 3.82280 3.52902 3.75230 3.03815 2.62398
2.57975 2.90066 3.12772 3.91645 2.93691 3.05484 2.18187 2.58195 2.78875 5.17871 3.89049
23 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01973 4.33131 5.05366 0.61958 0.77255 0.62772 0.76315
8 2.35670 5.14104 2.59023 2.29666 4.47219 2.93010 3.62820 3.94710 2.04764
3.43912 4.18729 2.84545 3.83264 2.55019 2.41265 2.56554 2.74894 3.52457 5.58079 4.17986
24 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01956 4.34008 5.06243 0.61958 0.77255 0.52419 0.89657
9 2.70329 4.59946 3.33128 2.77671 3.58063 3.60472 2.72765 2.94006 2.73677
2.77463 3.69458 2.14343 3.98982 3.07351 3.13881 2.83571 2.93476 2.52531 5.01301 2.57944
25 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01861 4.38940 5.11175 0.61958 0.77255 0.57190 0.83115
10 0.58061 4.39851 3.89198 3.70803 4.66940 3.05741 4.71068 4.00280 3.76833
3.77981 4.64326 3.71756 3.68666 4.04155 4.00008 2.69179 3.01786 3.44176 6.02272 4.86740
26 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01861 4.38940 5.11175 0.61958 0.77255 0.57190 0.83115
11 2.28535 5.06565 2.88471 2.36748 4.19761 3.27471 3.62729 3.53322 2.10760
3.18026 4.11808 2.80247 3.71214 2.51474 2.31369 2.57926 2.86084 3.38794 5.52458 3.98224
27 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01861 4.38940 5.11175 0.61958 0.77255 0.55657 0.85138
12 1.95678 4.83280 2.92821 2.43631 4.06399 2.95241 3.71153 3.30570 2.47325
3.04114 3.90855 3.04375 3.89352 2.78279 2.87396 2.61802 2.53741 2.71961 5.34398 4.01659
28 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01849 4.39559 5.11794 0.61958 0.77255 0.56314 0.84262
13 2.65884 4.25606 4.53713 3.95931 3.05007 4.05376 4.40064 1.21113 3.82028
2.25497 3.31657 4.10649 4.40020 4.01626 3.95164 3.36535 2.97633 1.88140 4.97279 3.28929
29 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01849 4.39559 5.11794 0.61958 0.77255 0.56314 0.84262
14 3.09624 4.49244 5.08148 4.54556 3.69891 4.61127 5.10139 1.09511 4.43687
2.08328 3.22577 4.70341 4.88972 4.64468 4.57704 3.97183 3.20262 1.33503 5.56774 4.38580
30 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01849 4.39559 5.11794 0.61958 0.77255 0.56314 0.84262
15 1.87078 5.06861 2.67006 2.34424 4.37045 3.16553 3.65393 3.82623 2.28226
3.35531 4.12231 2.87229 3.85367 2.70349 2.62439 2.49490 2.76661 3.35529 5.19663 4.14646
31 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01849 4.39559 5.11794 0.61958 0.77255 0.44025 1.03248
16 2.43366 4.90407 3.07169 1.93881 4.14929 3.51322 3.71660 3.38468 2.44374
3.14212 3.97548 3.04089 3.90532 2.38664 2.91529 2.71114 2.76736 2.33204 5.40352 4.06677
32 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01756 4.44649 5.16884 0.61958 0.77255 0.48576 0.95510
17 1.69111 4.40326 3.80425 3.41677 4.37951 1.19800 4.42086 3.72489 3.41793
3.46042 4.30219 3.40956 3.96367 3.70234 3.73859 2.67449 2.74965 2.61793 5.75300 4.54416
33 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01756 4.44649 5.16884 0.61958 0.77255 0.48576 0.95510
18 2.67801 5.17603 3.05013 2.31240 4.51586 3.49631 3.67694 3.96645 1.74435
3.22387 4.22607 2.91297 3.91428 2.52932 2.01448 2.64975 2.92944 3.35475 5.59394 4.23259
34 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01756 4.44649 5.16884 0.61958 0.77255 0.48576 0.95510
19 2.48895 5.18440 2.65300 2.21077 4.52329 3.29253 3.65271 4.00175 1.95386
3.48470 4.12914 2.89759 3.86079 2.50491 2.18622 2.57065 2.85720 3.57201 5.61837 4.21554
```

-continued

```
35 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01756 4.44649 5.16884 0.61958 0.77255 0.48576 0.95510
20 2.43351 4.88117 2.77074 2.22081 4.11935 3.46932 3.71513 3.38326 2.42344
2.62406 2.69401 3.04226 3.90131 2.82540 2.62123 2.56251 2.91163 3.14773 5.38359 3.90443
36 - -
2.68618 4.42225 2.77517 2.73121 3.46348 2.40513 3.72495 3.29354 2.67741
2.69355 4.24690 2.90347 2.73740 3.18147 2.89801 2.37887 2.77520 2.98519 4.58477 3.61503
0.04246 3.32766 5.16884 0.48651 0.95390 0.48576 0.95510
21 2.69712 5.18519 2.72756 2.39570 4.51082 1.98188 3.08098 3.97672 2.20957
3.47648 4.23700 2.82477 3.89080 2.76334 2.37850 2.67797 2.96922 3.56665 5.62338 4.23301
38 - -
2.68633 4.42243 2.77509 2.73132 3.46372 2.40492 3.72439 3.29372 2.67759
2.69347 4.24708 2.90365 2.73730 3.18093 2.89819 2.37883 2.77537 2.98501 4.58495 3.61521
0.10524 2.36234 5.16884 1.78389 0.18390 0.48576 0.95510
22 3.08450 4.42239 4.90061 4.32017 3.36955 4.33853 4.69926 1.58167 4.16773
1.61994 2.77727 4.43627 4.63435 4.05013 4.24780 3.66605 3.31710 1.41643 5.15040 3.90088
49 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01756 4.44649 5.16884 0.61958 0.77255 0.48576 0.95510
23 2.59988 4.75855 3.17066 2.72521 4.40766 2.14059 3.94805 3.84514 2.77802
3.44012 4.23907 3.03326 2.07393 2.98757 3.22451 2.01551 2.47915 3.41576 5.65635 4.33552
50 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01756 4.44649 5.16884 0.61958 0.77255 0.48576 0.95510
24 2.39242 5.12137 2.88795 2.13091 4.33191 3.46970 3.57957 3.90215 2.31739
3.35239 4.03851 2.90526 2.72477 2.72379 2.19066 2.50080 2.91724 3.45054 5.57111 4.18029
51 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01756 4.44649 5.16884 0.61958 0.77255 0.48576 0.95510
25 2.71674 5.18303 2.94981 2.39383 4.38247 3.46358 3.04209 3.88509 1.96661
3.38118 4.23031 2.98468 3.89750 2.14189 2.03986 2.68912 2.96595 3.57326 5.60356 4.22936
52 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01756 4.44649 5.16884 0.61958 0.77255 0.48576 0.95510
26 1.71921 4.45728 3.85035 3.71589 4.87129 0.76439 4.79418 4.28684 3.88233
4.01035 4.83765 3.73888 4.01975 4.11397 4.12696 2.72115 3.06866 3.62581 6.18704 5.04378
53 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01756 4.44649 5.16884 0.61958 0.77255 0.48576 0.95510
27 2.59152 2.48781 4.45380 3.85081 3.15329 3.82710 4.15011 1.84112 3.67495
1.97419 3.00019 3.92506 4.19158 3.38567 3.69697 3.13011 2.91063 2.23021 3.68826 3.44124
54 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01756 4.44649 5.16884 0.61958 0.77255 0.48576 0.95510
28 2.65209 3.96839 3.84226 3.11334 3.36636 3.72249 4.00157 2.32334 3.11605
2.17547 3.29883 3.58242 4.09639 2.77690 3.22956 2.96075 2.67088 1.76667 4.85107 3.53972
55 - -
2.68619 4.42226 2.77521 2.73124 3.46355 2.40514 3.72495 3.29355 2.67742
2.69356 4.24691 2.90341 2.73735 3.18147 2.89802 2.37888 2.77521 2.98519 4.58478 3.61490
0.03420 3.57804 5.16884 0.73477 0.65319 0.48576 0.95510
29 2.07224 4.45423 4.82417 4.28807 3.72902 4.39122 4.89895 1.15537 4.18214
2.34671 3.58878 4.46949 4.73704 4.42219 4.36253 3.74086 3.24252 1.52460 5.49002 4.28913
59 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01756 4.44649 5.16884 0.61958 0.77255 0.48576 0.95510
30 1.15453 3.74267 3.77490 3.26721 3.89912 2.36201 4.18636 3.24727 3.21520
2.97973 3.85757 3.52789 3.99672 3.50932 3.54238 2.73423 2.92343 2.74165 5.32643 3.69760
60 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01756 4.44649 5.16884 0.61958 0.77255 0.48576 0.95510
31 2.84534 4.33315 4.79654 4.21517 3.00397 4.21925 4.58222 1.49254 4.06138
1.49784 3.23805 4.07937 4.54078 4.22140 4.14680 3.54186 3.21703 1.75514 5.07561 3.90804
61 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01756 4.44649 5.16884 0.61958 0.77255 0.48576 0.95510
32 1.19836 4.20261 3.80733 3.28440 3.79916 3.46684 4.16982 3.08236 3.21815
2.85747 2.79726 3.55364 4.02738 3.51320 3.53422 2.61082 2.45216 2.77505 5.24805 4.03169
```

-continued

62 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01756 4.44649 5.16884 0.61958 0.77255 0.48576 0.95510
33 2.67861 4.43286 3.96982 3.42894 3.65753 3.77789 4.27411 2.58096 3.33280
2.44008 3.15099 3.73934 4.23535 3.64118 3.63033 3.09698 1.23658 2.16899 5.22762 4.01619
63 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
34 1.44620 4.53665 3.43775 2.81280 3.93249 2.34265 3.97126 3.24629 2.88857
2.99055 3.71572 3.31646 3.97140 3.21318 3.28442 2.63939 2.78238 2.66627 5.31139 4.05101
64 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
35 3.04606 4.42292 4.75886 4.16570 2.88260 4.22029 4.49891 2.34117 4.00836
1.03933 2.20271 4.29137 4.51739 4.12726 4.08499 3.42153 3.27084 2.49510 4.93841 3.26659
65 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
36 2.71461 4.59963 3.37734 2.81076 3.81249 3.60715 3.88255 3.10147 2.75570
2.84474 3.60963 3.28475 4.01656 1.92884 3.13739 2.77826 2.55554 1.85209 5.20271 3.93973
66 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
37 3.23633 5.68513 2.52859 0.74729 4.98392 3.53491 4.03390 4.51339 2.90426
4.00099 4.88649 3.02799 4.14144 2.82546 3.36929 3.14048 3.51910 4.11671 6.12487 4.69016
67 - -
2.68619 4.42226 2.77521 2.73122 3.46355 2.40510 3.72496 3.29355 2.67742
2.69356 4.24691 2.90348 2.73741 3.18143 2.89802 2.37884 2.77521 2.98516 4.58478 3.61504
0.03910 3.42113 5.17311 0.68213 0.70429 0.48576 0.95510
38 2.39513 4.11214 3.35820 3.20332 4.42695 3.26670 4.28663 3.82011 3.21286
3.50054 4.32164 3.46375 3.94681 3.51782 3.58241 0.93820 2.31575 3.34233 5.75692 4.51511
71 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
39 2.58578 5.14774 2.75533 2.34338 4.46814 2.68238 3.67933 3.93571 2.37780
3.44618 4.20504 2.13940 3.68658 2.77456 2.84780 2.37578 2.39625 3.52717 5.60429 4.20804
72 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
40 3.20020 4.54721 4.96249 4.36943 2.96426 4.39636 4.64583 2.10604 4.20651
0.83885 2.83629 4.48315 4.65449 4.27813 4.25147 3.71872 3.42034 2.57150 3.89377 3.67606
73 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
41 2.69560 4.72458 3.22090 2.63257 3.92297 3.56535 3.56009 2.72958 2.13988
2.63336 3.74365 3.14689 3.95072 2.89799 2.30477 2.78249 2.47712 3.01102 5.25331 3.23392
74 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
42 2.72660 4.33347 3.80539 3.20123 3.45879 3.75585 4.04605 2.31867 3.16049
2.48505 1.91296 2.34384 4.13604 3.45213 3.45614 2.98531 2.96321 2.24154 4.95867 3.74251
75 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
43 3.27737 4.67049 4.55145 4.06069 2.47355 4.24815 3.04419 3.15657 3.89846
1.64280 3.78329 4.07582 4.58700 4.03579 4.02494 3.55869 3.50219 2.88245 3.33803 1.24804
76 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
44 0.51810 4.44568 4.02569 3.87596 4.67377 3.25002 4.83448 3.91947 3.91283
3.77914 4.70430 3.82610 4.05779 4.19265 4.11231 2.69966 3.08739 3.40908 6.08181 4.89612
77 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
45 2.82915 4.93329 2.91029 2.80758 4.72631 3.36731 4.23890 4.33583 3.16837
3.93241 4.78070 0.84802 4.06265 3.45665 3.58212 2.30119 3.25191 3.81189 6.00977 4.62640

-continued

```
78 - -
2.68627 4.42234 2.77499 2.73132 3.46363 2.40491 3.72503 3.29363 2.67750
2.69350 4.24699 2.90356 2.73748 3.18111 2.89793 2.37896 2.77514 2.98527 4.58486 3.61512
0.05713 2.99842 5.17311 1.58281 0.22991 0.48576 0.95510
46 2.44557 5.15547 2.81273 2.27429 4.48469 3.15265 3.59265 3.95947 2.21519
3.45385 3.88587 2.75206 3.27069 2.59201 2.49640 2.15937 2.87349 3.48110 5.59762 4.05507
89 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
47 2.13454 5.00394 2.91686 2.45903 4.28160 2.96306 3.68619 3.67500 2.15235
3.28140 3.87376 2.63736 3.88029 2.80019 2.83287 2.41440 2.70755 2.87275 5.48352 4.11976
90 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
48 2.72141 4.35240 2.87142 3.17074 3.46488 3.73995 3.73692 2.49287 3.11195
2.30200 3.45239 3.53638 4.11660 3.40062 3.42677 3.00245 2.95465 1.43634 4.95481 3.60798
91 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
49 2.12915 4.48324 3.64290 3.40938 4.58739 3.18867 4.50853 3.96004 3.46395
3.53103 4.54098 3.58182 0.86537 3.78586 3.75910 2.64147 3.03200 3.44121 5.94006 4.71598
92 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
50 2.01164 5.32733 2.29923 1.57851 4.64741 3.27623 3.76224 4.13187 2.55344
3.62677 4.39593 2.92867 3.92919 2.69728 3.09144 2.54063 3.07699 3.70865 5.77773 4.35069
93 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
51 2.71221 4.62091 3.84225 3.72618 4.73636 3.34639 4.79405 4.36144 3.84443
4.04592 4.94233 3.81925 4.13886 4.14747 4.08008 0.47186 3.24139 3.75589 6.06282 4.83690
94 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
52 2.66443 4.20422 4.02877 3.41213 2.99738 3.77235 4.00427 2.62502 3.33273
1.34843 2.95964 3.64909 4.14137 3.15046 3.37243 3.05142 2.90210 2.37881 4.80399 3.44902
95 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
53 2.47713 5.18116 2.61739 2.34620 4.51729 3.13019 3.65365 3.99682 2.04882
3.48212 4.16874 2.22347 3.85828 2.41978 2.72356 2.58280 2.82696 3.48795 5.61851 4.21297
96 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
54 2.73893 4.19220 4.24842 3.53966 2.57306 3.84157 3.74088 2.33976 3.46086
1.99185 3.21748 3.83249 4.20652 3.73421 3.63828 3.13341 2.97029 2.44433 4.64684 1.75323
97 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
55 2.71240 5.13365 2.69940 2.43599 4.41459 3.50972 3.49117 3.85066 2.43114
3.37180 4.22210 3.01430 1.47487 2.86242 2.98711 2.79453 3.04627 3.49615 5.61591 4.25331
98 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
56 3.01695 4.95117 3.34848 2.93690 2.87628 3.79607 1.23282 3.57422 2.90391
3.12848 4.07095 2.86681 4.20183 3.25586 3.28583 3.07855 3.25131 3.31857 4.61908 2.76108
99 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
57 3.18894 5.84895 1.02997 1.80049 5.12950 3.38073 3.98591 4.67160 3.00026
4.12922 4.96533 2.84549 4.07391 2.43811 3.61066 3.05626 3.47306 4.21602 6.27452 4.73944
100 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
58 1.87056 5.02650 2.84164 2.46171 4.33046 2.29263 3.72123 3.76686 2.39089
3.23960 4.11787 3.01321 3.90717 2.85149 2.40724 2.72437 2.95880 3.40262 5.52546 4.16743
```

-continued

```
101 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
59 2.87296 4.29463 4.42304 3.69558 3.46367 4.04793 4.40439 2.07618 3.67094
2.05941 3.34949 4.05306 4.40386 3.95876 3.89843 3.10391 3.01800 1.11333 5.06040 3.86470
102 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
60 2.52335 4.51129 3.62019 3.55772 4.90051 0.60958 4.75107 4.41575 3.82700
4.10403 4.93001 3.66459 4.02959 4.06543 4.08722 2.50971 3.10678 3.71678 6.21996 5.01896
103 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
61 2.56709 4.93698 2.98607 2.45383 4.19080 3.24189 3.51161 3.61622 2.39299
3.20196 4.00362 2.98136 3.89479 2.84277 2.59044 1.74729 2.79854 3.27778 4.06346 3.72954
104 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
62 3.38324 5.87953 0.59437 2.43450 5.16499 3.51089 4.19299 4.82683 3.33417
4.31592 5.25707 3.02299 4.19831 3.13634 3.96628 3.25372 3.71690 4.38903 6.38048 4.86658
105 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
63 2.28041 4.89681 3.06750 2.53375 4.06796 2.85605 1.87529 3.55546 2.53845
3.16132 3.98206 3.01976 3.93000 2.75092 2.95635 2.75641 2.95343 3.23664 5.39946 3.72687
106 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
64 2.73536 5.16994 1.55165 2.40682 4.24291 3.11994 3.71533 3.93310 2.40910
3.28038 4.23100 2.48568 3.90074 2.83461 2.94504 2.72540 2.98937 3.53862 5.62732 3.93150
107 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
65 2.62666 4.61256 3.39176 3.21148 4.63783 3.28182 4.41739 4.20282 3.32467
3.84412 4.67922 3.16840 4.02180 3.67404 3.51687 0.68426 3.10405 3.63275 5.95670 4.66134
108 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
66 3.28127 4.55225 5.16566 4.64383 3.79600 4.71020 5.24685 1.56503 4.54047
1.99718 3.60026 4.80975 4.98633 4.76535 4.69380 4.08383 3.11988 0.89374 5.70699 4.51592
109 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
67 2.83680 4.79292 3.36129 3.31483 4.92387 0.56396 4.64949 4.54776 3.68201
4.17787 5.03927 2.99221 4.16071 3.94307 4.00415 2.97866 3.33903 3.92368 6.16418 4.94755
110 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
68 2.70449 4.13848 4.32502 3.73159 3.13755 3.83631 4.15179 2.03453 3.58574
1.52919 3.00530 3.87723 3.62487 3.66752 3.71454 2.91360 2.87147 2.05586 4.75960 3.51144
111 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
69 2.73703 4.50887 4.57967 4.02838 1.13149 4.19889 4.29405 2.61213 3.88343
1.97359 2.83383 4.17612 4.52379 4.04901 4.01988 3.51275 3.32702 2.56914 4.71360 3.20993
112 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
70 3.52506 5.43753 3.46574 3.27167 4.68799 3.87734 4.41883 4.45892 3.05955
3.89409 4.94547 3.72159 4.46342 0.47963 3.31382 3.56707 3.84071 4.16117 5.86192 4.62247
113 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
```

-continued 71 3.02299 5.04929 3.40906 2.92277 4.01409 3.75171 3.94381 3.49511 2.54678
2.80533 3.66251 3.37318 4.18320 1.04133 2.83982 3.09078 3.26561 3.31350 5.42159 4.07886
114 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
72 3.23277 5.37526 3.60226 2.97446 4.85343 3.84765 3.82756 4.21956 2.11769
3.65014 4.51048 3.38477 4.13356 2.19382 0.97246 3.05467 3.41202 3.88371 5.68623 4.50401
115 - -
2.68625 4.42237 2.77523 2.73135 3.46365 2.40496 3.72506 3.29355 2.67750
2.69364 4.24690 2.90336 2.73708 3.18158 2.89804 2.37895 2.77531 2.98487 4.58431 3.61515
0.36967 1.63266 2.17482 0.89983 0.52195 0.48576 0.95510
73 1.76091 4.60585 3.22695 2.66138 3.81873 3.21041 3.77958 3.20393 2.63580
2.87005 3.72561 3.15358 3.75753 2.86242 3.08379 2.38691 2.78816 2.67495 5.18090 3.39722
123 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01963 4.33652 5.05887 0.61958 0.77255 0.39638 1.11703
74 2.36188 4.66636 3.23919 2.64903 3.85241 3.48742 3.78659 3.17689 2.61741
2.87246 3.42621 3.16440 2.54039 2.70411 3.07610 2.15587 2.83967 2.88009 3.85405 3.79583
124 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
75 2.61045 4.23100 3.89390 3.31670 3.10119 2.37718 3.92350 2.41741 3.11684
2.43089 3.34271 3.57347 4.03101 3.48884 3.48808 2.78635 2.90801 2.39128 2.56930 3.00068
125 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
76 4.23911 5.35111 5.11059 4.88905 2.16141 4.82451 3.72509 3.97319 4.62130
3.22244 4.51964 4.46153 5.12779 4.55830 4.58510 4.24512 4.45234 3.88962 0.95146 1.31009
126 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
77 2.54730 4.84000 3.12323 2.67492 4.36810 1.48789 3.89014 3.79317 2.30863
3.38625 4.19529 3.14795 3.09597 3.04853 3.05662 2.71985 2.63434 3.40162 5.60425 4.28424
127 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
78 2.66228 5.17663 2.18695 2.38019 4.51071 3.46112 3.72860 3.97811 2.49394
3.49608 4.26544 2.46913 3.53684 2.84670 3.01297 2.30433 1.95746 3.57076 5.66185 4.26183
128 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
79 2.62597 3.72459 4.74145 4.16976 3.49514 4.17644 4.57946 1.53523 4.02504
2.06669 3.43633 4.27639 4.52278 4.21862 4.13372 3.37728 2.96630 1.32915 5.12648 3.93497
129 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
80 1.71018 5.09500 2.91003 2.28837 4.39860 3.20819 3.68055 3.85185 2.18117
3.38129 4.15199 2.97202 3.82904 2.59376 2.69863 2.63050 2.91871 3.35040 5.55436 4.17589
130 - -
2.68618 4.42225 2.77520 2.73123 3.46354 2.40513 3.72495 3.29354 2.67741
2.69355 4.24690 2.90347 2.73740 3.18146 2.89797 2.37887 2.77520 2.98518 4.58477 3.61503
0.02663 3.88177 5.17311 0.56218 0.84389 0.48576 0.95510
81 2.48394 3.10163 2.25908 2.04705 4.39152 3.47485 3.67962 3.84650 2.44021
3.37821 4.14764 2.96397 3.87525 2.41597 2.88073 2.68095 2.61892 3.42222 5.55416 4.17129
132 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
82 2.68177 3.55032 2.55328 2.65458 3.90044 3.55585 3.77777 3.23585 2.63297
2.14245 3.79147 3.07691 3.94510 2.97547 2.27756 2.59681 2.81043 2.92572 5.24224 3.94809
133 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
83 3.55146 5.02464 4.74999 4.42776 3.62483 4.31991 5.02933 2.86859 4.15961
2.16114 0.58493 4.62225 4.81483 4.51696 4.28820 3.94221 3.88517 2.93677 5.51590 4.31836
134 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
84 2.78950 5.27104 1.60171 2.36299 4.59227 3.42284 3.72878 4.07088 2.40039

-continued 3.56687 4.33046 2.53375 3.91054 2.77186 2.80759 2.59881 2.49679 3.65129 5.71587 4.30134
135 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
85 1.77249 4.42802 3.73213 3.25700 4.00890 3.41128 4.22625 3.23512 3.21280
2.95449 3.94696 3.53063 1.56755 3.52335 3.54799 2.70627 2.96075 2.25370 5.43619 4.20828
136 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
86 1.87784 5.02782 2.72866 2.33198 4.31028 3.19386 3.53042 3.75421 2.37531
3.26556 3.94889 2.98159 3.87619 2.75751 2.76120 2.54384 2.55560 3.23490 5.50000 3.78285
137 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
87 2.67637 2.87529 3.70049 3.09589 3.25828 3.44585 3.90857 2.60314 2.80465
2.33125 3.42306 3.49082 4.06803 3.27375 2.53060 2.91907 2.80152 2.55072 4.90754 2.46622
138 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
88 1.79992 4.78437 3.03555 2.72524 4.41183 3.38379 3.98195 3.84389 2.83464
3.45092 4.26320 2.85725 3.94926 2.98839 3.27815 1.35854 2.96383 3.42785 5.67722 4.35764
139 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
89 0.80355 4.37389 3.94778 3.56894 4.36811 3.25124 4.50693 3.63938 3.52971
3.44162 4.30193 3.48702 3.98332 3.81712 3.81331 2.60473 2.39172 2.87424 5.76557 4.57199
140 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
90 2.25481 5.11116 2.94963 2.41107 4.42260 2.57292 3.24732 3.87706 2.30147
3.39764 4.16527 2.97537 3.88387 2.61155 2.07107 2.60293 2.93976 3.41342 5.56165 4.18457
141 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
91 2.25875 4.65512 3.27561 2.71191 3.71913 3.58308 3.80002 3.21470 2.22262
2.23688 2.92970 3.19070 3.96792 2.32664 3.05287 2.79258 2.92381 2.93018 5.19763 3.91802
142 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
92 4.10061 5.33819 5.05020 4.90417 0.39707 4.58135 4.27801 3.59955 4.80953
2.84635 4.25771 4.72981 5.04948 4.82350 4.78408 4.31507 4.41322 3.62708 4.41534 2.73487
143 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
93 3.73347 4.97315 5.03984 4.66909 1.28357 4.63286 3.84974 3.24734 4.49074
2.00016 3.89704 4.40634 4.92154 4.43197 4.47846 3.98159 3.95025 3.15737 3.99370 1.21085
144 - -
2.68638 4.42247 2.77536 2.73135 3.46369 2.40447 3.72497 3.29375 2.67759
2.69372 4.24711 2.90334 2.73680 3.18155 2.89812 2.37878 2.77536 2.98540 4.58498 3.61517
0.11081 2.31033 5.17311 1.90953 0.16035 0.48576 0.95510
94 2.36046 5.18606 2.46437 2.08364 4.52401 3.06141 3.65211 4.00557 2.21277
3.47210 4.22927 2.71281 3.71770 2.67965 2.50031 2.53113 2.72851 3.53705 5.62257 4.21483
156 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
95 2.04461 5.10851 2.83785 2.25064 4.41932 2.69662 3.66732 3.77266 2.22782
3.39937 4.16115 2.95643 3.86815 2.74425 2.55833 2.39296 2.92164 3.37408 5.56407 4.17669
157 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
96 3.77195 5.02078 5.51168 4.93411 3.22586 5.09901 5.36604 2.28434 4.77671
0.68399 1.90625 5.18303 5.15259 4.73558 4.79347 4.47651 3.97588 2.64824 5.44208 4.46890
158 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510

-continued

```
97 2.27665 4.54429 3.31069 2.67276 3.77380 3.58986 3.81443 3.12693 2.13922
2.16378 3.62025 3.19158 3.97401 3.01825 2.81563 2.81424 2.79037 2.51297 5.15297 3.55805
159 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
98 2.49488 5.19607 2.45038 2.24856 4.53529 3.23631 3.65787 4.01546 1.90310
3.49690 4.24001 2.83925 3.86393 2.61300 2.31130 2.64491 2.75545 3.58392 5.62980 4.22437
160 - -
2.68620 4.42244 2.77520 2.73124 3.46373 2.40506 3.72514 3.29342 2.67743
2.69374 4.24709 2.90323 2.73741 3.18123 2.89767 2.37906 2.77520 2.98503 4.58496 3.61522
0.09568 2.45835 5.17311 1.90622 0.16092 0.48576 0.95510
99 2.64610 4.19287 4.51782 3.92763 2.77711 3.97094 4.30822 1.78813 3.57005
2.08485 3.28244 4.04333 4.32451 3.95582 3.66707 3.27791 3.03016 1.43763 4.87494 3.69158
175 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.02184 4.45077 4.61181 0.61958 0.77255 0.48576 0.95510
100 2.57644 5.19801 2.27538 2.38818 4.52814 3.35083 3.68719 4.00392 2.23129
3.50058 4.25504 2.58839 2.30709 2.79494 2.80539 2.41521 2.96353 3.58321 5.64771 4.24193
176 - -
2.68622 4.42229 2.77523 2.73127 3.46358 2.40516 3.72498 3.29358 2.67744
2.69359 4.24693 2.90350 2.73743 3.18150 2.89804 2.37890 2.77523 2.98522 4.58481 3.61363
0.19911 1.74384 5.16884 0.21958 1.62384 0.48146 0.96202
101 2.99688 5.49109 2.31693 2.34426 4.82026 1.50085 3.89510 4.31373 2.80362
3.81760 4.62442 1.94387 4.01089 2.75286 3.34734 2.82386 3.26700 3.89190 5.98283 4.52864
178 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
102 2.70284 4.52919 3.24032 2.96189 3.71775 3.56073 3.97139 3.17965 2.94172
2.87349 3.75897 3.21460 4.03711 3.27740 3.29933 2.53512 2.46622 2.91647 1.54333 3.85468
179 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.02978 4.45077 4.03581 0.61958 0.77255 0.48576 0.95510
103 2.61665 5.23073 2.48892 1.93564 4.56747 3.45738 3.61649 4.05178 2.24240
3.53134 4.27684 2.80050 3.64002 1.94619 2.84919 2.64239 2.89577 3.61752 5.66449 4.25113
180 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01770 4.43869 5.16104 0.61958 0.77255 0.50512 0.92491
104 2.50715 5.12699 2.77810 2.33590 4.44582 3.30582 3.61595 3.91337 2.30426
3.35320 4.17496 2.61050 3.85772 2.65896 2.39675 2.29108 2.36063 3.50352 5.57542 3.76373
181 - -
2.68618 4.42225 2.77515 2.73124 3.46354 2.40513 3.72495 3.29354 2.67741
2.69355 4.24690 2.90347 2.73740 3.18147 2.89801 2.37884 2.77520 2.98519 4.58477 3.61503
0.03088 3.70193 5.16104 0.63198 0.75831 0.47385 0.97446
105 2.60454 4.24739 3.87526 3.29633 3.36055 3.57144 3.72308 2.65342 3.19345
2.14470 1.84807 3.60313 4.10632 3.35860 3.01033 3.00275 2.85663 2.18919 4.84814 3.64240
184 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
106 2.39134 5.15060 2.35146 2.27357 4.47362 3.41528 3.68003 3.94208 2.43822
3.37742 4.20939 2.86965 2.78407 2.78921 2.79582 2.01297 2.86585 3.53191 5.60823 4.21105
185 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
107 2.62098 4.25013 3.87151 3.29482 3.36602 3.73620 3.93542 2.37557 2.91952
2.03620 3.23025 3.60470 2.54484 3.47456 3.42600 3.00516 2.82863 1.90641 4.85591 3.64926
186 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
108 2.06052 4.40686 3.81765 3.48760 4.63190 1.17260 4.52999 4.05972 3.52970
3.73232 4.53659 3.59957 3.80588 3.79688 3.84625 2.40774 1.76640 3.46863 5.96429 4.76728
187 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
109 2.30528 5.00504 2.79584 2.32132 4.28012 3.35093 3.68460 3.71938 2.30210
3.20302 4.06501 2.97029 3.87976 2.52168 2.83814 2.53315 2.26799 2.84934 4.56909 4.11805
188 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
```

-continued

```
110 1.74241 4.18228 4.15006 3.56681 3.06887 3.80169 3.83739 2.56132 3.44556
1.80992 3.28778 3.77234 4.16953 3.66514 3.62758 3.08801 2.93731 2.40159 3.19051 3.11867
189 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
111 1.15417 2.40052 3.43268 3.31342 3.94825 3.05617 4.23524 3.29134 3.27802
2.88728 3.90490 3.55144 3.99881 3.56368 3.59756 2.72050 2.93186 2.96489 5.37506 4.15892
190 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
112 3.26861 5.44238 2.97663 2.64398 4.75892 3.69012 4.06288 4.30148 2.66362
3.78982 4.71915 3.28643 4.23921 0.76296 2.96287 3.24618 3.53605 3.96409 5.86880 4.56259
191 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
113 1.91522 4.95047 2.97467 2.39757 4.20895 3.50202 3.70112 3.61309 2.14870
3.19155 3.18272 3.01748 3.89338 2.73359 2.84536 2.53242 2.55518 3.29391 5.43928 4.09037
192 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
114 3.29634 4.59962 5.14480 4.67781 3.93848 4.66858 5.40358 1.71382 4.56710
2.45181 3.72266 4.84032 5.02031 4.85191 4.75526 4.08284 3.33697 0.67655 5.91411 4.69288
193 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
115 3.15567 5.44348 2.80271 2.49407 4.78415 3.60247 3.94943 4.28979 2.58206
3.78846 4.65575 2.96667 4.14360 0.91366 2.91447 3.11238 3.41462 3.91870 5.87574 4.52658
194 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
116 2.71563 4.90409 3.12545 2.55928 4.14921 2.85289 3.44680 3.05862 2.22913
3.15932 3.97583 3.07155 3.92680 2.53911 2.16870 2.75050 2.94327 2.44686 5.39558 4.07226
195 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
117 2.19207 4.40484 3.86126 3.64147 4.76639 3.17370 4.68117 4.15367 3.70231
3.88127 4.70113 3.67352 3.97014 3.97418 3.96685 0.66193 2.77617 3.52234 6.10860 4.92572
196 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
118 1.23716 4.99590 2.82777 2.30137 4.34451 3.20483 3.85483 3.76823 2.68928
3.36557 4.18982 3.06501 3.97138 2.91804 3.03321 2.75915 3.06515 3.41893 5.59981 4.25545
197 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
119 2.63152 4.27604 4.03648 3.47068 1.69703 3.81555 3.85315 2.68413 3.36748
2.44928 3.39118 3.31828 4.18646 3.53607 3.59165 3.09668 2.86423 2.46901 4.64999 2.19303
198 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
120 3.10050 4.93865 3.89438 3.80685 5.08138 2.93213 4.95457 4.68524 3.99850
4.30514 5.22080 4.02495 0.41952 4.31180 4.23729 3.27299 3.60547 4.11129 6.18106 5.18331
199 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
121 2.63821 5.16765 1.71131 2.06185 4.48005 3.20764 3.58490 3.94854 2.45253
3.45931 4.22038 2.80491 3.88069 2.79852 2.94579 2.60137 2.82264 3.54145 4.92801 3.93756
200 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
122 1.86376 4.90237 3.28241 2.68163 4.15144 3.62338 3.62925 3.54290 2.36576
2.72221 3.98901 3.18063 4.00712 2.90768 1.74335 2.86644 3.03069 3.24561 5.38278 4.04754
201 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
```

-continued

```
0.01749 4.45077 5.17311 0.61958 0.77255 0.48576 0.95510
123 4.19177 5.36263 4.97401 4.78151 2.11394 4.76326 3.76878 3.89368 4.60093
3.15403 4.48829 4.44462 5.10497 4.55202 4.59461 4.21077 4.43309 3.83039 3.88657 0.47676
202 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01749 4.45077 5.17311 0.61958 0.77255 0.48576 0.95510
124 1.79635 5.14532 2.26839 2.39026 4.45744 3.24099 3.34639 3.84057 2.35322
3.43625 4.19753 2.81236 3.87618 2.60394 2.87095 2.67589 2.92156 3.51869 5.59711 4.13300
203 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.02128 4.45077 4.66879 0.61958 0.77255 0.48576 0.95510
125 2.49141 5.20122 2.74864 2.18402 4.54180 3.39680 3.60493 4.01898 1.78979
3.49991 4.24589 2.89607 3.84714 2.16259 2.63607 2.67773 2.87195 3.59004 5.63139 4.23074
204 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.02321 4.44704 4.48894 0.61958 0.77255 0.49180 0.94553
126 2.70259 4.78288 3.10316 2.62084 3.23014 3.55717 2.77689 3.39328 2.58605
3.02278 3.86371 3.04868 3.94378 2.53415 2.11061 2.76991 2.93283 3.10180 3.35180 3.35576
205 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01765 4.44148 5.16383 0.61958 0.77255 0.50070 0.93168
127 2.64699 4.39217 3.56865 2.05763 3.29481 3.66295 3.91739 2.60538 2.95345
2.50897 2.59486 3.40402 4.04141 3.00636 3.30409 2.90867 2.78869 2.22561 4.97634 3.56924
206 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01765 4.44148 5.16383 0.61958 0.77255 0.50070 0.93168
128 2.15651 5.08647 2.66218 2.31635 4.38993 2.79836 3.66501 3.84743 2.38128
3.37411 4.13923 2.89371 2.92678 2.67029 2.83170 2.46722 2.70744 3.45474 4.50984 4.16121
207 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01765 4.44148 5.16383 0.61958 0.77255 0.50070 0.93168
129 2.47139 5.13557 2.73837 1.94974 4.45770 3.46490 3.60456 3.85623 2.21863
2.88369 4.18268 2.94198 3.82238 2.40411 2.53877 2.63956 2.79959 3.31420 5.58153 4.18624
208 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.01765 4.44148 5.16383 0.61958 0.77255 0.50070 0.93168
130 0.54170 4.41455 3.99487 3.83758 4.67181 3.21702 4.80217 3.94160 3.87765
3.78720 4.68767 3.78860 4.02574 4.15301 4.08310 2.61480 3.04914 3.40878 6.07441 4.88693
209 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.04858 4.44148 3.33421 0.61958 0.77255 0.50070 0.93168
131 2.47060 5.10222 2.92302 2.23845 4.41518 3.31163 3.65256 3.83300 2.30764
3.39268 4.15289 2.86002 3.85601 2.39911 2.32759 2.51827 2.29611 3.30596 5.55412 4.16668
210 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.03356 4.41110 3.86983 0.61958 0.77255 0.54715 0.86416
132 2.26873 5.14785 2.83342 2.18702 4.47827 3.38243 3.63990 3.95273 2.07133
3.41537 4.19342 2.78721 3.84499 2.33511 2.64759 2.45499 2.67363 3.49865 5.58841 4.18815
211 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.03225 4.39603 3.94192 0.61958 0.77255 0.56894 0.83500
133 3.29475 4.59909 5.27958 4.75843 3.67853 4.82300 5.34776 1.05587 4.65842
1.73667 3.38036 4.93089 5.04836 4.83561 4.78636 4.20753 3.60004 1.39603 5.69975 4.55067
212 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.19685 4.38251 1.79460 0.61958 0.77255 0.58780 0.81091
134 2.59525 2.26255 4.26037 3.68225 3.24006 3.81148 4.16702 2.18927 3.54565
2.25647 3.24248 3.85052 4.18879 3.76123 3.70265 3.11792 2.92528 1.72461 4.80046 2.95881
213 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.04263 4.20800 3.61724 0.61958 0.77255 0.77092 0.62099
135 2.12293 5.06795 2.53477 2.27785 4.37789 3.30834 3.61326 3.84072 2.22403
3.35911 4.12421 2.69439 3.80736 2.57158 2.81142 2.37052 2.76704 3.41396 5.52424 4.13208
214 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477 3.61503
0.05033 4.19589 3.38058 0.61958 0.77255 0.78725 0.60714
```

```
136  1.41298  4.54007  3.16784  2.67479  3.96764  3.28514  3.85979  3.32496  2.60972
     2.92660  3.87024  3.16231  3.88002  3.04176  3.09126  2.66015  2.58267  3.00986  5.31055  4.04058
215  - -
     2.68596  4.42247  2.77539  2.73143  3.46365  2.40403  3.72516  3.29358  2.67762
     2.69335  4.24680  2.90368  2.73761  3.18168  2.89806  2.37907  2.77541  2.98531  4.58498  3.61491
     0.51189  0.91469  *        1.07030  0.41993  0.00000  *
//
```

Example 11: Method of Determining the Lysozyme Enhancing Domain by HMM

SEQ ID NOs: 188 to 316 were aligned using the software program MUSCLE v3.8.31 with the default settings. Using this alignment, the HMM was constructed using the software program 'hmmbuild' from the package HMMER 3.0 (March 2010) (hmmer.org/) and the software was invoked using the default settings by the command: hmmscan3--tblout output.dat model.hmm sequences.fasta. The lysozyme enhancing domain HMM profile thereby generated for subsequent loading into the software program 'hmmscan' is given below.

```
HMMER3/b [3.0 | March 2010]
NAME  lysozyme_enhancing_domain
LENG  73
ALPH  amino
RF    no
CS    no
MAP   yes
DATE  Tue Feb. 3 15:29:15 2015
NSEQ  129
EFFN  1.263702
CKSUM 3302514446
STATS LOCAL MSV     -9.1036 0.71868
STATS LOCAL VITERBI -9.7357 0.71868
STATS LOCAL FORWARD -3.7686 0.71868
HMM        A        C        D        E        F        G        H        I
           K        L        M        N        P        Q        R        S        T        V        W        Y
           m->m     m->i     m->d     i->m     i->i     d->m     d->d
COMPO   2.64236  3.16005  2.87141  2.79417  3.60706  2.63596  3.86157  2.94229  2.65279
        2.95816  3.97690  3.11757  3.46392  3.12498  3.11011  2.56828  2.58627  2.58086  4.17029  3.04296
        2.68618  4.42225  2.77519  2.73123  3.46354  2.40513  3.72494  3.29354  2.67741  2.69355
        4.24690  2.90347  2.73739  3.18146  2.89801  2.37887  2.77519  2.98518  4.58477  3.61503
        0.17958  4.32413  1.88959  0.61958  0.77255  0.00000  *
    1   3.80107  5.04040  4.67499  4.39045  1.81828  4.48873  3.56285  3.50991  4.23379  2.82560
        4.11380  4.16131  4.81340  4.22617  4.28030  3.87997  4.03091  3.43577  3.70270  0.73371  1 - -
        2.68618  4.42225  2.77519  2.73123  3.46354  2.40513  3.72494  3.29354  2.67741  2.69355
        4.24690  2.90347  2.73739  3.18146  2.89801  2.37887  2.77519  2.98518  4.58477  3.61503
        0.02327  4.16783  4.89017  0.61958  0.77255  0.67437  0.71228
    2   2.33952  4.44593  3.23890  3.02979  4.35083  3.16321  4.20776  3.67603  3.02584  3.40031
        4.31198  3.32021  1.10553  3.46227  3.39562  2.64660  2.86963  3.24503  5.70138  4.44714  2 - -
        2.68618  4.42225  2.77519  2.73123  3.46354  2.40513  3.72494  3.29354  2.67741  2.69355
        4.24690  2.90347  2.73739  3.18146  2.89801  2.37887  2.77519  2.98518  4.58477  3.61503
        0.02327  4.16783  4.89017  0.61958  0.77255  0.58149  0.81886
    3   2.99224  4.47028  5.00531  4.50059  3.72470  4.59877  5.18674  1.10701  4.40105  2.19903
        3.51509  4.69439  4.89181  4.65354  4.58483  3.98375  3.44715  1.21838  5.67709  4.47722  3 - -
        2.68618  4.42225  2.77519  2.73123  3.46354  2.40513  3.72494  3.29354  2.67741  2.69355
        4.24690  2.90347  2.73739  3.18146  2.89801  2.37887  2.77519  2.98518  4.58477  3.61503
        0.02218  4.21548  4.93783  0.61958  0.77255  0.62351  0.76800
    4   2.67119  4.76820  3.04982  2.54195  4.12069  3.43519  3.75916  3.51149  2.19874  3.13703
        3.97428  2.96845  3.89558  2.93360  2.89915  2.57877  1.61288  3.10281  5.38435  4.08520  4 - -
        2.68618  4.42225  2.77519  2.73123  3.46354  2.40513  3.72494  3.29354  2.67741  2.69355
        4.24690  2.90347  2.73739  3.18146  2.89801  2.37887  2.77519  2.98518  4.58477  3.61503
        0.02491  4.21548  4.62159  0.61958  0.77255  0.52151  0.90048
    5   2.37234  5.08464  2.49824  2.21575  4.41120  1.99198  3.58111  3.86677  2.52882  3.41126
        4.20120  2.81325  3.86140  2.84200  3.02691  2.42476  2.83819  3.48001  5.60144  4.21122  5 - -
        2.68618  4.42225  2.77519  2.73123  3.46354  2.40513  3.72494  3.29354  2.67741  2.69355
        4.24690  2.90347  2.73739  3.18146  2.89801  2.37887  2.77519  2.98518  4.58477  3.61503
        0.02114  4.26301  4.98536  0.61958  0.77255  0.56183  0.84436
    6   2.63301  5.17310  2.09015  2.17272  4.49463  3.27178  3.65545  3.97097  2.38584  3.47241
        4.23433  2.52660  3.34330  2.76874  2.94084  2.41690  2.44683  3.55393  5.62559  4.21427  6 - -
        2.68618  4.42225  2.77519  2.73123  3.46354  2.40513  3.72494  3.29354  2.67741  2.69355
        4.24690  2.90347  2.73739  3.18146  2.89801  2.37887  2.77519  2.98518  4.58477  3.61503
        0.07099  4.26555  2.90975  0.61958  0.77255  0.56422  0.84119
    7   2.61111  4.85146  2.70126  2.41033  4.02944  2.66646  3.65077  3.52514  2.43178  3.11934
        3.92649  2.77281  3.83428  2.77300  2.91547  2.42718  2.41739  2.79685  5.35415  3.75427  7 - -
        2.68619  4.42226  2.77521  2.73124  3.46355  2.40511  3.72496  3.29355  2.67742  2.69356
        4.24691  2.90348  2.73741  3.18147  2.89802  2.37888  2.77504  2.98519  4.58478  3.61504
        0.09494  2.48394  4.93906  0.38374  1.14353  0.52245  0.89910
    8   3.16563  4.52406  5.00410  4.47860  3.59477  4.61318  5.11093  1.75130  4.36399  1.66390
```

-continued 3.39589 4.68330 4.88103 4.58179 4.52924 3.98371 3.48258 0.98654 5.56065 4.39116 9 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.02108 4.26555 4.98790 0.61958 0.77255 0.56422 0.84119
9 2.74568 5.18103 2.62071 2.37499 4.50785 3.44148 3.43386 3.97009 2.14487 3.46738
4.24084 1.77122 3.86903 2.77625 2.44752 2.65464 2.97757 3.56615 5.60976 4.22640 10 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.02108 4.26555 4.98790 0.61958 0.77255 0.43965 1.03356
10 3.21633 0.35479 4.79708 4.65548 4.57914 3.72194 5.20787 3.82938 4.49870 3.70850
4.85167 4.53077 4.45916 4.82584 4.53365 3.48556 3.72159 3.53505 5.86530 4.85631 11 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
11 3.30119 5.31389 3.73668 3.09114 4.51121 3.86969 3.13217 4.16018 2.10415 3.58751
4.49408 3.45992 4.26052 2.99924 0.83233 3.31264 3.47550 3.85705 5.50391 4.26079 12 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
12 2.24421 4.51545 3.30473 2.81428 4.39051 3.23670 4.14928 3.77491 3.04692 3.44962
4.27960 3.30747 3.89875 3.36729 3.42822 1.05895 2.51437 3.31859 5.70279 4.43964 13 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
13 2.69468 4.75034 2.89429 2.56341 4.66767 0.94912 4.20148 4.12822 3.15097 3.75743
4.60332 3.20872 3.96757 3.42394 3.55601 2.47312 3.12631 3.62410 5.94365 4.63448 14 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
14 2.67424 4.69741 3.65691 3.53445 4.63811 3.40395 4.65858 4.09486 3.63150 3.77181
4.76683 3.75211 0.59051 3.99224 3.88152 2.99980 3.31792 3.64480 5.92609 4.77080 15 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
15 2.26323 4.51933 3.21961 2.94036 4.47411 1.38422 4.14822 3.91245 3.06085 3.54037
4.34588 2.97288 3.87499 3.35219 3.46854 1.96711 2.52323 3.40350 5.76384 4.49002 16 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
16 2.20668 4.36145 3.82003 3.56662 4.41076 3.20360 4.55272 3.51597 3.53768 3.41304
4.35967 3.64187 3.96341 3.86648 3.78744 2.68079 0.81042 3.10831 5.83931 4.64399 17 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
17 2.61570 5.10849 2.62653 2.38205 4.43252 2.78078 3.60811 3.89018 2.47426 3.42628
4.20945 2.71231 3.87390 2.61734 2.99949 1.64993 2.94705 3.49936 5.60799 4.21799 18 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
18 2.58292 4.58689 3.02231 2.68583 3.00245 3.32285 2.97170 3.14564 2.67302 2.81683
3.67939 2.99852 3.79428 3.00246 3.09283 2.65865 2.82740 2.88473 5.11794 2.25478 19 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
19 2.02971 5.05961 2.68453 2.36019 4.37471 3.26819 3.65420 3.83090 2.10672 3.36092
4.13132 2.92980 3.45060 2.77060 2.82369 2.16905 2.88648 3.43886 5.53518 4.15201 20 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
20 3.16684 4.47509 4.98151 4.48359 3.78153 4.52597 5.13073 1.23357 4.37208 2.38350
3.60515 4.64947 4.86068 4.63385 4.54770 3.62858 3.43521 1.03896 5.65865 4.43929 21 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
21 2.67985 4.50015 3.40866 2.83947 3.66095 3.60615 3.61051 2.50038 2.12953 2.71143
3.59755 3.27678 3.98763 2.81347 3.06211 2.85030 2.83675 1.92294 5.06195 3.81377 22 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
22 2.57540 5.16214 3.25351 2.63376 4.54584 3.62294 3.69980 3.93939 1.30635 3.43432
4.24813 3.13299 4.00544 2.78831 2.11440 2.89381 2.74985 3.58326 5.55169 4.27942 23 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
23 2.54455 4.73655 3.02733 2.59505 4.05985 3.44683 3.70095 3.46466 2.60056 3.09418

-continued

```
3.92399 3.08417 3.89235 2.67009 3.04116 2.11836 1.78482 2.95974 5.35882 4.04770 24 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
24 3.40982 4.75103 4.67192 4.22624 1.97308 4.35966 3.81417 3.04888 4.07862 2.38151
3.72579 4.16721 4.67838 4.14717 4.17038 3.68839 3.63576 2.47365 4.02768 0.99393 25 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
25 2.33607 5.05721 2.94517 2.24042 4.36369 3.44673 3.55543 3.81754 1.82729 3.31948
4.11325 2.80831 3.17764 2.75227 2.78214 2.58400 2.65726 3.32087 5.51479 4.13659 26 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
26 2.36555 5.04925 3.04993 2.35049 4.35720 3.51989 3.68369 3.71551 1.45376 3.06828
4.12214 3.00561 3.91721 2.74243 2.72409 2.73518 2.95391 3.42066 5.49677 4.16815 27 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
27 2.61202 4.80098 2.75023 2.62858 4.42906 1.32629 3.93435 3.86483 2.78346 3.46292
4.27988 3.09911 3.91159 3.10786 2.85440 2.43819 2.91018 3.44468 5.68001 4.35178 28 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
28 2.39518 5.06692 2.42469 2.35324 4.15968 3.22653 3.04826 3.83188 2.39351 3.35617
4.12096 2.82671 3.83411 2.52507 2.87979 2.43622 2.35726 3.41027 5.52582 4.13893 29 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
29 2.56098 5.10975 1.84700 2.22610 4.41970 3.43432 3.64564 3.82090 2.31577 3.39892
4.16246 2.88269 3.84241 2.68525 2.69153 2.62766 2.81515 3.48193 5.56120 3.47482 30 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
30 2.71289 4.20867 4.05384 3.08944 3.32534 3.70711 4.11635 2.10460 3.37170 2.31376
3.31881 3.74286 4.18005 3.62760 3.59433 3.09939 2.94743 1.40821 4.85949 3.10435 31 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
31 2.56066 3.98356 2.83917 2.26935 4.26245 3.45019 3.65582 3.70207 1.96206 3.26063
4.04582 2.95679 3.84786 2.75603 2.89654 2.30158 2.29348 3.33728 5.46026 4.09624 32 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
32 2.98261 4.34033 4.74407 4.16222 2.74015 4.19374 4.48870 1.33722 4.00888 1.70186
3.16247 4.27271 4.50036 4.14592 4.09048 3.51345 3.21313 1.97755 4.93581 3.15765 33 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
33 2.50714 4.52249 3.32761 2.73441 3.99413 2.87824 3.93263 3.37611 2.83014 3.05077
3.89907 3.20556 3.90546 3.15647 3.23473 2.09891 1.66153 2.58887 5.34950 4.08041 34 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
34 2.73372 0.86170 4.21080 3.82223 3.72250 3.51687 4.43487 3.14732 3.50989 2.93675
3.97687 3.88251 4.17078 3.93344 3.44432 2.99564 3.14856 2.89652 5.25169 3.70577 35 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
35 2.78221 4.93521 3.15849 2.72873 3.66991 3.61431 3.78500 3.57206 2.57323 3.13265
4.05241 3.20038 4.05162 1.36867 2.92156 2.93601 3.12692 3.29834 5.09768 2.57435 36 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
36 2.39232 4.68655 3.16574 2.46000 3.89951 3.51768 3.74742 2.86223 2.34831 2.93724
3.78511 3.11031 3.91433 2.90991 3.00803 2.69966 1.85059 2.95170 5.23226 3.93826 37 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
37 2.38712 4.95526 2.95139 2.14292 4.22581 3.30071 3.48757 3.66208 2.41922 3.22834
4.01725 2.96015 3.42523 2.64575 2.85382 2.40915 2.33462 3.08668 5.43599 3.59495 38 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
38 3.32493 5.03100 4.08842 4.05521 5.14287 0.28143 5.12256 4.87721 4.29611 4.46333
```

-continued 5.45951 4.25516 4.43330 4.58529 4.45932 3.51325 3.84001 4.31766 6.09414 5.26815 39 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
39 2.77845 5.16916 2.50798 1.90461 4.47239 3.42576 3.73520 3.92893 2.55535 3.46812
4.26082 2.91770 3.47218 2.74953 3.05304 2.74879 1.68968 3.54385 5.65411 4.25701 40 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
40 2.55637 3.36322 2.86419 2.49420 4.07854 3.43147 3.53651 3.49427 2.36324 3.10007
3.91410 2.51497 3.86778 2.83786 2.95074 2.24490 2.43049 3.00556 5.34651 3.93774 41 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
41 3.32262 4.56891 5.24679 4.77118 3.84175 4.81012 5.48421 1.14831 4.68143 2.30177
3.60891 4.94823 5.08094 4.93596 4.85577 4.22682 3.58792 0.99460 5.88795 4.67682 42 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
42 2.65825 5.10541 2.72992 2.15627 3.98363 3.31023 3.53625 3.89170 2.18852 3.23731
4.15424 2.23857 3.82936 2.65748 2.86654 2.25743 2.79796 3.48165 5.55380 4.15800 43 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
43 2.61182 4.52680 3.60621 3.51889 4.78008 0.61583 4.68006 4.23876 3.72062 3.95294
4.83622 3.66170 4.02536 4.00392 3.97409 2.79132 2.85714 3.64017 6.05621 4.90618 44 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
44 2.79049 5.22667 2.25221 2.33027 4.53369 3.27947 3.53614 4.00930 2.56097 3.52971
4.31450 1.59788 3.89352 2.86397 3.06987 2.39242 3.03945 3.49407 5.69864 4.13140 45 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
45 2.49378 3.36932 2.74714 2.42229 4.10830 3.46961 3.68039 3.52770 2.44255 3.12654
3.93602 2.51463 3.86384 2.82770 2.94369 2.19290 2.51568 3.13211 5.36588 3.76024 46 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
46 2.69732 4.16858 4.15640 3.57668 3.28068 3.80998 4.13366 1.64485 3.45403 1.84904
3.26899 3.79253 3.96991 3.68559 3.64246 2.81777 2.62992 2.15853 4.82146 3.52063 47 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
47 4.19233 5.38393 4.84605 4.67977 3.27817 4.29458 4.57157 4.26819 4.41284 3.57367
4.87507 4.74845 4.85287 4.77414 4.45256 4.39169 4.52083 4.16862 0.32020 3.26075 48 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
48 3.20149 5.67973 0.78816 2.34486 4.76934 3.43076 3.17601 4.55895 3.07436 4.04716
4.94146 2.92732 4.07402 3.21129 3.65781 3.08955 3.50632 4.14006 6.03658 4.51417 49 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
49 2.76346 4.98544 3.15831 2.56957 4.01057 3.55403 3.68400 3.67589 1.47331 2.89158
4.05158 3.07047 3.93382 2.56322 2.45400 2.78078 2.98070 3.34485 5.41794 3.49426 50 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
50 2.64257 4.43619 3.56736 3.08202 3.77537 3.52079 4.05811 2.42620 3.00927 2.79176
3.72810 2.99222 4.03030 3.35753 3.34645 2.85418 1.35329 2.62966 5.23131 3.98292 51 - -
2.68619 4.42226 2.77521 2.73124 3.46340 2.40514 3.72496 3.29355 2.67742 2.69356
4.24691 2.90348 2.73741 3.18148 2.89802 2.37888 2.77521 2.98520 4.58478 3.61472
0.08832 2.54971 5.04648 0.37639 1.15942 0.48576 0.95510
51 2.52068 4.47414 3.35565 2.74391 3.33968 3.48613 3.81115 3.00228 2.76056 2.69538
3.20591 3.24034 3.68619 2.82417 3.12828 2.08694 2.32290 2.59916 4.31681 3.78415 53 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
52 2.77860 4.87789 1.42239 2.56155 3.13731 3.54366 3.74371 3.49507 2.67769 3.09585
3.97167 3.06454 3.97169 2.99708 3.12924 2.82286 3.01884 3.20614 4.04928 3.59798 54 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
53 2.94931 5.28328 2.08563 2.39481 4.84632 1.16425 4.00151 4.36230 3.01231 3.90219
4.74326 2.45548 3.99074 3.18038 3.56729 2.91382 3.29175 3.89959 6.06470 4.62009 55 - -
2.68621 4.42228 2.77522 2.73126 3.46357 2.40509 3.72497 3.29357 2.67727 2.69358

-continued

```
4.24693 2.90346 2.73742 3.18149 2.89804 2.37878 2.77522 2.98521 4.58480 3.61506
0.08509 2.58845 5.04648 0.73284 0.65497 0.48576 0.95510
54 3.21633 0.35479 4.79708 4.65548 4.57914 3.72194 5.20787 3.82938 4.49870 3.70850
4.85167 4.53077 4.45916 4.82584 4.53365 3.48556 3.72159 3.53505 5.86530 4.85631 59 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
55 4.07603 5.22780 4.94333 4.71701 1.81696 4.70604 3.64405 3.73694 4.54415 3.00155
4.31962 4.34626 5.01267 4.44587 4.52415 4.10863 4.29875 3.67538 3.75731 0.60600 60 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
56 3.29932 4.57114 5.13914 4.65306 3.79025 4.73170 5.36042 1.62171 4.54191 2.21256
3.57888 4.84627 5.01963 4.80796 4.72647 4.13701 3.56571 0.76183 5.80720 4.58938 61 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
57 1.40302 4.31490 3.77731 3.44350 4.52474 3.10962 4.46137 3.90675 3.45708 3.61908
4.43729 3.53676 3.86941 3.73557 3.76041 1.18441 2.55005 3.34107 5.86901 4.67381 62 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
58 3.16638 5.52729 0.80512 2.42994 5.07620 2.30005 4.12607 4.65042 3.22647 4.16769
5.05164 2.99972 4.08759 3.32219 3.82773 3.09290 3.51563 4.17606 6.23444 4.80691 63 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
59 3.11990 4.36544 4.32127 3.81191 2.17745 4.09367 3.78203 3.04592 3.23806 2.64903
3.67717 3.91110 4.44159 3.85035 3.84946 3.39383 3.34718 2.77912 3.74216 1.06936 64 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
60 3.51146 4.91649 4.45325 4.08004 2.02567 4.31163 3.69403 3.46524 3.96389 2.92976
4.07889 4.05659 4.68281 4.07537 4.10672 2.99801 3.75887 3.31559 3.91189 0.78971 65 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01987 4.32413 5.04648 0.61958 0.77255 0.48576 0.95510
61 2.72553 4.31253 4.16671 3.66674 3.67680 3.72642 4.41126 2.29394 3.56150 2.58708
3.60951 3.86666 4.24179 3.84789 3.80334 2.76599 2.38224 1.10833 5.25833 4.04936 66 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.02985 4.32413 4.12501 0.61958 0.77255 0.48576 0.95510
62 2.51216 5.16569 2.33791 2.35923 4.49437 3.19374 3.66109 3.96480 1.64210 3.46558
4.22781 2.83561 3.85394 2.71011 2.84192 2.54559 2.88860 3.55105 5.61534 4.21583 67 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.02007 4.31435 5.03670 0.61958 0.77255 0.49963 0.93333
63 2.49188 4.38955 3.59551 3.16295 4.09719 3.28177 4.17679 3.38911 3.04040 3.15453
4.02841 3.43067 3.92288 3.44894 3.44644 2.11805 1.20176 2.68117 5.48692 4.25411 68 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.02007 4.31435 5.03670 0.61958 0.77255 0.49963 0.93333
64 1.89508 4.31720 3.70048 3.48388 4.63634 0.95179 4.55159 4.00807 3.58485 3.73760
4.55934 3.55250 3.87506 3.84242 3.86415 2.56592 2.50453 3.40204 5.97883 4.79808 69 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.03953 4.31435 3.67355 0.61958 0.77255 0.49963 0.93333
65 2.63597 3.39258 3.14566 2.45530 3.91792 3.49097 3.54341 3.31288 2.40023 2.95698
3.79792 3.08785 3.89316 2.92081 3.00148 1.97899 2.29007 2.96915 5.24220 3.94276 70 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.02046 4.29528 5.01763 0.61958 0.77255 0.52575 0.89432
66 2.59137 4.97540 2.68695 2.29850 4.05453 3.34590 3.64946 3.59380 2.42308 3.26160
4.04572 2.57932 3.83844 2.77492 2.90216 1.98570 2.44689 3.22530 5.46068 4.09334 71 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.02046 4.29528 5.01763 0.61958 0.77255 0.52575 0.89432
67 2.36239 3.82492 3.07537 2.52645 4.05085 1.94430 3.77137 3.45853 2.53920 3.08721
3.91418 2.86394 3.87403 2.94691 3.05153 2.46988 2.65768 3.12923 5.35184 4.04208 72 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.02046 4.29528 5.01763 0.61958 0.77255 0.52575 0.89432
68 2.51473 4.23017 3.73065 3.15738 2.96324 3.66009 3.93184 2.62617 3.08387 2.43082
2.74387 3.49391 3.33993 3.35931 3.14679 2.64784 2.86016 2.49302 4.81896 2.22311 73 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.02046 4.29528 5.01763 0.61958 0.77255 0.52575 0.89432
69 2.33893 4.26290 4.21737 3.66773 3.27773 3.87203 4.32579 2.12233 3.56960 2.41061
```

```
-continued
3.43058 3.89614 4.28394 3.82133 3.79298 2.87144 3.03565 1.21453 5.06701 3.86005 74 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.02293 4.29528 4.70670 0.61958 0.77255 0.52575 0.89432
70 2.49593 4.60476 3.23381 2.52485 3.79749 3.53767 3.76569 3.14297 2.26081 2.40764
3.70182 3.15412 3.92810 2.98301 3.03430 2.76728 2.09050 2.55846 5.16115 3.88294 75 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.02051 4.29287 5.01521 0.61958 0.77255 0.52898 0.88967
71 2.60687 5.12624 2.52016 2.23382 4.44833 2.55208 3.64005 3.91884 2.12896 3.37075
4.18386 2.86694 3.03933 2.74997 2.89501 2.33562 2.83629 3.50672 5.58015 4.17955 76 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.02051 4.29287 5.01521 0.61958 0.77255 0.52898 0.88967
72 2.57816 5.12677 2.87095 2.24649 4.45454 3.41210 3.40077 3.91086 1.59193 3.41242
4.17909 2.90547 3.85681 2.60853 2.68264 2.65653 2.67555 3.50960 5.55782 4.18309 77 - -
2.68618 4.42225 2.77520 2.73117 3.46354 2.40513 3.72495 3.29354 2.67741 2.69355
4.24690 2.90347 2.73740 3.18147 2.89801 2.37887 2.77520 2.98519 4.58477 3.61503
0.09497 3.41028 2.85473 0.52137 0.90068 0.52898 0.88967
73 3.08258 0.42515 4.66004 4.49479 4.42412 3.61311 5.06351 3.64868 4.33208 3.53771
4.67608 4.38809 4.34603 4.66309 4.38494 3.35266 3.58099 3.36315 5.74041 4.70439 79 - -
2.68618 4.42225 2.77519 2.73123 3.46354 2.40513 3.72494 3.29354 2.67741 2.69355
4.24690 2.90347 2.73739 3.18146 2.89801 2.37887 2.77519 2.98518 4.58477 3.61503
0.01461 4.23357 * 0.61958 0.77255 0.00000 *
//
```

Example 12: Determination of DomT Scores

The DomT scores for the LAD domain and the LED domain of the LYS polypeptides of the invention were determined using the LAD Catalytic Domain HMM from Example 10 and the Lysozyme Enhancing Domain HMM from Example 11 as described herein are presented in table 5 below.

TABLE 5

DomT scores for LAD and LED domains

| | LAD domain | | LED domain | |
|---|---|---|---|---|
| Sequence | Amino acid numbers | DomT score | Amino acid numbers | DomT score |
| SEQ ID NO: 3 | 84 to 226 | 202.5 | 1 to 73 | 118.3 |
| SEQ ID NO: 6 | 84 to 226 | 195.4 | 1 to 73 | 118.5 |
| SEQ ID NO: 9 | 81 to 220 | 199.2 | 1 to 73 | 116.7 |
| SEQ ID NO: 12 | 161 to 304 | 193.4 | 1 to 72 | 108.7 |
| | | | 76 to 147 | 104.6 |
| SEQ ID NO: 15 | 85 to 228 | 200.1 | 1 to 73 | 125.2 |
| SEQ ID NO: 18 | 88 to 230 | 205.3 | 1 to 73 | 119.7 |
| SEQ ID NO: 21 | 87 to 230 | 201.4 | 1 to 73 | 116.9 |
| SEQ ID NO: 24 | 90 to 232 | 201.5 | 1 to 73 | 119.1 |
| SEQ ID NO: 27 | 85 to 228 | 199.8 | 1 to 73 | 123 |
| SEQ ID NO: 30 | 85 to 228 | 202.8 | 1 to 73 | 122.6 |
| SEQ ID NO: 33 | 84 to 226 | 198.2 | 1 to 73 | 115.2 |
| SEQ ID NO: 36 | 83 to 222 | 194.9 | 1 to 73 | 113.1 |
| SEQ ID NO: 39 | 82 to 225 | 203.0 | 1 to 72 | 117.4 |
| SEQ ID NO: 42 | 161 to 303 | 192.6 | 1 to 73 | 115.8 |
| | | | 77 to 149 | 111.2 |
| SEQ ID NO: 45 | 85 to 227 | 208.3 | 1 to 73 | 124.9 |
| SEQ ID NO: 329 | 4 to 146 | 205.3 | — | — |

All of the claimed LYS polypeptides have a LAD DomT score of at least 170, indicating good homology to the LAD HMM model. Likewise all claimed LYS polypeptides have a LED, had a LED DomT score of at least 100, indicating good homology to the LED HMM model.

Example 13: Activity of LYS Polypeptides as Determined Using Reducing Ends Assay The LYS polypeptides of the invention were tested according to Example 1 at two enzyme concentrations and the results are shown in tables 6 to 8 below.

TABLE 6

OD Drop of SEQ ID NO: 3

| LYS polypeptide | OD Drop (5.0 µg/ml)[1] | OD Drop (0.7 µg/ml)[1] |
|---|---|---|
| SEQ ID NO: 3 | 5.4 | 2.4 |

[1]enzyme concentration

TABLE 7

OD Drop of SEQ ID NO: 6 to 45

| LYS polypeptide | OD Drop (5.0 µg/ml)[1] | OD Drop (0.7 µg/ml)[1] |
|---|---|---|
| SEQ ID NO: 6 | 4.4 | 2.0 |
| SEQ ID NO: 9 | 5.2 | 2.7 |
| SEQ ID NO: 12 | 2.4 | 1.4 |
| SEQ ID NO: 15 | 6.7 | 3.2 |
| SEQ ID NO: 21 | 3.9 | 2.2 |
| SEQ ID NO: 24 | 3.1 | 1.8 |
| SEQ ID NO: 27 | 7.8 | 4.6 |
| SEQ ID NO: 30 | 8.7 | 6.0 |
| SEQ ID NO: 33 | 8.6 | 5.7 |
| SEQ ID NO: 36 | 5.4 | 2.9 |
| SEQ ID NO: 39 | 7.8 | 4.8 |
| SEQ ID NO: 42 | 5.1 | 3.1 |
| SEQ ID NO: 45 | 8.5 | 3.9 |
| SEQ ID NO: 329 | 5.0 | 2.3 |

[1]enzyme concentration

As can be seen, the LYS polypeptides of the invention display lysozyme activity as determined using the reducing ends assay.

Example 14: Activity of LYS Polypeptides as Determined Using OD Drop Assay

The LYA polypeptides of the invention were tested according to Example 2 at pH4 and the results are shown in tables 8 and 9 below.

TABLE 8

OD Drop against *M. luteus*

| LYS polypeptide | OD Drop *M. luteus* 1 h, pH 4 |
|---|---|
| SEQ ID NO: 3 | 0.116 |
| SEQ ID NO: 6 | 0.151 |
| SEQ ID NO: 9 | 0.121 |
| SEQ ID NO: 12 | 0.177 |
| SEQ ID NO: 15 | 0.125 |
| SEQ ID NO: 21 | 0.113 |
| SEQ ID NO: 24 | 0.121 |
| SEQ ID NO: 27 | 0.071 |
| SEQ ID NO: 30 | 0.081 |
| SEQ ID NO: 33 | 0.052 |
| SEQ ID NO: 36 | 0.171 |
| SEQ ID NO: 39 | 0.154 |
| SEQ ID NO: 42 | 0.162 |

TABLE 9

OD Drop against *M. luteus*

| LYS polypeptide | OD Drop *M. luteus* 1 h, pH 4 |
|---|---|
| SEQ ID NO: 18 | 0.078 |
| SEQ ID NO: 329 | 0.063 |

As can be seen, the LYS polypeptides of the invention display lysozyme activity as determined using the traditional OD drop assay against *M luteus*.

Example 19: Animal Feed and Animal Feed Additives Comprising a LYS Polypeptide

Animal Feed Additive

A formulation comprising the LYS polypeptide of the invention (e.g. SEQ ID NO: 3, 6, 9, 12, 15, 18, 21, 24, 27, 30, 33, 36, 39, 42, 45 or 239) containing 0.01 g to 10 g enzyme protein is added to the following premix (per kilo of premix):

| 5000000 | IE | Vitamin A |
|---|---|---|
| 1000000 | IE | Vitamin D3 |
| 13333 | mg | Vitamin E |
| 1000 | mg | Vitamin K3 |
| 750 | mg | Vitamin B1 |
| 2500 | mg | Vitamin B2 |
| 1500 | mg | Vitamin B6 |
| 7666 | mcg | Vitamin B12 |
| 12333 | mg | Niacin |
| 33333 | mcg | Biotin |
| 300 | mg | Folic Acid |
| 3000 | mg | Ca-D-Panthothenate |
| 1666 | mg | Cu |
| 16666 | mg | Fe |
| 16666 | mg | Zn |
| 23333 | mg | Mn |
| 133 | mg | Co |
| 66 | mg | I |
| 66 | mg | Se |
| 5.8 | % | Calcium |
| 25 | % | Sodium |

Animal Feed

This is an example of an animal feed (broiler feed) comprising the animal feed additive as described above:

62.55% Maize 33.8% Soybean meal (50% crude protein)

1.0% Soybean oil 0.2% DL-Methionine 0.22% DCP (dicalcium phosphate)

0.76% CaCO$_3$ (calcium carbonate)

0.32% Sand 0.15% NaCl (sodium chloride)

1% of the above Premix

The ingredients are mixed, and the feed is pelleted at the desired temperature, e.g. 60, 65, 75, 80, 85, 90 or even 95 Q C.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure, including definitions, will control.

What is claimed is:

1. A composition comprising a plant material and at least 0.01 mg of a polypeptide per kilogram of said composition, wherein the polypeptide has lysozyme activity and is selected from the group consisting of:

(a) polypeptides having at least 80% sequence identity to the polypeptide of SEQ ID NO: 18;
   (b) variants of SEQ ID NO: 18 that comprise one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;
   (c) polypeptides comprising a polypeptide of (a) or (b) and a N-terminal and/or C-terminal His-tag and/or HQ-tag;
   (d) polypeptides comprising a polypeptide of (a) or (b) and a N-terminal and/or C-terminal extension of up to 10 amino acids, e.g. 1, 2, 3, 4, 5, 6, 7, 8, 9 or 10 amino acids; and
   (e) fragments of the polypeptides of (a) or (b) having lysozyme activity and having at least 90% of the length of the polypeptide of which it is a fragment.

2. The composition of claim 1, wherein the polypeptide comprises one or more motifs selected from the group consisting of (a) motif I:
   (SEQ ID NO: 317)
   AG[I/L]AT[A/G][I/L][T/V]ES;

(b) motif II
   (SEQ ID NO: 318)
   V[G/A]XLCQXVQXSAYP;
   and (c) motif III:
   (SEQ ID NO: 319)
   [CGY][YF][VIL][ASTP][DG]X[YF][VIT]X[TS][GAN].

3. The composition of claim 1, wherein the polypeptide is a variant of SEQ ID NO: 18 that comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions.

4. The composition of claim 1, wherein the polypeptide comprises an N-terminal and/or C-terminal His-tag and/or HQ-tag.

5. The composition of claim 1, wherein the polypeptide is a fragment of SEQ ID NO: 18 having at least 90% of the length of SEQ ID NO: 18.

6. The composition of claim 1, wherein the plant material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, fava bean, chickpea, lentil, peanut, Spanish peanut, canola, oilseed rape, rice, beet, cabbage, sugar beet, spinach, quinoa, and pea, and any combination thereof.

7. The composition of claim 1, wherein the plant material comprises soybean meal and/or rapeseed meal.

8. The composition of claim 1, wherein the plant material comprises one or more vegetable proteins.

9. The composition of claim 1, further comprising whey.

10. The composition of claim 1, further comprising an animal protein.

11. The composition of claim 10, wherein said animal protein comprises a meat and bone meal, a feather meal and/or a fish meal.

12. The composition of claim 1, further comprising a formulating agent selected from the group consisting of glycerol, ethylene glycol, 1,2-propylene glycol, 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose.

13. The composition of claim 1, further comprising one or more additional enzymes selected from the group consisting of acetyl xylan esterase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lipase, lysophospholipase, lysozyme, mannanase, alpha-mannosidase, beta-mannosidase, phytase, phospholipase A1, phospholipase A2, phospholipase C, phospholipase D, protease, pullulanase, pectinase, pectin lyase, xylanase, beta-xylosidase and any combination thereof.

14. The composition of claim 1, further comprising one or more vitamins, one or more minerals, one or more amino acids, one or more prebiotics, one or more organic acids, and/or one or more phytogenics.

15. The composition of claim 1, in the form of a pellet or granule.

16. The composition of claim 1, wherein the polypeptide is selected from:
(i) polypeptides having at least 85% sequence identity to the polypeptide of SEQ ID NO: 18;
(ii) polypeptides comprising a polypeptide of (i) and a N-terminal and/or C-terminal His-tag and/or HQ-tag;
(iii) polypeptides comprising a polypeptide of (i) and a N-terminal and/or C-terminal extension of up to 10 amino acids, e.g. 1, 2, 3, 4, 5, 6, 7, 8, 9 or 10 amino acids; and
(iv) fragments of the polypeptides of (i) having lysozyme activity and having at least 90% of the length of the polypeptide of which it is a fragment.

17. The composition of claim 1, wherein the polypeptide is selected from:
(i) polypeptides having at least 90% sequence identity to the polypeptide of SEQ ID NO: 18;
(ii) polypeptides comprising a polypeptide of (i) and a N-terminal and/or C-terminal His-tag and/or HQ-tag;
(iii) polypeptides comprising a polypeptide of (i) and a N-terminal and/or C-terminal extension of up to 10 amino acids, e.g. 1, 2, 3, 4, 5, 6, 7, 8, 9 or 10 amino acids; and
(iv) fragments of the polypeptides of (i) having lysozyme activity and having at least 90% of the length of the polypeptide of which it is a fragment.

18. The composition of claim 1, wherein the polypeptide is selected from:
(i) polypeptides having at least 95% sequence identity to the polypeptide of SEQ ID NO: 18;
(ii) polypeptides comprising a polypeptide of (i) and a N-terminal and/or C-terminal His-tag and/or HQ-tag;
(iii) polypeptides comprising a polypeptide of (i) and a N-terminal and/or C-terminal extension of up to 10 amino acids, e.g. 1, 2, 3, 4, 5, 6, 7, 8, 9 or 10 amino acids; and
(iv) fragments of the polypeptides of (i) having lysozyme activity and having at least 90% of the length of the polypeptide of which it is a fragment.

19. The composition of claim 1, wherein the polypeptide is selected from:
(i) polypeptides having at least 97% sequence identity to the polypeptide of SEQ ID NO: 18;
(ii) polypeptides comprising a polypeptide of (i) and a N-terminal and/or C-terminal His-tag and/or HQ-tag;
(iii) polypeptides comprising a polypeptide of (i) and a N-terminal and/or C-terminal extension of up to 10 amino acids, e.g. 1, 2, 3, 4, 5, 6, 7, 8, 9 or 10 amino acids; and
(iv) fragments of the polypeptides of (i) having lysozyme activity and having at least 90% of the length of the polypeptide of which it is a fragment.

20. The composition of claim 1, wherein the polypeptide is selected:
(i) polypeptides having at least 99% sequence identity to the polypeptide of SEQ ID NO: 18;
(i) polypeptides comprising a polypeptide of (i) and a N-terminal and/or C-terminal His-tag and/or HQ-tag;
(i) polypeptides comprising a polypeptide of (i) and a N-terminal and/or C-terminal extension of up to 10 amino acids, e.g. 1, 2, 3, 4, 5, 6, 7, 8, 9 or 10 amino acids; and
(iv) fragments of the polypeptides of (i) having lysozyme activity and having at least 90% of the length of the polypeptide of which it is a fragment.

21. An animal feed comprising the composition of claim 1.

22. A method comprising administering the composition of claim 1 to an animal.

23. The method of claim 22, wherein said animal is monogastric.

24. The method of claim 22, wherein said animal is a swine.

25. The method of claim 22, wherein said animal is a poultry.

26. The composition of claim 1, wherein the polypeptide is selected from:
(i) polypeptides having 100% sequence identity to the polypeptide of SEQ ID NO: 18;
(ii) polypeptides comprising a polypeptide of (i) and a N-terminal and/or C-terminal His-tag and/or HQ-tag;
(iii) polypeptides comprising a polypeptide of (i) and a N-terminal and/or C-terminal extension of up to 10 amino acids, e.g. 1, 2, 3, 4, 5, 6, 7, 8, 9 or 10 amino acids; and (iv) fragments of the polypeptides of (i) having lysozyme activity and having at least 90% of the length of the polypeptide of which it is a fragment.

* * * * *